(12) United States Patent
Jun et al.

(10) Patent No.: US 10,121,974 B2
(45) Date of Patent: *Nov. 6, 2018

(54) CONDENSED-CYCLIC COMPOUND AND ORGANIC LIGHT-EMITTING DEVICE COMPRISING THE SAME

(71) Applicant: SAMSUNG DISPLAY CO., LTD., Yongin, Gyeonggi-Do (KR)

(72) Inventors: Mieun Jun, Yongin (KR); Sooyon Kim, Yongin (KR); Youngkook Kim, Yongin (KR); Seokhwan Hwang, Yongin (KR); Seunggak Yang, Yongin (KR)

(73) Assignee: Samsung Display Co., Ltd., Yongin, Gyeonggi-do (KR)

( * ) Notice: Subject to any disclaimer, the term of this patent is extended or adjusted under 35 U.S.C. 154(b) by 449 days.

This patent is subject to a terminal disclaimer.

(21) Appl. No.: 14/743,217

(22) Filed: Jun. 18, 2015

(65) Prior Publication Data

US 2016/0190449 A1 Jun. 30, 2016

(30) Foreign Application Priority Data

Dec. 31, 2014 (KR) .......................... 10-2014-0195957

(51) Int. Cl.
*H01L 51/00* (2006.01)
*C07F 5/02* (2006.01)
(Continued)

(52) U.S. Cl.
CPC ............ *H01L 51/008* (2013.01); *C07F 5/027* (2013.01); *C07F 7/082* (2013.01); *C09K 11/06* (2013.01);
(Continued)

(58) Field of Classification Search
None
See application file for complete search history.

(56) References Cited

U.S. PATENT DOCUMENTS 7,053,255 B2 6/2006 Ikeda et al.
7,233,019 B2 6/2007 Ionkin et al.
(Continued)

FOREIGN PATENT DOCUMENTS

JP 2000-294373 10/2000
JP 2007-16237 1/2007
(Continued)

OTHER PUBLICATIONS

Machine Translation of JP 2000-294373 A. (Year: 2000).*

*Primary Examiner* — Kevin M Bernatz
(74) *Attorney, Agent, or Firm* — Lee & Morse, P.C.

(57) ABSTRACT

A condensed-cyclic compound is represented by Formula 1:

<Formula 1> where X, $L_1$ to $L_3$, $R_1$ to $R_3$, $Ar_1$ to $Ar_6$, c1 to c3, a1 to a2, and b1 to b3 are as defined in the specification.

12 Claims, 1 Drawing Sheet

(51) Int. Cl.
*C09K 11/06* (2006.01)
*C07F 7/08* (2006.01)
*H01L 51/50* (2006.01)

(52) U.S. Cl.
CPC ........ *H01L 51/009* (2013.01); *H01L 51/0072* (2013.01); *H01L 51/0073* (2013.01); *H01L 51/0074* (2013.01); *H01L 51/0094* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *C09K 2211/1096* (2013.01); *H01L 51/5012* (2013.01); *H01L 51/5056* (2013.01)

(56) References Cited

U.S. PATENT DOCUMENTS

| | | | | |
|---|---|---|---|---|
| 9,425,416 | B2* | 8/2016 | Jung | H01L 51/0094 |
| 9,831,445 | B2* | 11/2017 | Kim | H01L 51/008 |
| 9,991,445 | B2* | 6/2018 | Haketa | H01L 51/0054 |
| 9,991,452 | B2* | 6/2018 | Kim | H01L 51/008 |
| 2003/0157366 | A1* | 8/2003 | Matsuura | C09K 11/06 |
| | | | | 428/690 |
| 2005/0156164 | A1 | 7/2005 | Sotoyama | |
| 2007/0015005 | A1 | 1/2007 | Chen et al. | |
| 2007/0207343 | A1* | 9/2007 | Funahashi | C09K 11/06 |
| | | | | 428/690 |
| 2007/0237984 | A1 | 10/2007 | Matsuura et al. | |
| 2008/0100208 | A1* | 5/2008 | Shin | C07C 13/62 |
| | | | | 313/504 |
| 2009/0004485 | A1* | 1/2009 | Zheng | C07C 255/09 |
| | | | | 428/446 |
| 2009/0026930 | A1* | 1/2009 | Shin | C07C 13/62 |
| | | | | 313/504 |
| 2009/0261717 | A1* | 10/2009 | Buesing | C07C 13/62 |
| | | | | 313/504 |
| 2010/0032658 | A1* | 2/2010 | Lee | C09K 11/06 |
| | | | | 257/40 |
| 2010/0163852 | A1* | 7/2010 | Nagao | H05B 33/14 |
| | | | | 257/40 |
| 2011/0006289 | A1 | 1/2011 | Mizuki et al. | |
| 2013/0306958 | A1 | 11/2013 | Ito et al. | |
| 2016/0072064 | A1* | 3/2016 | Tada | H01L 51/0059 |
| | | | | 252/301.16 |
| 2016/0155951 | A1* | 6/2016 | Kim | C09K 11/06 |
| | | | | 257/40 |
| 2016/0172594 | A1* | 6/2016 | Kim | H01L 51/008 |
| | | | | 257/40 |
| 2016/0190448 | A1* | 6/2016 | Kim | H01L 51/008 |
| | | | | 257/40 |

FOREIGN PATENT DOCUMENTS

| | | |
|---|---|---|
| JP | 2007-119454 | 5/2007 |
| JP | 2007-123863 | 5/2007 |
| JP | 2010-056190 | 3/2010 |
| KR | 10-2006-0006760 | 1/2006 |
| KR | 10-2009-0010763 | 1/2009 |
| KR | 10-2009-0111355 | 10/2009 |
| KR | 10-2010-0097182 | 9/2010 |
| KR | 10-2014-0032948 | 3/2014 |

* cited by examiner

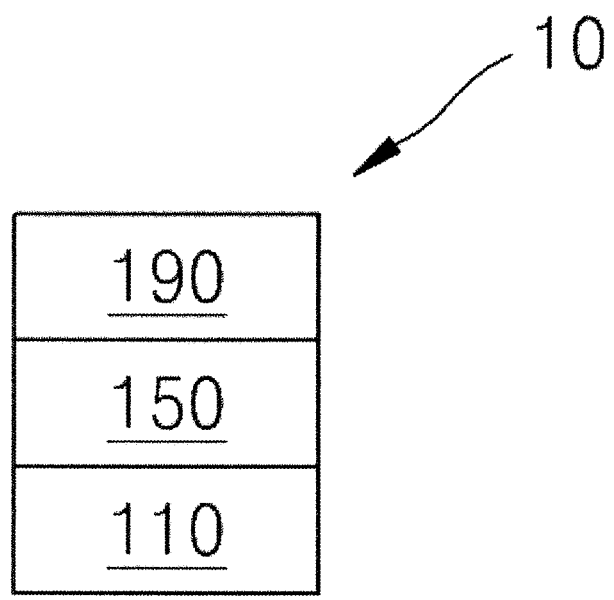

CONDENSED-CYCLIC COMPOUND AND ORGANIC LIGHT-EMITTING DEVICE COMPRISING THE SAME

CROSS-REFERENCE TO RELATED APPLICATION

Korean Patent Application No. 10-2014-0195957, filed on Dec. 31, 2014, in the Korean Intellectual Property Office, and entitled: "Condensed-Cyclic Compound and Organic Light-Emitting Device Comprising The Same," is incorporated by reference herein in its entirety.

BACKGROUND

1. Field

Embodiments relate to a condensed-cyclic compound and an organic light-emitting device including the same.

2. Description of the Related Art

Organic light-emitting devices (OLEDs) are self-emission devices that have wide viewing angles, high contrast ratios, and short response times. In addition, the OLEDs exhibit excellent luminance, driving voltage, and response speed characteristics, and produce full-color images.

The organic light-emitting device may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. The holes and the electrons are recombined in the emission layer to produce excitons. These excitons change from an excited state to a ground state to thereby generate light.

SUMMARY

Embodiments are directed to a condensed-cyclic compound represented by Formula 1:

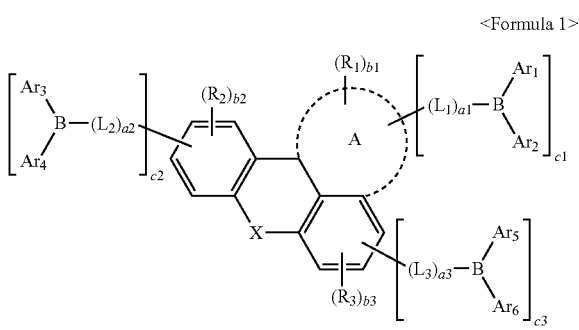

<Formula 1>

In Formula 1,

X is selected from O, S, $N(R_{11})$, $Si(R_{12})(R_{13})(R_{14})$, and $C(R_{15})(R_{16})$;

$L_1$ to $L_3$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 to a3 are each independently selected from 0, 1, 2, and 3, when a1 is two or more, a plurality of $L_1$(s) are identical to or different from each other, when a2 is two or more, a plurality of $L_2$(s) are identical to or different from each other, and when a3 is two or more, a plurality of $L_3$(s) are identical to or different from each other;

$Ar_1$ to $Ar_6$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

c1 to c3 are each independently selected from 0, 1, and 2, provided that a sum of c1, c2, and c3 is 1 or more;

$R_1$ to $R_3$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, and —$N(Q_4)(Q_5)$;

b1 to b3 are each independently an integer selected from 0 to 3;

$R_{11}$ to $R_{16}$ are each independently selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

A is a $C_6$-$C_{20}$ aromatic ring, provided that when A is a benzene, X is not $C(R_{15})(R_{16})$;

at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), and —N($Q_{14}$)($Q_{15}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), and N($Q_{24}$)($Q_{25}$); and —Si($Q_{31}$)($Q_{32}$)($Q_{33}$) and —N($Q_{34}$)($Q_{35}$);

wherein $Q_1$ to $Q_5$, $Q_{11}$ to $Q_{15}$, $Q_{21}$ to $Q_{25}$, and $Q_{31}$ to $Q_{35}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to one or more exemplary embodiments, an organic light-emitting device includes: a first electrode; a second electrode facing the first electrode; and an organic layer that is disposed between the first electrode and the second electrode and including an emission layer; wherein the organic layer includes at least one condensed-cyclic compound described above.

BRIEF DESCRIPTION OF THE DRAWING

Features will become apparent to those of skill in the art by describing in detail exemplary embodiments with reference to the attached drawing in which:

FIG. 1 illustrates a schematic view of an organic light-emitting device according to an embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

As used herein, the term "and/or" includes any and all combinations of one or more of the associated listed. Expressions such as "at least one of" when preceding a list of elements, modify the entire list of elements and do not modify the individual elements of the list.

A condensed-cyclic compound may be represented by Formula 1 below:

<Formula 1>

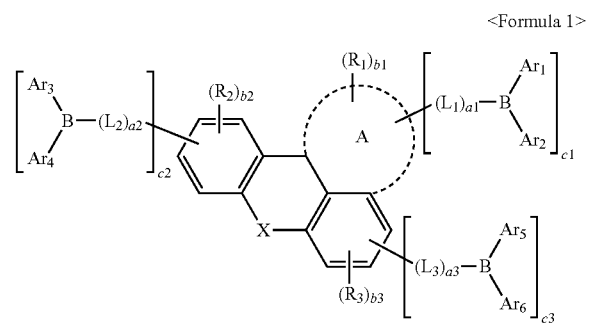

In Formula 1,

X may be selected from O, S, N($R_{11}$), Si($R_{12}$)($R_{13}$)($R_{14}$), and C($R_{15}$)($R_{16}$).

Here, when A, which may be a $C_6$-$C_{20}$ aromatic ring, is a benzene, X may not be C($R_{15}$)($R_{16}$).

B refers to boron.

In some embodiments, in Formula 1, X may be oxygen (O) or sulfur (S).

wherein, in Formula 1, $L_1$ to $L_3$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In some embodiments, in Formula 1, $L_1$ to $L_3$ may be each independently selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a phenylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

In some embodiments, in Formula 1, $L_1$ to $L_3$ may be each independently selected from a group represented by one of Formulae 3-1 to 3-33 below:

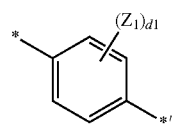

Formula 3-1

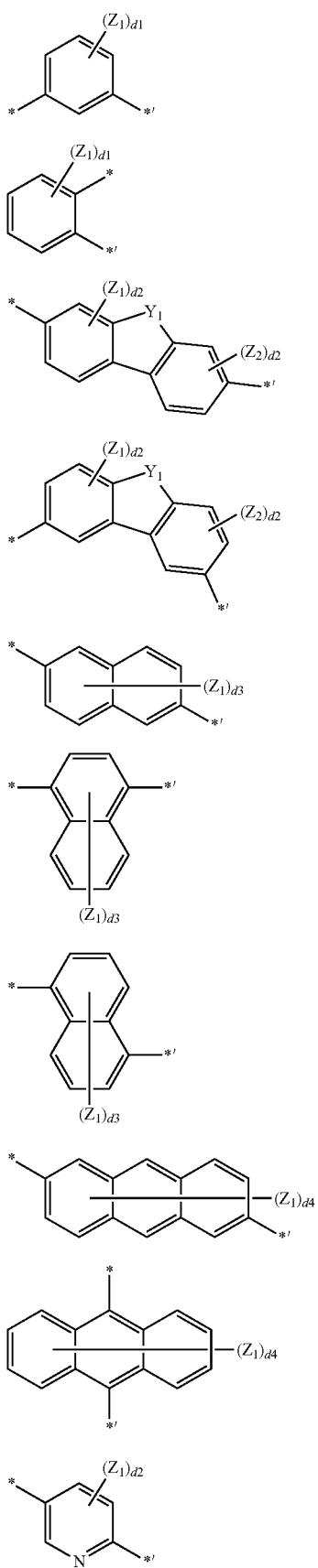
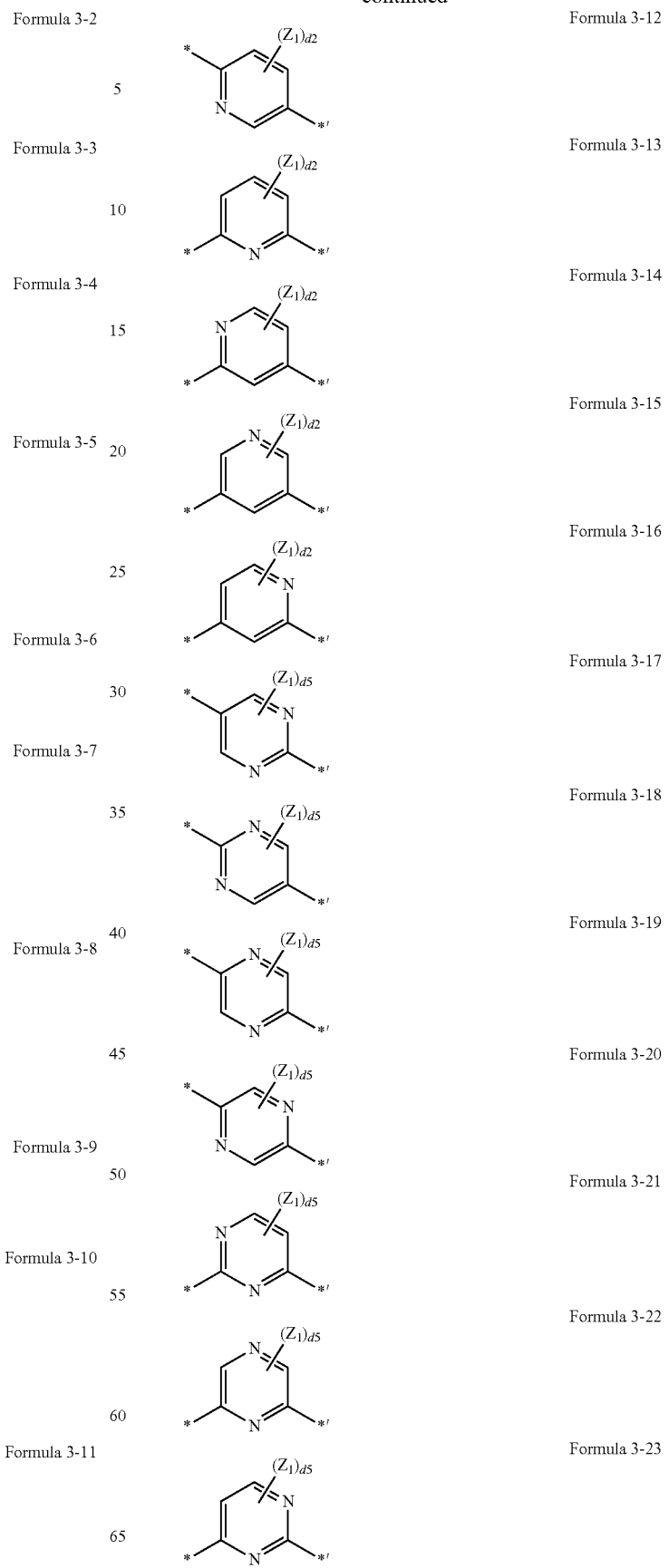

-continued

Formula 3-24
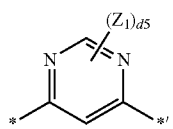

Formula 3-25
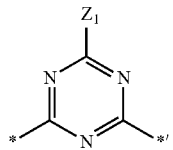

Formula 3-26
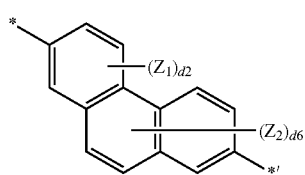

Formula 3-27
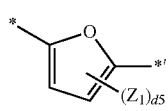

Formula 3-28
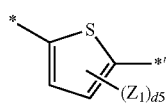

Formula 3-29
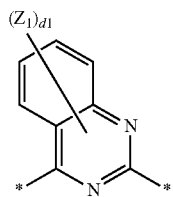

Formula 3-30
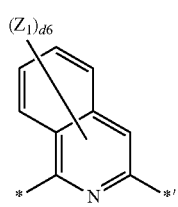

Formula 3-31
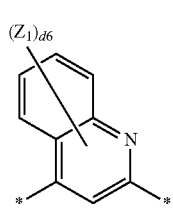

Formula 3-32
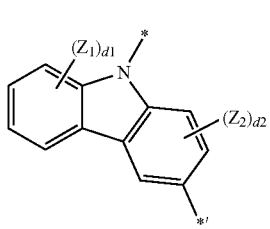

Formula 3-33
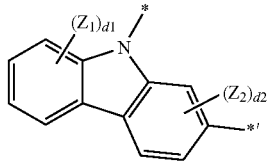

wherein, in Formulae 3-1 to 3-33, $Y_1$ may be selected from O, S, $C(Z_3)(Z_4)$, $N(Z_5)$, and $Si(Z_6)(Z_7)$;

$Z_1$ to $Z_7$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

d1 may be an integer selected from 1 to 4; d2 may be an integer selected from 1 to 3; d3 may be an integer selected from 1 to 6; d4 may be an integer selected from 1 to 8; d5 may be an integer selected from 1 and 2; d6 may be an integer selected from 1 to 5; and * and *' each indicate a binding site to an adjacent atom.

In some embodiments, in Formula 1, $L_1$ to $L_3$ may be each independently selected from a group represented by one of Formulae 4-1 to 4-28 below, as examples:

Formula 4-1
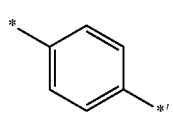

Formula 4-2
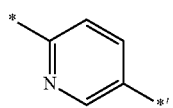

Formula 4-3
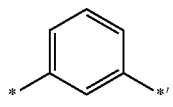

Formula 4-4
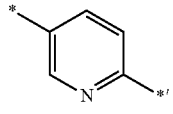

Formula 4-5
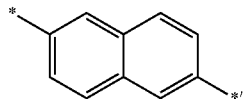

Formula 4-6
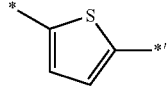

-continued
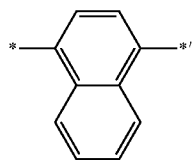
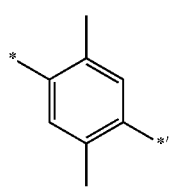
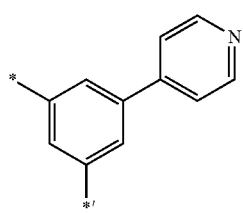
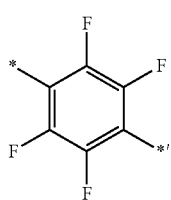
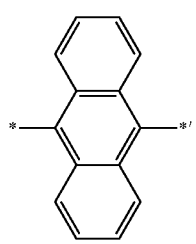
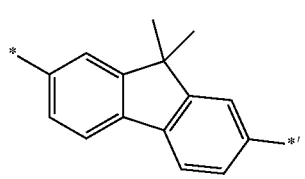
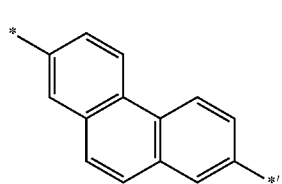
-continued
Formula 4-7
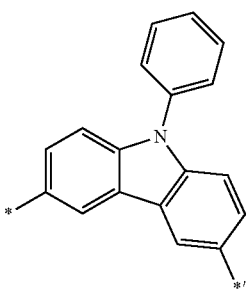
Formula 4-8
Formula 4-9
Formula 4-10
Formula 4-11
Formula 4-12
Formula 4-13
Formula 4-14
Formula 4-15
Formula 4-16
Formula 4-17
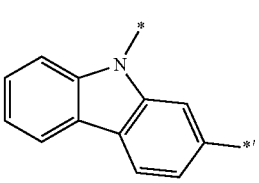
Formula 4-18
Formula 4-19
Formula 4-20
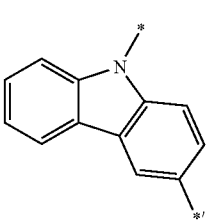
Formula 4-21

-continued

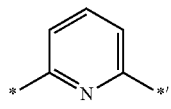
Formula 4-22

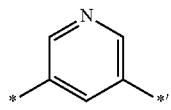
Formula 4-23

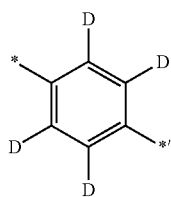
Formula 4-24

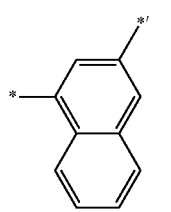
Formula 4-25

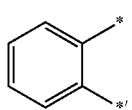
Formula 4-26

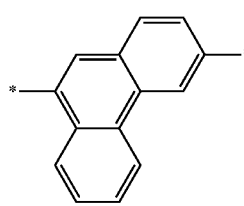
Formula 4-27

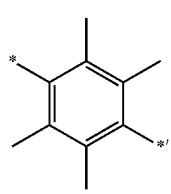
Formula 4-28 in Formulae 4-1 to 4-28, * and *' each indicate a binding site to an adjacent atom.

In Formula 1, a1 to a3 may be each independently selected from 0, 1, 2, and 3. a1 in Formula 1 indicates the number of $L_1$s. When a1 is two or more, a plurality of $L_1(s)$ may be identical to or different from each other. When a1 is 0, *-$(L_1)_{a1}$-*' may be a single bond. a2 in Formula 1 indicates the number of $L_2$s. When a2 is two or more, a plurality of $L_2(s)$ may be identical to or different from each other. When a2 is 0, *-$(L_2)_{a2}$-*' may be a single bond. a3 in Formula 1 indicates the number of $L_3$s. When a3 is two or more, a plurality of $L_3(s)$ may be identical to or different from each other. When a3 is 0, *-$(L_3)_{a3}$-*' may be a single bond.

In some embodiments, in Formula 1, a1 to a3 may be each independently selected from 0 and 1 as examples.

In Formulae 1, $Ar_1$ to $Ar_6$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formula 1, An to $Ar_6$ may be each independently selected from a cyclohexyl group, a norbornanyl group, a norpinanyl group, a pyrrolydinyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group; and a cyclohexyl group, a norbornanyl group, a norpinanyl group, a pyrrolydinyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$);

wherein $Q_{31}$ to $Q_{33}$ may be each independently selected from a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group.

In some embodiments, in Formula 1, $Ar_1$ to $Ar_6$ may be each independently selected from a group represented by one of Formulae 5-1 to 5-18 below:

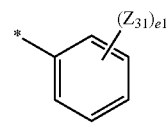

Formula 5-1

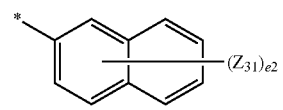

Formula 5-2

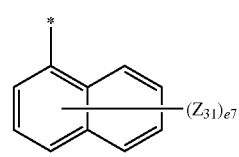

Formula 5-3

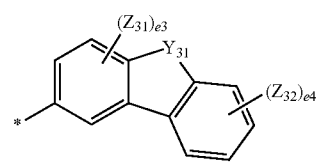

Formula 5-4

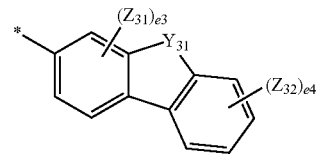

Formula 5-5

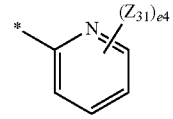

Formula 5-6

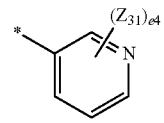

Formula 5-7

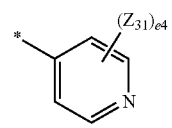

Formula 5-8

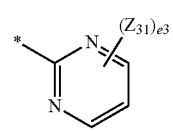

Formula 5-9

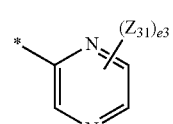

Formula 5-10

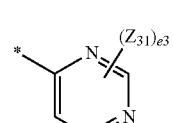

Formula 5-11

-continued

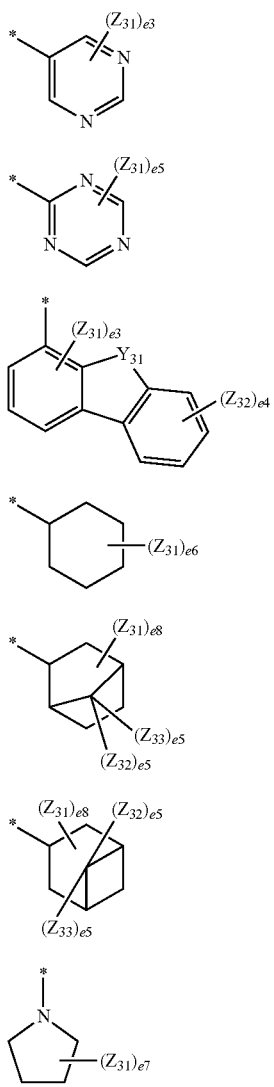

Formula 5-12

Formula 5-13

Formula 5-14

Formula 5-15

Formula 5-16

Formula 5-17

Formula 5-18 wherein, in Formulae 5-1 to 5-18, $Y_{31}$ may be selected from O, S, $C(Z_{34})(Z_{35})$, $N(Z_{36})$, and $Si(Z_{37})(Z_{38})$;

$Z_{31}$ to $Z_{38}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

e1 may be an integer selected from 1 to 5, e2 may be an integer selected from 1 to 7, e3 may be an integer selected from 1 to 3, e4 may be an integer selected from 1 to 4, e5 may be an integer selected from 1 and 2, e6 may be an integer selected from 1 to 10, e7 may be an integer selected from 1 to 8, e8 may be an integer selected from 1 to 9, and

* indicates a binding site to a neighboring atom.

In some embodiments, in Formula 1, $Ar_1$ to $Ar_6$ may be each independently selected from a group represented by one of Formulae 6-1 to 6-28, as examples:

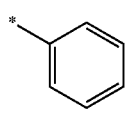

Formula 6-1

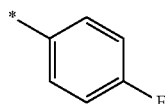

Formula 6-2

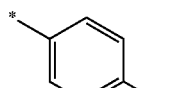

Formula 6-3

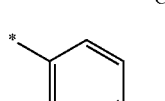

Formula 6-4

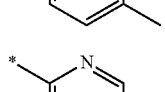

Formula 6-5

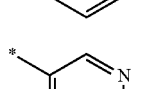

Formula 6-6

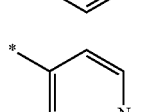

Formula 6-7

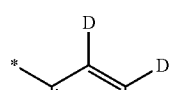

Formula 6-8

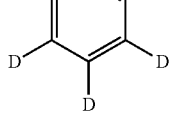

Formula 6-9

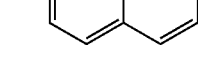

Formula 6-10

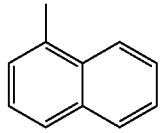

Formula 6-11

-continued

Formula 6-12
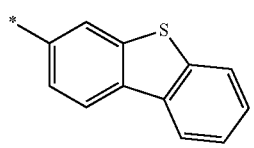

Formula 6-13
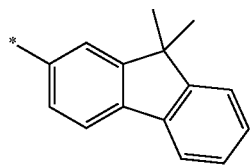

Formula 6-14
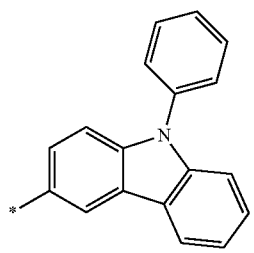

Formula 6-15
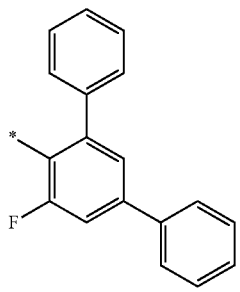

Formula 6-16
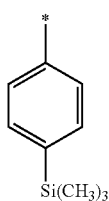

Formula 6-17
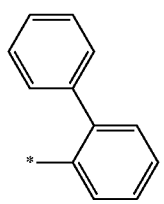

Formula 6-18
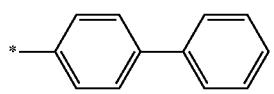

Formula 6-19
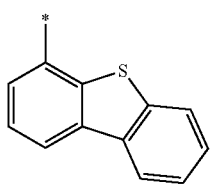

-continued

Formula 6-20
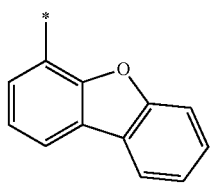

Formula 6-21
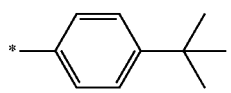

Formula 6-22
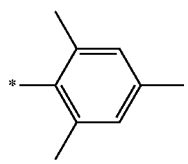

Formula 6-23
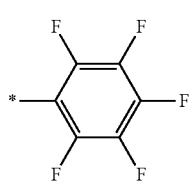

Formula 6-24
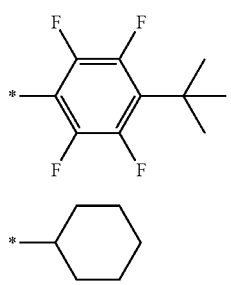

Formula 6-25
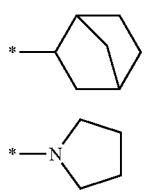

Formula 6-26
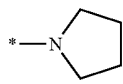

Formula 6-27

Formula 6-28 wherein, in Formulae 6-1 to 6-28, * indicates a binding site to an adjacent atom.

In some embodiments, in Formula 1, $Ar_1$ to $Ar_6$ may be each independently selected from a group represented by one of Formulae 6-1 to 6-8 and Formula 6-21 to 6-28.

In some embodiments, in Formula 1, $Ar_1$ and $Ar_e$ may be identical to or different from each other, $Ar_3$ and $Ar_4$ may be identical to or different from each other, or $Ar_5$ and $Ar_6$ may be identical to or different from each other.

In some embodiments, in Formula 1, $Ar_1$ and $Ar_e$ may be identical to each other, $Ar_3$ and $Ar_4$ may be identical to each other, or $Ar_5$ and $Ar_6$ may be identical to each other.

In Formula 1, c1 to c3 each indicate the number of $*\text{-}[(L_1)_{a1}\text{-}B(Ar_1)(Ar_2)]$, $*\text{-}[(L_2)_{a2}\text{-}B(Ar_3)(Ar_4)]$, and $*\text{-}[(L_3)_{a3}\text{-}B(Ar_5)(Ar_6)]$ in Formula 1, and c1 to c3 may be each independently selected from 0, 1, and 2. Here, a sum of c1, c2, and c3 may be 1 or more.

In some embodiments, in Formula 1, a sum of c1, c2, and c3 may be selected from 1 and 2.

In some embodiments, in Formula 1, c1 may be 1, and c2 and c3 may both be 0, or c1 and c2 may both be 1, and c3 may be 0.

In Formula 1, $R_1$ to $R_3$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1\text{-}C_{60}$ alkyl group, a substituted or unsubstituted $C_2\text{-}C_{60}$ alkenyl group, a substituted or unsubstituted $C_2\text{-}C_{60}$ alkynyl group, a substituted or unsubstituted $C_1\text{-}C_{60}$ alkoxy group, a substituted or unsubstituted $C_3\text{-}C_{10}$ cycloalkyl group, a substituted or unsubstituted $C_1\text{-}C_{10}$ heterocycloalkyl group, a substituted or unsubstituted $C_3\text{-}C_{10}$ cycloalkenyl group, a substituted or unsubstituted $C_1\text{-}C_{10}$ heterocycloalkenyl group, a substituted or unsubstituted $C_6\text{-}C_{60}$ aryl group, a substituted or unsubstituted $C_6\text{-}C_{60}$ aryloxy group, a substituted or unsubstituted $C_6\text{-}C_{60}$ arylthio group, a substituted or unsubstituted $C_1\text{-}C_{60}$ heteroaryl group, a substituted or unsubstituted monovalent non-aromatic condensed polycyclic group, a substituted or unsubstituted monovalent non-aromatic condensed heteropolycyclic group, $-\text{Si}(Q_1)(Q_2)(Q_3)$, and $-\text{N}(Q_4)(Q_5)$.

In some embodiments, in Formula 1, $R_1$ to $R_3$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1\text{-}C_{20}$ alkyl group, and a $C_1\text{-}C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, and a dibenzocarbazolyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1\text{-}C_{20}$ alkyl group, a $C_1\text{-}C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, a dibenzocarbazolyl group, and $-\text{Si}(Q_{31})(Q_{32})(Q_{33})$; and $-\text{Si}(Q_1)(Q_2)(Q_3)$;

wherein $Q_1$ to $Q_3$ and $Q_{31}$ to $Q_{33}$ may be each independently selected from a $C_1\text{-}C_{10}$ alkyl group, a $C_1\text{-}C_{10}$ alkoxy group, a phenyl group, and a naphthyl group.

In some embodiments, in Formula 1, $R_1$ to $R_3$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1\text{-}C_{20}$ alkyl group, and a $C_1\text{-}C_{20}$ alkoxy group;

a phenyl group, a naphthyl group, an anthracenyl group, a pyrenyl group, a chrysenyl group, a pyridinyl group, a pyrazinyl group, a pyrimidinyl group, a pyridazinyl group, and a triazinyl group; and a phenyl group, a naphthyl group, an anthracenyl group, a pyrenyl group, a chrysenyl group, a pyridinyl group, a pyrazinyl group, a pyrimidinyl group, a pyridazinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1\text{-}C_{20}$ alkyl group, a $C_1\text{-}C_{20}$ alkoxy group, a phenyl group, a naphthyl group, and $-\text{Si}(Q_{31})(Q_{32})(Q_{33})$; and $-\text{Si}(Q_1)(Q_2)(Q_3)$;

wherein $Q_1$ to $Q_3$ and $Q_{31}$ to $Q_{33}$ may be each independently selected from a $C_1\text{-}C_{10}$ alkyl group, a $C_1\text{-}C_{10}$ alkoxy group, a phenyl group, and a naphthyl group.

In Formula 1, b1 to b3 each indicate the number of $R_1$s to $R_3$s in Formula 1, and b1 to b3 may be each independently an integer selected from 0 to 3.

In Formula 1, $R_{11}$ to $R_{16}$ may be each independently selected from:

a substituted or unsubstituted $C_1\text{-}C_{60}$ alkyl group, a substituted or unsubstituted $C_2\text{-}C_{60}$ alkenyl group, a substituted or unsubstituted $C_2\text{-}C_{60}$ alkynyl group, a substituted or unsubstituted $C_1\text{-}C_{60}$ alkoxy group, a substituted or unsubstituted $C_3\text{-}C_{10}$ cycloalkyl group, a substituted or unsubstituted $C_1\text{-}C_{10}$ heterocycloalkyl group, a substituted or unsubstituted $C_3\text{-}C_{10}$ cycloalkenyl group, a substituted or unsubstituted $C_1\text{-}C_{10}$ heterocycloalkenyl group, a substituted or unsubstituted $C_6\text{-}C_{60}$ aryl group, a substituted or unsubstituted $C_1\text{-}C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formula 1, $R_{11}$ to $R_{16}$ may be each independently selected from:

a $C_1\text{-}C_{20}$ alkyl group and a $C_1\text{-}C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, and a chrysenyl group.

In some embodiments, in Formula 1, A may be a $C_6$-$C_{20}$ aromatic ring.

In some embodiments, in Formula 1, A may be selected from a benzene, a naphthalene, an anthracene, a phenanthrene, a chrysene, and a pyrene.

In Formula 1, when A is a benzene, X may not be $C(R_{15})(R_{16})$.

In some embodiments, in Formula 1, A may be selected from a benzene, a naphthalene, and a phenanthrene.

In some embodiments, the condensed-cyclic compound may be represented by one of Formulae 1A to 1C below:

wherein, in Formulae 1A to 1C, X may be selected from O, S, $N(R_{11})$, $Si(R_{12})(R_{13})(R_{14})$, and $C(R_{15})(R_{16})$, and $L_1$ to $L_3$, a1 to a3, $Ar_1$ to $Ar_6$, c1 to c3, $R_1$ to $R_3$, b1 to b3 and $R_{11}$ to $R_{16}$ may be understood by referring to the description provided herein, provided that X is not $C(R_{15})(R_{16})$ in Formula 1A.

In some embodiments, the condensed-cyclic compound may be represented by one of Formulae 1-1 to 1-3 and Formulae 2-1 to 2-3 below:

<Formula 1-1>

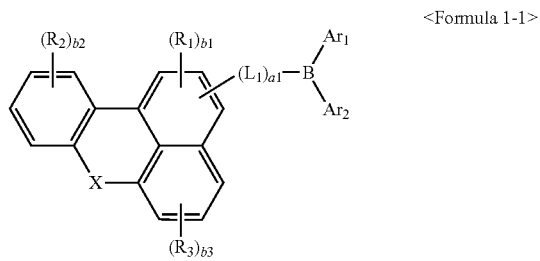

<Formula 1A>

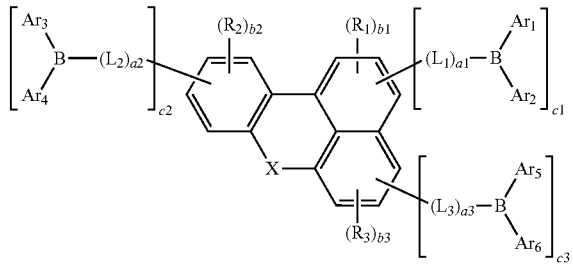

<Formula 1B>

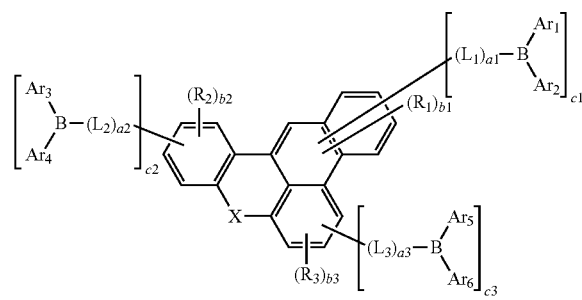

<Formula 1C>

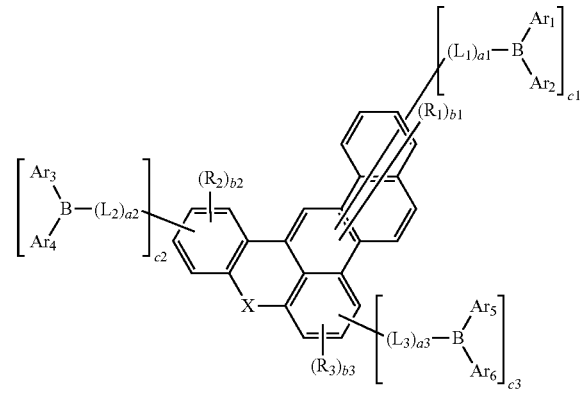

<Formula 1-2>

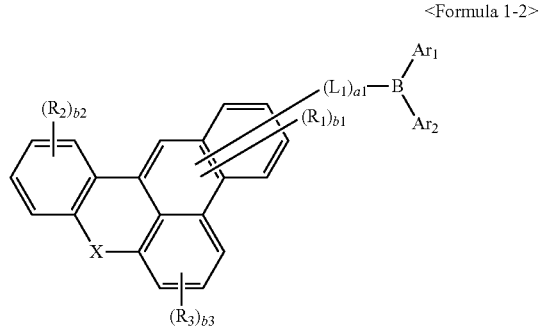

<Formula 1-3>

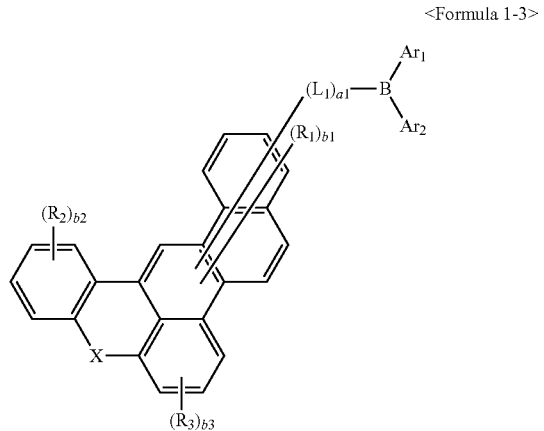

<Formula 2-1>

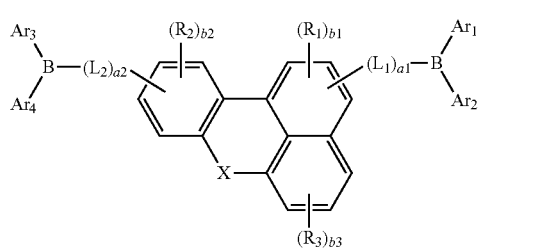

<Formula 2-2>

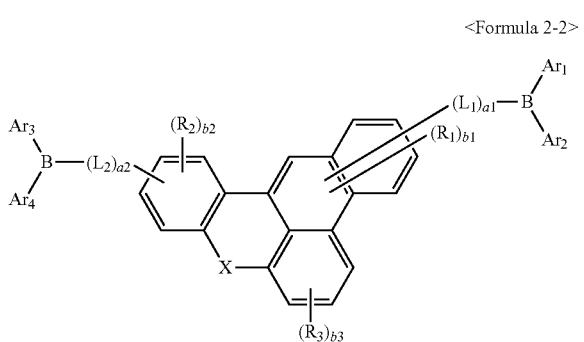

<Formula 2-3>

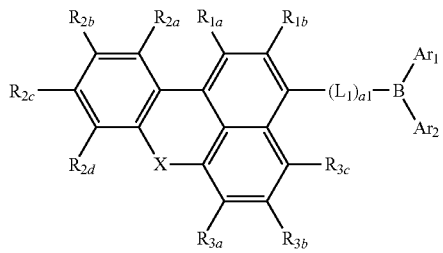

wherein, in Formulae 1-1 to 1-3 and Formulae 2-1 to 2-3, X may be selected from O, S, $N(R_{11})$, $Si(R_{12})(R_{13})(R_{14})$, and $C(R_{15})(R_{16})$, and $L_1$, $L_2$, a1, a2, $Ar_1$ to $Ar_4$, $R_1$ to $R_3$, b1 to b3 and $R_{11}$ to $R_{16}$ may be understood by referring to the description provided herein, provided that X is not $C(R_{15})(R_{16})$ in Formulae 1-1 and 2-1.

In some embodiments, the condensed-cyclic compound may be represented by one of Formulae 1-1(1) to 1-3(1) and Formulae 2-1(1) to 2-3(1) below:

<Formula 1-1(1)>

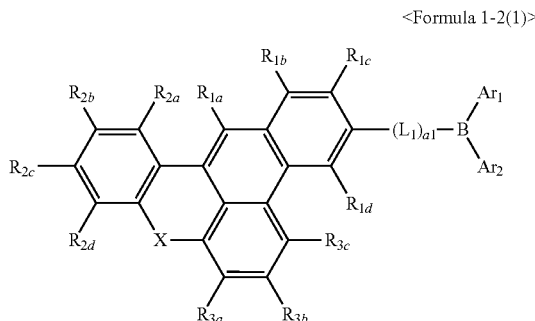

<Formula 1-2(1)>

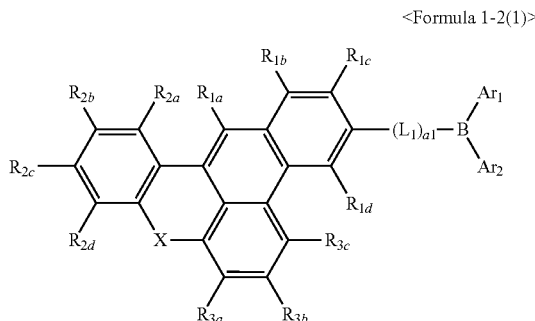

-continued

<Formula 1-3(1)>

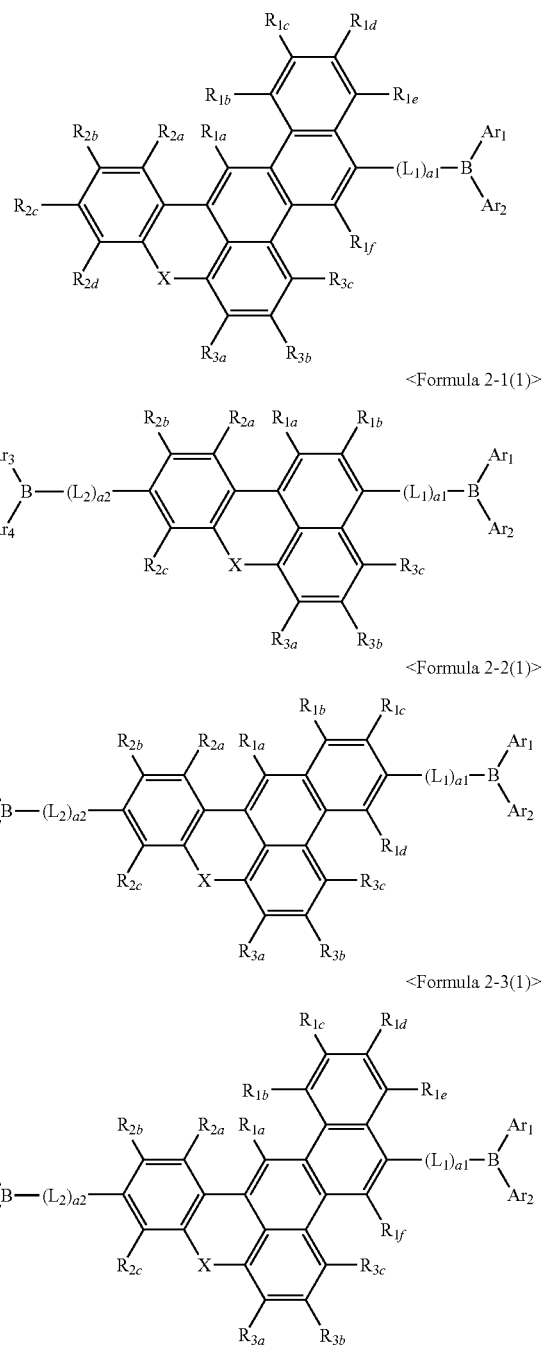

<Formula 2-1(1)>

<Formula 2-2(1)>

<Formula 2-3(1)> wherein, in Formulae 1-1(1) to 1-3(1) and Formulae 2-1(1) to 2-3(1), X may be selected from O, S, $N(R_{11})$, $Si(R_{12})(R_{13})(R_{14})$, and $C(R_{15})(R_{16})$, $L_1$, $L_2$, a1, a2, and $Ar_1$ to $Ar_4$ and $R_{11}$ to $R_{16}$ may be understood by referring to the description provided herein, and $R_{1a}$ to $R_{1f}$, $R_{2a}$ to $R_{2c}$, and $R_{3a}$ to $R_{1c}$ are the same as defined in connection with $R_1$ herein, provided that X is not $C(R_{15})(R_{16})$ in Formulae 1-1(1) and 2-1(1).

In some embodiments, in Formulae 1-1(1) to 1-3(1) and Formulae 2-1(1) to 2-3(1), $R_{1a}$ to $R_{1f}$, $R_{2a}$ to $R_{2c}$, and $R_{3a}$ to $R_{1c}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, and a group represented by one of Formulae 6-1 to 6-24 above.

In some embodiments, in Formulae 1-1(1) to 1-3(1) and Formulae 2-1(1) to 2-3(1), $Ar_1$ to $Ar_4$ may be each independently selected from a group represented by one of Formulae 6-1 to 6-28 above, and $R_1$, to $R_{1f}$, $R_{2a}$ to $R_{2c}$, and $R_{3a}$ to $R_{3c}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, and a group represented by one of Formulae 6-1 to 6-24 above.

In some embodiments, the condensed-cyclic compound may be represented by one of Formulae 1-1(1)A, 1-1(1)B, 1-2(1)A, 1-2(1)B, 1-3(1)A, 1-3(1)B, 2-1(1)A to 2-1(1)D, 2-2(1)A to 2-2(1)D, and 2-3(1)A to 2-3(1)D below:

<Formula 1-1(1)A>

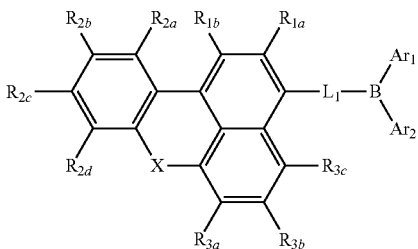

<Formula 1-1(1)B>

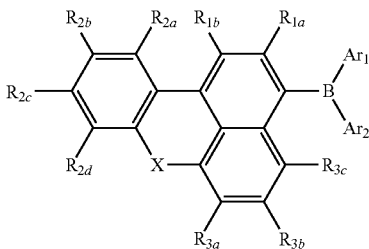

<Formula 1-2(1)A>

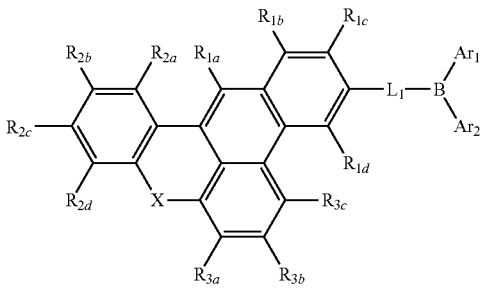

<Formula 1-2(1)B>
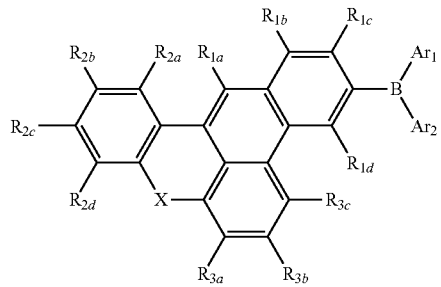
<Formula 1-3(1)A>
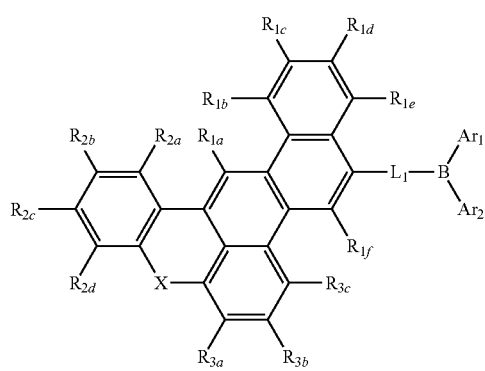
<Formula 1-3(1)B>
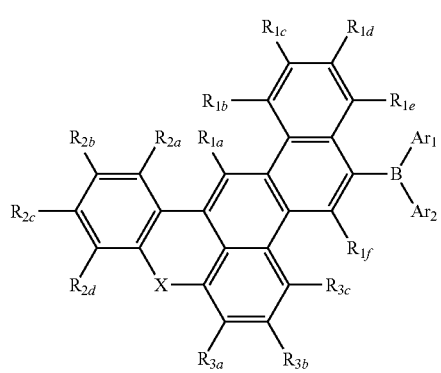
<Formula 2-1(1)A>
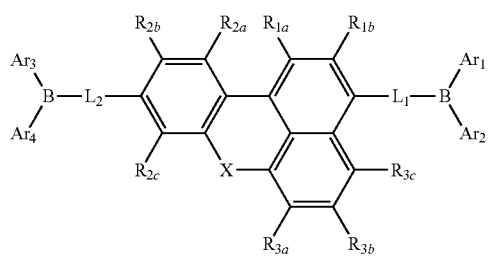
<Formula 2-1(1)B>
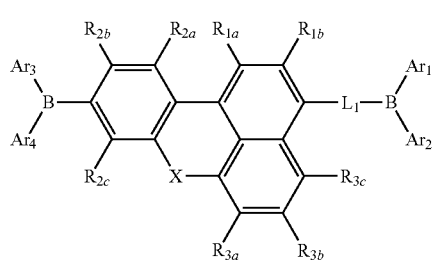
<Formula 2-1(1)C>
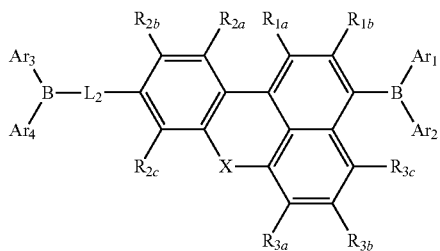
<Formula 2-1(1)D>
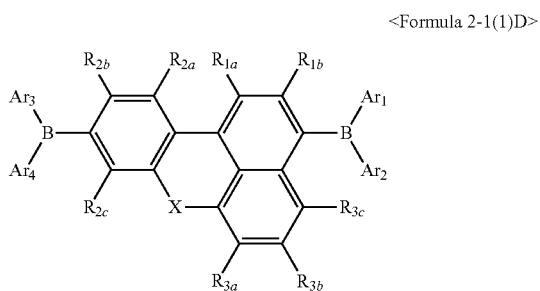
<Formula 2-2(1)A>
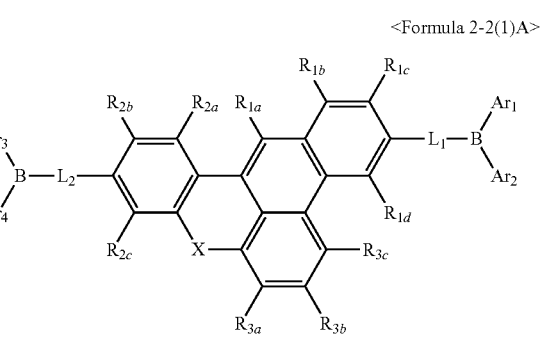
<Formula 2-2(1)B>
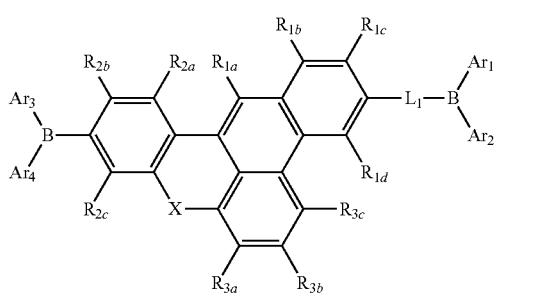
<Formula 2-2(1)C>
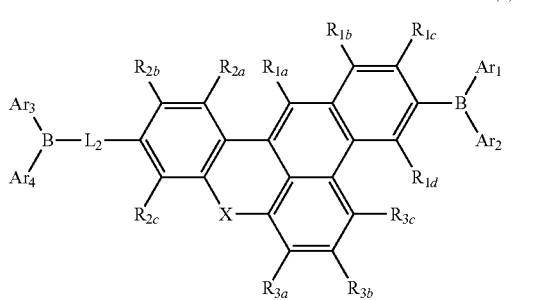

<Formula 2-2(1)D>

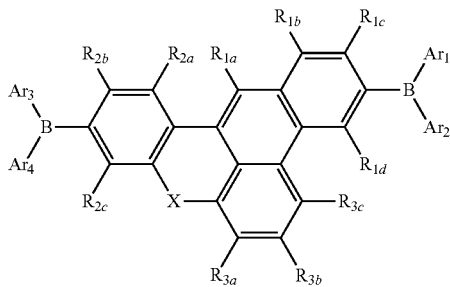

<Formula 2-3(1)A>

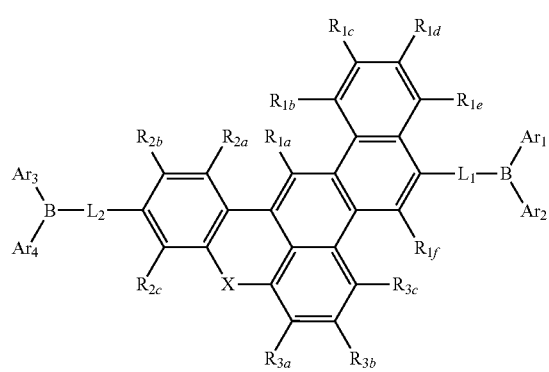

<Formula 2-3(1)B>

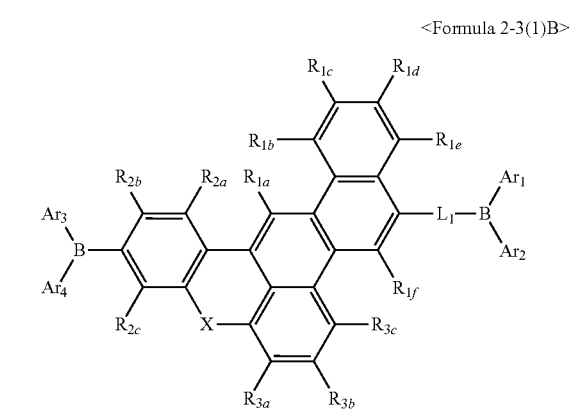

<Formula 2-3(1)C>

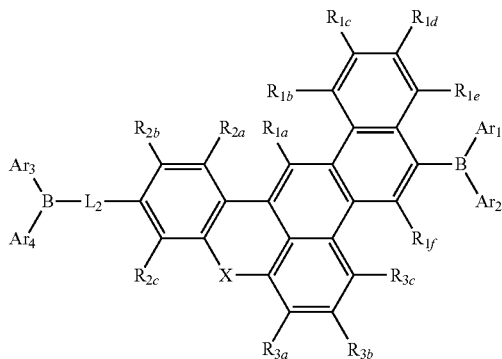

<Formula 2-3(1)D>

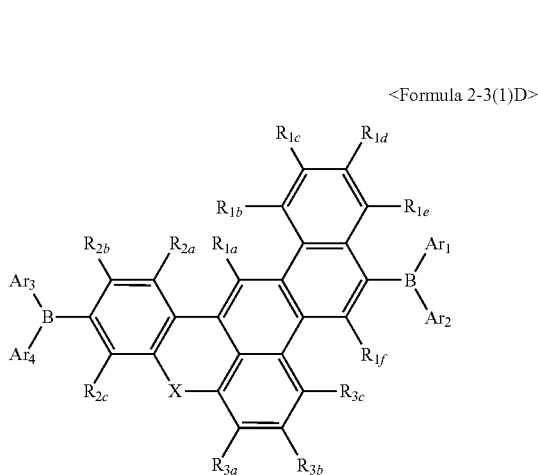

wherein X in Formulae 1-1(1)A, 1-1(1)B, 1-2(1)A, 1-2(1)B, 1-3(1)A, 1-3(1)B, 2-1(1)A to 2-1(1)D, 2-2(1)A to 2-2(1)D, and 2-3(1)A to 2-3(1)D may be selected from O, S, $N(R_{11})$, $Si(R_{12})(R_{13})(R_{14})$, and $C(R_{15})(R_{16})$, $L_1$, $L_2$, $Ar_1$ to $Ar_4$ and $R_{11}$ to $R_{16}$ may be understood by referring to the description provided herein, and $R_{1a}$ to $R_{1f}$, $R_{2a}$ to $R_{2c}$ and $R_{3a}$ to $R_{3c}$ may each be understood by referring to $R_1$ described herein, provided that X is not $C(R_{15})(R_{16})$ in Formulae 1-1(1)A, 1-1(1)B, 2-1(1)A, 2-1(1)B, 2-1(1)C, and 2-1(1)D.

The condensed-cyclic compound represented by Formula 1 may be represented by one of Compounds 1 to 231 below, as examples:

1

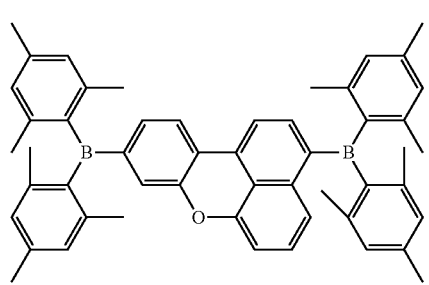

2

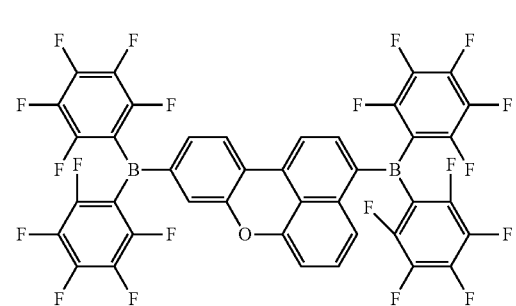

-continued
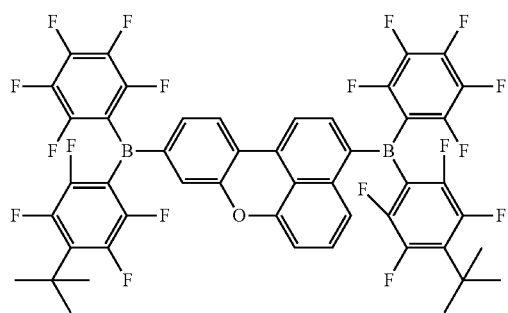
3
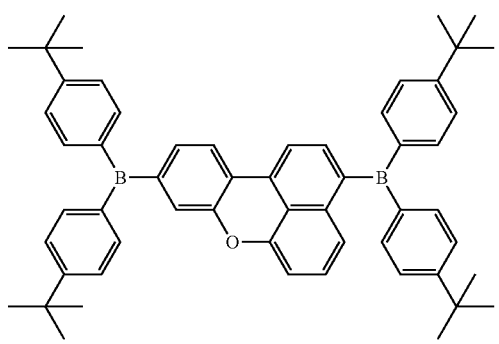
4
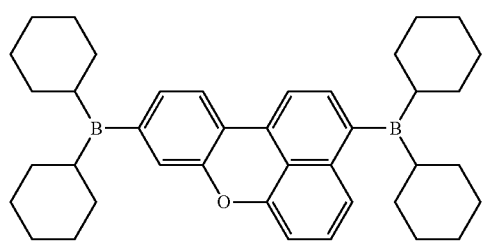
5
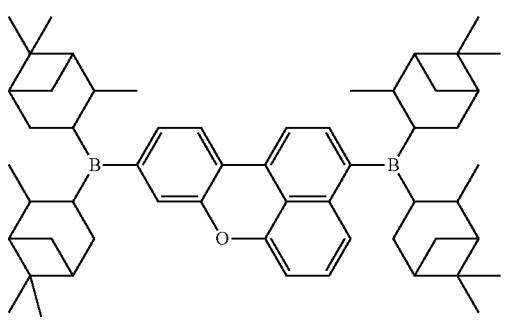
6
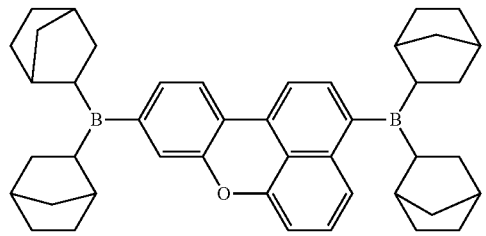
7
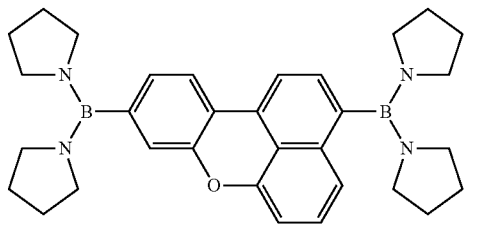
8
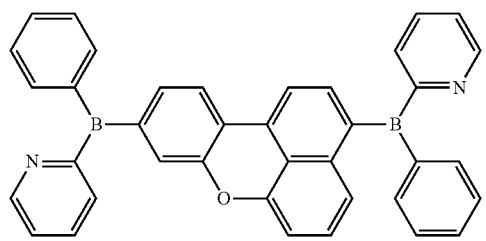
9
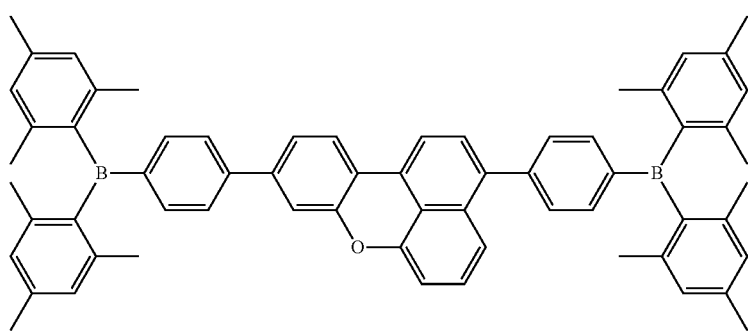
10

-continued
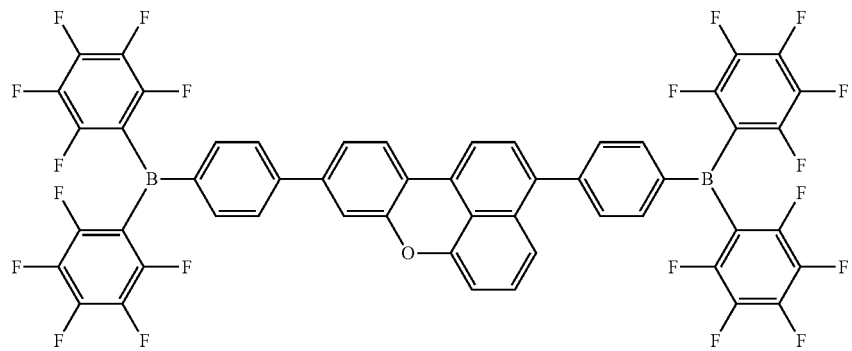
11
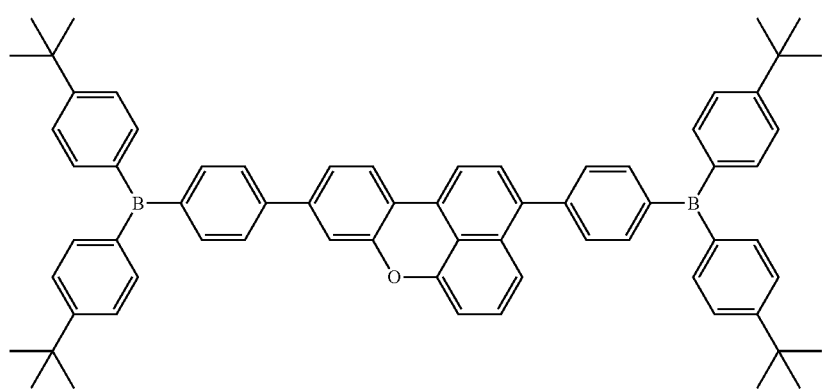
12
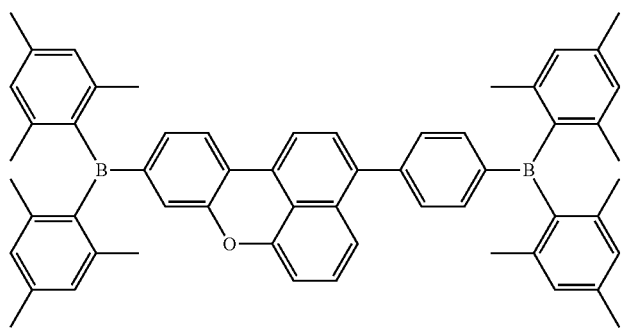
13
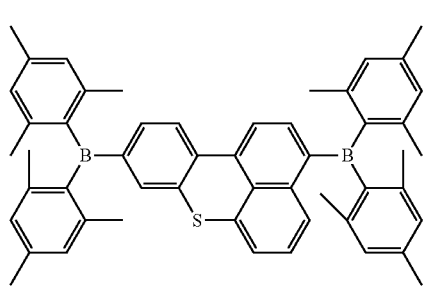
14
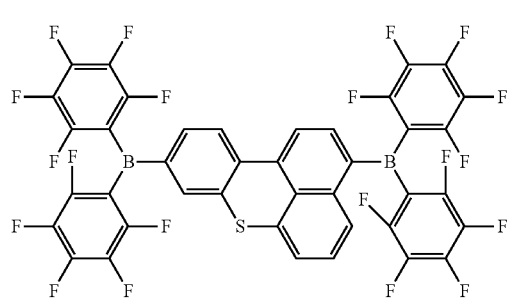
15

-continued
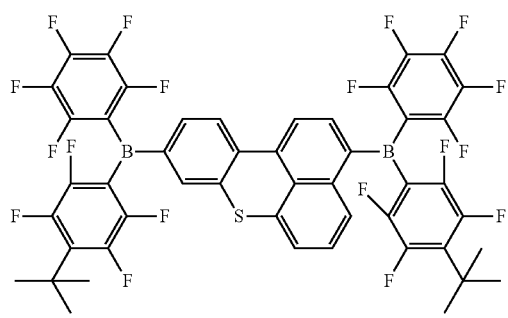
16
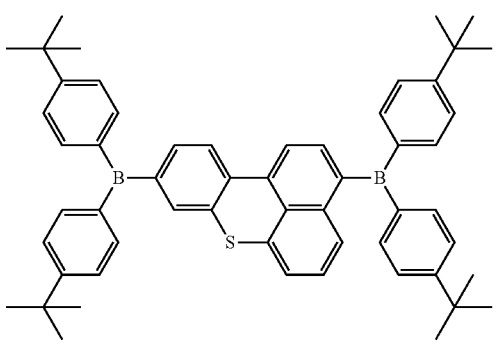
17
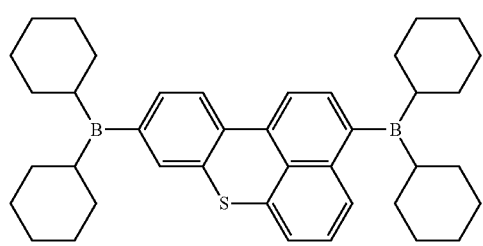
18
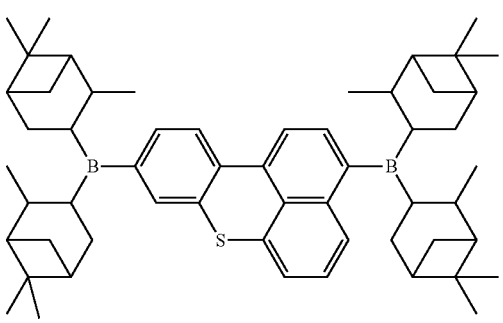
19
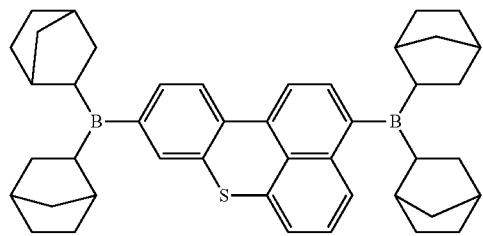
20
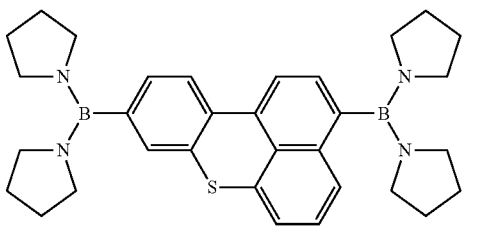
21
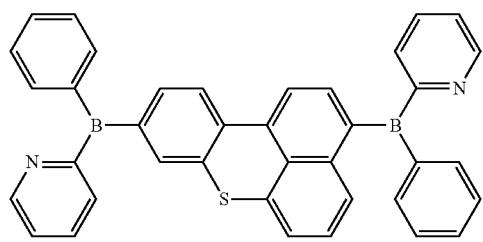
22
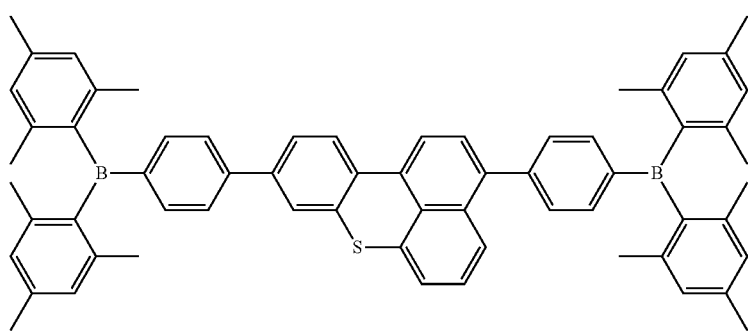
23

-continued
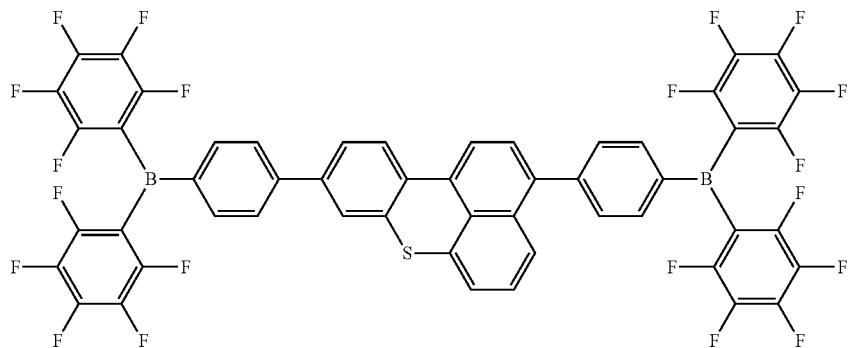
24
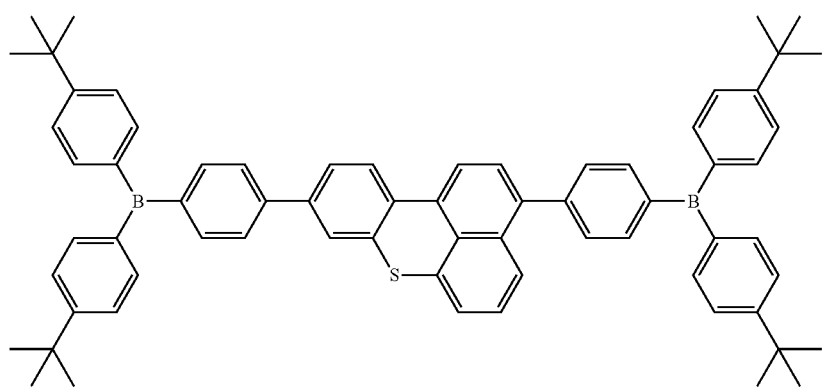
25
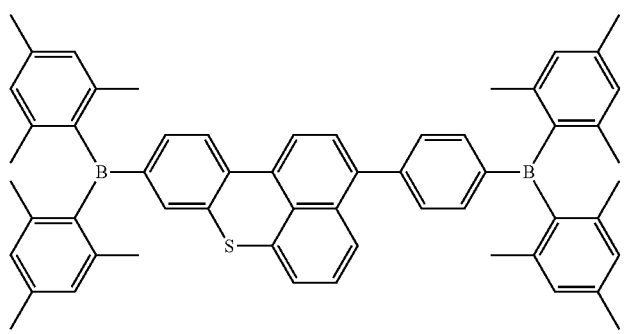
26
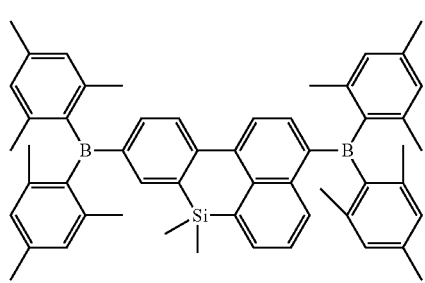
27
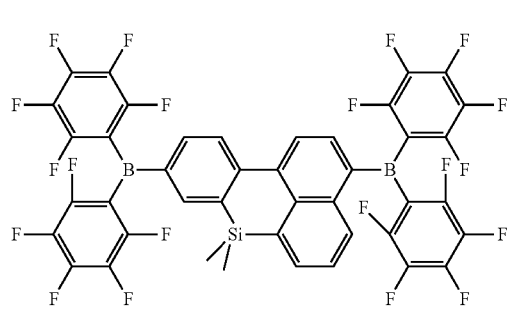
28

-continued
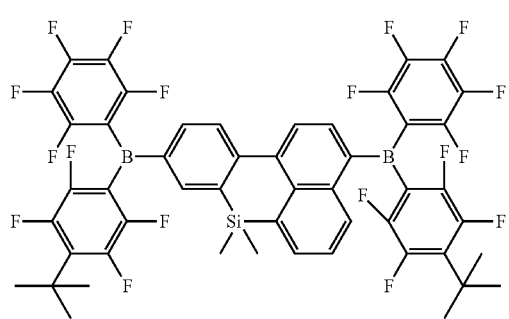
29
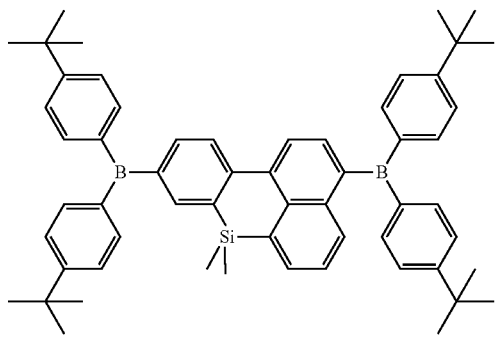
30
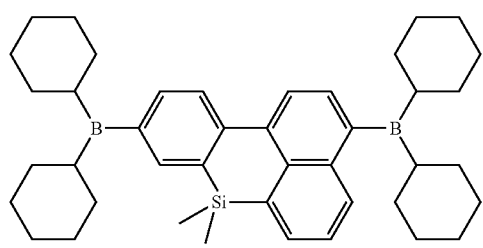
31
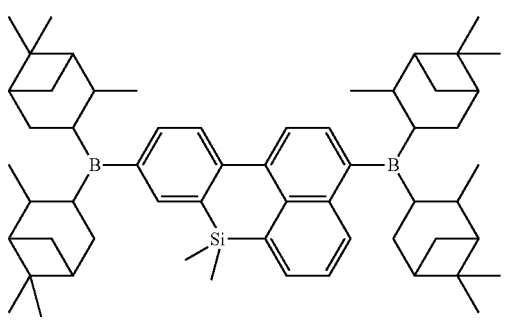
32
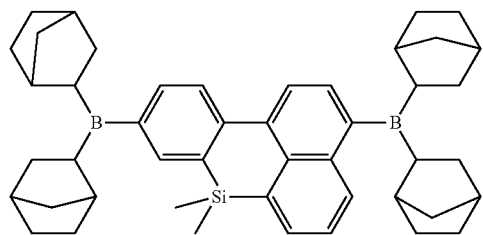
33
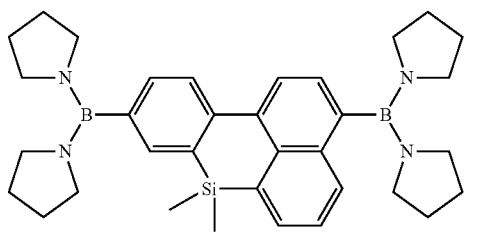
34
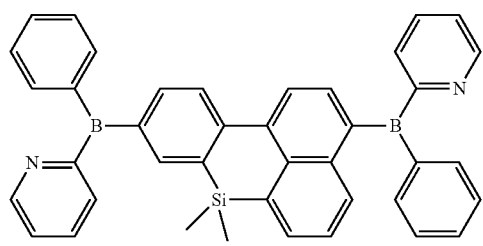
35
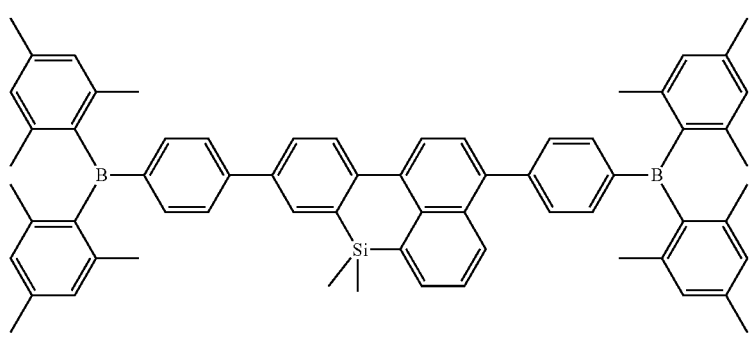
36

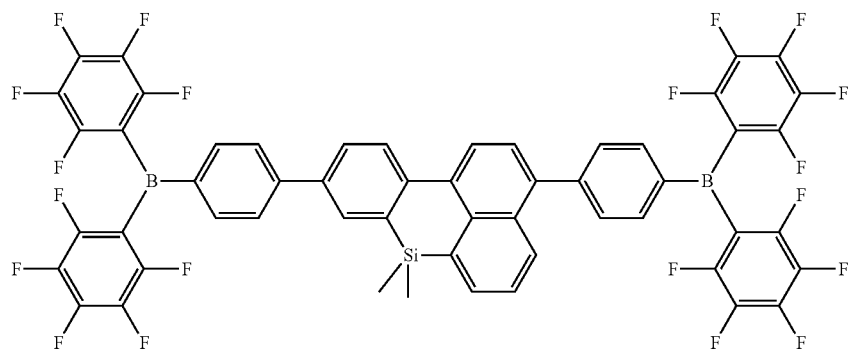
37
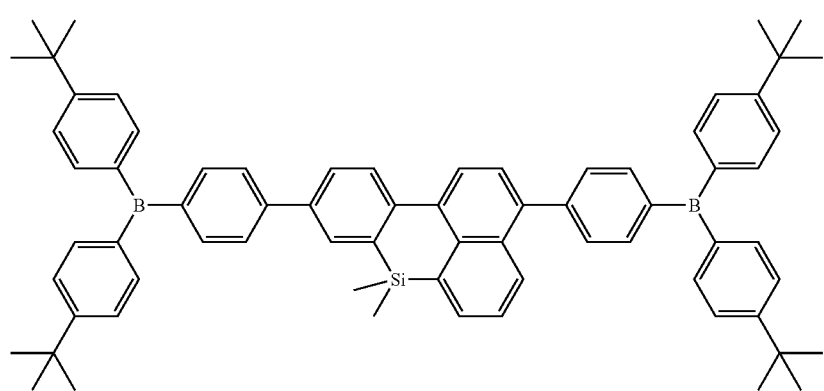
38
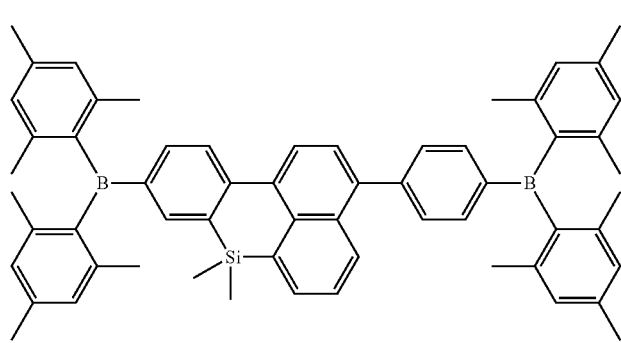
39
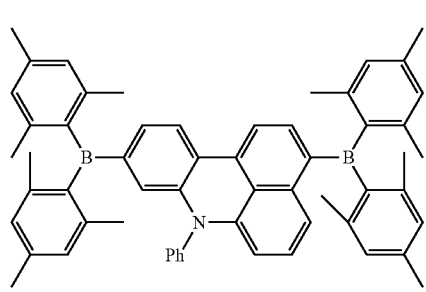
40
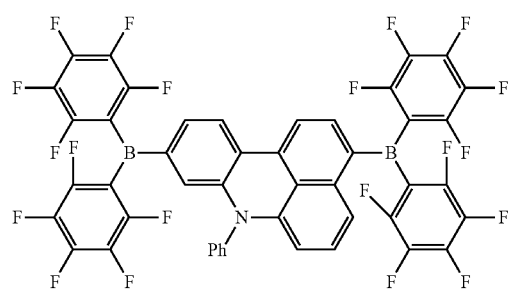
41

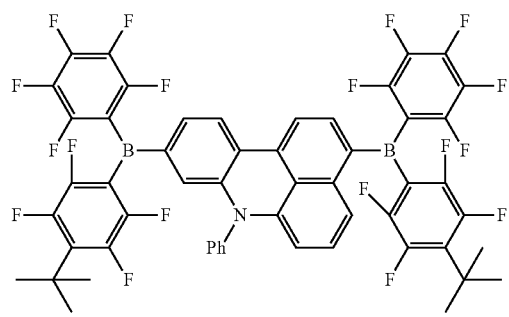
42
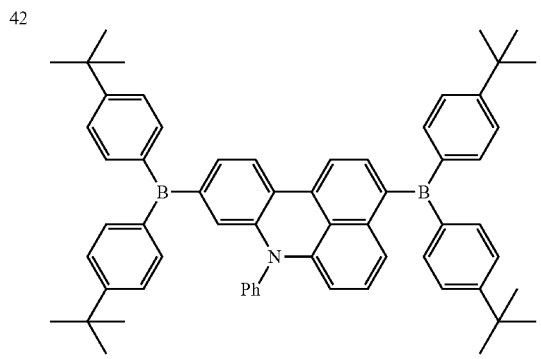
43
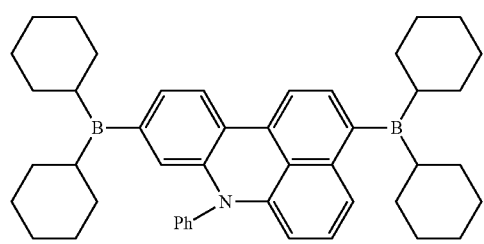
44
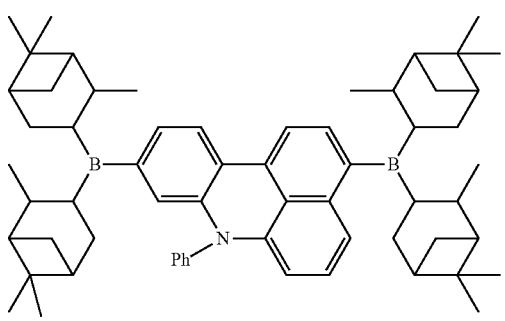
45
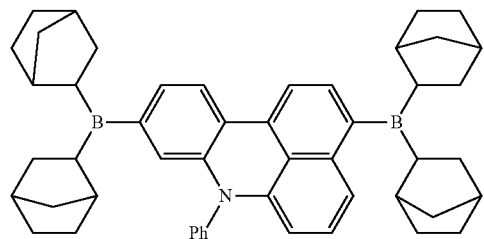
46
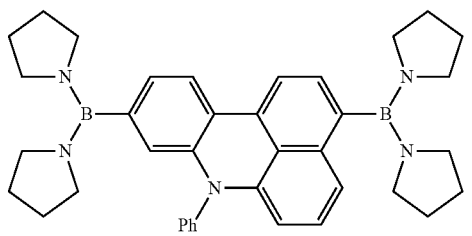
47
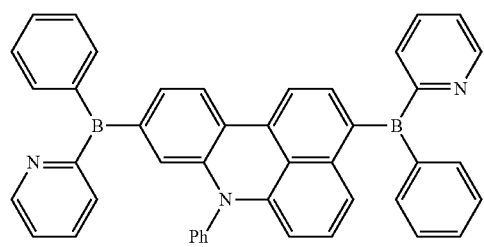
48
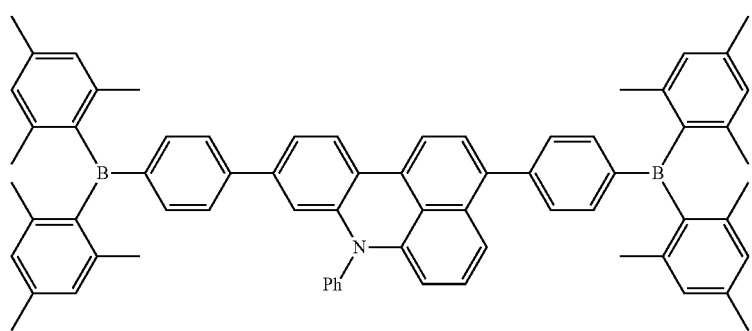
49

-continued
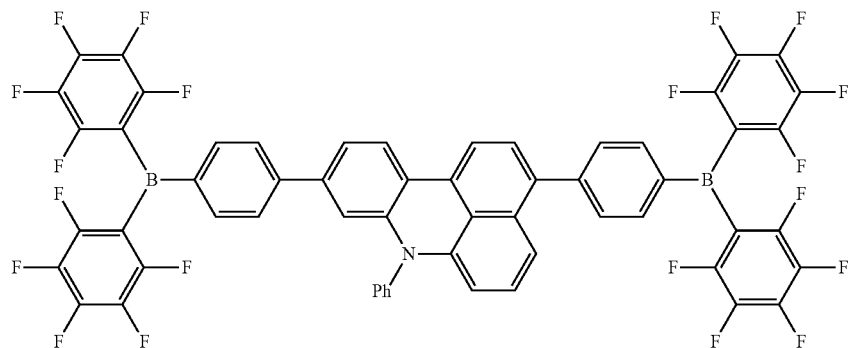
50
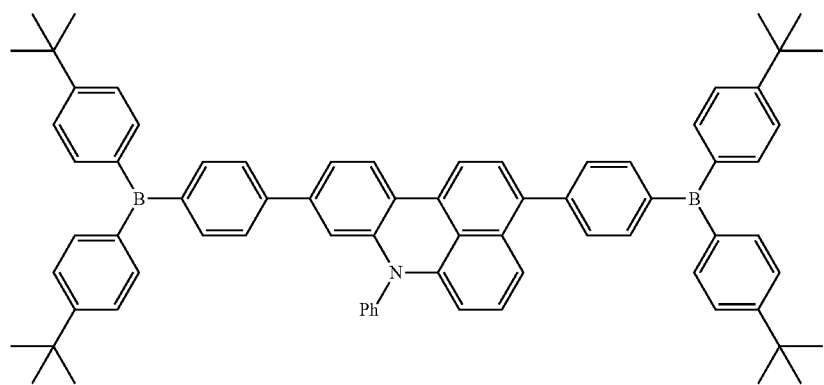
51
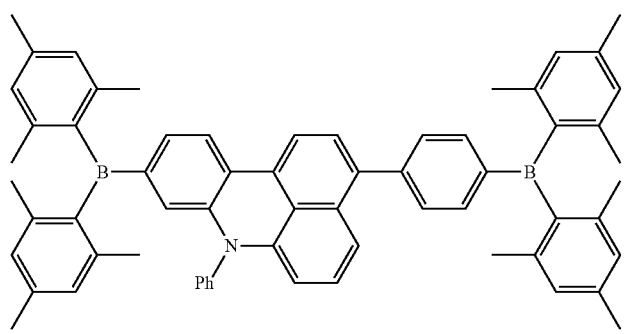
52
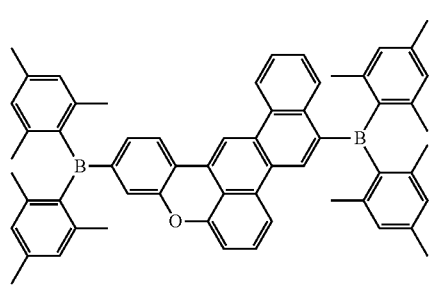
53
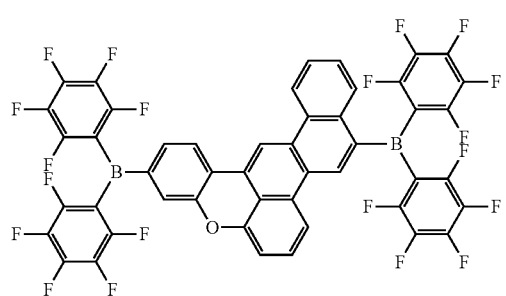
54

-continued
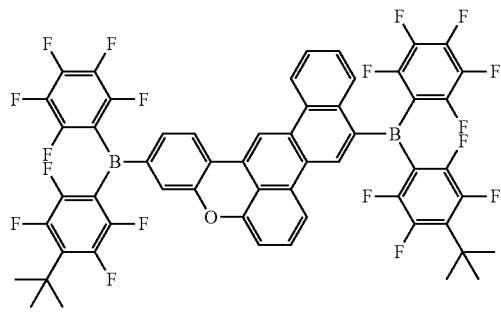
55
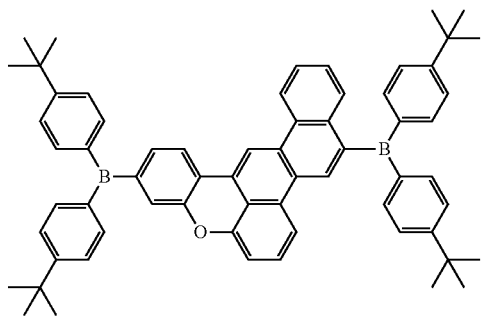
56
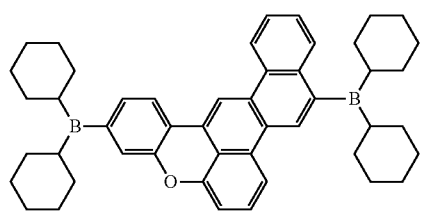
57
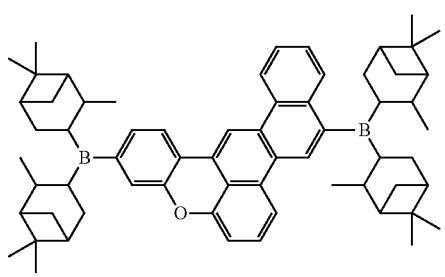
58
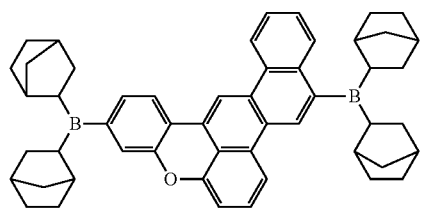
59
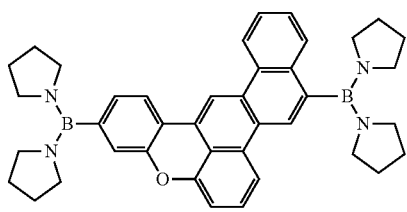
60
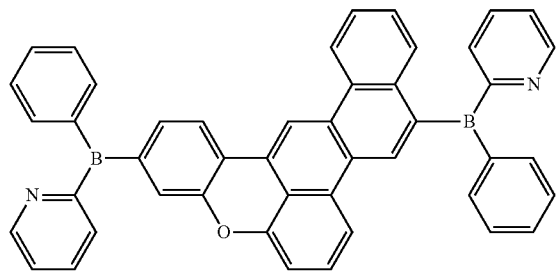
61
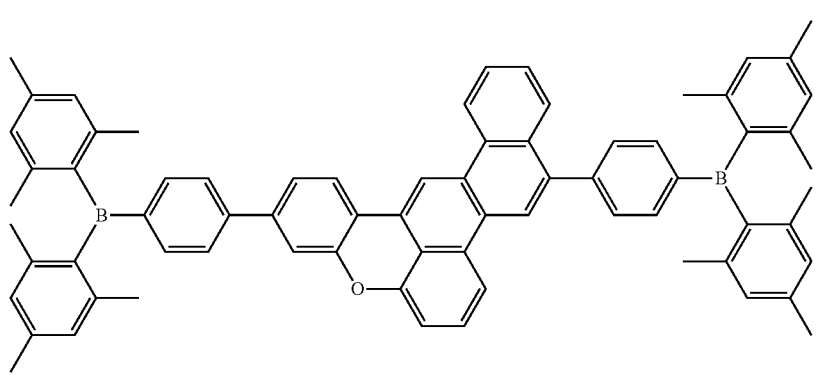
62

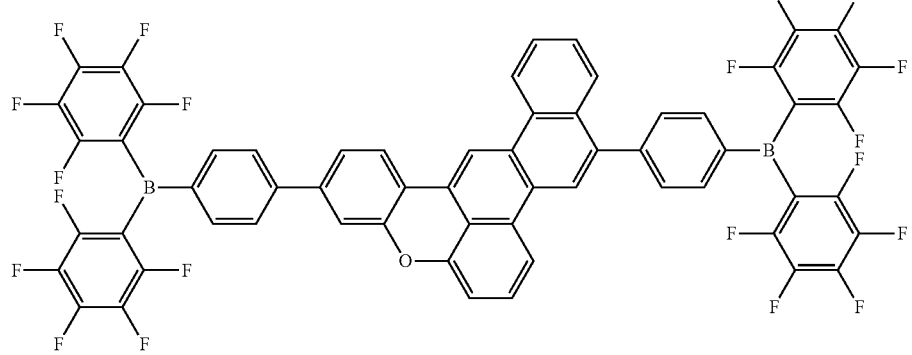
63
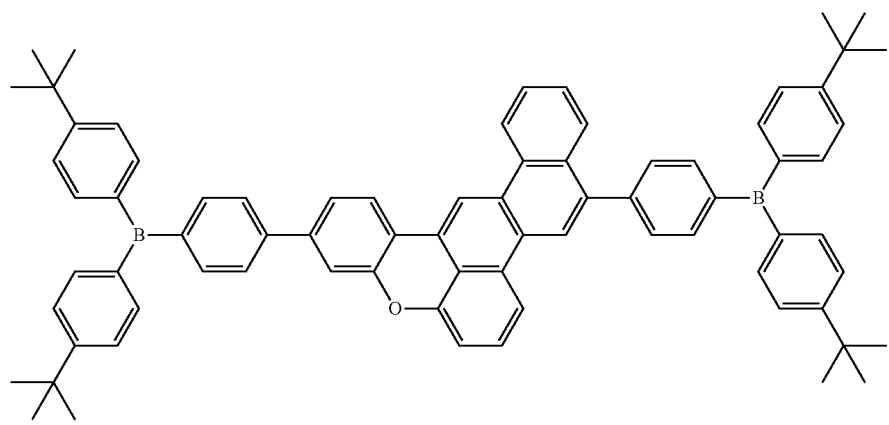
64
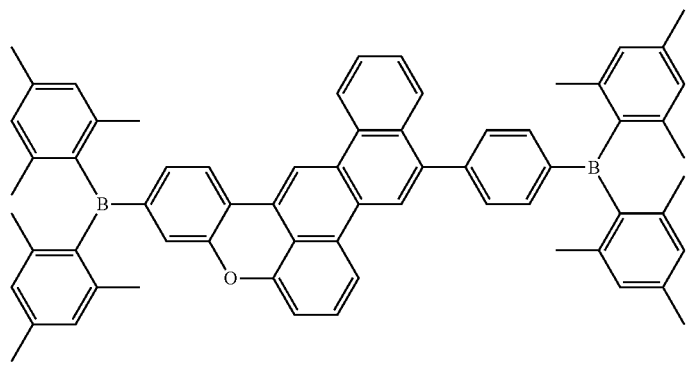
65
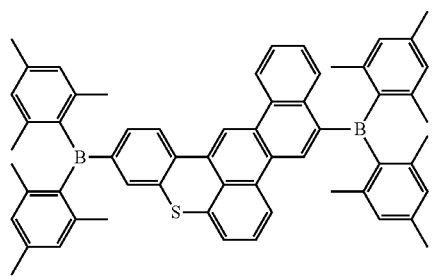
66
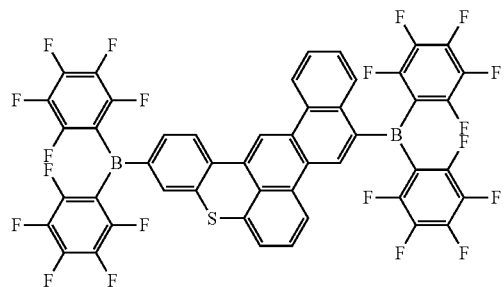
67

-continued
68
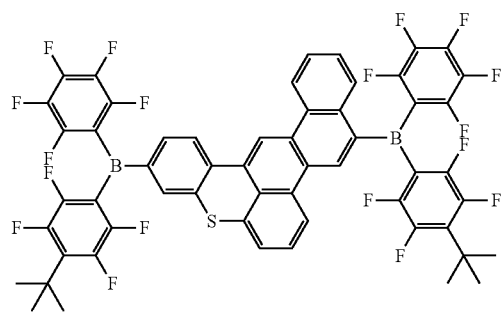
69
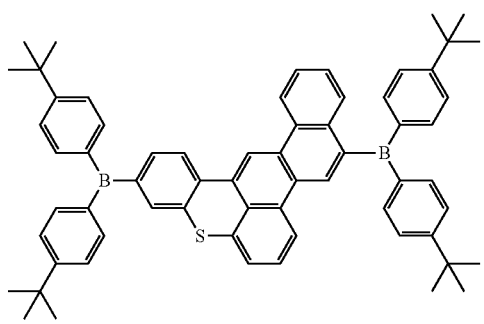
70
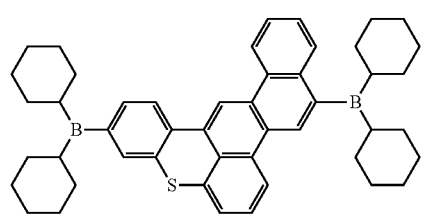
71
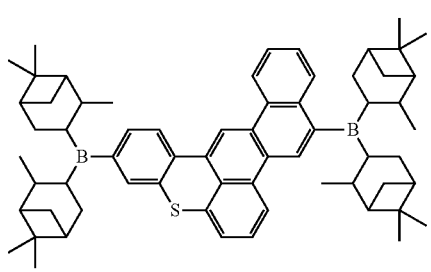
72
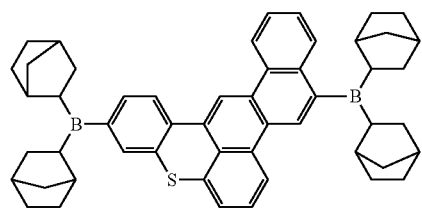
73
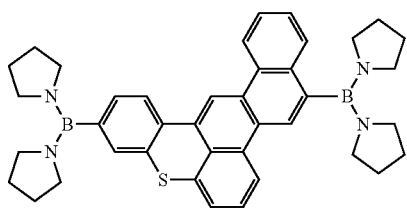
74
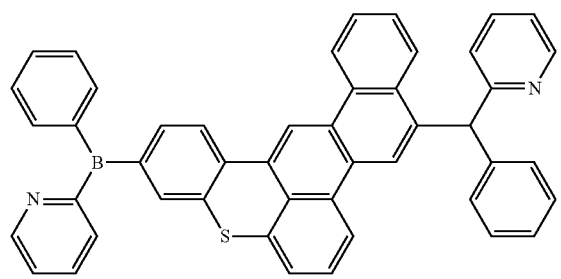
75
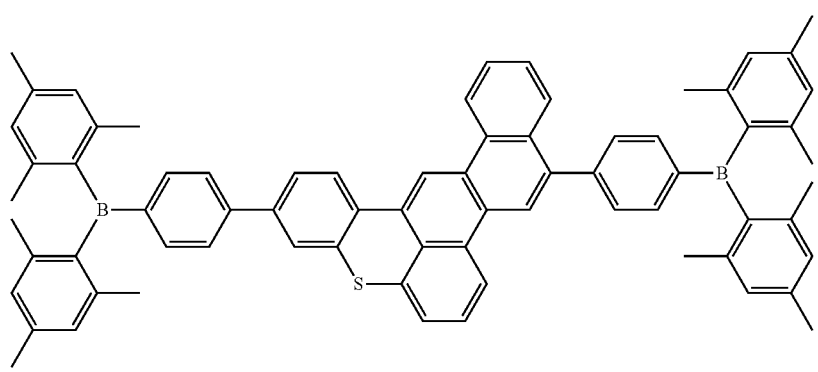

-continued
76
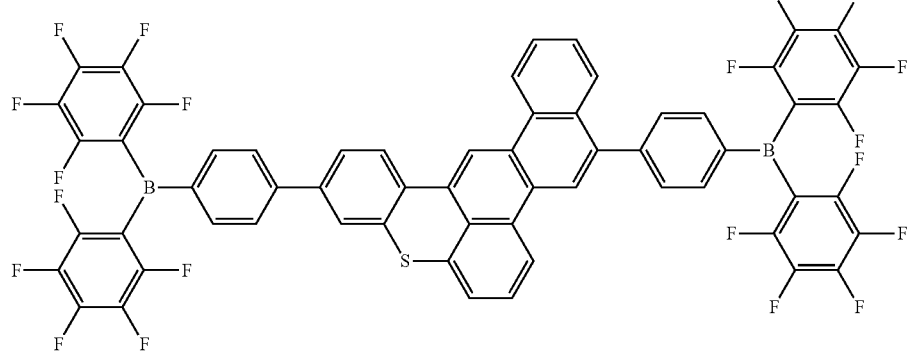
77
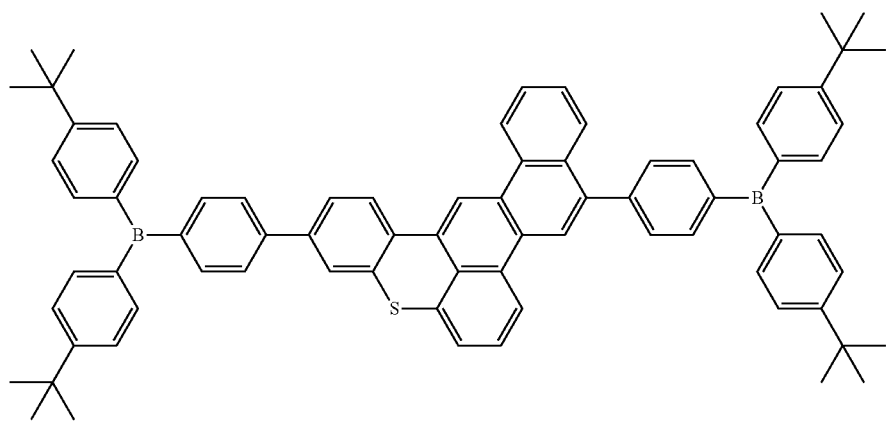
78
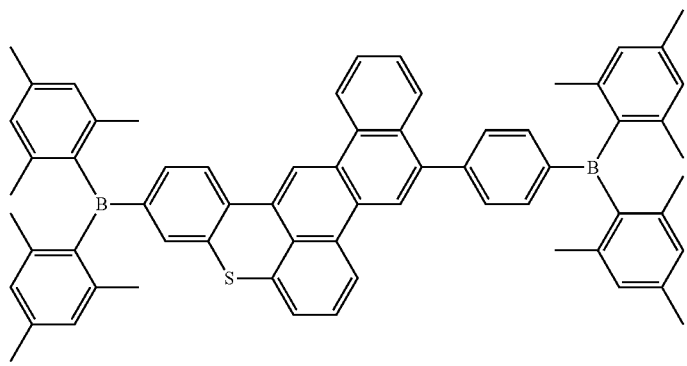
79
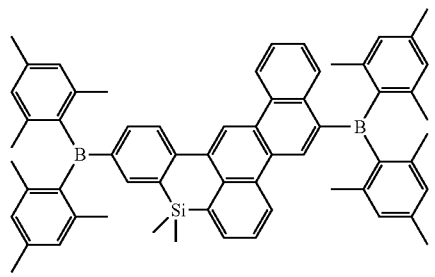
80
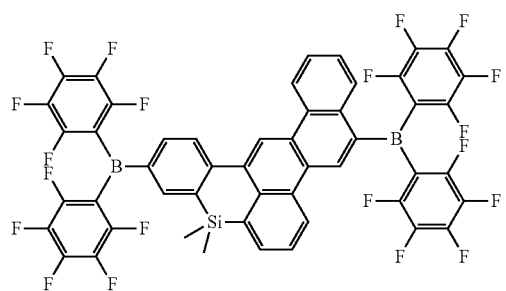

-continued
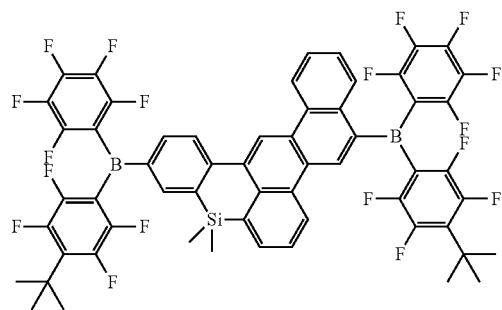
81
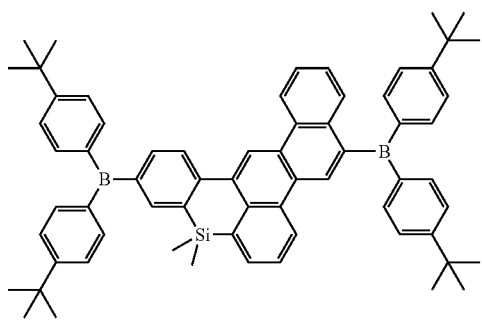
82
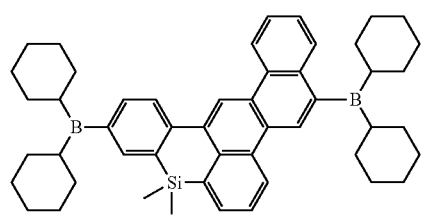
83
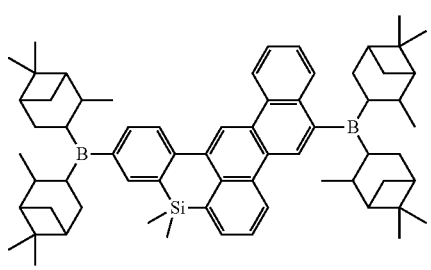
84
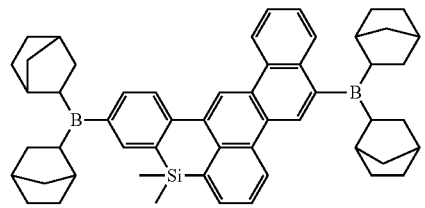
85
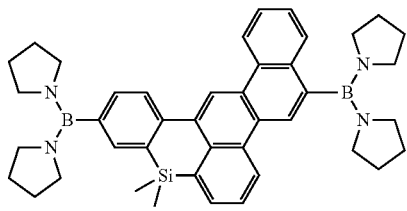
86
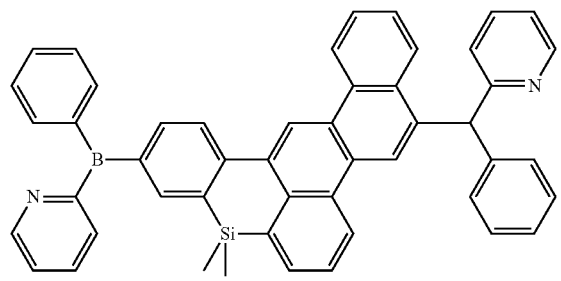
87
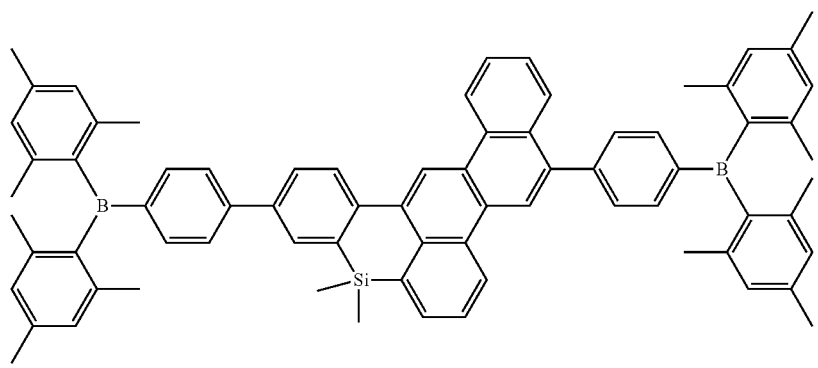
88

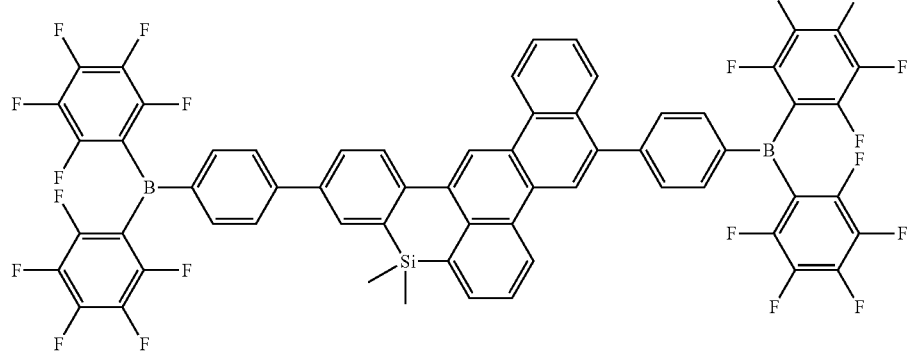
89
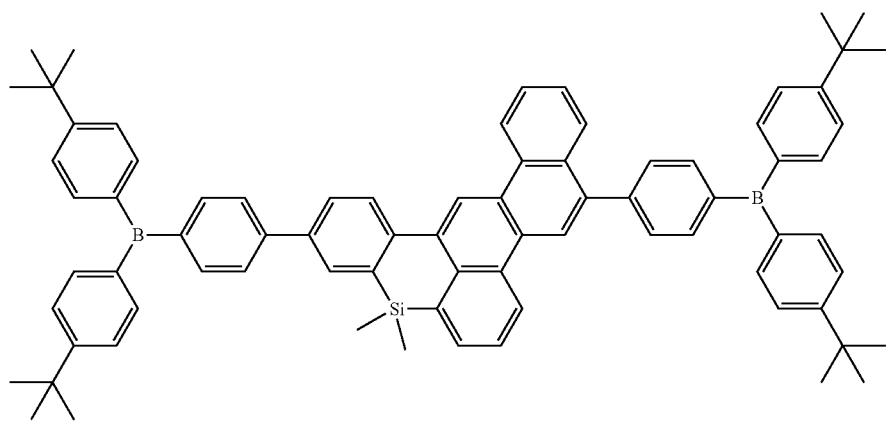
90
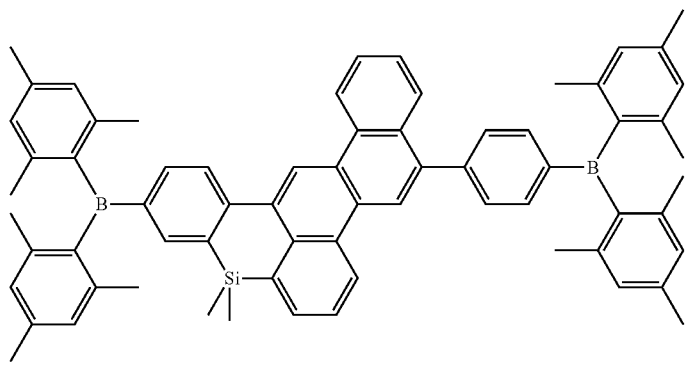
91
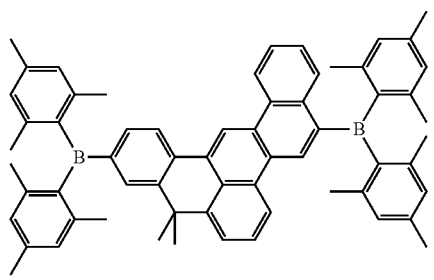
92
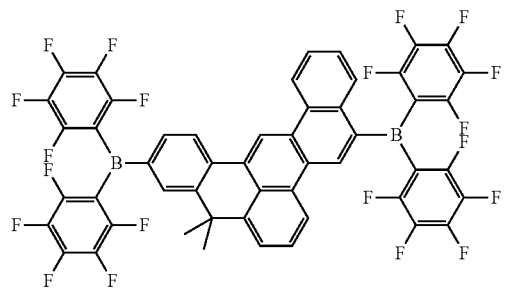
93

-continued
94 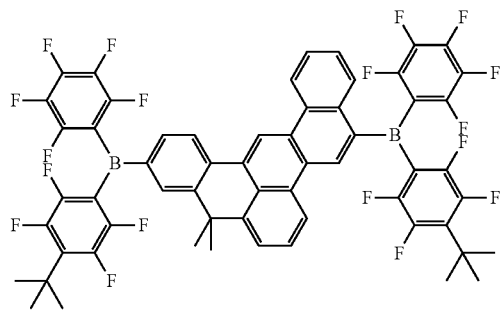
95 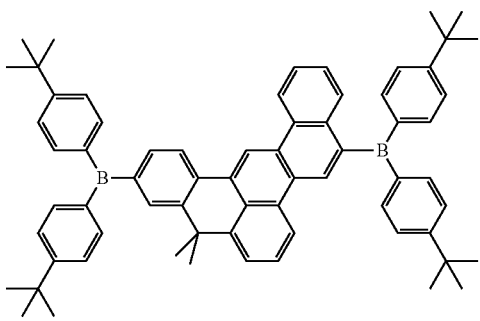
96 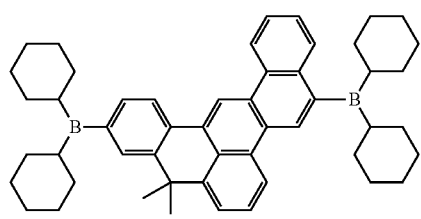
97 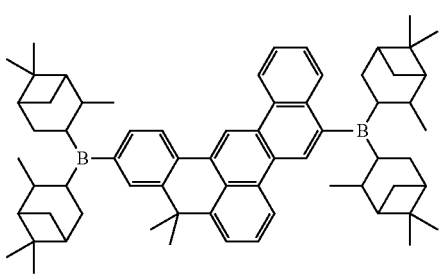
98 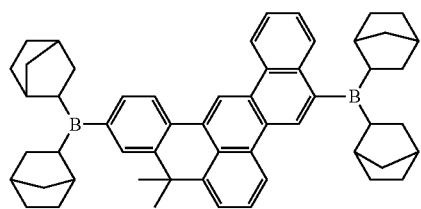
99 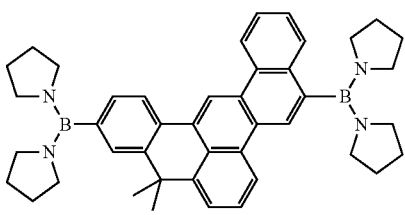
100 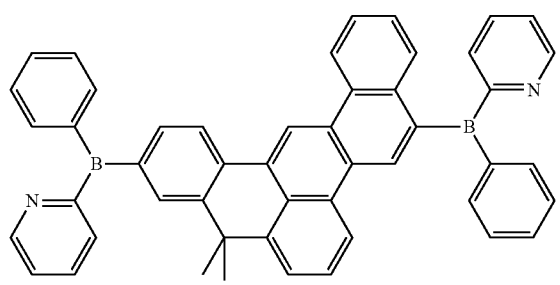
101 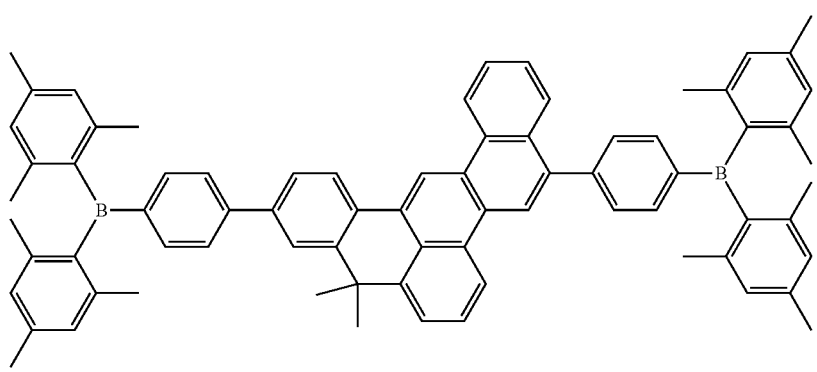

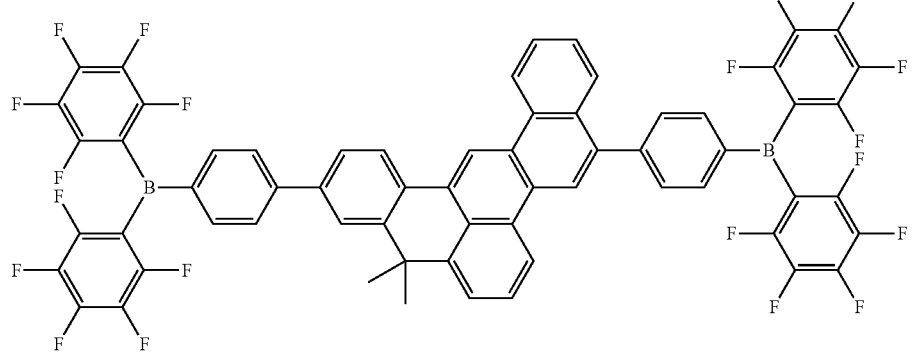
102
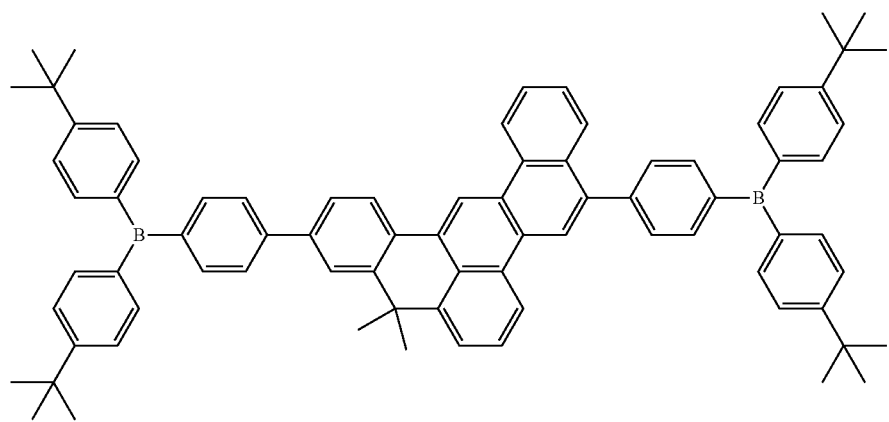
103
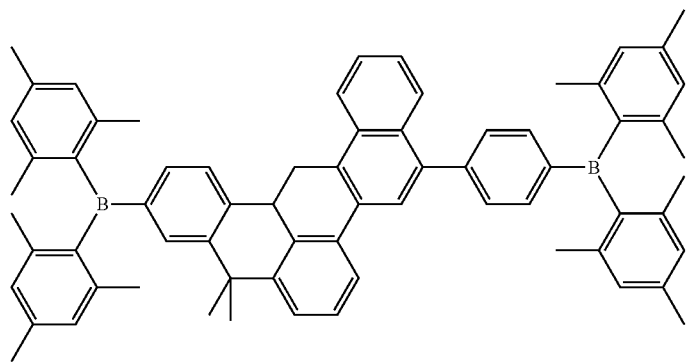
104
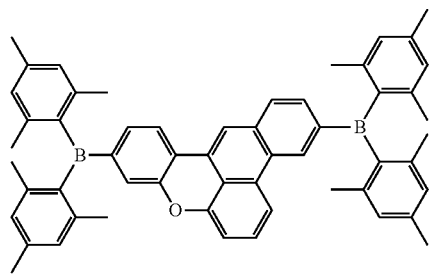
105
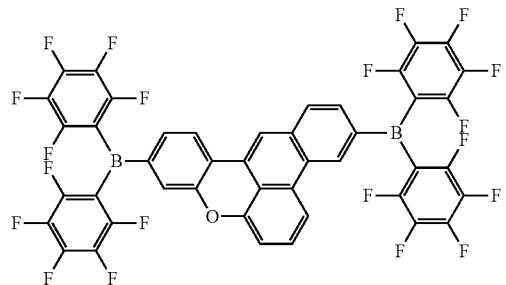
106

-continued
107
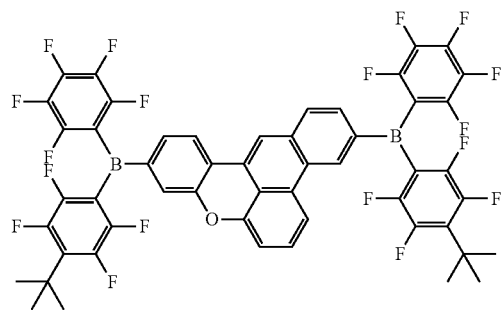
108
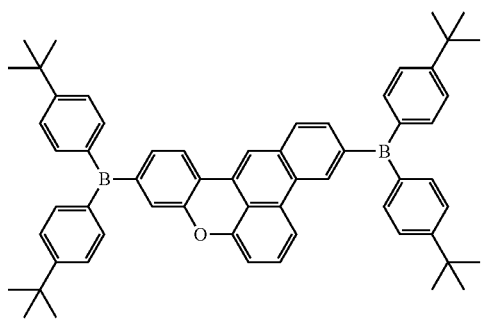
109
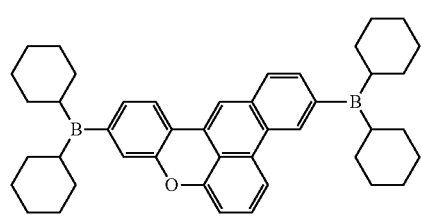
110
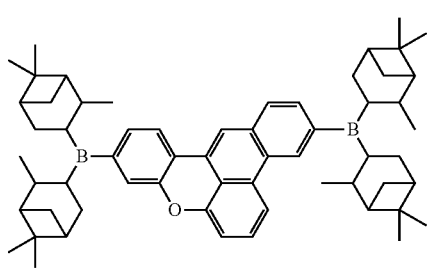
111
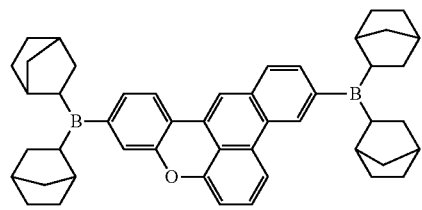
112
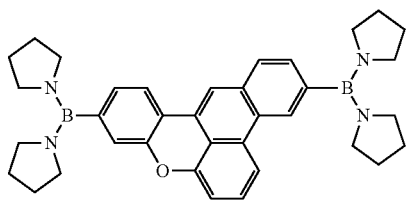
113
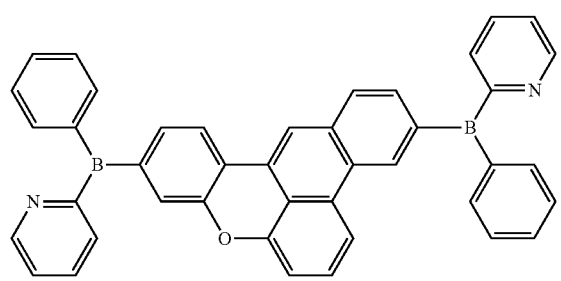
114
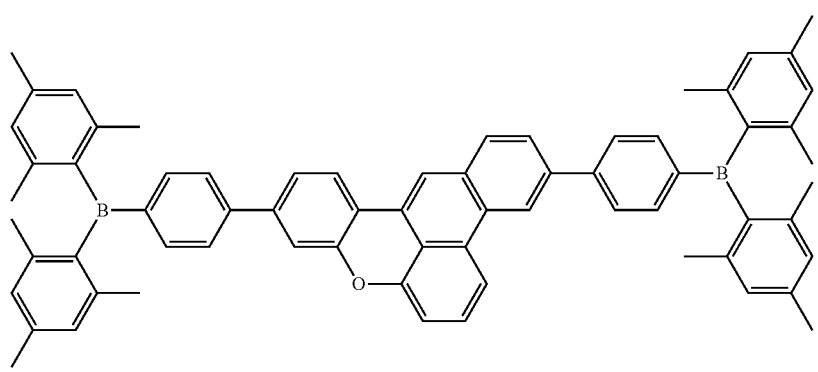

115
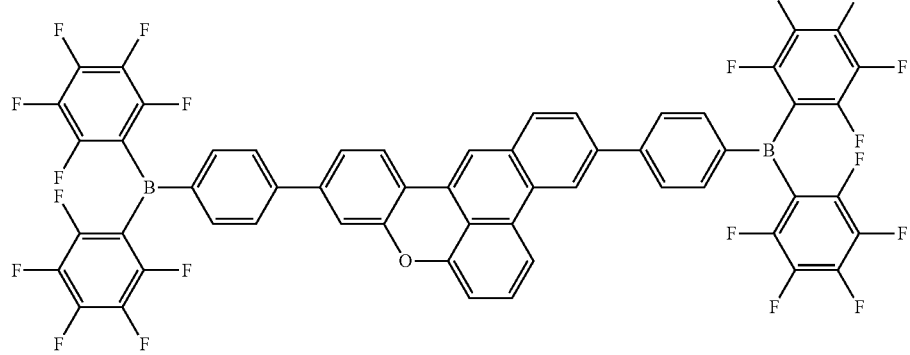
116
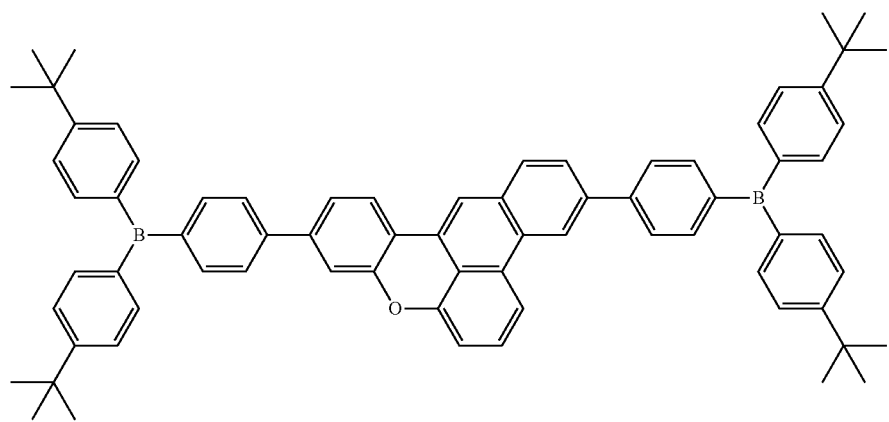
117
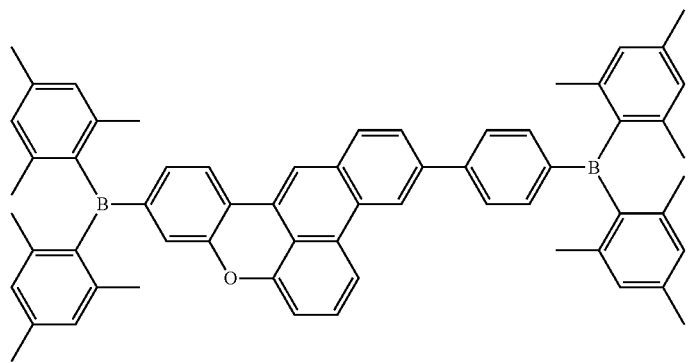
118
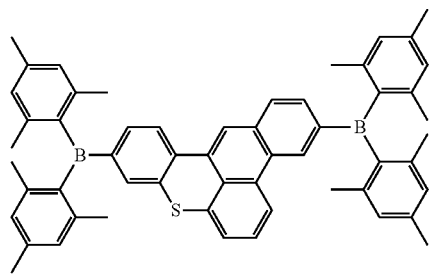
119
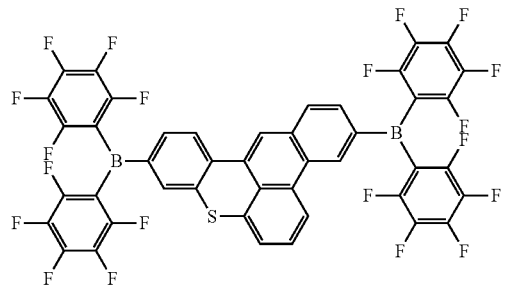

-continued
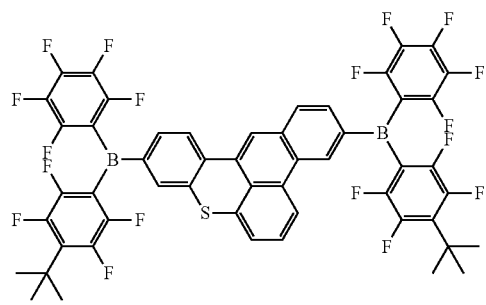
120
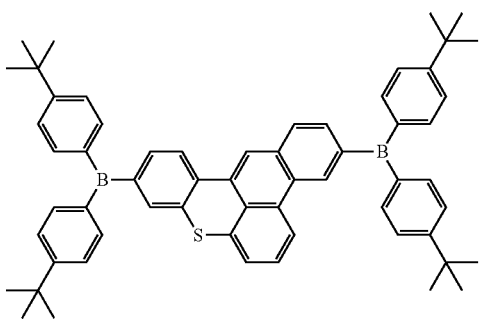
121
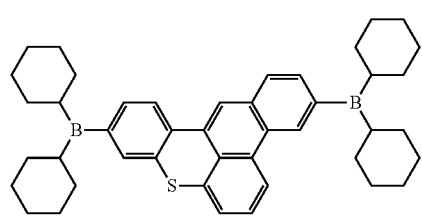
122
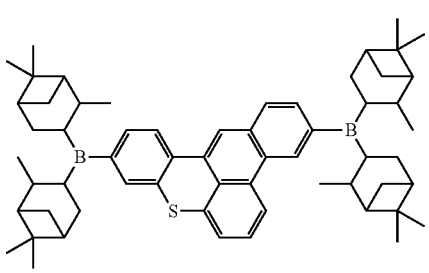
123
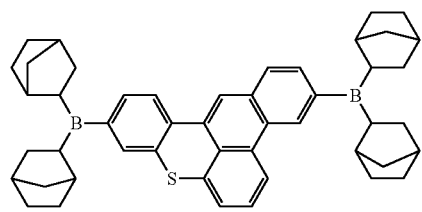
124
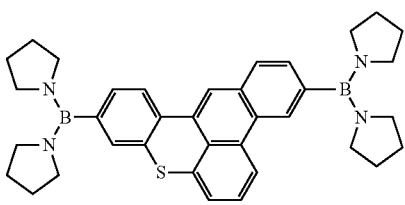
125
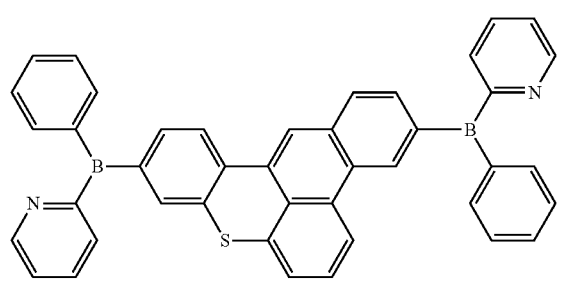
126
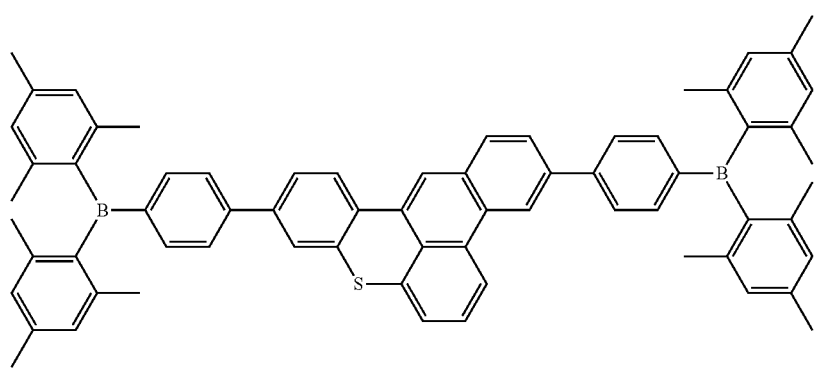
127

128
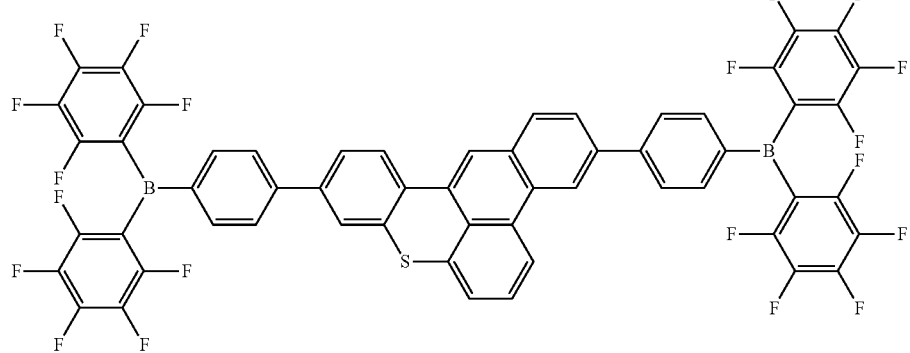
129
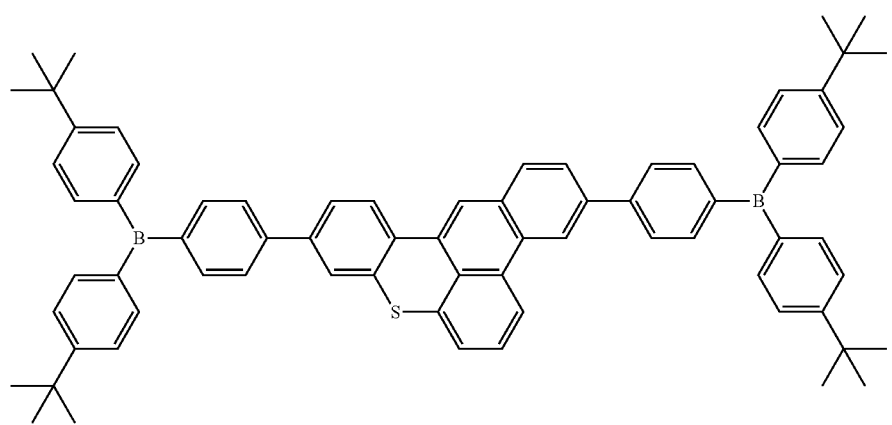
130
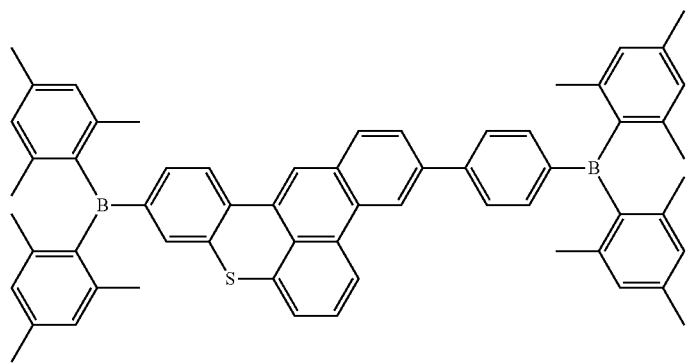
131
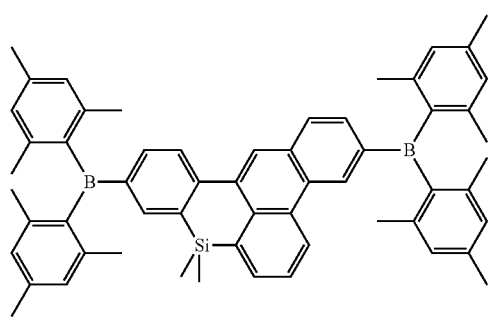
132
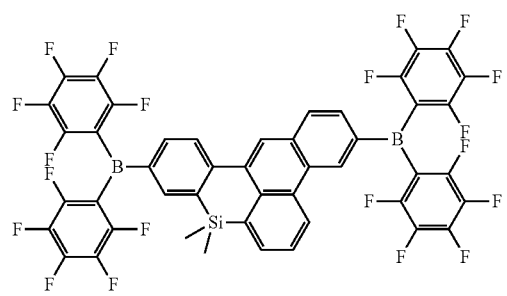

133 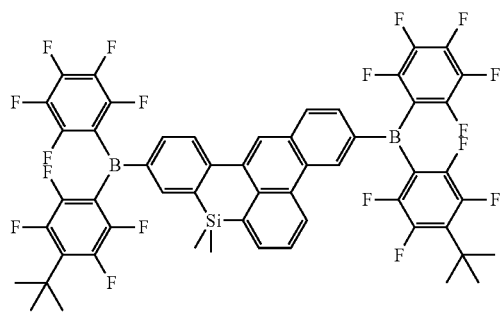
134 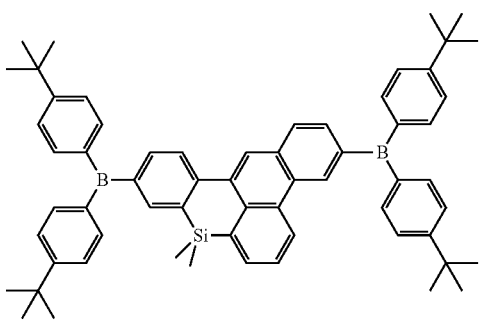
135 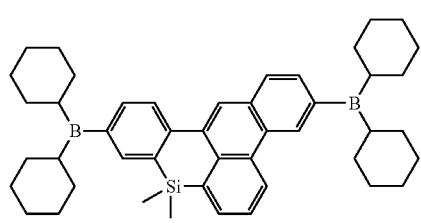
136 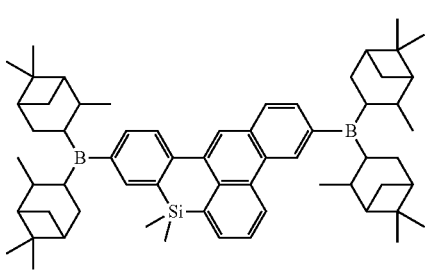
137 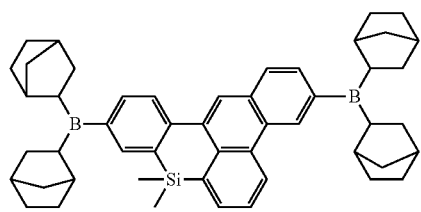
138 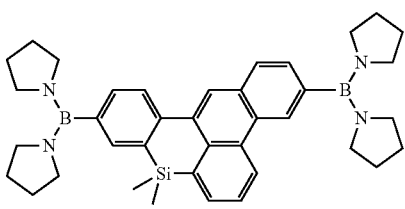
139 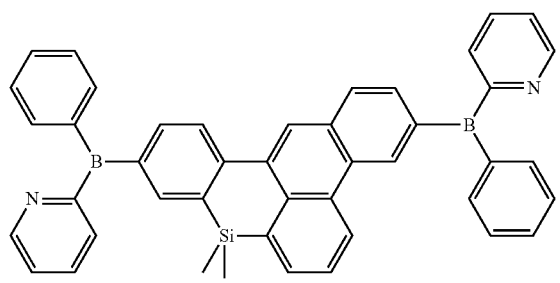
140 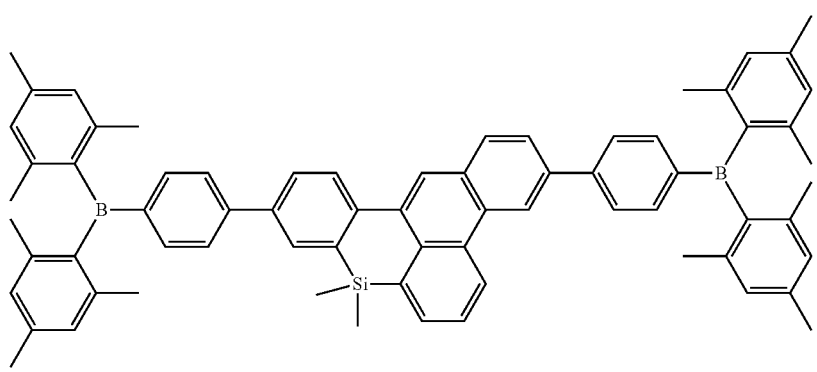

-continued
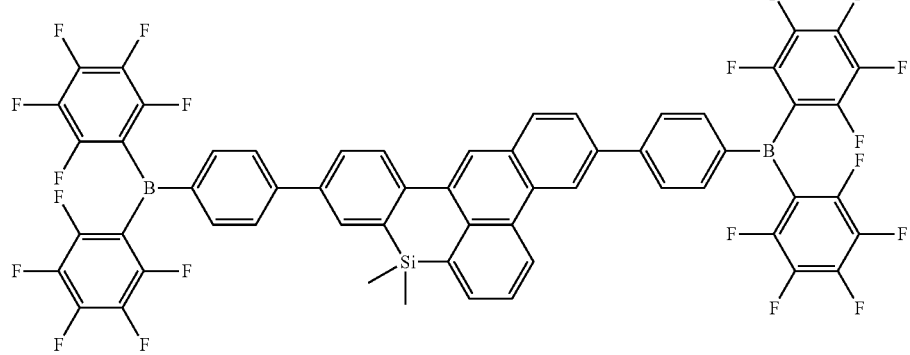
141
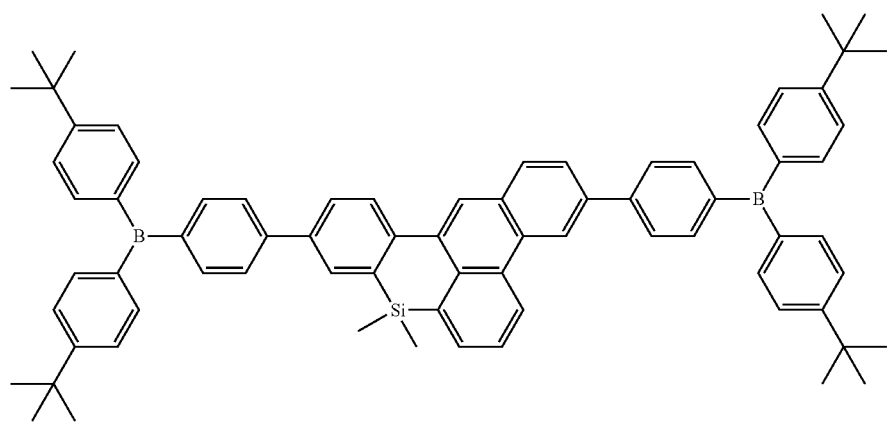
142
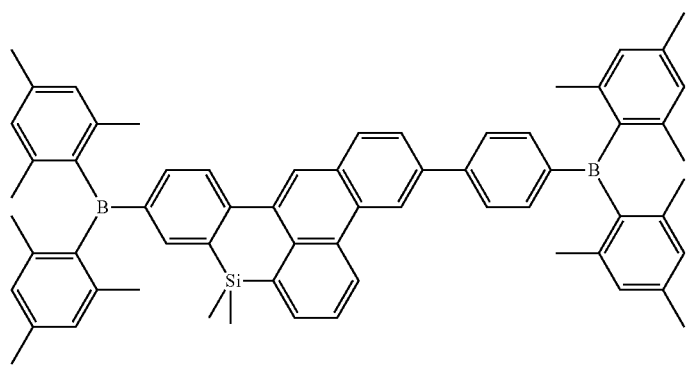
143
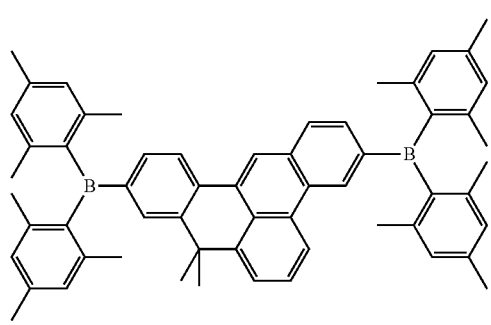
144
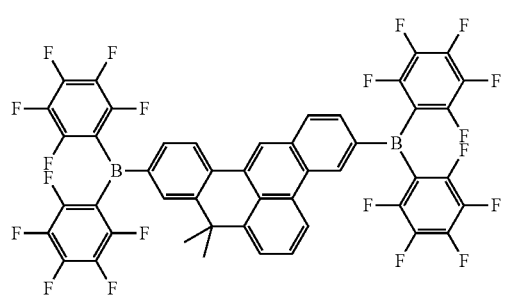
145

146 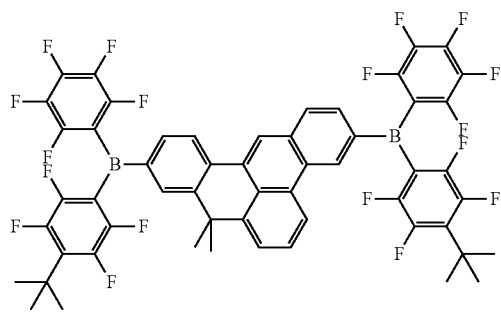
147 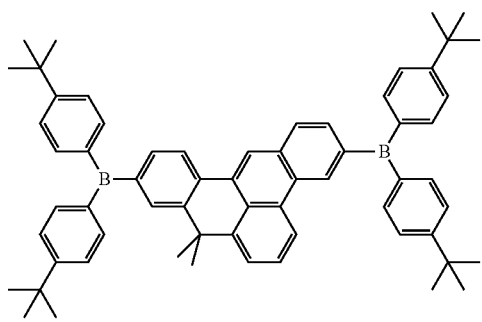
148 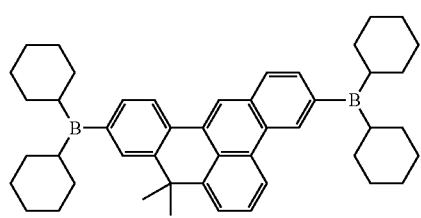
149 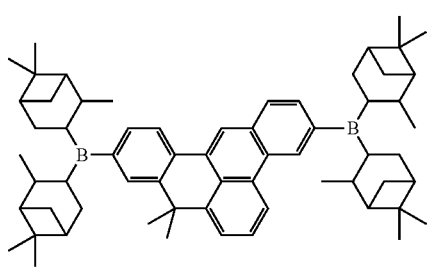
150 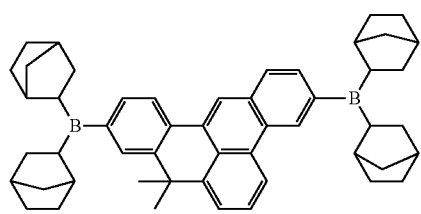
151 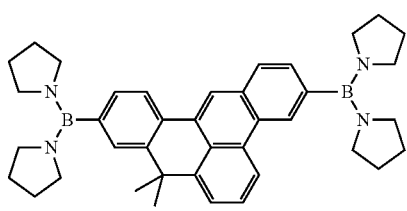
152 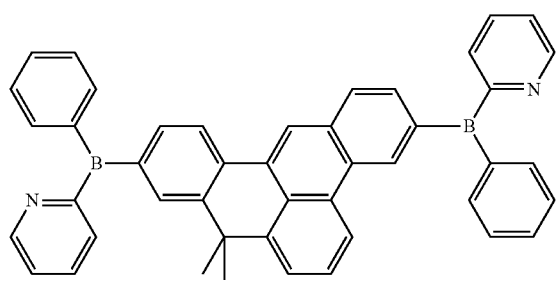
153 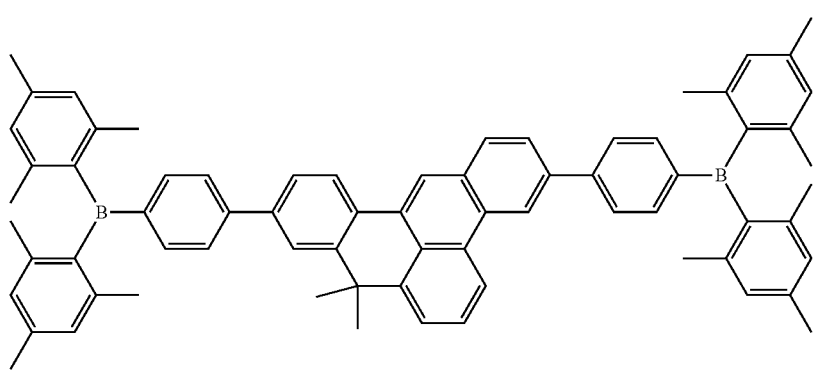

-continued
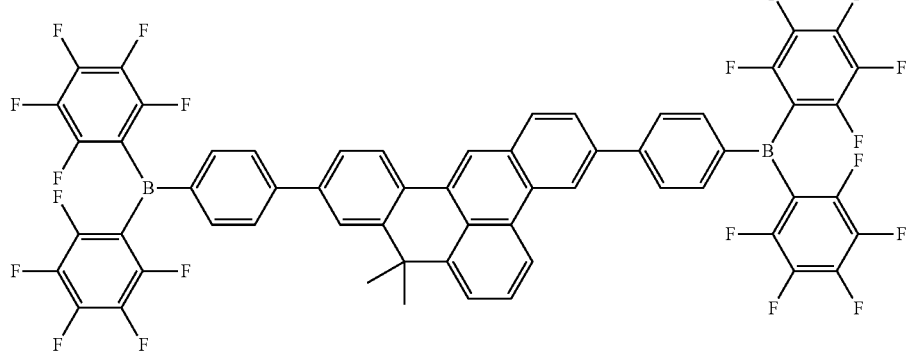
154
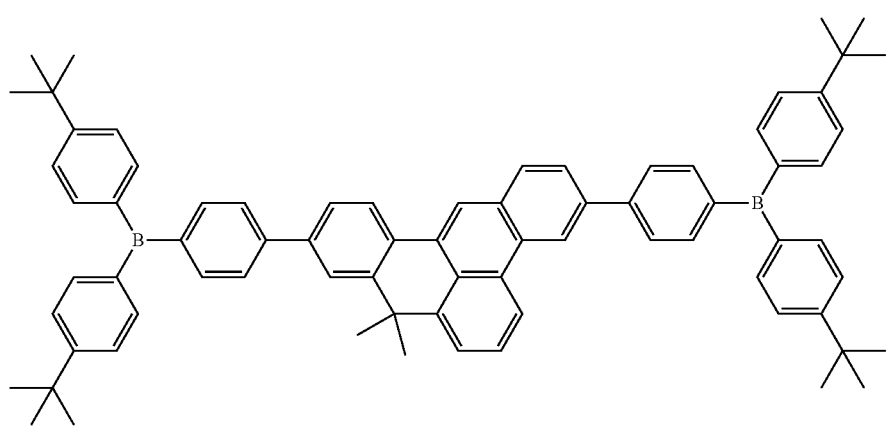
155
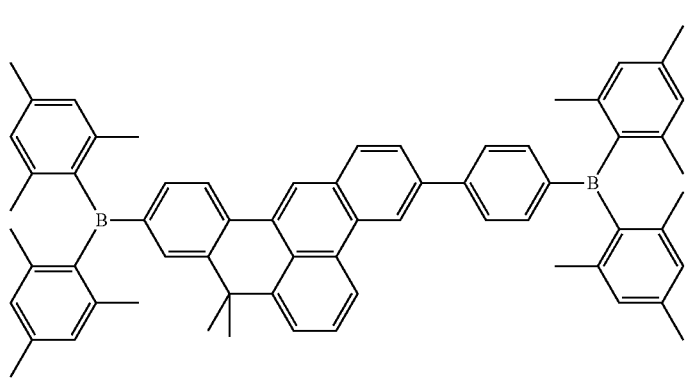
156
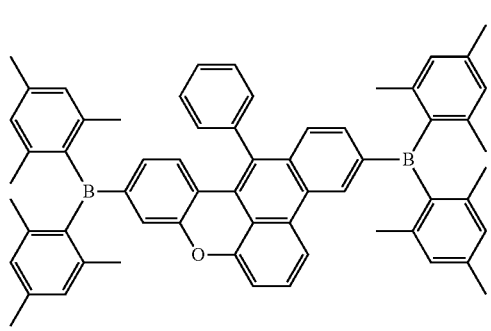
157
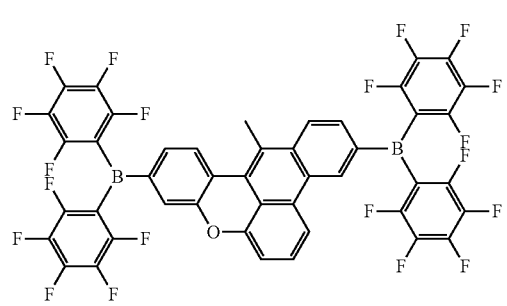
158

-continued
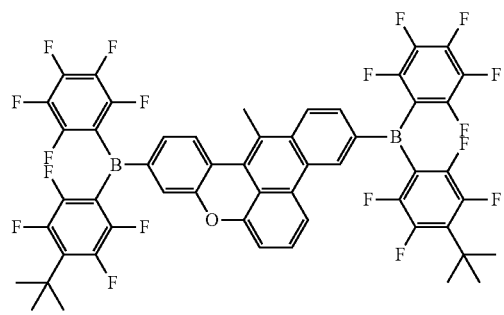
159
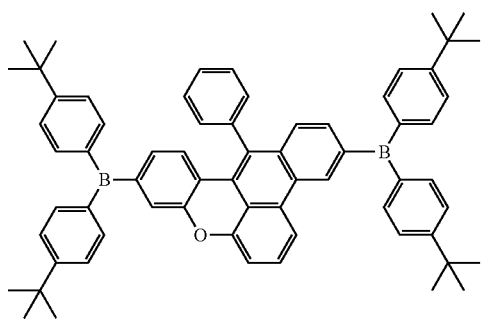
160
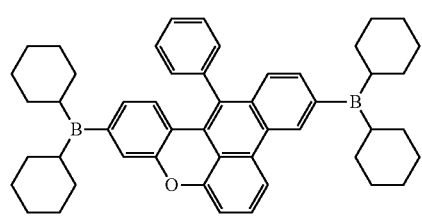
161
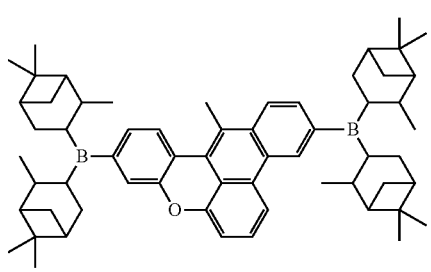
162
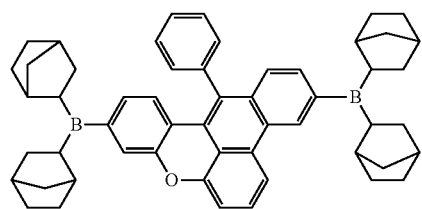
163
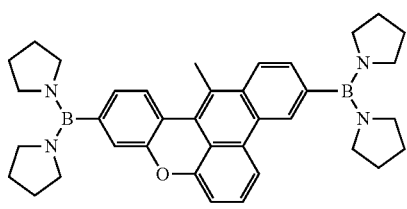
164
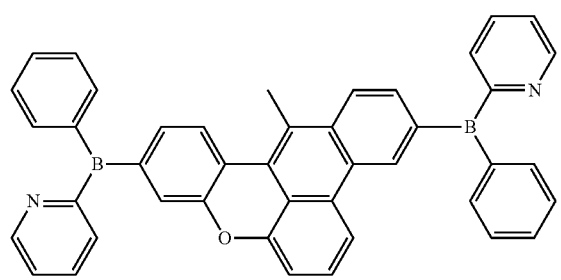
165
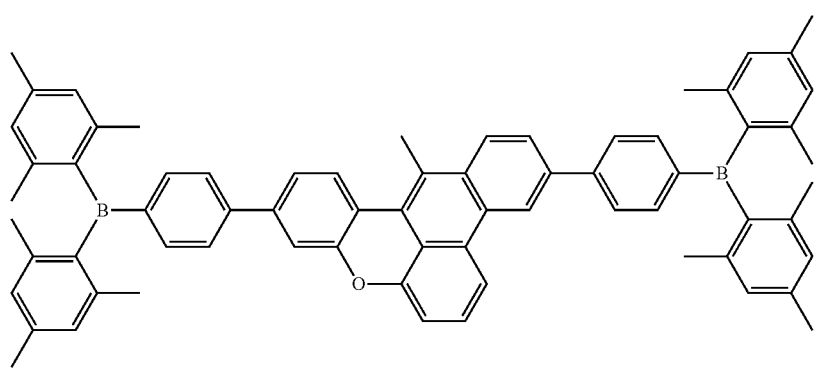
166

167
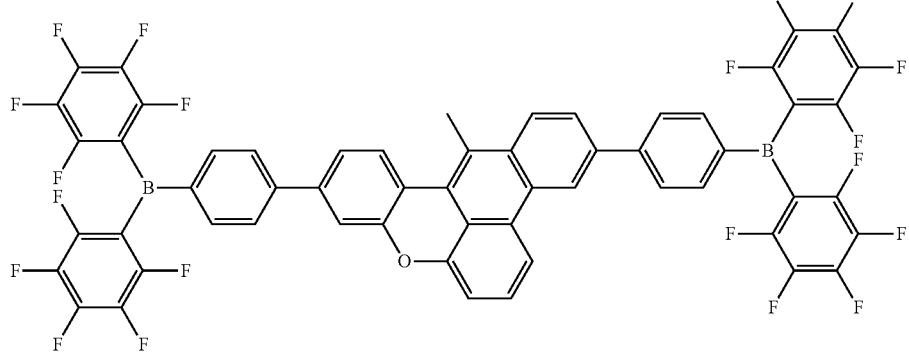
168
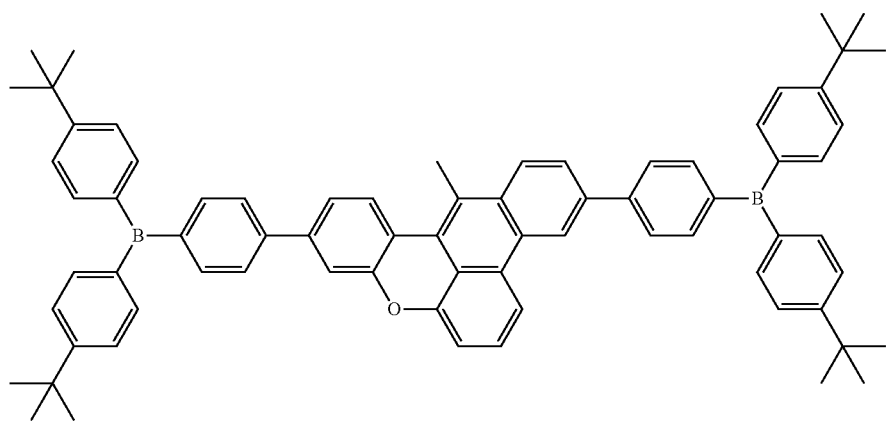
169
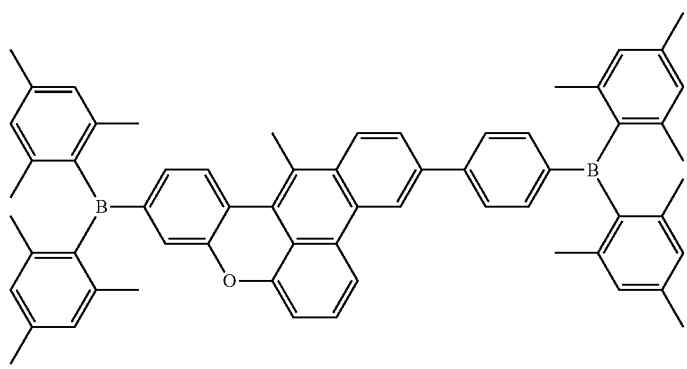
170
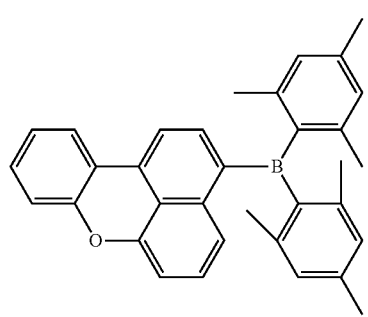
171
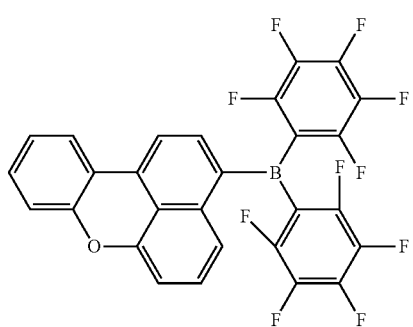

172
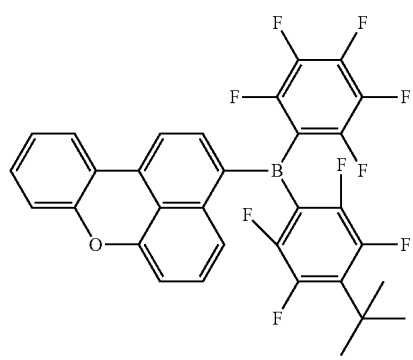
173
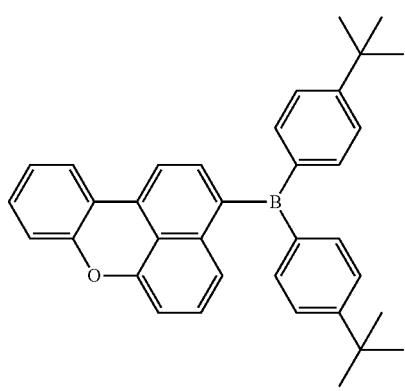
174
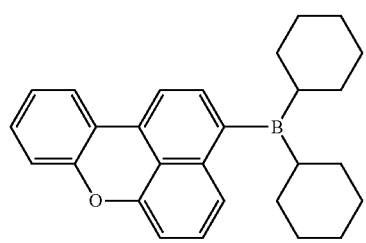
175
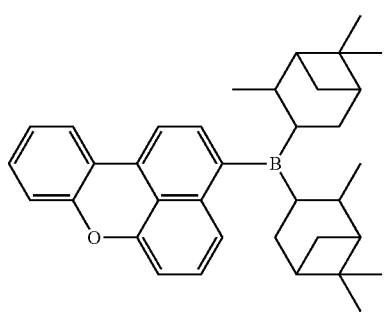
176
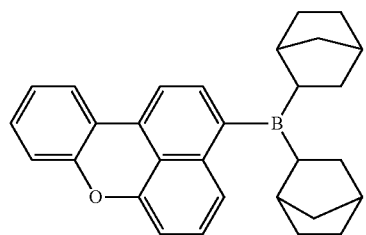
177
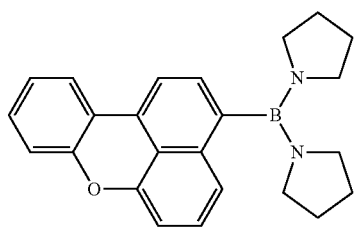
178
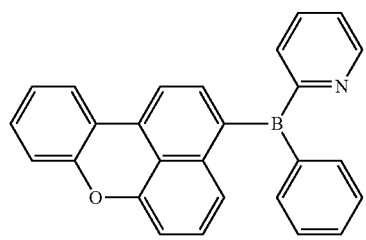
179
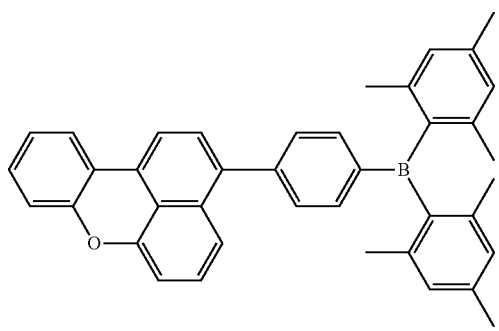

-continued
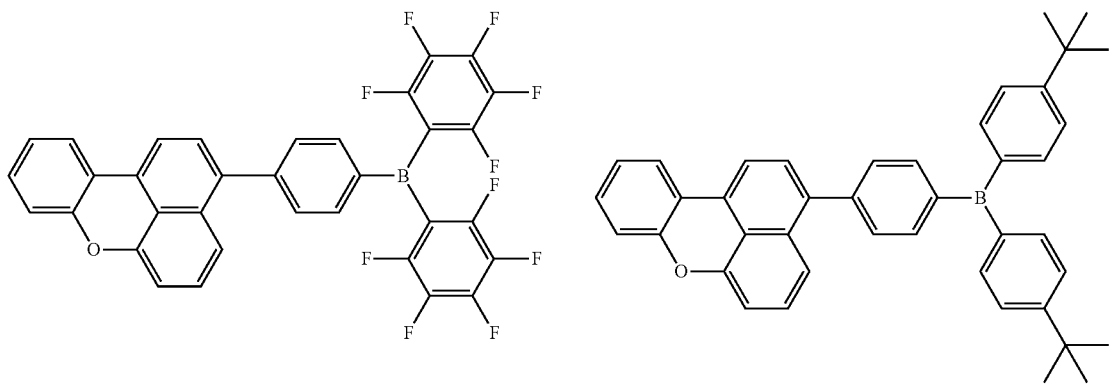
180 181
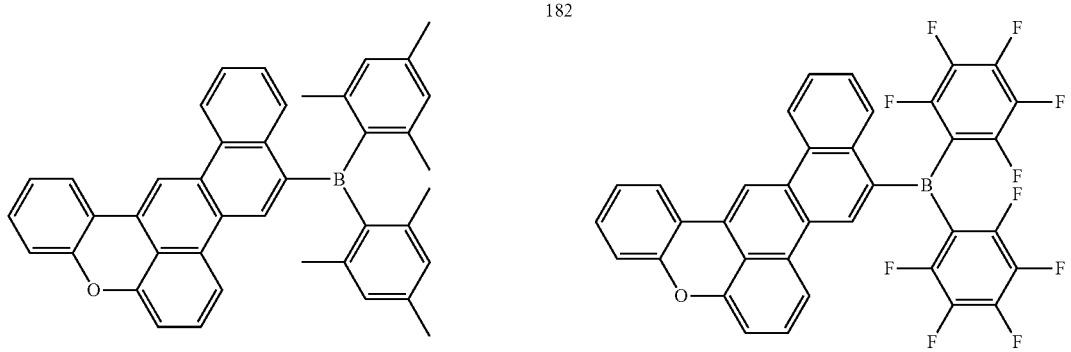
182 183
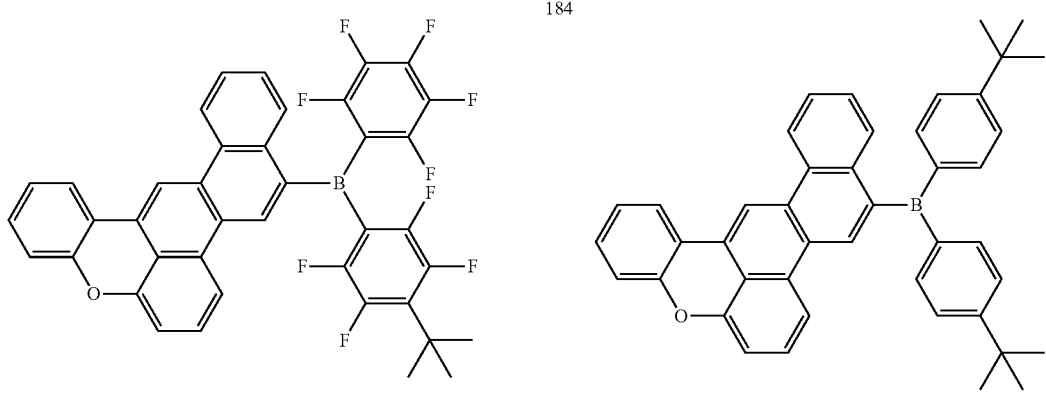
184 185
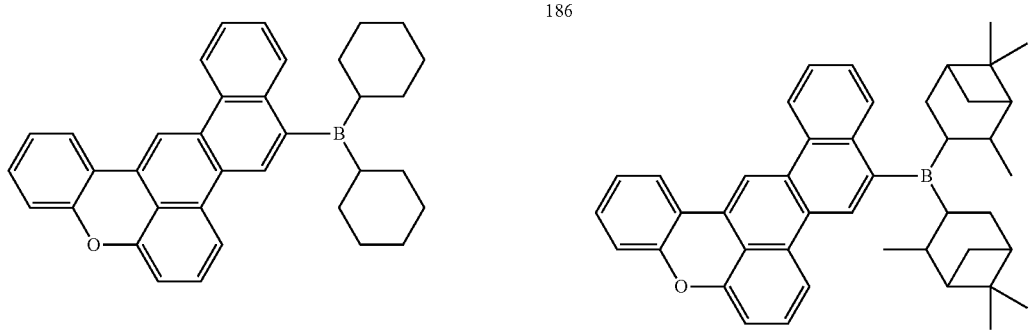
186 187

-continued
188
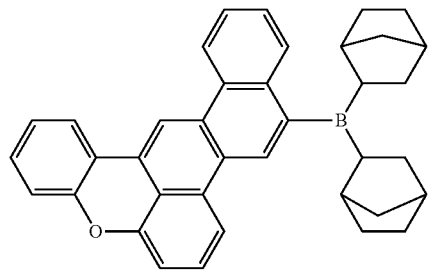
189
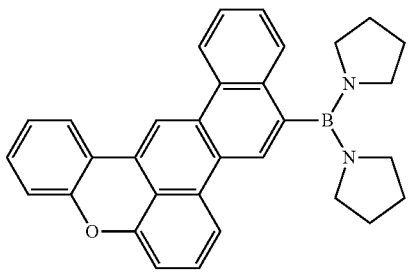
190
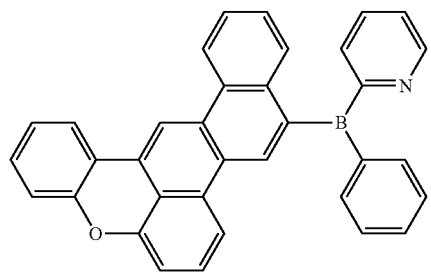
191
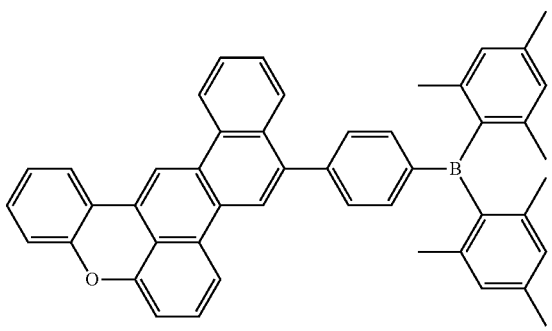
192
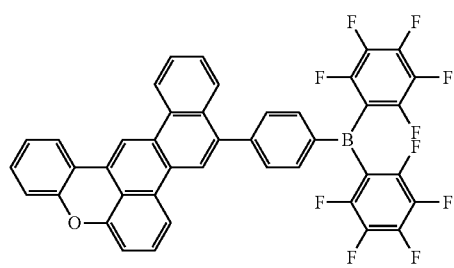
193
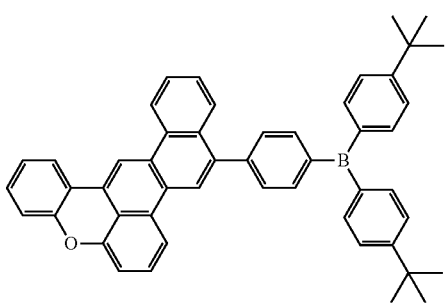
195
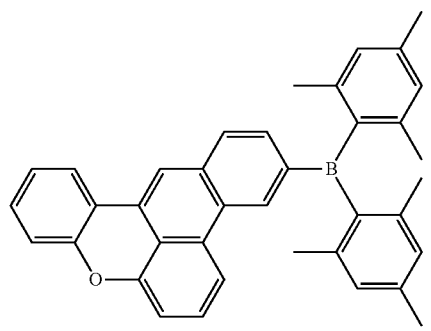
194
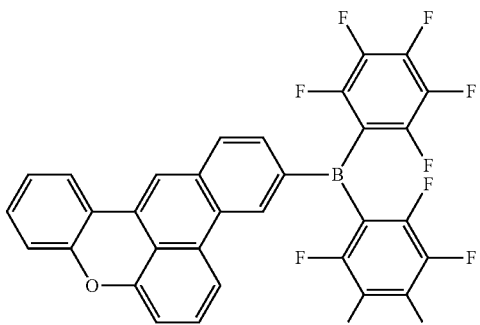
196
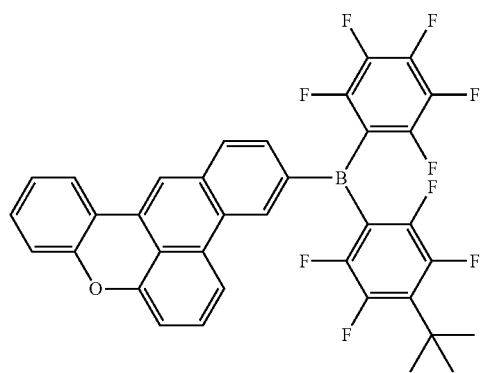
197
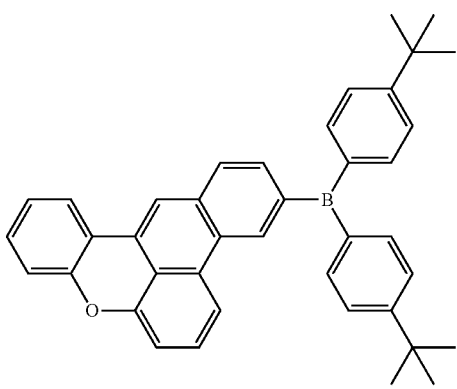

-continued
198 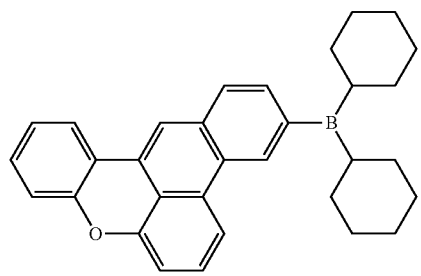
199 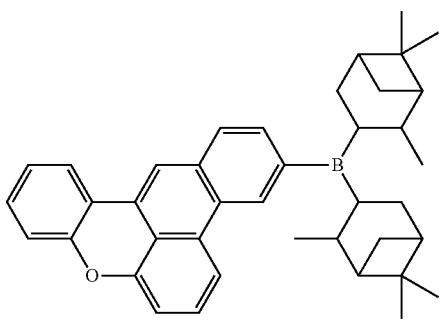
200 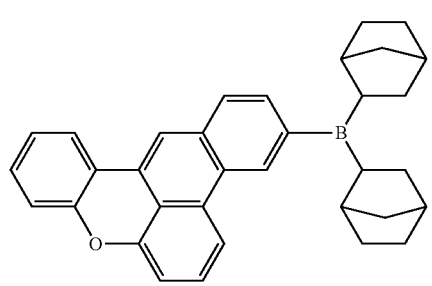
201 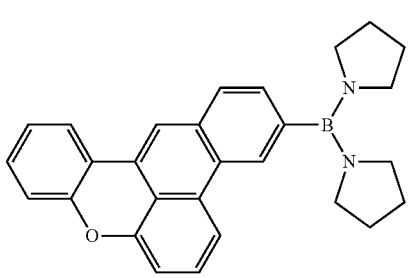
202 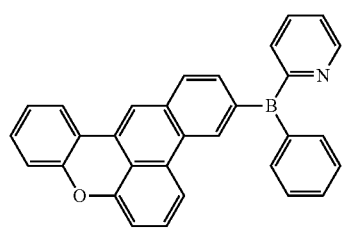
203 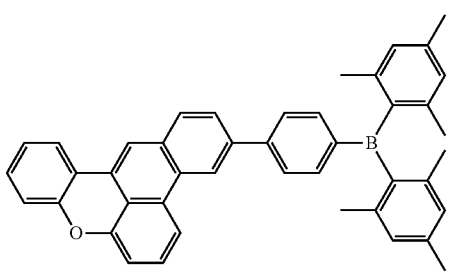
204 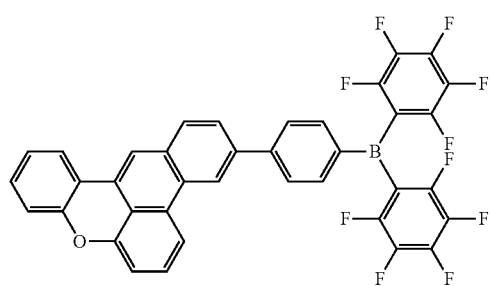
205 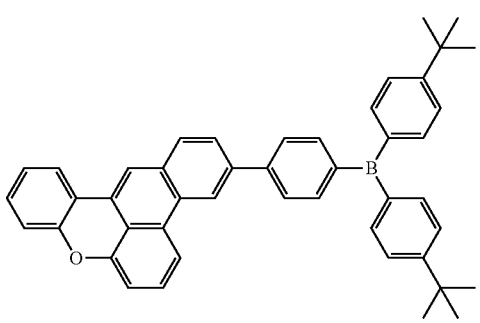
206 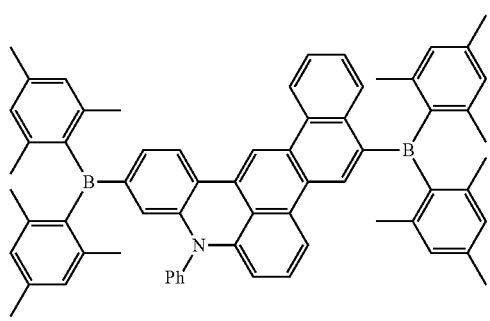
207 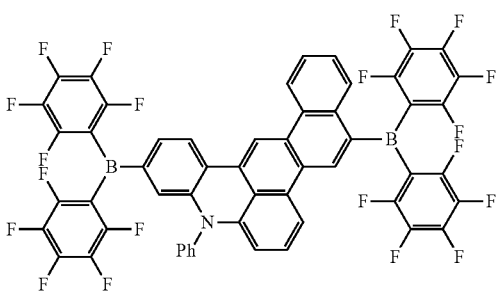

-continued
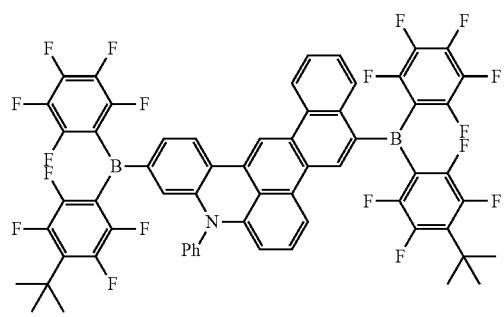
208
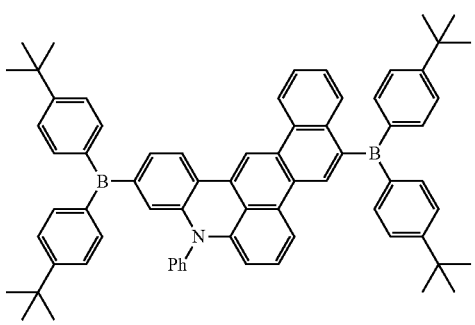
209
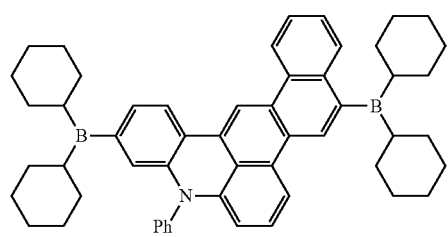
210
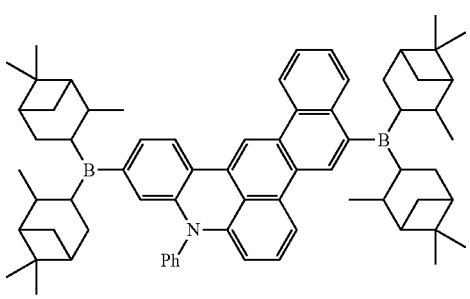
211
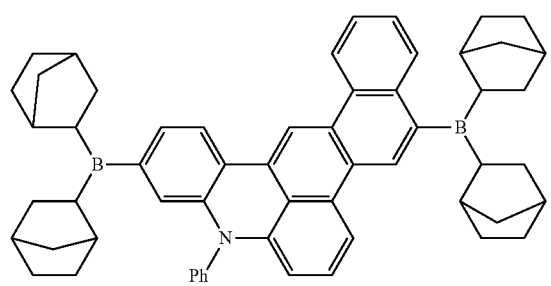
212
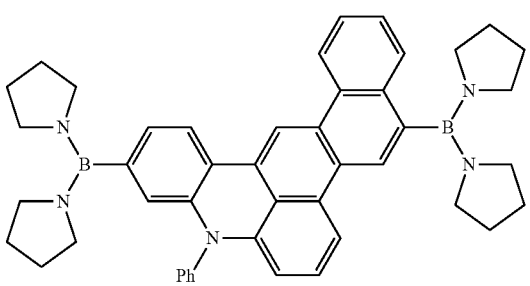
213
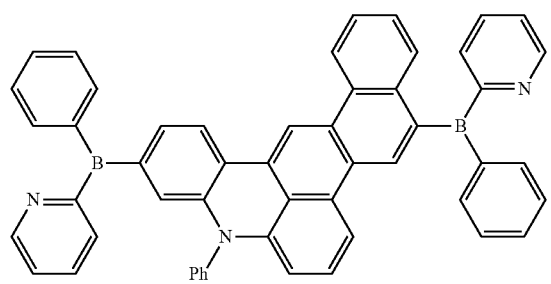
214
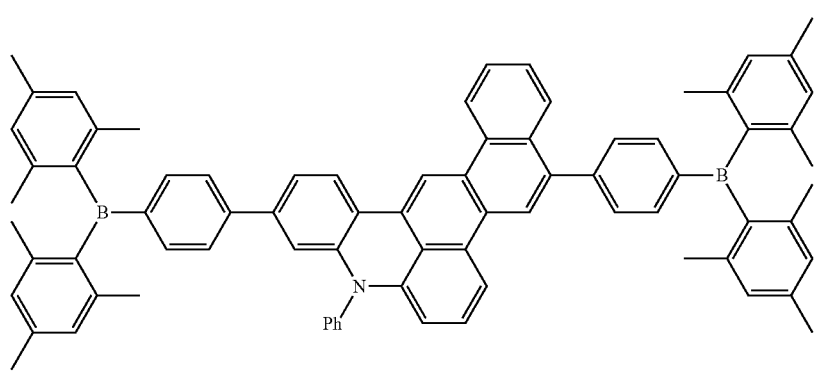
215

-continued
216
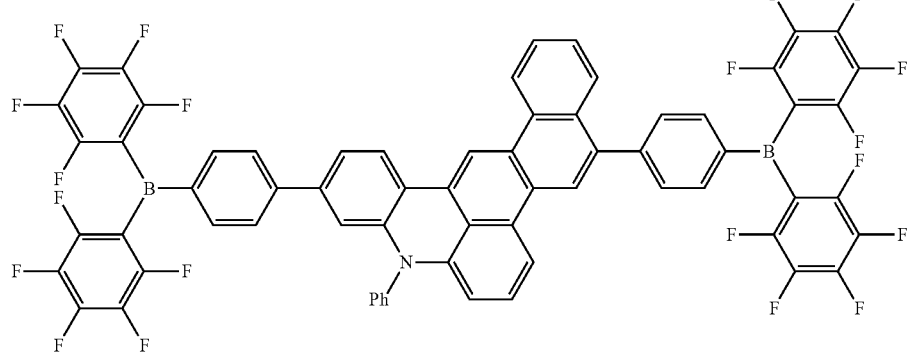
217
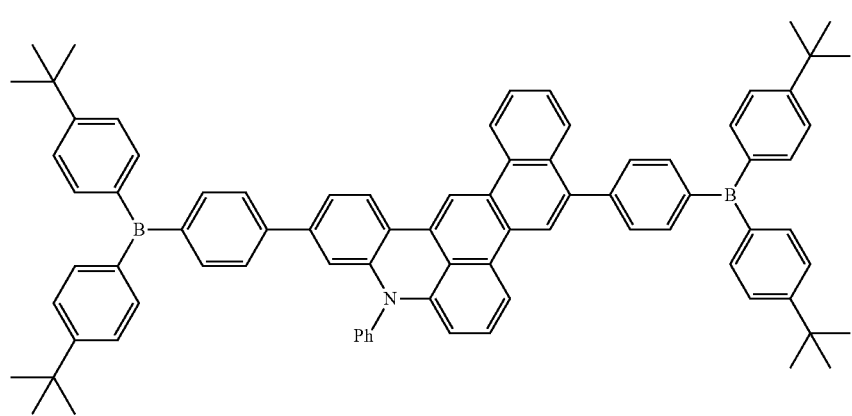
218
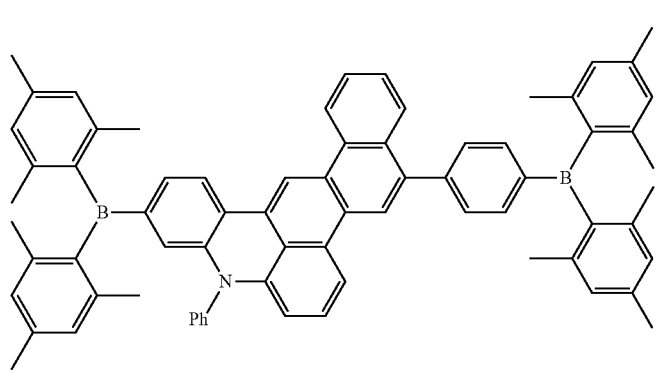
219
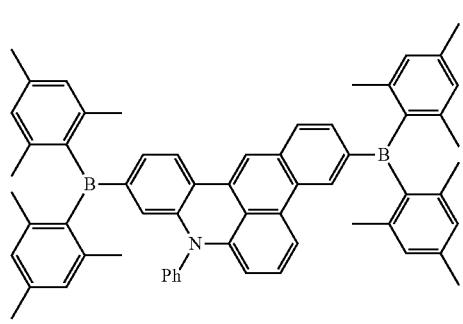
220
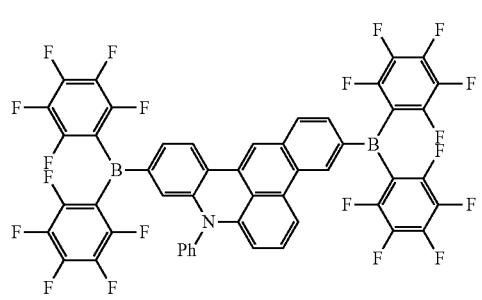

-continued
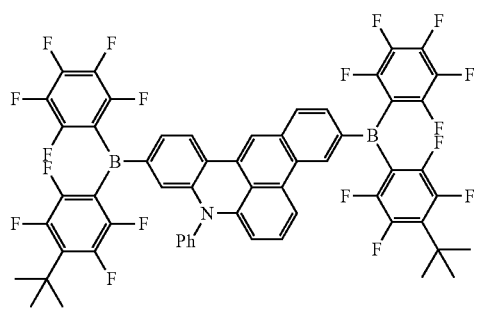
221
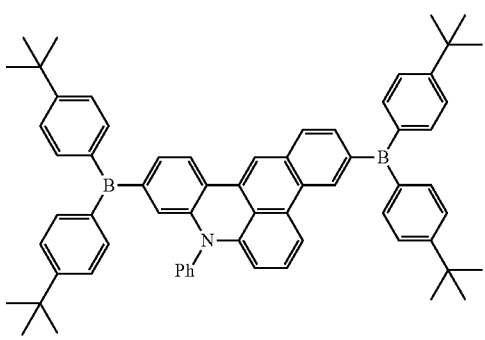
222
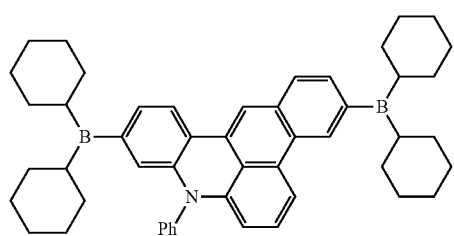
223
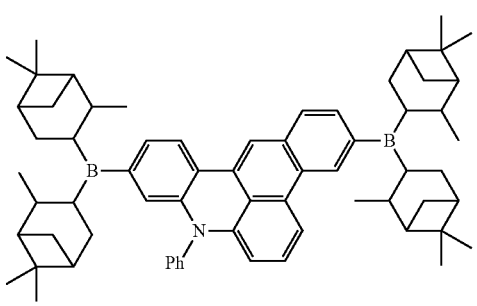
224
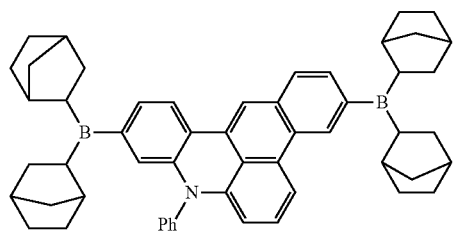
225
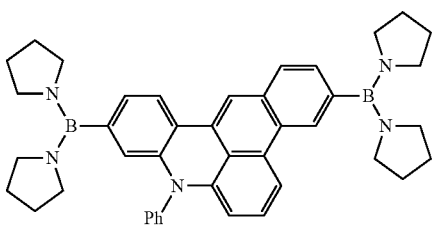
226
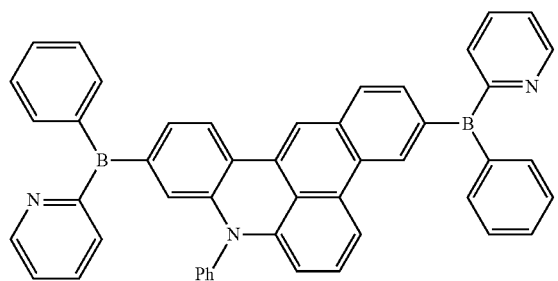
227
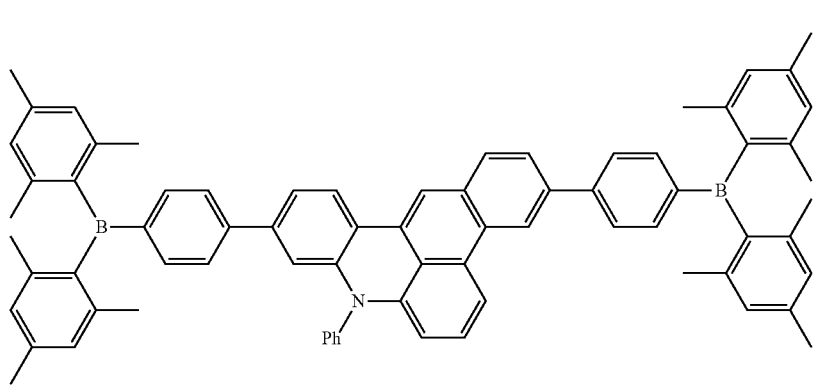
228

-continued

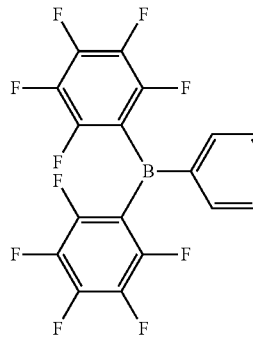

229

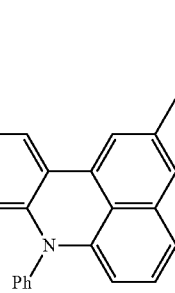

230

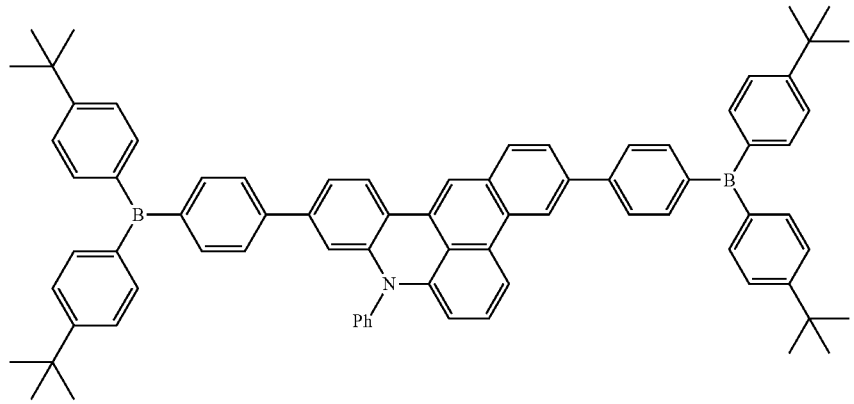

231

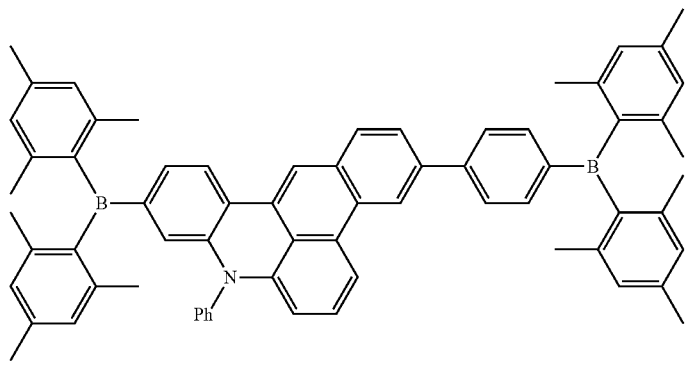

The condensed-cyclic compound represented by Formula 1 may be synthesized by using a suitable organic synthetic method. Such a method of synthesizing the condensed-cyclic compound may be understood by referring to examples used herein.

At least one condensed-cyclic compound represented by Formula 1 may be used in between a pair of electrodes in an organic light-emitting device. For example, the condensed-cyclic compound may be included in a hole transport region, for example, in a hole transport layer. In some embodiments, the condensed-cyclic compound may be included in a emission layer. Accordingly, an organic light-emitting device includes: a first electrode; a second electrode facing the first electrode; and an organic layer that is disposed between the first electrode and the second electrode and includes an emission layer; wherein the organic layer includes at least one condensed-cyclic compound represented by Formula 1.

As used herein, the expression the "(organic layer) includes at least one condensed-cyclic compound" may be construed as meaning the "(organic layer) may include one condensed-cyclic compound represented by Formula 1 or two different condensed-cyclic compounds represented by Formula 1".

For example, the organic layer may include only Compound 1 as the condensed-cyclic compound. In this regard, Compound 1 may be included in a hole transport layer or an emission layer of the organic light-emitting device. In some embodiments, the organic layer may include Compound 1 and Compound 2 as the condensed-cyclic compounds. In this regard, Compound 1 and Compound 2 may be situated in the same layer (for example, both Compound 1 and Compound 2 may be situated in a hole transport layer), or in different layers (for example, Compound 1 may be situated in an emission layer and Compound 2 may be situated in a hole transport layer).

The organic layer may include i) a hole transport region disposed between the first electrode (anode) and the emission layer and including at least one selected from a hole injection layer, a hole transport layer, a buffer layer, and an electron blocking layer and ii) an electron transport region that is disposed between the emission layer and the second electrode (cathode) and that includes at least one selected from a hole blocking layer, an electron transport layer, and an electron injection layer. At least one selected from the hole transport region and the emission layer may include at least one condensed-cyclic compound represented by Formula 1. In some embodiments, the hole transport region may include a hole transport layer, wherein the hole transport layer may include the at least one condensed-cyclic compound represented by Formula 1.

In some embodiments, the emission layer in the organic light-emitting device may include the condensed-cyclic compound represented by Formula 1. In the emission layer, the condensed-cyclic compound represented by Formula 1 may serve as a dopant, and the emission layer may further include a host.

In some embodiments, the hole transport region (for example, the hole transport layer in the hole transport region) and emission layer may each include the condensed-cyclic compound. The condensed-cyclic compound included in the hole transport region (for example, the hole transport layer in the hole transport region) and condensed-cyclic compound included in the emission layer may be different from each other.

As used herein, the term the "organic layer" refers to a single and/or a plurality of layers disposed between the first electrode and the second electrode in an organic light-emitting device. A material included in the "organic layer" may include other materials besides an organic material.

FIG. 1 illustrates a schematic view of an organic light-emitting device 10 according to an embodiment. The organic light-emitting device 10 may include a first electrode 110, an organic layer 150, and a second electrode 190.

Hereinafter, a structure and a method of manufacturing the organic light-emitting device according to an embodiment will be described with reference to FIG. 1.

Referring to FIG. 1, a substrate may be additionally disposed under the first electrode 110 or on the second electrode 190. The substrate may be substrate with excellent mechanical strength, thermal stability, transparency, surface smoothness, ease of handling, and water resistance, such as a glass substrate or transparent plastic substrate.

The first electrode 110 may be formed by depositing or sputtering a material for forming the first electrode on the substrate. When the first electrode 110 is an anode, the material for the first electrode may be selected from materials with a high work function to make holes be easily injected. The first electrode 110 may be a reflective electrode, a semi-transmissive electrode, or a transmissive electrode. The material for the first electrode may be a transparent and highly conductive material. Examples of such a material include indium tin oxide (ITO), indium zinc oxide (IZO), tin oxide ($SnO_2$), and zinc oxide (ZnO). When the first electrode 110 is a semi-transmissive electrode or a reflective electrode, as a material for forming the first electrode, at least one selected from magnesium (Mg), aluminum (Al), aluminum-lithium (Al—Li), calcium (Ca), magnesium-indium (Mg—In), and magnesium-silver (Mg—Ag) may be used.

The first electrode 110 may have a single-layer structure, or a multi-layer structure including a plurality of layers. For example, the first electrode 110 may have a triple-layer structure of ITO/Ag/ITO.

The organic layer 150 may be disposed on the first electrode 110. The organic layer 150 may include an emission layer.

The organic layer 150 may further include a hole transport region disposed between the first electrode and the emission layer, and an electron transport region disposed between the emission layer and the second electrode.

The hole transport region may include at least one selected from a hole injection layer (HIL), a hole transport layer (HTL), a buffer layer, and an electron blocking layer (EBL). The electron transport region may include at least one selected from a hole blocking layer (HBL), an electron transport layer (ETL), and an electron injection layer (EIL), as examples.

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, or a structure of hole injection layer/hole transport layer, a structure of hole injection layer/hole transport layer/buffer layer, a structure of hole injection layer/buffer layer, a structure of hole transport layer/buffer layer, or a structure of hole injection layer/hole transport layer/electron blocking layer, wherein layers of each structure are sequentially stacked from the first electrode 110 in this stated order.

When the hole transport region includes a hole injection layer, the hole injection layer may be formed on the first electrode 110 by a suitable method, such as vacuum-deposition, spin coating, casting, Langmuir-Blodgett (LB) method, ink-jet printing, laser-printing, or laser-induced thermal imaging (LITI).

When the hole injection layer is formed by vacuum-deposition, for example, the vacuum-deposition may be performed at a deposition temperature of about 100° C. to about 500° C., at a vacuum degree of about $10^{-8}$ Torr to about $10^{-3}$ Torr, and at a vacuum-deposition rate in a range of about 0.01 Å/sec to about 100 Å/sec in consideration of a compound for the hole injection layer to be deposited, and the structure of the hole injection layer to be formed.

When a hole injection layer is formed by spin coating, the spin coating may be performed at a coating rate of about 2,000 rpm to about 5,000 rpm, and at a temperature of about 80° C. to 200° C. in consideration of a compound for a hole injection layer to be deposited, and the structure of a hole injection layer to be formed.

When the hole transport region includes a hole transport layer, the hole transport layer may be formed on the first electrode 110 or the hole injection layer by a suitable method, such as vacuum-deposition, spin coating, casting, LB method, ink-jet printing, laser-printing, or LITI. When the hole transport layer is formed by vacuum-deposition or spin coating, conditions for vacuum-deposition and coating may be similar to the above-described vacuum-deposition and coating conditions for forming the hole injection layer.

The hole transport region may include the condensed-cyclic compound represented by Formula 1. In some embodiments, the hole transport region may include a hole transport layer, wherein the hole transport layer may include the condensed-cyclic compound represented by Formula 1.

The hole transport region may include at least one selected from m-MTDATA, TDATA, 2-TNATA, NPB, β-NPB, TPD, a spiro-TPD, a spiro-NPB, α-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201, and a compound represented by Formula 202:

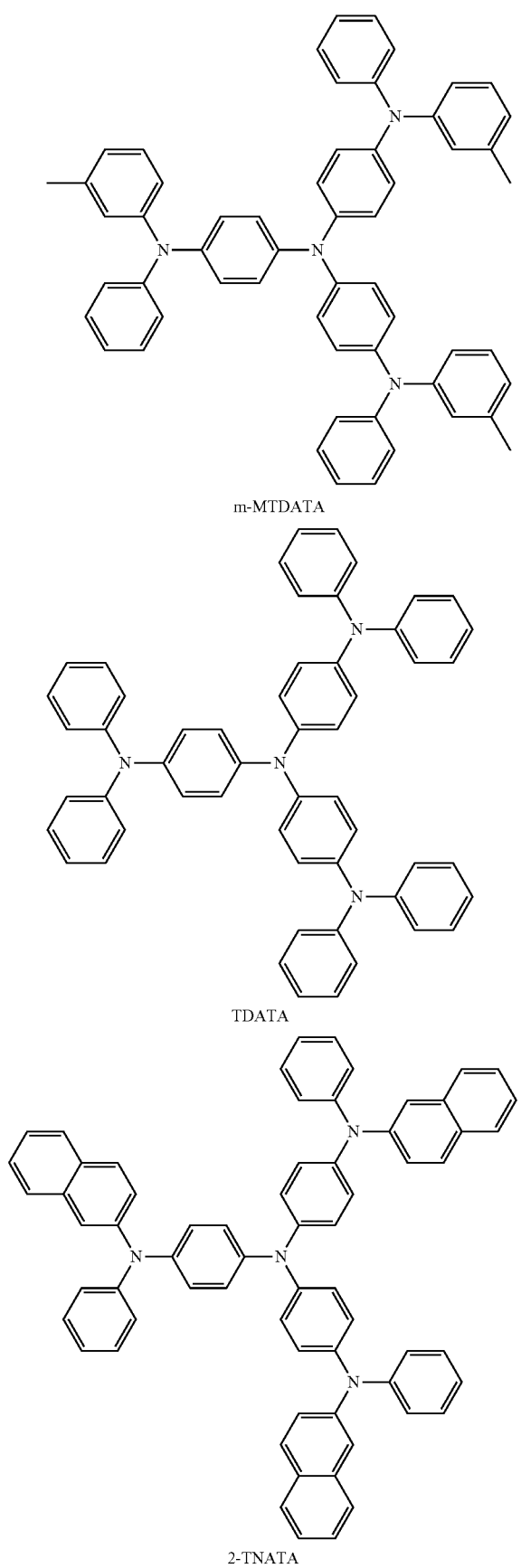
m-MTDATA
TDATA
2-TNATA
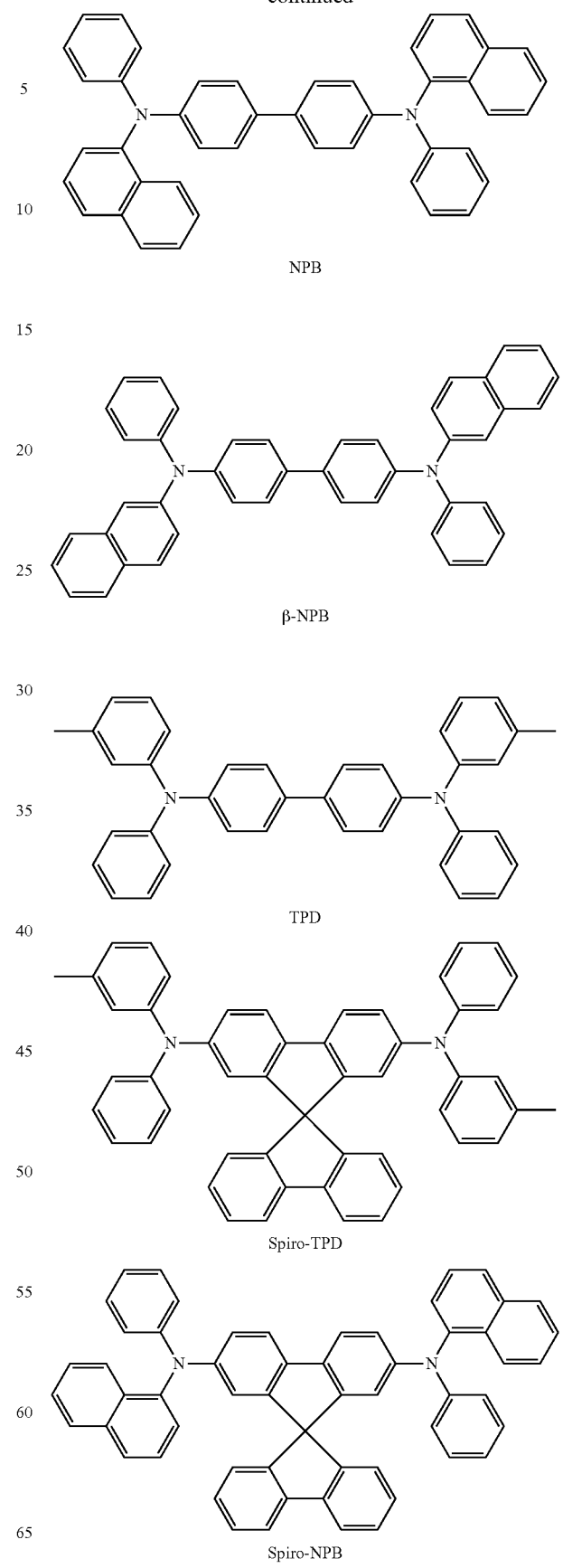
NPB
β-NPB
TPD
Spiro-TPD
Spiro-NPB

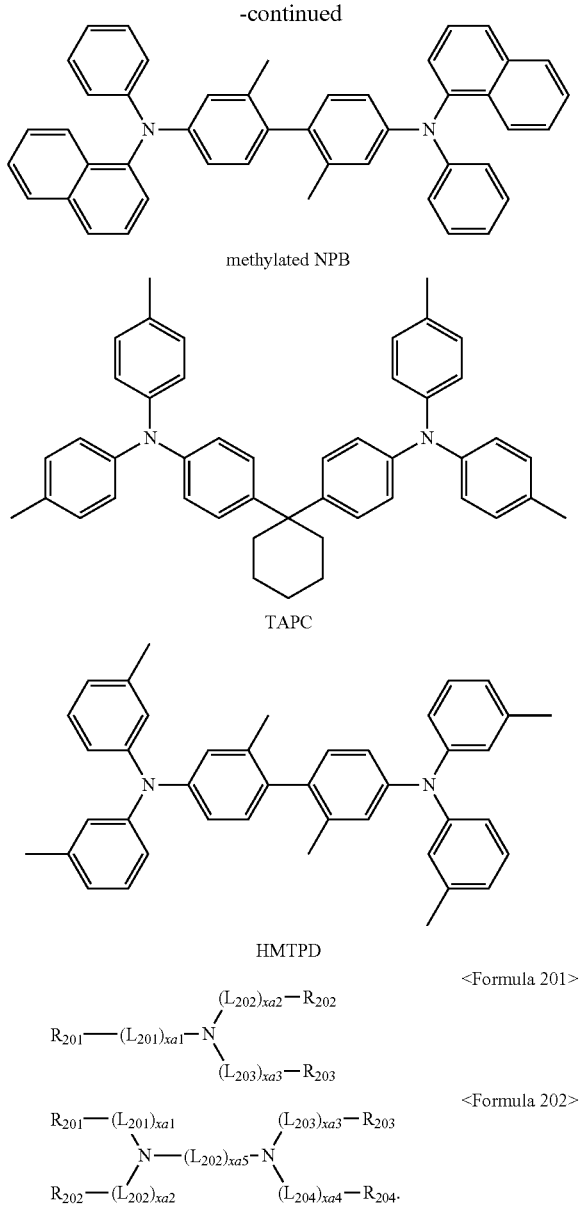

In Formulae 201 and 202.

$L_{201}$ to $L_{205}$ may be the same as defined in connection with $L_1$ provided herein;

xa1 to xa4 may be each independently selected from 0, 1, 2, and 3; and xa5 may be selected from 1, 2, 3, 4, and 5;

$R_{201}$ to $R_{204}$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formulae 201 and 202, $L_{201}$ to $L_{205}$ may be each independently selected from:
a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently selected from 0, 1, and 2;

xa5 may be selected from 1, 2, and 3;

$R_{201}$ to $R_{204}$ may be each independently selected from:
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

The compound represented by Formula 201 may be represented by Formula 201A:

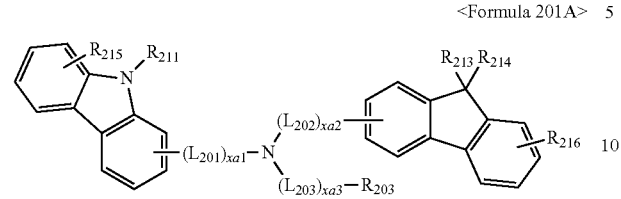

<Formula 201A>

In some embodiments, the compound represented by Formula 201 may be represented by Formula 201A-1:

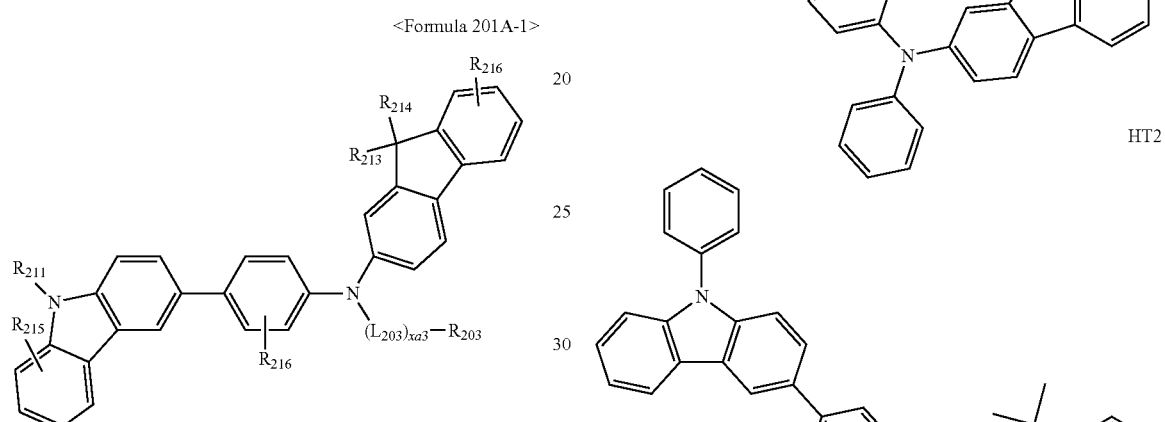

<Formula 201A-1>

In some embodiments, the compound represented by Formula 202 may be represented by Formula 202A:

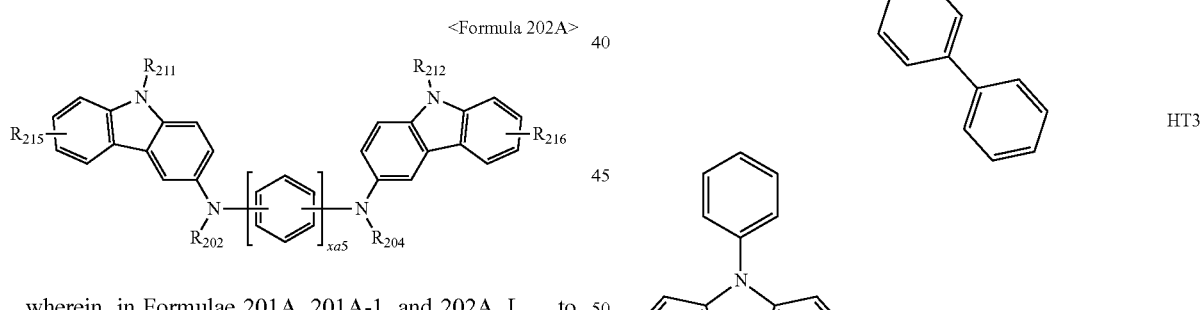

<Formula 202A> wherein, in Formulae 201A, 201A-1, and 202A, $L_{201}$ to $L_{203}$, xa1 to xa3, xa5, and $R_{202}$ to $R_{204}$ may be understood by referring to the description provided herein, and $R_{211}$ may be the same as defined in connection with $R_{203}$; and $R_{213}$ to $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

The compound represented by Formula 201 and the compound represented by Formula 202 may include Compounds HT1 to HT20:

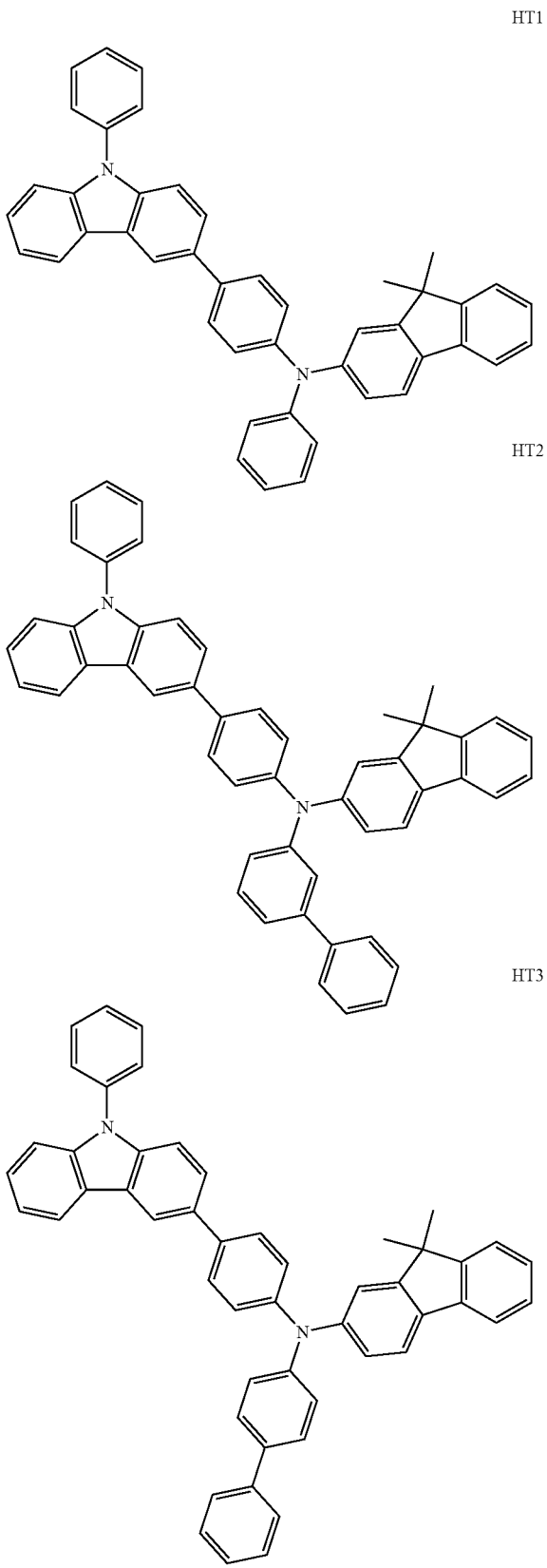

HT4
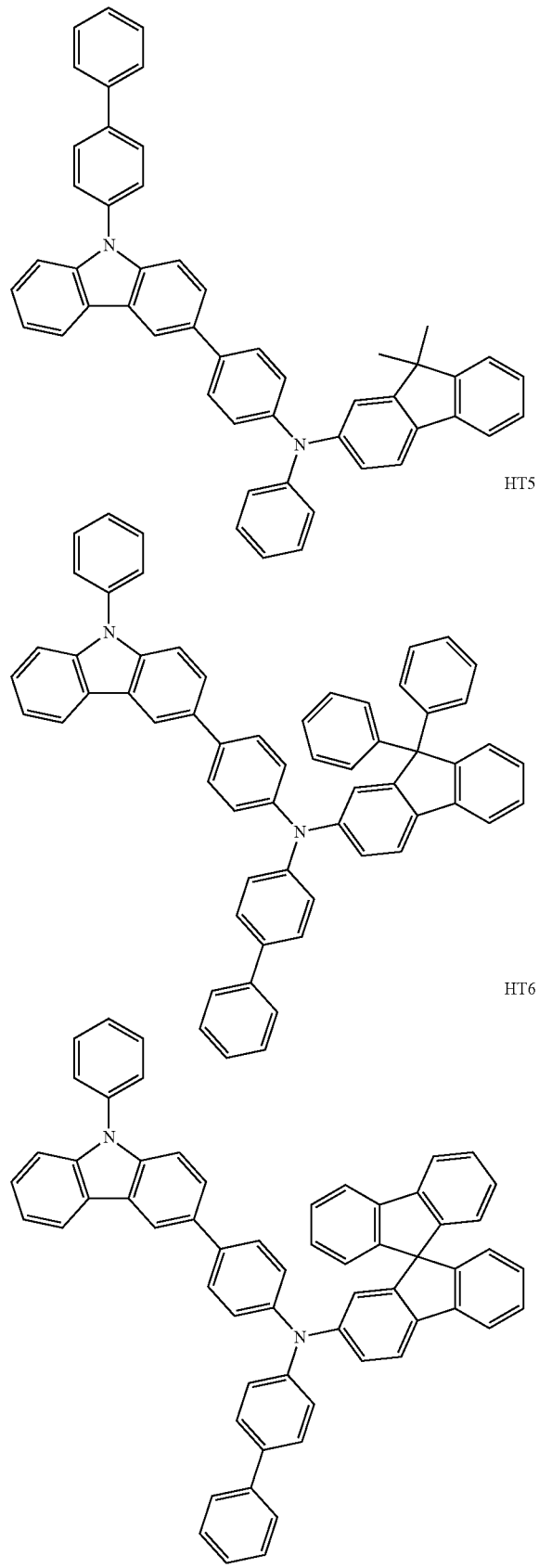
HT5
HT6
HT7
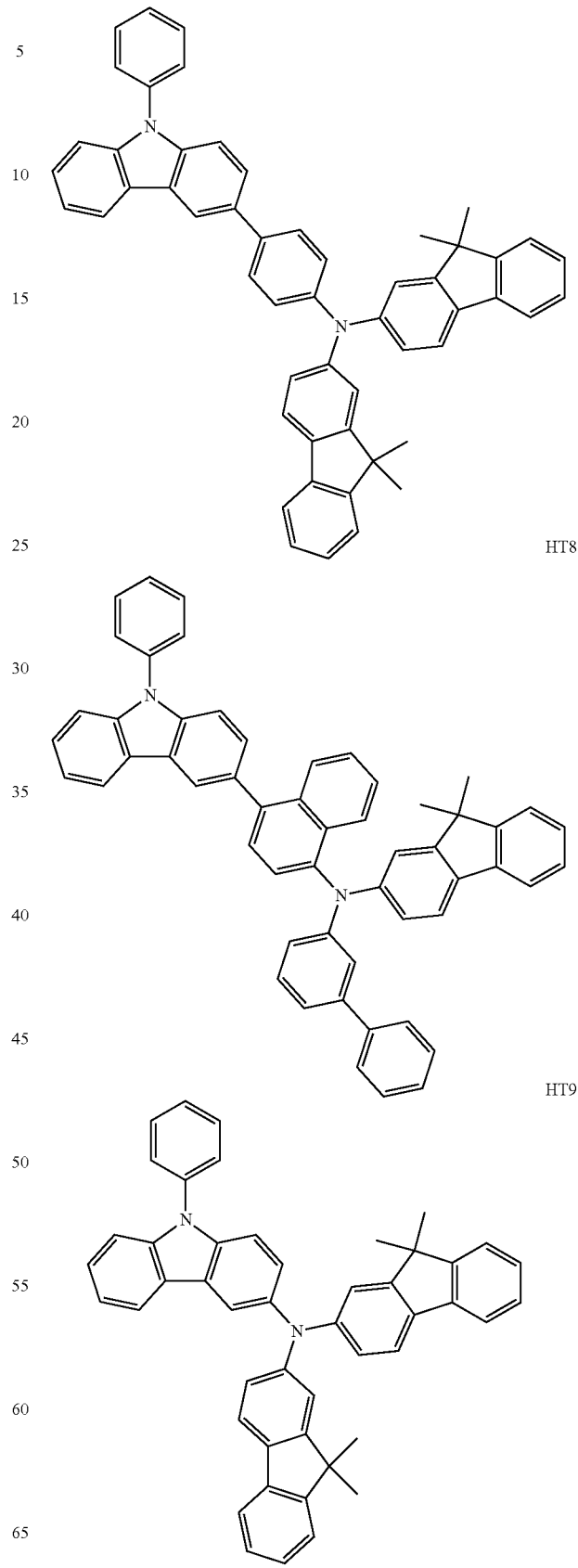
HT8
HT9

HT10
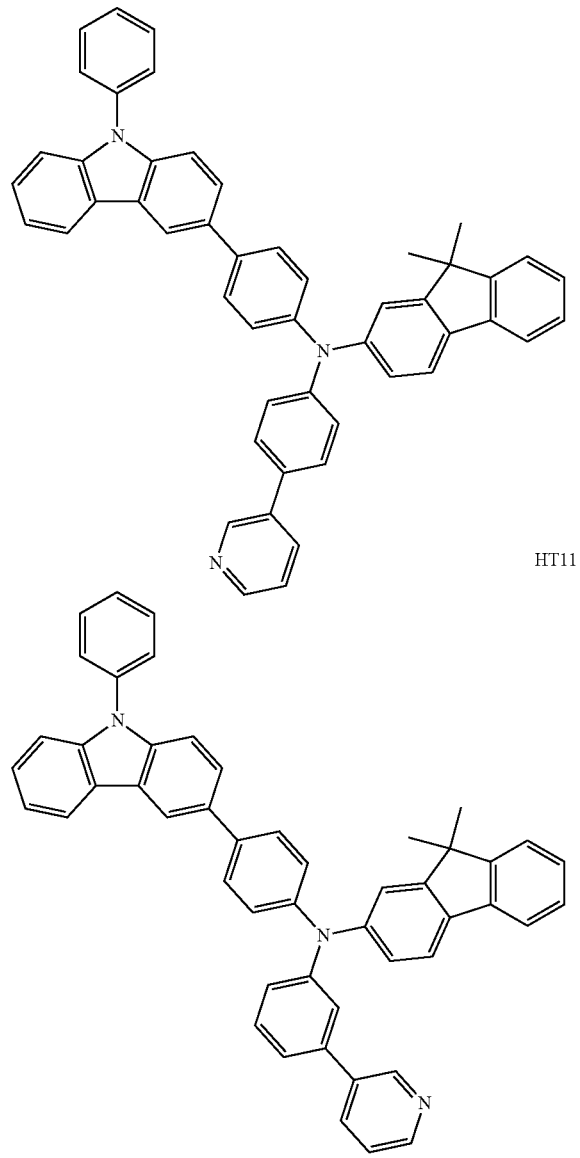
HT11
HT12
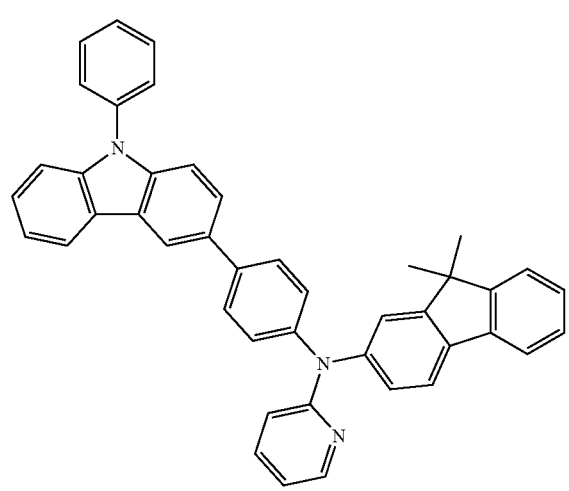
HT13
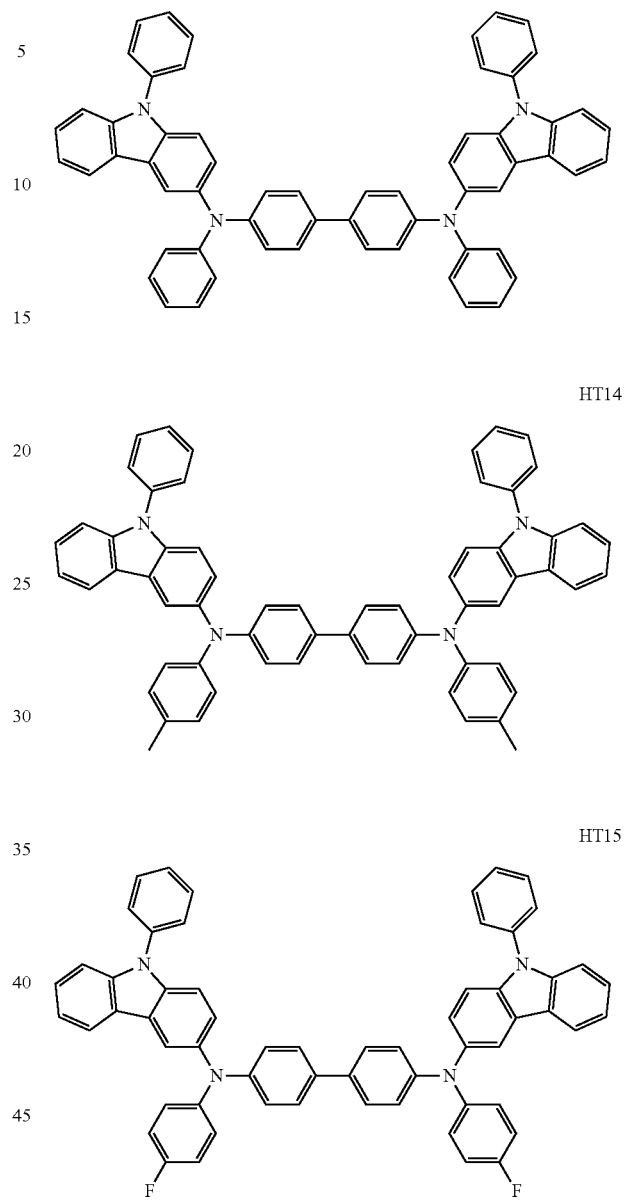
HT14
HT15
HT16
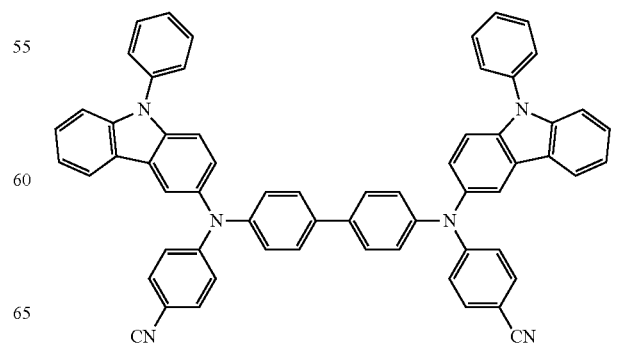

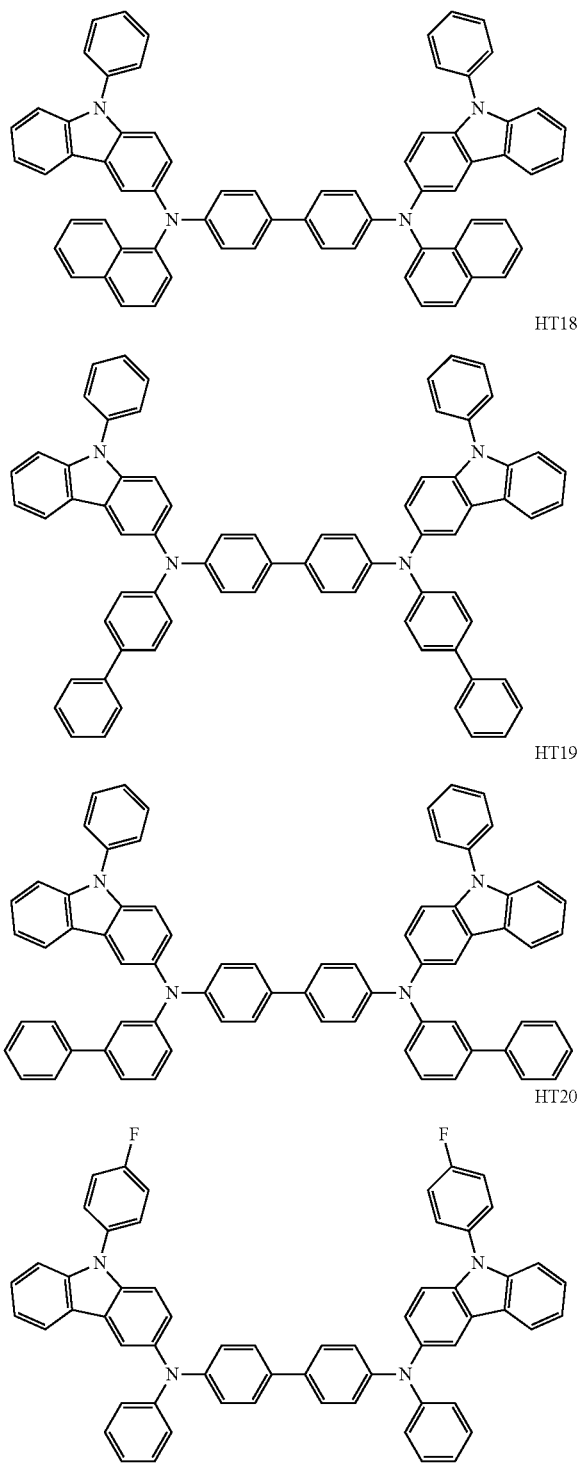

about 100 Å to about 1,500 Å. When the thicknesses of the hole transport region, the hole injection layer, and the hole transport layer are within these ranges, excellent hole transport characteristics may be obtained without a substantial increase in driving voltage.

The hole transport region may further include, in addition to the mentioned materials above, a charge-generating material to improve conductive properties. The charge-generating material may be homogeneously or non-homogeneously dispersed throughout the hole transport region.

The charge-generating material may be, for example, a p-dopant. The p-dopant may be one selected from a quinone derivative, a metal oxide, and a cyano group-containing compound, as examples. Examples of the p-dopant may include a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide, and Compound HT-D1 illustrated below.

<Compound HT-D1>

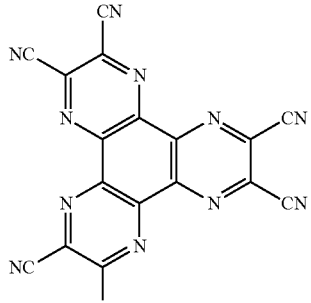

<F4-TCNQ>

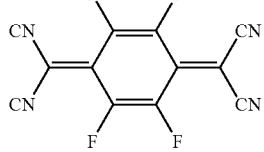

The hole transport region may further include, in addition to the hole injection layer and the hole transport layer, at least one selected from a buffer layer and an electron blocking layer. The buffer layer may compensate for an optical resonance distance according to a wavelength of light emitted from the emission layer. Accordingly, the light-emission efficiency of a formed organic light-emitting device may be improved. As a material included in the buffer layer, materials that are included in the hole transport region may be used. The electron blocking layer may prevent injection of electrons from the electron transport region.

An emission layer may be formed on the first electrode 110 or the hole transport region by a suitable method, such as vacuum-deposition, spin coating, casting, LB method, ink-jet printing, laser-printing, or LITI. When the emission layer is formed by vacuum-deposition or spin coating, deposition and coating conditions for the emission layer may be determined by referring to the deposition and coating conditions for the hole injection layer.

When the organic light-emitting device 10 is a full color organic light-emitting device, the emission layer may be patterned into a red emission layer, a green emission layer, or a blue emission layer, according to a sub pixel. In some implementations, the emission layer may have a stacked A thickness of the hole transport region may be in a range of about 100 Å to about 10,000 Å, or, for example, about 100 Å to about 1,000 Å. When the hole transport region includes a hole injection layer and a hole transport layer, the thickness of the hole injection layer may be in a range of about 100 Å to about 10,000 Å, or, for example, about 100 Å to about 1,000 Å, and the thickness of the hole transport layer may be in a range of about 50 Å to about 2,000 Å, or, for example, structure of a red emission layer, a green emission layer, and a blue emission layer, or may include a red-light emission material, a green-light emission material, and a blue-light emission material, which are mixed with each other in a single layer, to emit white light.

The emission layer may include a host and a dopant.

The host may include a compound represented by Formula 301:

$$Ar_{301}\text{-}[(L_{301})_{xb1}\text{-}R_{301}]_{xb2} \qquad \text{<Formula 301>}$$

wherein, in Formula 301, $Ar_{301}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$);

wherein $Q_{301}$ to $Q_{303}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group;

$L_{301}$ may be the same as defined in connection with $L_1$;

$R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3;

xb2 may be selected from 1, 2, 3, and 4;

In some embodiments, in Formula 301, $L_{301}$ may be selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium. —F, —Cl, —Br, —I, a hydroxyl group, a cyano group, a nitro group, an amino group, an amidino group, a hydrazine group, a hydrazone group, a carboxylic acid or a salt thereof a sulfonic acid or a salt thereof a phosphoric acid or a salt thereof, a $C_1$-$C_{20}$ alkyl group, a $C_1$-$C_{20}$ alkoxy group, a phenyl group, a naphthyl group, a fluorenyl group, a spirofluorenyl group, a benzofluorenyl group, a dibenzofluorenyl group, a phenanthrenyl group, an anthracenyl group, a pyrenyl group, and a chrysenyl group.

In some embodiment, the host may include a compound represented by Formula 301A:

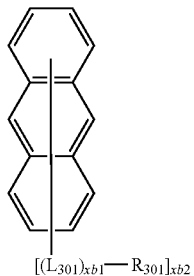

<Formula 301A>

The descriptions for Formula 301A may be understood by referring to the descriptions provided herein.

The compound represented by Formula 301 may include at least one compound selected from Compounds H1 to H42 below, as examples:

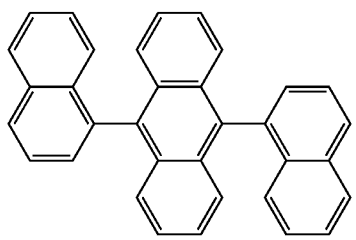
H1

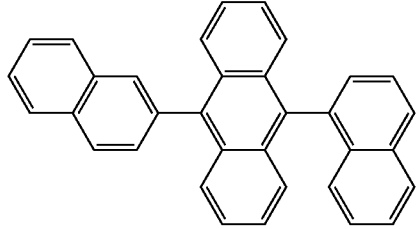
H2

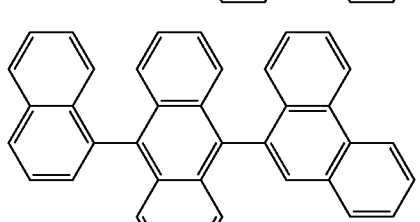
H3

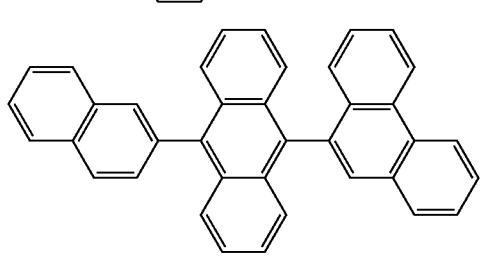
H4

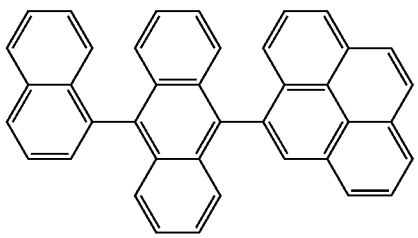
H5

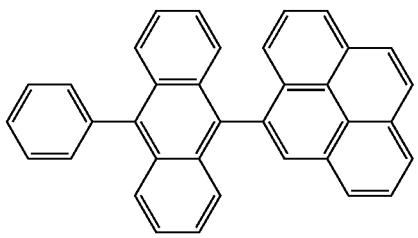
H6

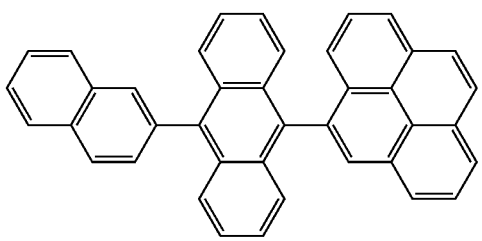
H7

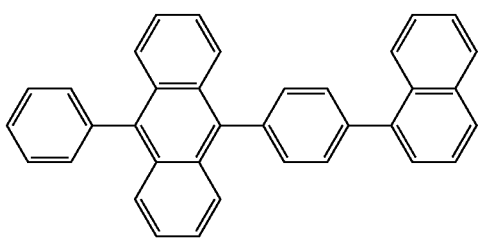
H8

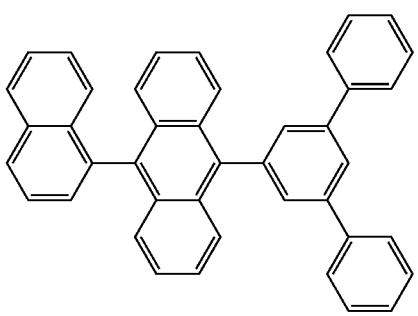
H9

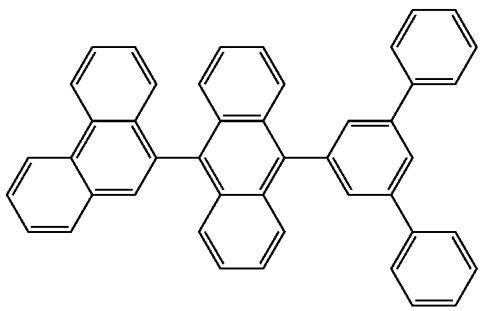
H10

H11
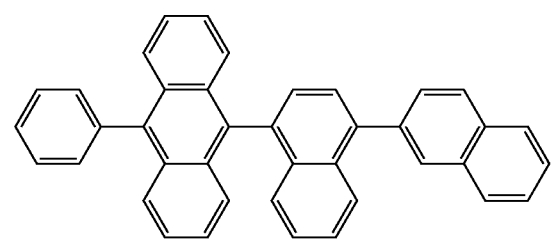
H12
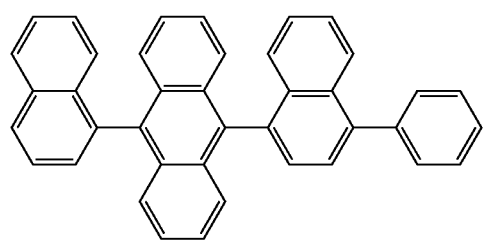
H13
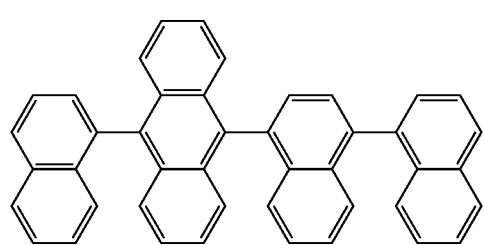
H14
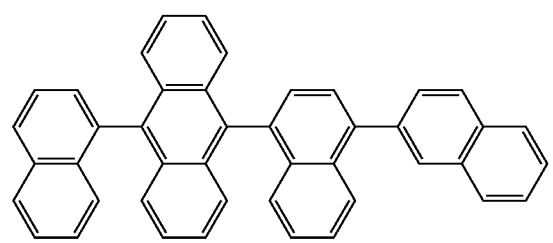
H15
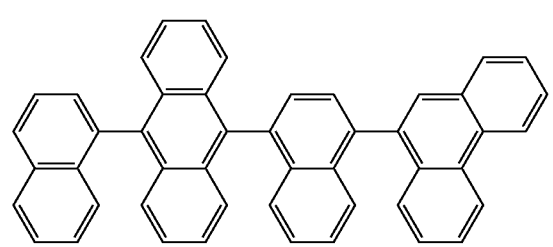
H16
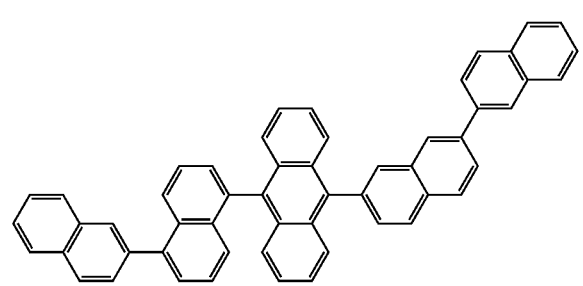
H17
H18
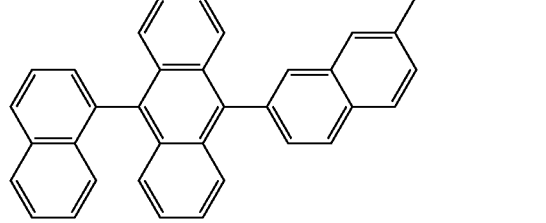
H19
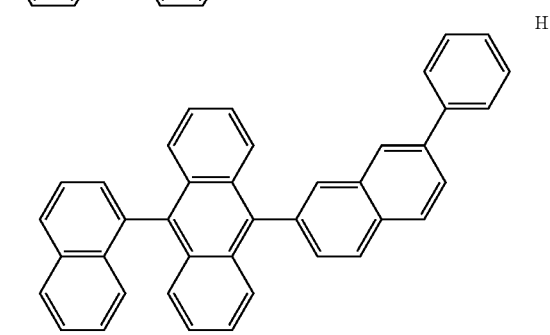
H20
H21
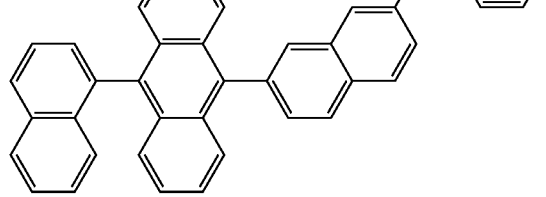

H22
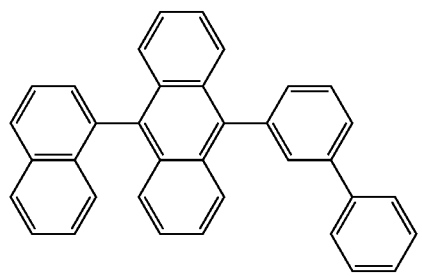
H23
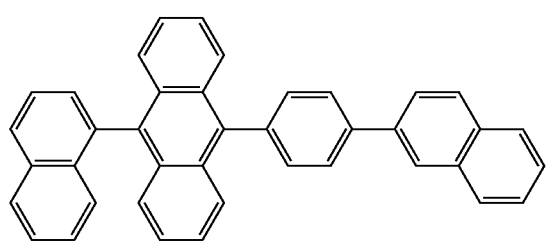
H24
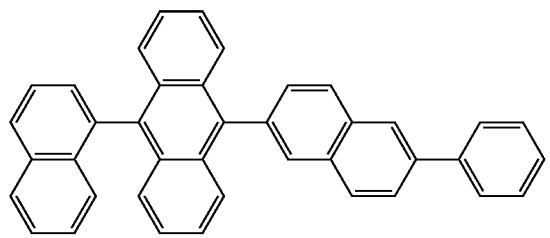
H25
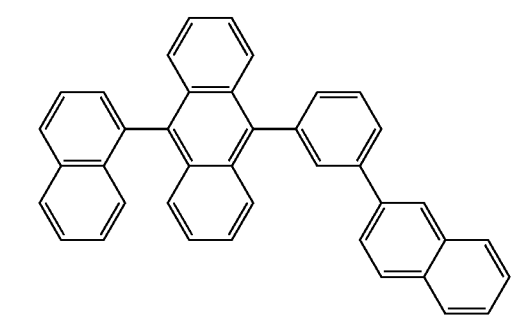
H26
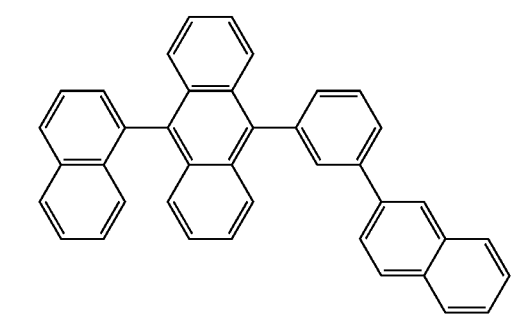
H27
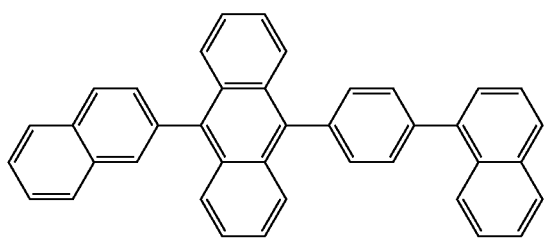
H28
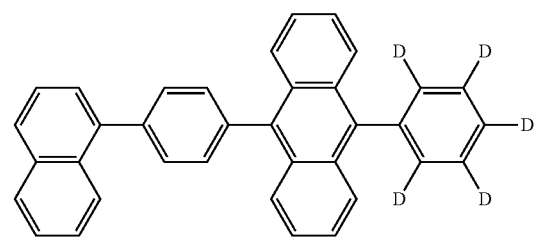
H29
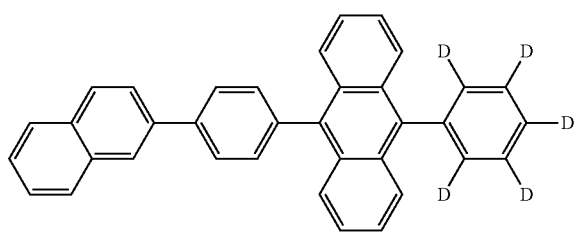
H30
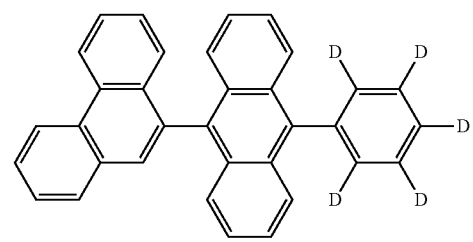
H31
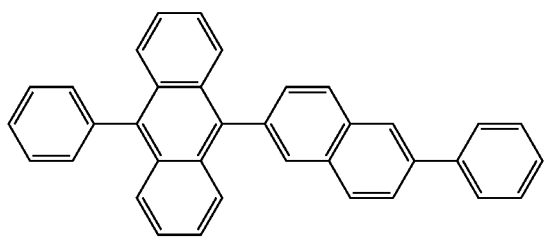
H32
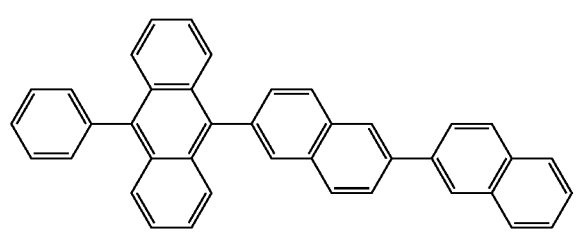

123
-continued
H33
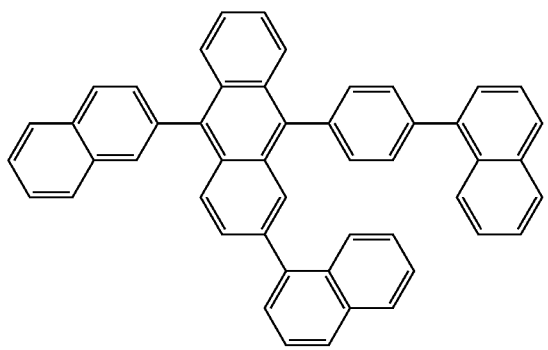
H34
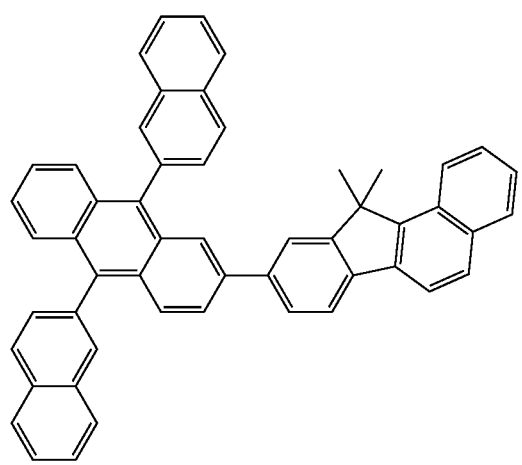
H35
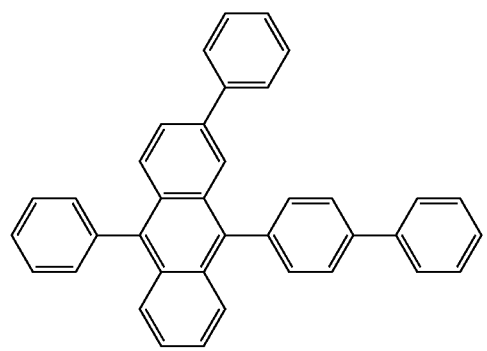
124
-continued
H36
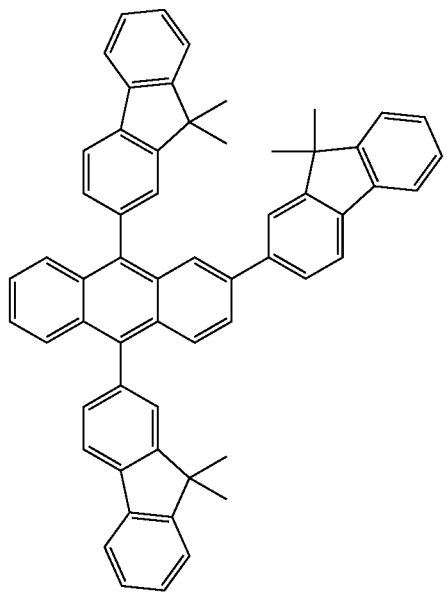
H37
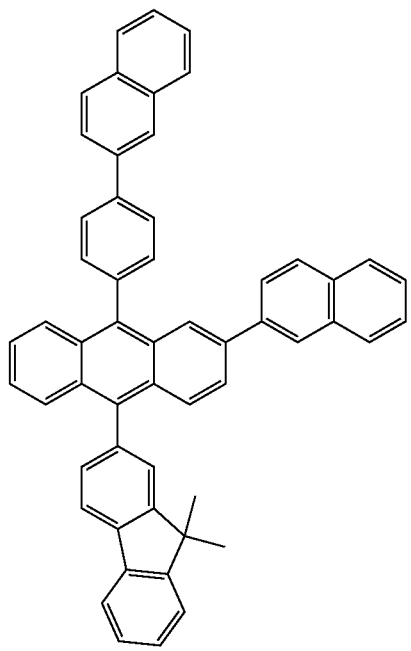
H38
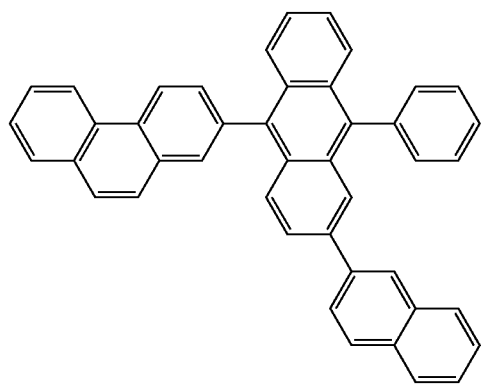

H39
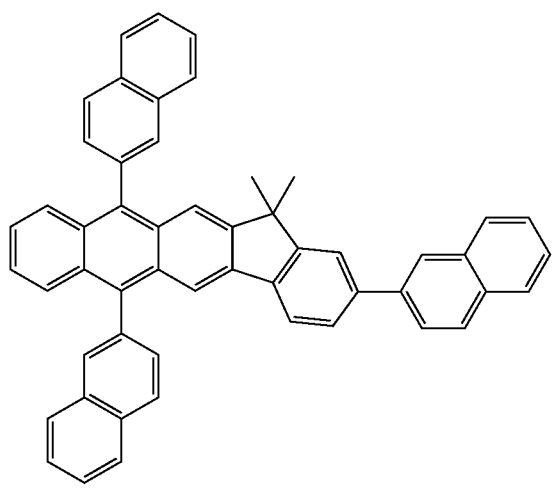
H42
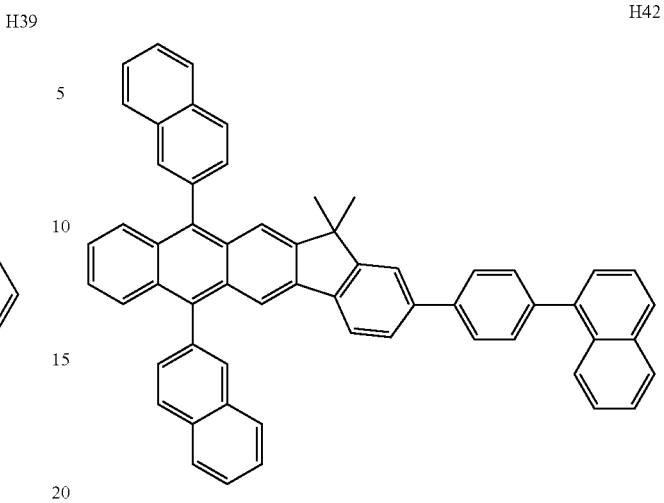
In some embodiments, the host may include at least one selected from Compounds H43 to H49 below:
H40
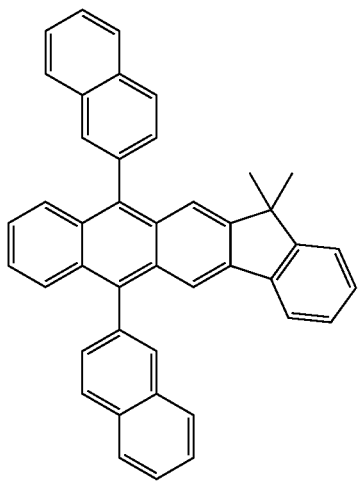
H43
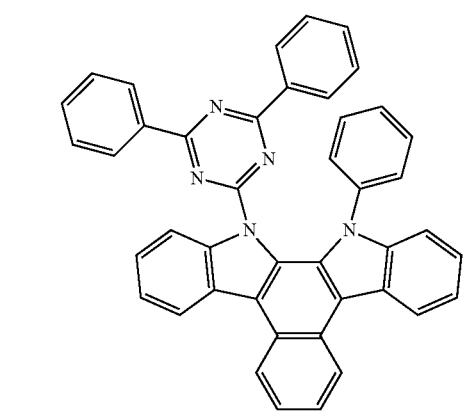
H41
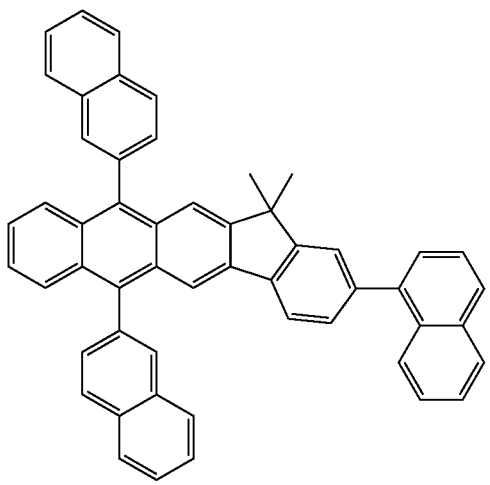
H44
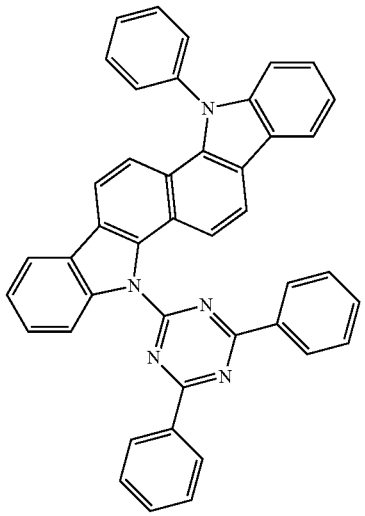

H45

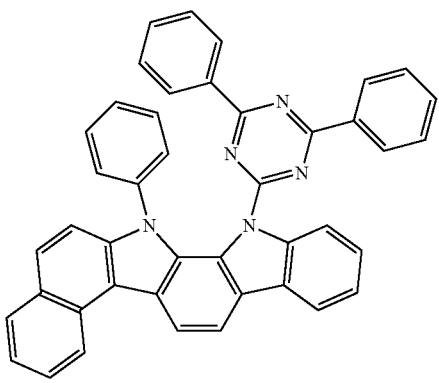

H46

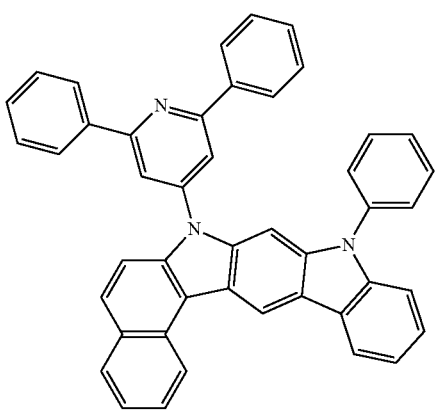

H47

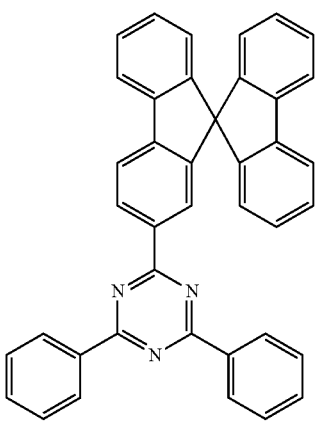

H48

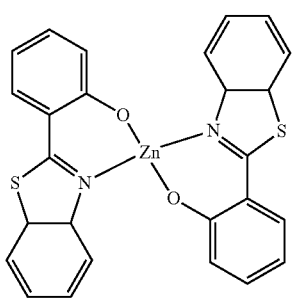

H49

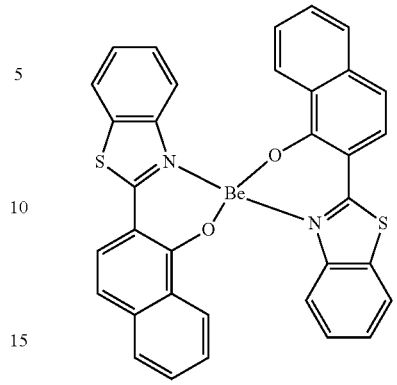

The dopant may include the condensed-cyclic compound represented by Formula 1.

In some embodiments, the dopant may include a compound represented by Formula 501:

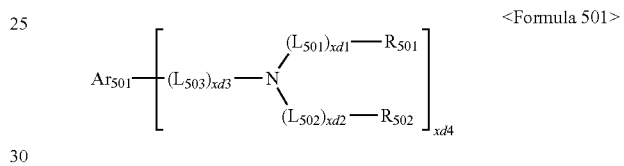

<Formula 501> wherein, in Formula 501, $Ar_{501}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) ($Q_{501}$ to $Q_{503}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

$L_{501}$ to $L_{503}$ may be the same as defined in connection with $L_1$ provided herein;

$R_{501}$ and $R_{502}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group;

xd1 to xd3 may be each independently selected from 0, 1, 2, and 3; and xb4 may be selected from 1, 2, 3, and 4.

An amount of the dopant in the emission layer may be, for example, in a range of about 0.01 part by weight to about 15 parts by weight based on 100 parts by weight of the host.

A thickness of the emission layer may be in a range of about 100 Å to about 1,000 Å, or, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer (ETL), and an electron injection layer.

For example, the electron transport region may have a structure of electron transport layer/electron injection layer or a structure of hole blocking layer/electron transport layer/electron injection layer, wherein layers of each structure are sequentially stacked from the emission layer in the stated order.

In some embodiments, the organic layer 150 of the organic light-emitting device may include an electron transport region disposed between the emission layer and the second electrode 190.

When the electron transport region includes a hole blocking layer, the hole blocking layer may be formed on the emission layer by a suitable method, such as vacuum-deposition, spin coating, casting, LB method, ink-jet printing, laser-printing, or LITI. When the hole blocking layer is formed by vacuum-deposition or spin coating, deposition and coating conditions for the hole blocking layer may be determined by referring to the deposition and coating conditions for the hole injection layer.

The hole blocking layer may include, for example, at least one selected from BCP and Bphen.

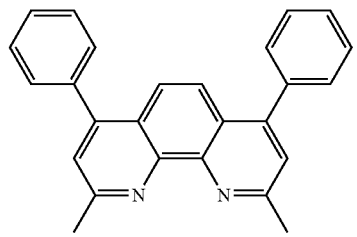

BCP

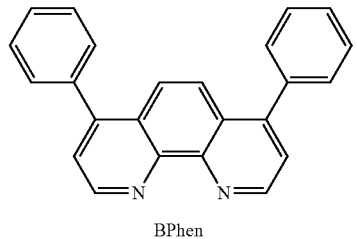

BPhen

A thickness of the hole blocking layer may be in a range of about 20 Å to about 1,000 Å, or, for example, about 30 Å to about 300 Å. When the thickness of the hole blocking layer is within this range, excellent hole blocking characteristics may be obtained without a substantial increase in driving voltage.

The electron transport region may include an electron transport layer. The electron transport layer may be formed on the emission layer or the hole blocking layer by using various methods, such as vacuum deposition, spin coating, casting, LB method, ink-jet printing, laser-printing, or LITI. When the electron transport layer is formed by using vacuum deposition or spin coating, vacuum deposition and coating conditions for the electron transport layer may be determined by referring to the vacuum deposition and coating conditions for the hole injection layer.

In some embodiments, the electron transport layer may include at least one selected from a compound represented by Formula 601 and a compound represented by Formula 602:

$$Ar_{601}\text{-}[(L_{601})_{xe1}\text{-}E_{601}]_{xe2} \qquad \text{<Formula 601>}$$

wherein, in Formula 601, $Ar_{601}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$);

wherein $Q_{301}$ to $Q_{303}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group;

$L_{601}$ may be the same as defined in connection with $L_{201}$;

$E_{601}$ may be selected from:

a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

xe1 may be selected from 0, 1, 2, and 3; and xe2 may be selected from 1, 2, 3, and 4.

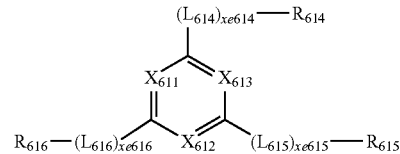

<Formula 602> wherein, in Formula 602, $X_{611}$ may be N or C-($L_{611}$)$_{xe611}$-$R_{611}$, $X_{612}$ may be N or C-($L_{612}$)$_{xe612}$-$R_{612}$, $X_{613}$ may be N or C-($L_{613}$)$_{xe613}$-$R_{613}$, and at least one selected from $X_{611}$ to $X_{613}$ may be N;

$L_{611}$ to $L_{616}$ may be each the same as defined in connection with $L_1$ provided herein;

$R_{611}$ to $R_{616}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xe611 to xe616 may be each independently selected from 0, 1, 2, and 3.

The compound represented by Formula 601 and the compound represented by Formula 602 may be each independently selected from Compounds ET1 to ET15:

ET1 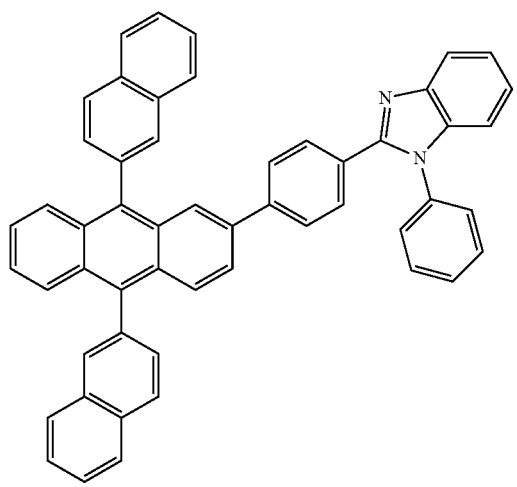
ET2 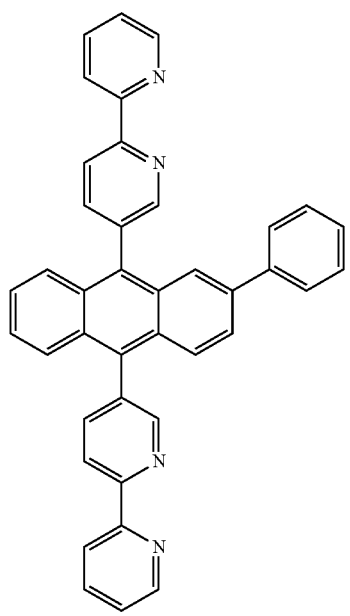
ET3 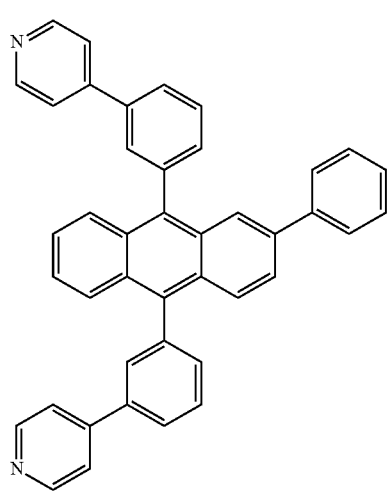
ET4 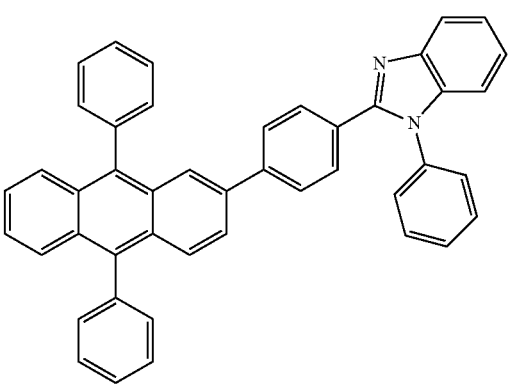
ET5 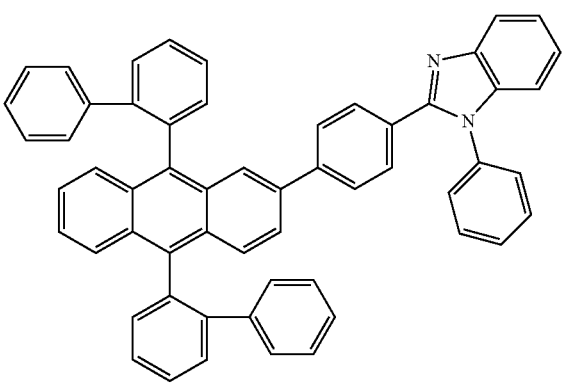
ET6 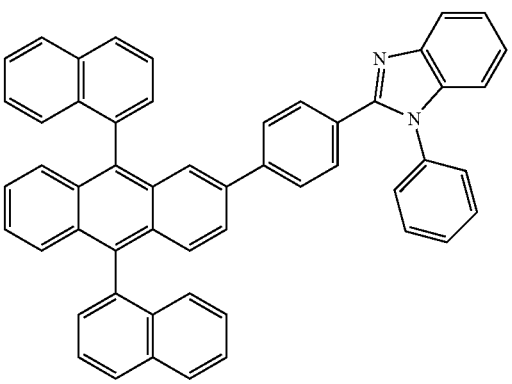

ET7
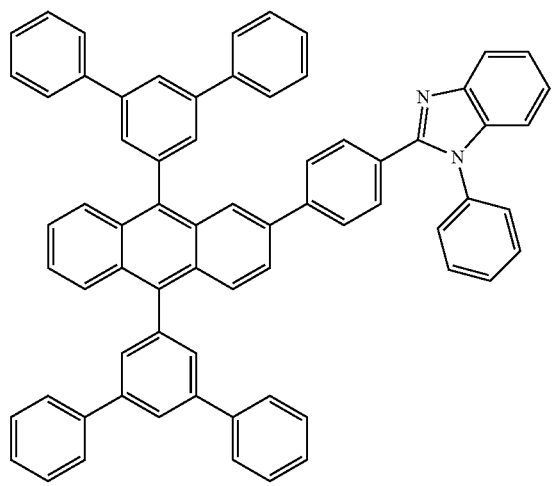
ET8
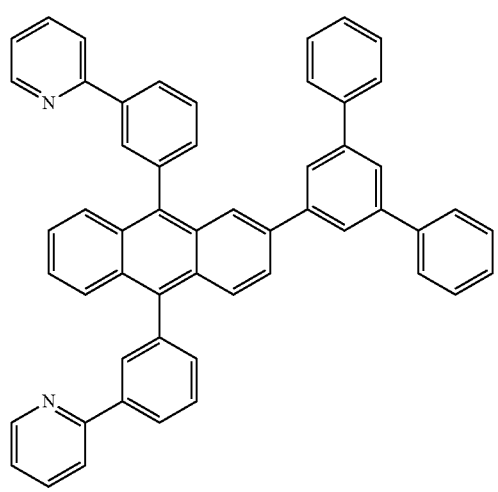
ET9
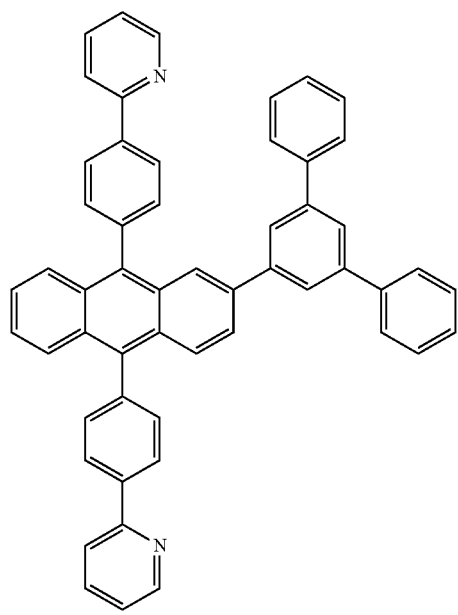
ET10
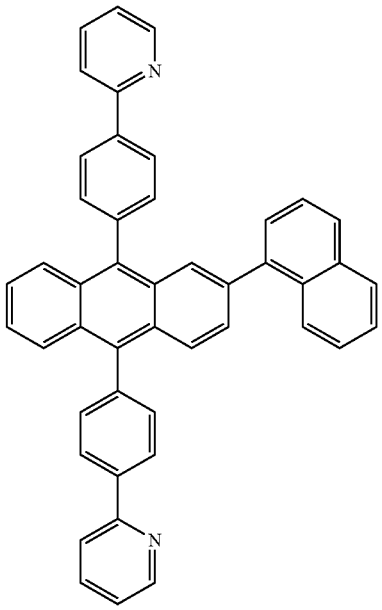
ET11
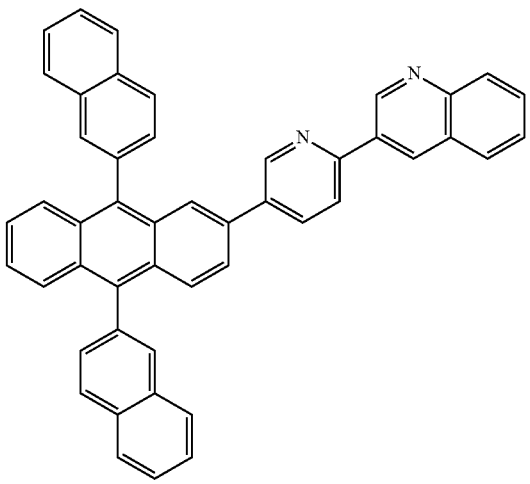
ET12
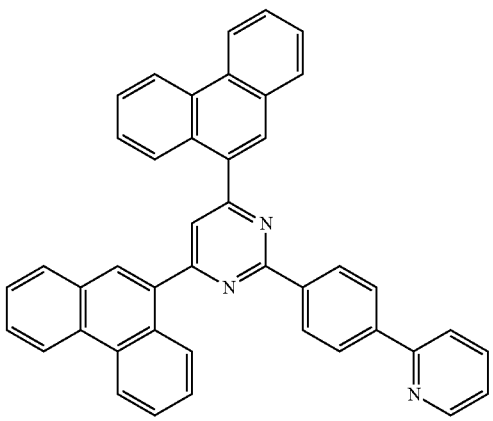

ET13

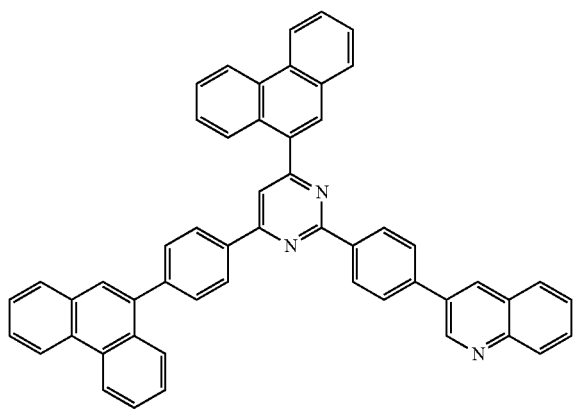

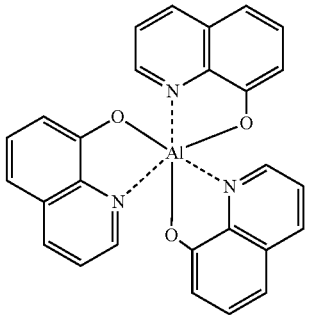

Alq₃

ET14

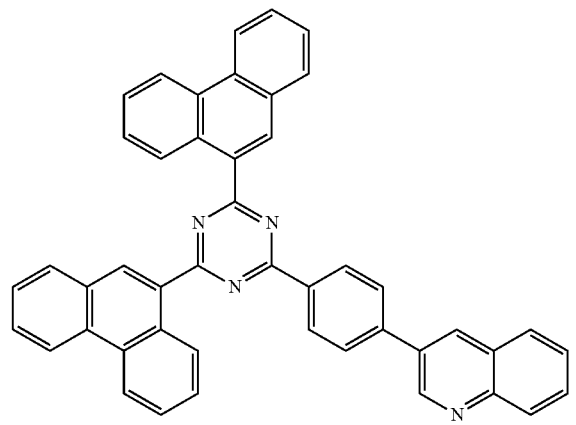

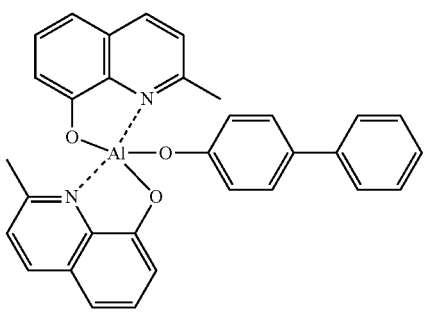

BAlq

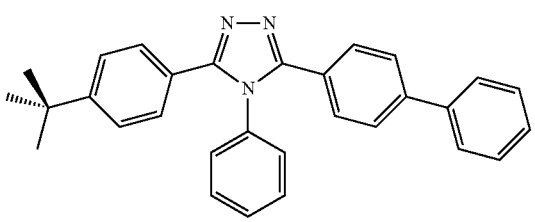

TAZ

ET15

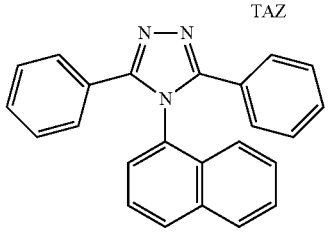

NTAZ

A thickness of the electron transport layer may be in a range of about 100 Å to about 1,000 Å, or, for example, about 150 Å to about 500 Å. When the thickness of the electron transport layer is within this range, excellent electron transport characteristics may be obtained without a substantial increase in driving voltage.

The electron transport layer may further include a metal-containing material in addition to the materials described above.

In some embodiments, the electron transport layer may include at least one selected from BCP, Bphen, Alq₃, BAlq, TAZ, and NTAZ.

The metal-containing material may include a Li complex. The Li complex may include, for example, Compound ET-D1 (lithium quinolate, LiQ) or ET-D2.

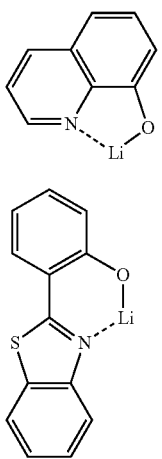

ET-D1

ET-D2

The electron transport region may include an electron injection layer that facilitates electron injection from the second electrode 190.

The electron injection layer may be formed on the electron transport layer by a suitable method, such as vacuum-deposition, spin coating, casting, LB method, ink-jet printing, laser-printing, or LITI. When the electron injection layer is formed by vacuum-deposition or spin coating, vacuum-deposition and coating conditions for the electron injection layer may be determined by referring to the vacuum-deposition and coating conditions for the hole injection layer.

The electron injection layer may include at least one selected from, LiF, NaCl, CsF, Li$_2$O, BaO, and LiQ.

A thickness of the electron injection layer may be in a range of about 1 Å to about 100 Å, or, for example, about 3 Å to about 90 Å. When the thickness of the electron injection layer is within this range, excellent electron injection characteristics may be obtained without a substantial increase in driving voltage.

The second electrode 190 is disposed on the organic layer 150. The second electrode 190 may be a cathode that is an electron injection electrode, and in this regard, a material for forming the second electrode 190 may be a material having a low work function, and such a material may be metal, alloy, an electrically conductive compound, or a mixture thereof. Examples of the second electrode 190 include lithium (Li), magnesium (Mg), aluminum (Al), aluminum-lithium (Al—Li), calcium (Ca), magnesium-indium (Mg—In), and magnesium-silver (Mg—Ag). In some embodiments, the material for forming the second electrode 190 may be ITO or IZO. The second electrode 190 may be a semi-transmissive electrode or a transmissive electrode.

Hereinbefore, the organic light-emitting device has been described with reference to FIG. 1, but the organic light-emitting device may have various structures.

The term "$C_1$-$C_{60}$ alkyl group" used herein refers to a linear or branched aliphatic hydrocarbon monovalent group having 1 to 60 carbon atoms. Examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" used herein refers to a divalent group having the same structure as a $C_1$-$C_{60}$ alkyl group.

The term "$C_1$-$C_{60}$ alkoxy group" used herein refers to a monovalent group represented by —OA$_{101}$ (wherein A$_{101}$ is the $C_1$-$C_{60}$ alkyl group). Examples thereof include a methoxy group, an ethoxy group and an isopropyloxy group.

The term "$C_2$-$C_{60}$ alkenyl group" used herein refers to a hydrocarbon group formed by substituting at least one carbon double bond in the middle or at the terminal of the $C_2$-$C_{60}$ alkyl group. Examples thereof include an ethenyl group, a propenyl group, and a butenyl group. The term "$C_2$-$C_{60}$ alkenylene group" used herein refers to a divalent group having the same structure as a $C_2$-$C_{60}$ alkenyl group.

The term "$C_2$-$C_{60}$ alkynyl group" used herein refers to a hydrocarbon group formed by substituting at least one carbon triple bond in the middle or at the terminal of the $C_2$-$C_{60}$ alkyl group. Examples thereof include an ethynyl group and a propynyl group. The term "$C_2$-$C_{60}$ alkynylene group" used herein refers to a divalent group having the same structure as a $C_2$-$C_{60}$ alkynyl group.

The term "$C_3$-$C_{10}$ cycloalkyl group" used herein refers to a monovalent monocyclic saturated hydrocarbon group including 3 to 10 carbon atoms. Examples thereof include a cyclopropyl group, a cyclobutyl group, a cyclopentyl group, a cyclohexyl group, and a cycloheptyl group. The term "$C_3$-$C_{10}$ cycloalkylene group" used herein refers to a divalent group having the same structure as a $C_3$-$C_{10}$ cycloalkyl group.

The term "$C_1$-$C_{10}$ heterocycloalkyl group" used herein refers to a monovalent monocyclic group including at least one hetero atom selected from N, O, Si, P, and S as a ring-forming atom and 1 to 10 carbon atoms. Examples thereof include a tetrahydrofuranyl group and a tetrahydrothiophenyl group. The term "$C_1$-$C_{10}$ heterocycloalkylene group" used herein refers to a divalent group having the same structure as a $C_1$-$C_{10}$ heterocycloalkyl group.

The term "$C_3$-$C_{10}$ cycloalkenyl group" used herein refers to a monovalent monocyclic group that has 3 to 10 carbon atoms and at least one double bond in its ring, and which is not aromatic. Examples thereof include a cyclopentenyl group, a cyclohexenyl group, and a cycloheptenyl group. The term "$C_3$-$C_{10}$ cycloalkenylene group" used herein refers to a divalent group having the same structure as a $C_3$-$C_{10}$ cycloalkenyl group.

The term "$C_1$-$C_{10}$ heterocycloalkenyl group" used herein refers to a monovalent monocyclic group including at least one hetero atom selected from N, O, Si, P, and S as a ring-forming atom, 1 to 10 carbon atoms, and at least one double bond in its ring. Examples of the $C_1$-$C_{10}$ heterocycloalkenyl group include a 2,3-hydrofuranyl group and a 2,3-hydrothiophenyl group. The term "$C_1$-$C_{10}$ heterocycloalkenylene group" used herein refers to a divalent group having the same structure as a $C_1$-$C_{10}$ heterocycloalkenyl group.

The term "$C_6$-$C_{60}$ aryl group" used herein refers to a monovalent group including a carbocyclic aromatic system having 6 to 60 carbon atoms. The term "$C_6$-$C_{60}$ arylene group" used herein refers to a divalent group including a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include a plurality of rings, the rings may be fused to each other.

The term "$C_1$-$C_{60}$ heteroaryl group" used herein refers to a monovalent group having a carbocyclic aromatic system including at least one hetero atom selected from N, O, Si, P, and S as a ring-forming atom and 1 to 60 carbon atoms. The term "$C_1$-$C_{60}$ heteroarylene group" used herein refers to a divalent group having a carbocyclic aromatic system including at least one hetero atom selected from N, O, P, and S as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include a plurality of rings, the rings may be fused to each other.

The term "$C_6$-$C_{60}$ aryloxy group" used herein indicates —$OA_{102}$ (wherein $A_{102}$ is the $C_6$-$C_{60}$ aryl group). The term "$C_6$-$C_{60}$ arylthio group" used herein indicates —$SA_{103}$ (wherein $A_{103}$ is the $C_6$-$C_{60}$ aryl group).

The term "monovalent non-aromatic condensed polycyclic group" used herein refers to a monovalent group that has two or more rings condensed to each other, only carbon atoms (for example, the number of carbon atoms may be in a range of 8 to 60) as ring forming atoms, wherein the molecular structure as a whole is non-aromatic in the entire molecular structure. An example of the monovalent non-aromatic condensed polycyclic group is a fluorenyl group. The term "divalent non-aromatic condensed polycyclic group" used herein refers to a divalent group having the same structure as the monovalent non-aromatic condensed polycyclic group.

The term "monovalent non-aromatic condensed heteropolycyclic group" used herein refers to a monovalent group that has a plurality of rings condensed to each other and a hetero atom selected from N, O, P, Si, and S, other than carbon atoms (for example, the number of carbon atoms may be in a range of 1 to 60), as a ring-forming atom, wherein the molecular structure as a whole is non-aromatic in the entire molecular structure. An example of a monovalent non-aromatic condensed heteropolycyclic group is a carbazolyl group. The term "divalent non-aromatic condensed heteropolycyclic group" used herein refers to a divalent group having the same structure as the monovalent non-aromatic condensed hetero-polycyclic group.

At least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_6$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, and —$N(Q_{14})(Q_{15})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, and —$N(Q_{24})(Q_{25})$; and —$Si(Q_{31})(Q_{32})(Q_{33})$ and —$N(Q_{34})(Q_{35})$;

wherein $Q_{11}$ to $Q_{15}$, $Q_{21}$ to $Q_{25}$, and $Q_{31}$ to $Q_{35}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

"Ph" used herein refers to a phenyl group, "Me" refers to a methyl group, "Et" refers to an ethyl group, and "ter-Bu" or "But" refers to a tert-butyl group.

Hereinafter, an organic light-emitting device according to an embodiment will be described in detail with reference to Synthesis Examples and Examples. The wording "B was used instead of A" used in describing Synthesis Examples means that a molar equivalent of A was identical to a molar equivalent of B.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLE

Synthesis Example

Synthesis Example 1: Synthesis of Compound 1

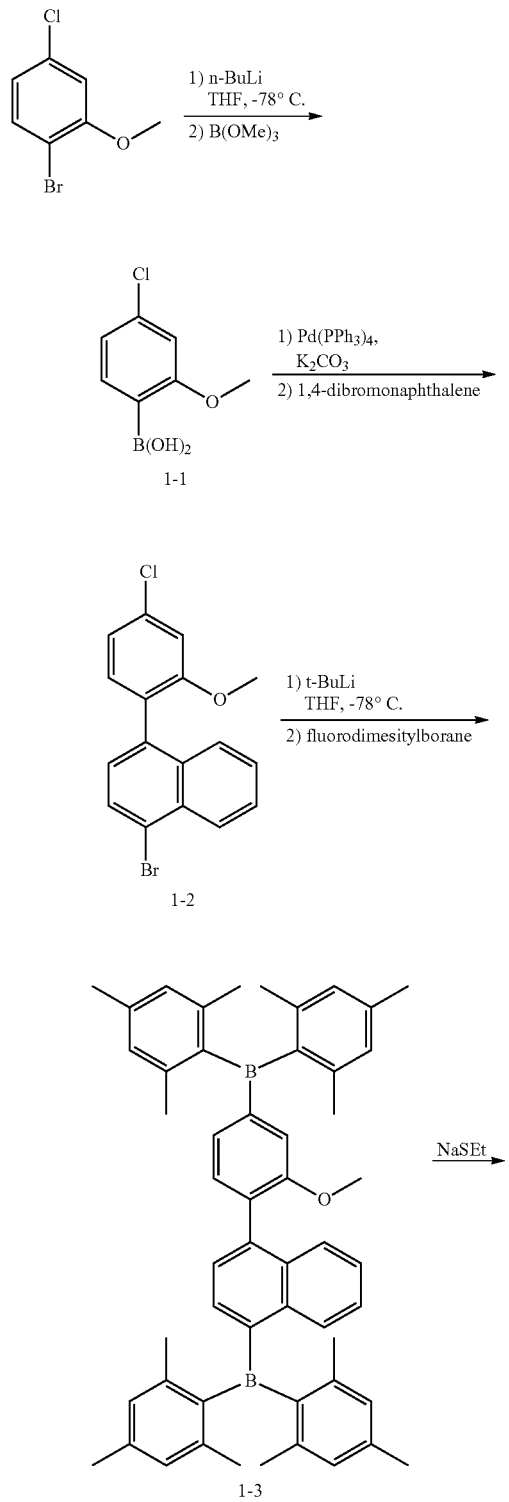

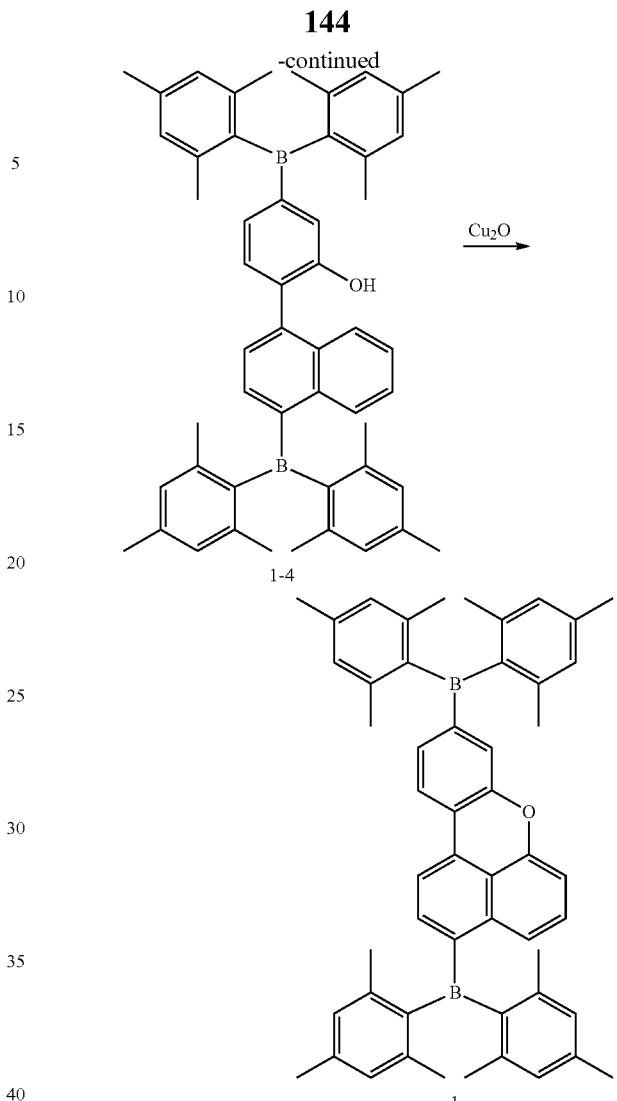

Synthesis of Intermediate 1-1

5.2 g (23.6 mmol) of 2-bromo-5-chloroanisole was dissolved in 100 mL of tetrahydrofuran (THF). 10 mL (25.0 mmol) of n-BuLi (2.5M in hexane) was slowly added dropwise thereto at −78° C. The result was stirred at the same temperature for 1 hour. Then, 9.3 mL (50.0 mmol) of trimethyl borate was slowly added dropwise thereto, and stirred for 24 hours at room temperature. Once the reaction was complete, 10% aqueous HCl solution was added thereto to adjust pH to about 5. Then, an organic layer was extracted three times therefrom by using diethylether. The obtained organic layer was dried by using magnesium sulfate (MgSO$_4$). Then, a solvent was removed therefrom by evaporation. The obtained residue was purified by recrystallization, thereby obtaining 3.15 g of Intermediate 1-1 (yield: 50%).

Synthesis of Intermediate 1-2

5.90 g (22.0 mmol) of Intermediate 1-1, 16.9 g (44.0 mmol) of 1,4-dibromonaphthalene, 1.27 g (1.1 mmol) of tetrakis(triphenylphosphine)palladium (Pd(PPh$_3$)$_4$), and 4.50 g (33 mmol) of K$_2$CO$_3$ were dissolved in 200 mL of a mixture solution of THF/H₂O (at a volume ratio of 2:1), and stirred at 70° C. for 5 hours. The resulting solution was allowed to cool to room temperature. Then, an organic layer was extracted three times therefrom by using each of 60 mL of water and 60 mL of ethylether. The obtained organic layer was dried by using MgSO₄. Then, a solvent was removed therefrom by evaporation. The obtained residue was separated and purified through a silica gel chromatography to thereby obtain 6.30 g of Intermediate 1-2 (yield: 64%).

Synthesis of Intermediate 1-3

8.92 g (20.0 mmol) of Intermediate 1-2 was dissolved in 100 mL of THF. 200 mL (50.0 mmol) of t-BuLi (2.5M in hexane) was slowly added dropwise thereto at −78° C. The result was stirred at the same temperature for 1 hour. Then, 9.3 mL (50.0 mmol) of fluorodimesitylborane was slowly added dropwise thereto, and stirred for 24 hours at room temperature. Once the reaction was complete, an organic layer was extracted three times therefrom by using water and diethylether. The obtained organic layer was dried by using MgSO₄. Then, a solvent was removed therefrom by evaporation. The obtained residue was purified through a column chromatography to thereby obtain 12.5 g of Intermediate 1-3 (yield: 75%).

Synthesis of Intermediate 1-4

1.62 g (2.00 mmol) of Intermediate 1-3 and 8.4 g (10 mmol) sodium ethanthiolate were dissolved in 10 mL of dimethylformamide (DMF), and stirred at 150° C. for 24 hours. Once the reaction was complete, the resulting solution was added to ice water. Then, the obtained solid was filtrated. An organic layer was extracted three times from the filtered resulting solution by using water and diethyl ether. The obtained organic layer was dried by using MgSO₄. Then, a solvent was removed therefrom by evaporation. The obtained residue was separated and purified through a silica gel chromatography to thereby obtain 1.20 g of Intermediate 1-4 (yield: 75%).

Synthesis of Compound 1

1.60 g (2.00 mmol) of Intermediate 1-4 was dissolved in 10 mL of DMF, and then, 0.48 g (6.0 mmol) of Cu₂O was added dropwise thereto at room temperature. The resulting solution was stirred for 48 hours at 140° C. Once the reaction was complete, an organic layer was filtrated by using a celite filter. An organic layer was extracted three times therefrom by using each of 10 mL of H₂O and 10 mL of ethyl acetate. The obtained organic layer was dried by using MgSO₄. Then, a solvent was removed therefrom by evaporation. The obtained residue was separated and purified through a silica gel chromatography to obtain 1.39 g of Compound 1.

Synthesis Example 2: Synthesis of Compound 5

Compound 5 was obtained in the same manner as in Synthesis of Compound 1, except that in synthesizing Intermediate 1-3, dicyclohexylfluoroborane was used instead of fluorodimesitylborane.

Synthesis Example 3: Synthesis of Compound 7

Compound 7 was obtained in the same manner as in Synthesis of Compound 1, except that in synthesizing Intermediate 1-3, di(bicyclo[2.2.1]heptan-2-yl)fluoroborane was used instead of fluorodimesitylborane.

Synthesis Example 4: Synthesis of Compound 8

Compound 8 was obtained in the same manner as in Synthesis of Compound 1, except that in synthesizing Intermediate 1-3, 1-(fluoro(pyrrolidin-1-yl)boryl)pyrrolidine was used instead of fluorodimesitylborane.

Synthesis Example 5: Synthesis of Compound 166

Compound 166 was obtained in the same manner as in Synthesis of Compound 1, except that in synthesizing Intermediate 1-2, 3,9-dibromo-10-methylphenanthrene was used instead of 1,4-dibromonaphthalene, and in synthesizing Intermediate 1-3, (4-fluorophenyl)dimesitylborane was used instead of fluorodimesitylborane.

Synthesis Example 6: Synthesis of Compound 191

Compound 191 was obtained in the same manner as in Synthesis of Compound 1, except that in synthesizing Intermediate 1-1, 1-bromo-2-methoxybenzene was used instead of 2-bromo-5-chloroanisole, in synthesizing Intermediate 1-2, 6,12-dibromochrysene was used instead of 1,4-dibromonaphthalene was used instead of 2-bromo-chloroanisole, in synthesizing Intermediate 1-2, 6,12-dibromochrysene was used instead of 1,4-dibromonaphthalene, and in synthesizing Intermediate 1-3, (4-fluorophenyl)dimesitylborane was used instead of fluorodimesitylborane.

Synthesis Example 7: Synthesis of Compound 2

Compound 2 was obtained in the same manner as in Synthesis of Compound 1, except that in synthesizing Intermediate 1-3, fluorobis(perfluorophenyl)borane was used instead of fluorodimesitylborane.

Synthesis Example 8: Synthesis of Compound 9

Compound 9 was obtained in the same manner as in Synthesis of Compound 1, except that in synthesizing Intermediate 1-3, 2-(fluoro(phenyl)boryl)pyridine was used instead of fluorodimesitylborane.

Synthesis Example 9: Synthesis of Compound 26

Compound 26 was obtained in the same manner as in Synthesis of Compound 1, except that in synthesizing Intermediate 1-1, (2-bromo-5-chlorophenyl)(methyl)sulfane was used instead of 2-bromo-5-chloroanisole, and in synthesizing Intermediate 1-2, 1-bromo-4-(4-bromophenyl)naphthalene was used instead of 1,4-dibromonaphthalene.

Synthesis Example 10: Synthesis of Compound 29

Compound 29 was obtained in the same manner as in Synthesis of Compound 1, except that in synthesizing Intermediate 1-1, (2-bromo-5-chlorophenyl)trimethylsilane was used instead of 2-bromo-5-chloroanisole, and in synthesizing Intermediate 1-3, (4-tert-butyl-2,3,5,6-tetrafluorophenyl)fluoro(perfluorophenyl)borane was used instead of fluorodimesitylborane.

Synthesis Example 11: Synthesis of Compound 30

Compound 30 was obtained in the same manner as in Synthesis of Compound 1, except that in synthesizing Intermediate 1-1, (2-bromo-5-chlorophenyl)trimethylsilane was used instead of 2-bromo-5-chloroanisole, and in synthesizing Intermediate 1-3, bis(4-tert-butylphenyl)fluoroborane was used instead of fluorodimesitylborane.

Synthesis Example 12: Synthesis of Compound 38

Compound 38 was obtained in the same manner as in Synthesis of Compound 1, except that in synthesizing Intermediate 1-1, (2-bromo-5-chlorophenyl)trimethylsilane was used instead of 2-bromo-5-chloroanisole, and in synthesizing Intermediate 1-3, bis(4-tert-butylphenyl)(4-fluorophenyl)borane was used instead of fluorodimesitylborane.

Synthesis Example 13: Synthesis of Compound 54

Compound 54 was obtained in the same manner as in Synthesis of Compound 1, except that in synthesizing Intermediate 1-2, 6,12-dibromochrysene was used instead of 1,4-dibromonaphthalene, and in synthesizing Intermediate 1-3, fluorobis(perfluorophenyl)borane was used instead of fluorodimesitylborane.

Synthesis Example 14: Synthesis of Compound 88

Compound 88 was obtained in the same manner as in Synthesis of Compound 1, except that in synthesizing Intermediate 1-1, (2-bromo-5-chlorophenyl)trimethylsilane was used instead of 2-bromo-5-chloroanisole, in synthesizing Intermediate 1-2, 6,12-dibromochrysene was used instead of 1,4-dibromonaphthalene, and in synthesizing Intermediate 1-3, (4-fluorophenyl)dimesitylborane was used instead of fluorodimesitylborane.

The $^1$H nuclear magnetic resonance (NMR) results, mass spectroscopy/fast atom bombardment (MS/FAB) results, and yields of the prepared compounds are shown in Table 1.

TABLE 1

| Compound | $^1$H NMR (CDCl$_3$, 400 MHz) | MS/FAB found | MS/FAB calc. | Yield (%) |
|---|---|---|---|---|
| 1 | δ = 7.73 (d, 1H), 7.18 (d, 1H), 8.09 (d, 1H), 8.02 (d, 1H), 7.81-7.77 (m, 1H), 7.63-7.48 (m, 5H), 7.12-7.02 (m, 9H), 6.76-6.74 (m, 1H), 6.66-6.61 (m, 4H), 6.50 (dd, 1H), 6.30-6.25 (m, 4H), 6.15-6.10 (m, 4H) | 714.63 | 714.61 | 72 |
| 2 | δ = 8.72 (d, 1H), 8.22 (d, 1H), 8.06-8.03 (m, 2H), 7.98 (d, 1H), 7.88-7.82 (m, 2H), 7.70-7.54 (m, 4H), 7.48-7.40 (m, 4H), 7.32-7.19 (m, 4H), 7.05-6.94 (m, 6H), 6.63-6.61 (m, 2H), 6.24-6.22 (m, 2H), 6.06-6.04 (m, 2H), 2.77 (s, 3H), 2.56 (s, 3H) | 905.99 | 906.09 | 66 |
| 5 | δ = 8.72 (d, 1H), 8.22 (d, 1H), 8.04-8.05 (m, 2H), 7.98 (d, 1H), 7.88-7.86 (m, 2H), 7.76 (d, 1H), 7.56-7.54 (m, 3H), 7.48-7.32 (m, 5H), 7.23-7.17 (m, 4H), 7.04-7.02 (m, 4H), 6.66-6.62 (m, 4H), 6.07-6.02 (m, 4H), 2.77 (s, 3H), 2.56 (s, 3H) | 570.99 | 570.42 | 49 |
| 7 | δ = 7.95 (d, 1H), 7.73-7.69 (m, 2H), 7.63-7.48 (m, 5H), 7.12-7.02 (m, 9H), 6.76-6.74 (m, 1H), 6.66-6.61 (m, 4H), 6.50 (dd, 1H), 6.30-6.25 (m, 4H), 6.15-6.10 (m, 4H), 1.40-2.19 (m, 40H) | 652.26 | 652.25 | 63 |
| 8 | δ = 8.72 (d, 1H), 8.22 (d, 1H), 8.04 (d, 1H), 7.97-7.80 (m, 3H), 7.67-7.63 (m, 4H), 7.56 (d, 1H), 7.49-7.46 (m, 3H), 7.39-7.41 (m, 2H), 7.32-7.30 (m, 2H), 7.05-6.94 (m, 8H), 6.63-6.61 (m, 2H), 2.77 (s, 3H), 2.56 (s, 3H) | 519.12 | 518.34 | 57 |
| 9 | δ = 8.66 (d, 1H), 8.42 (d, 1H), 8.96-8.94 (m, 2H), 7.83-7.81 (m, 2H), 7.70-7.54 (m, 7H), 7.49-7.46 (m, 2H), 7.42-7.37 (m, 3H), 7.07-7.01 (m, 4H), 6.99-6.82 (m, 6H), 6.64-6.60 (m, 2H), 6.29-6.22 (m, 4H) | 548.35 | 548.22 | 67 |
| 26 | δ = 8.56 (d, 1H), 8.36 (d, 1H), 8.08-8.01 (m, 3H), 7.96 (t, 1H), 7.59-7.49 (m, 6H), 7.33-7.32 (m, 2H), 7.26-7.21 (m, 6H), 7.03-7.00 (m, 4H), 6.62-6.59 (m, 4H), 6.09-6.07 (m, 4H), 4.38 (q, 1H), 4.14 (q, 1H), 1.44 (d, 6H), 1.37 (d, 6H), 0.36-0.30 (m, 12H) | 806.43 | 807.12 | 70 |

TABLE 1-continued

| Compound | $^1$H NMR (CDCl$_3$, 400 MHz) | MS/FAB found | MS/FAB calc. | Yield (%) |
|---|---|---|---|---|
| 29 | δ = 8.66 (d, 1H), 8.48 (d, 1H), 8.36 (t, 1H), 8.10 (t, 1H), 8.00 (d, 1H), 7.66-7.62 (m, 2H), 7.56-7.54 (m, 2H), 7.33 (t, 1H), 7.07-7.03 (m, 4H), 6.64-6.62 (m, 2H), 6.19-6.15 (m, 4H), 2.84 (s, 3H) | 1024.27 | 1024.22 | 65 |
| 30 | δ = 8.27 (d, 1H), 8.02 (d, 1H), 7.61-7.57 (m, 4H), 7.12-7.02 (m, 9H), 6.76-6.74 (m, 1H), 6.70-6.65 (m, 4H), 6.50 (dd, 1H), 6.30-6.25 (m, 4H), 6.15-6.10 (m, 4H) | 812.77 | 812.87 | 84 |
| 38 | δ = 8.57 (d, 1H), 8.37 (d, 1H), 8.19 (d, 1H), 7.99 (t, 1H), 7.68-7.50 (m, 11H), 7.41-7.38 (m, 1H), 7.34 (t, 1H), 7.31 (d, 1H), 7.09-7.04 (m, 7H), 7.63-7.60 (m, 3H), 6.13-6.11 (m, 4H), 6.06-6.04 (m, 2H), 0.47 (s, 9H), 0.41 (s, 9H) | 965.77 | 965.57 | 70 |
| 54 | δ = 7.18 (d, 1H), 8.09 (d, 1H), 8.02 (d, 1H), 7.81-7.77 (m, 1H), 7.63-7.48 (m, 5H), 7.12-7.02 (m, 9H), 6.76-6.74 (m, 1H), 6.66-6.61 (m, 4H), 6.50 (dd, 1H), 6.30-6.25 (m, 4H), 6.15-6.10 (m, 4H) | 652.26 | 652.25 | 67 |
| 88 | δ = 8.23-8.21 (m, 1H), 8.09 (d, 1H), 8.02 (d, 1H), 7.81-7.77 (m, 1H), 7.63-7.48 (m, 5H), 7.12-7.02 (m, 9H), 6.76-6.74 (m, 1H), 6.66-6.61 (m, 4H), 6.50 (dd, 1H), 6.30-6.25 (m, 4H), 6.15-6.10 (m, 4H) | 652.26 | 652.25 | 44 |
| 166 | δ = 8.66 (d, 1H), 8.36 (d, 1H), 8.28 (d, 1H), 7.74-7.49 (m, 14H), 7.40-7.34 (m, 4H), 7.70-7.01 (m, 7H), 6.64-6.58 (m, 3H), 6.18-6.08 (m, 6H) | 931.11 | 930.51 | 82 |
| 191 | δ = 8.23-8.21 (m, 1H), 8.09 (d, 1H), 8.02 (d, 1H), 7.81-7.77 (m, 1H), 7.63-7.48 (m, 5H), 7.12-7.02 (m, 9H), 6.76-6.74 (m, 1H), 6.66-6.61 (m, 4H), 6.50 (dd, 1H), 6.30-6.25 (m, 4H), 6.15-6.10 (m, 4H) | 652.26 | 652.25 | 73 |

Example 1

A 15 Ohms per square centimeter (Ω/cm$^2$) (1,200 Å (Angstroms)) ITO glass substrate (available from Corning Co., Ltd) was cut to a size of 50 millimeters (mm)×50 mm×0.7 mm, sonicated in isopropyl alcohol and pure water for 5 minutes in each solvent, cleaned with ultraviolet rays for 30 minutes, and then ozone, and was mounted on a vacuum deposition apparatus.

2-TNATA was vacuum-deposited on the ITO anode of the glass substrate to form a hole injection layer having a thickness of about 600 Å. Then, Compound 1 was vacuum-deposited on the hole injection layer to form a hole transport layer having a thickness of about 300 Å, thereby forming a hole transport region.

9,10-di-naphthalene-2-yl-anthracene (ADN), which is a host, and N,N,N',N'-tetraphenyl-pyrene-1,6-diamine (TPD), which is a dopant, were co-deposited on the hole transport region at a weight ratio of about 98:2, thereby forming an emission layer having a thickness of about 300 Å.

Alq$_3$ was vacuum-deposited on the emission layer to form an electron transport layer having a thickness of about 300 Å. Then, LiF was vacuum-deposited on the electron transport layer to form an electron injection layer having a thickness of about 10 Å, thereby forming an electron transport region.

Aluminum was vacuum-deposited on the electron transport region to form a cathode having a thickness of about 3,000 Å, thereby completing the manufacture of an organic light-emitting device.

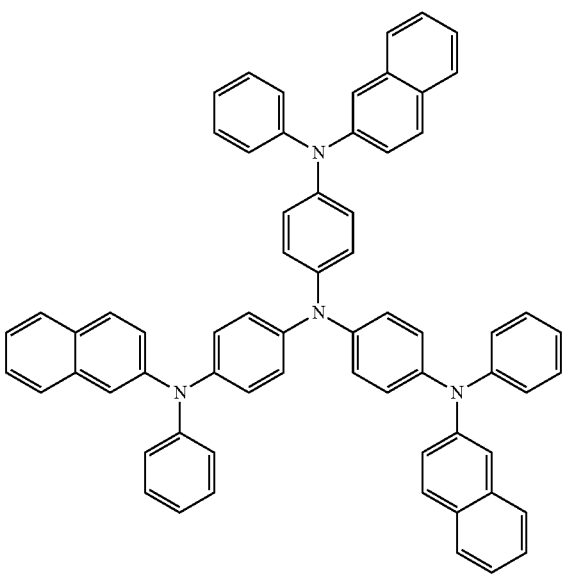

2-TNATA

-continued

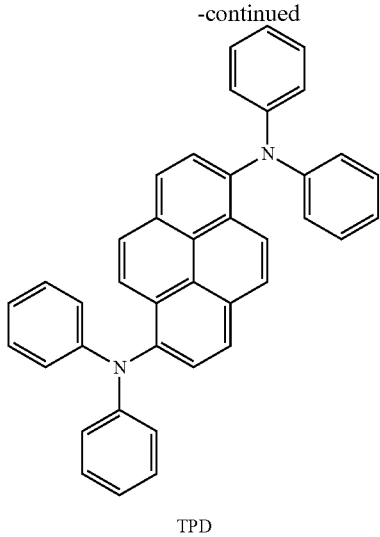

TPD

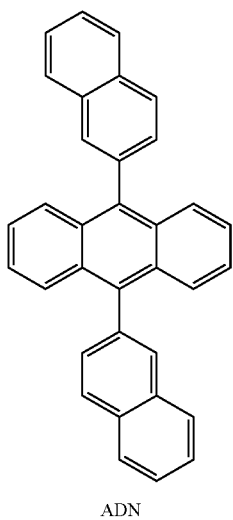

ADN

Example 2

An organic light-emitting device was manufactured in the same manner as in Example 1, except that in forming a hole transport layer, Compound 5 was used instead of Compound 1.

Example 3

An organic light-emitting device was manufactured in the same manner as in Example 1, except that in forming a hole transport layer. Compound 7 was used instead of Compound 1.

Example 4

An organic light-emitting device was manufactured in the same manner as in Example 1, except that in forming a hole transport layer, Compound 8 was used instead of Compound 1.

Example 5

An organic light-emitting device was manufactured in the same manner as in Example 1, except that in forming a hole transport layer, Compound 166 was used instead of Compound 1.

Example 6

An organic light-emitting device was manufactured in the same manner as in Example 1, except that in forming a hole transport layer, Compound 191 was used instead of Compound 1.

Comparative Example 1

An organic light-emitting device was manufactured in the same manner as in Example 1, except that in forming a hole transport layer, NPB was used instead of Compound 1.

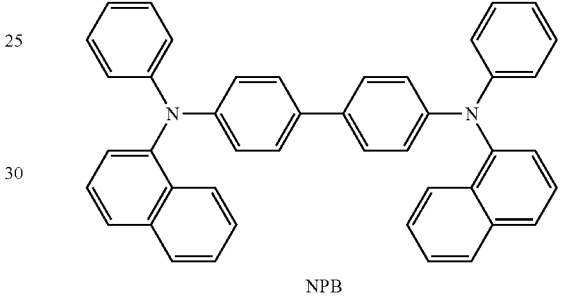

NPB

Comparative Example 2

An organic light-emitting device was manufactured in the same manner as in Example 1, except that in forming a hole transport layer, Compound A was used instead of Compound 1.

<Compound A>

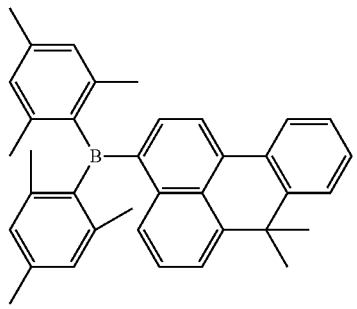

Comparative Example 3

An organic light-emitting device was manufactured in the same manner as in Example 1, except that in forming a hole transport layer, Compound B was used instead of Compound 1.

<Compound B>

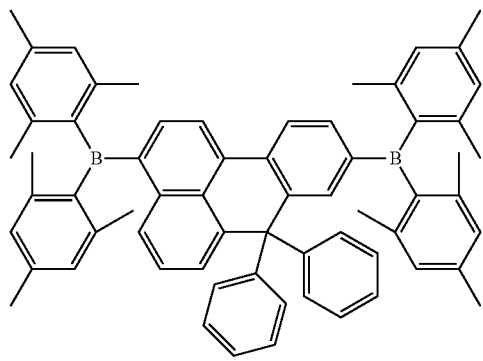

Evaluation Example 1

The driving voltage, current density, luminance, efficiency, and half-lifespan of the organic light-emitting devices manufactured according to Examples 1 to 6 and Comparative Examples 1 to 3 were measured by using Keithley 236 Source Measure (SMU) and a PR650 luminance meter. The results thereof are shown in Table 2. The half-lifespan indicates a period of time required for the luminance of the organic light-emitting device to reach 50% with respect to an initial luminance.

TABLE 2

|  | Hole transport layer | Driving voltage (V) | Current Density (mA/cm$^2$) | luminance (cd/m$^2$) | Efficiency (cd/A) | Emission color | Half lifespan (hr @100 mA/cm$^2$) |
|---|---|---|---|---|---|---|---|
| Example 1 | Compound 1 | 5.79 | 50 | 3206 | 6.64 | blue | 364 |
| Example 2 | Compound 5 | 5.64 | 50 | 3309 | 6.69 | blue | 349 |
| Example 3 | Compound 7 | 5.76 | 50 | 3216 | 6.49 | blue | 280 |
| Example 4 | Compound 8 | 5.79 | 50 | 3290 | 6.49 | blue | 340 |
| Example 5 | Compound 166 | 5.67 | 50 | 3254 | 6.60 | blue | 370 |
| Example 6 | Compound 191 | 5.66 | 50 | 3206 | 6.50 | blue | 371 |
| Comparative Example 1 | NPB | 7.01 | 50 | 2645 | 5.29 | blue | 258 |
| Comparative Example 2 | Compound A | 6.21 | 50 | 3097 | 6.27 | blue | 334 |
| Comparative Example 3 | Compound B | 6.04 | 50 | 3208 | 6.55 | blue | 295 |

Referring to Table 2, it was found that the organic light-emitting devices manufactured according to Examples 1 to 6 exhibited improved driving voltage, improved luminance, improved efficiency, and improved half-lifespan, compared to those of the organic light-emitting devices manufactured according to Comparative Examples 1 to 3.

Example 7

An organic light-emitting device was manufactured in the same manner as in Example 1, except that in forming a hole transport layer, NPB was used instead of Compound 1, and Compound 2 was used as a dopant instead of TPD.

Example 8

An organic light-emitting device was manufactured in the same manner as in Example 7, except that in forming an emission layer, Compound 9 was used as a dopant instead of Compound 2.

Example 9

An organic light-emitting device was manufactured in the same manner as in Example 7, except that in forming an emission layer, Compound 26 was used as a dopant instead of Compound 2.

Example 10

An organic light-emitting device was manufactured in the same manner as in Example 7, except that in forming an emission layer, Compound 29 was used as a dopant instead of Compound 2.

Example 11

An organic light-emitting device was manufactured in the same manner as in Example 7, except that in forming an emission layer, Compound 30 was used as a dopant instead of Compound 2.

Example 12

An organic light-emitting device was manufactured in the same manner as in Example 7, except that in forming an emission layer, Compound 38 was used as a dopant instead of Compound 2.

Example 13

An organic light-emitting device was manufactured in the same manner as in Example 7, except that in forming an emission layer, Compound 54 was used as a dopant instead of Compound 2.

Example 14

An organic light-emitting device was manufactured in the same manner as in Example 7, except that in forming an emission layer, Compound 88 was used as a dopant instead of Compound 2.

Example 15

An organic light-emitting device was manufactured in the same manner as in Example 1, except that in forming a hole transport layer, Compound 191 was used instead of Compound 1, and Compound 2 was used as a dopant instead of TPD.

Example 16

An organic light-emitting device was manufactured in the same manner as in Example 15, except that in forming an emission layer, Compound 38 was used as a dopant instead of Compound 2.

Comparative Example 4

An organic light-emitting device was manufactured in the same manner as in Example 7, except that in forming an emission layer, Compound C was used as a dopant instead of Compound 2.

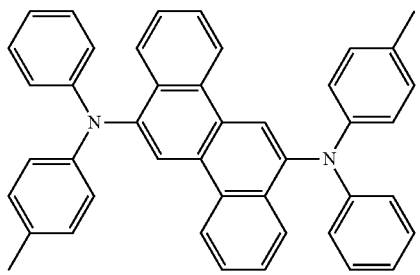

<Compound C>

Comparative Example 5

An organic light-emitting device was manufactured in the same manner as in Example 7, except that in forming an emission layer, Compound B was used as a dopant instead of Compound 2.

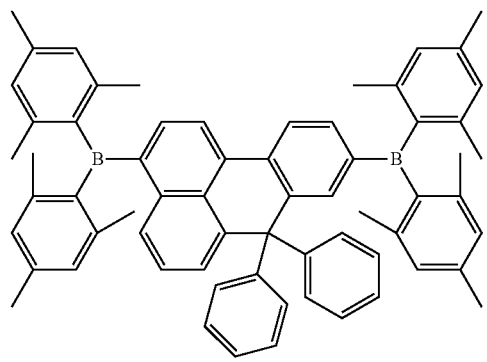

<Compound B>

Evaluation Example 2

The driving voltage, current density, luminance, efficiency, and half-lifespan of the organic light-emitting devices manufactured according to Examples 7 to 16 and Comparative Examples 4 and 5 were measured by using Keithley 236 Source-Measure Unit (SMU) and a PR650 luminance meter. Results thereof are shown in Table 3. The half-lifespan indicates a period of time required for the luminance of the organic light-emitting device to reach 50% with respect to an initial luminance.

TABLE 3

| | Hole transport layer | Dopant | Driving voltage (V) | Current Density (mA/cm$^2$) | luminance (cd/m$^2$) | Efficiency (cd/A) | Emission color | Half lifespan (hr @100 mA/cm$^2$) |
|---|---|---|---|---|---|---|---|---|
| Example 7 | NPB | Compound 2 | 6.87 | 50 | 3455 | 7.13 | blue | 336 |
| Example 8 | NPB | Compound 9 | 6.83 | 50 | 3460 | 6.92 | blue | 349 |
| Example 9 | NPB | Compound 26 | 6.86 | 50 | 3525 | 7.09 | blue | 348 |
| Example 10 | NPB | Compound 29 | 6.81 | 50 | 3545 | 7.01 | blue | 329 |
| Example 11 | NPB | Compound 30 | 6.89 | 50 | 3560 | 6.72 | blue | 333 |
| Example 12 | NPB | Compound 38 | 6.81 | 50 | 3565 | 7.14 | blue | 318 |
| Example 13 | NPB | Compound 54 | 6.86 | 50 | 3505 | 6.93 | blue | 356 |
| Example 14 | NPB | Compound 88 | 6.84 | 50 | 3570 | 7.15 | blue | 342 |
| Example 15 | Compound 191 | Compound 2 | 5.56 | 50 | 3690 | 7.38 | blue | 397 |
| Example 16 | Compound 191 | Compound 38 | 5.56 | 50 | 3755 | 7.51 | blue | 328 |
| Comparative Example 4 | NPB | Compound C | 6.95 | 50 | 2420 | 4.84 | blue | 250 |
| Comparative Example 5 | NPB | Compound B | 6.88 | 50 | 2366 | 5.16 | blue | 294 |

Referring to Table 3, it was found that the organic light-emitting devices manufactured according to Examples 7 to 16 exhibited improved driving voltage, improved luminance, improved efficiency, and improved half-lifespan, compared to those of the organic light-emitting devices manufactured according to Comparative Examples 4 and 5.

As described above, according to one or more of the exemplary embodiments, the organic light-emitting device including the condensed-cyclic compound may have a low driving voltage, high efficiency, high luminance, and a long lifespan.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A condensed-cyclic compound represented by one of Formula 1, 1B, and 1C:

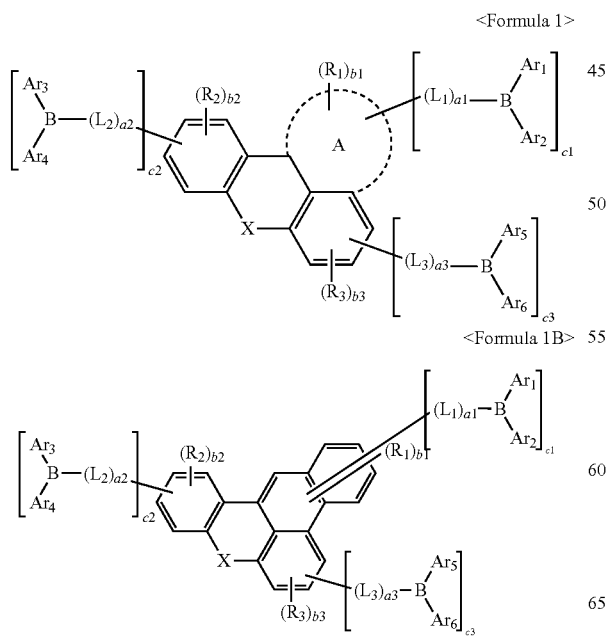

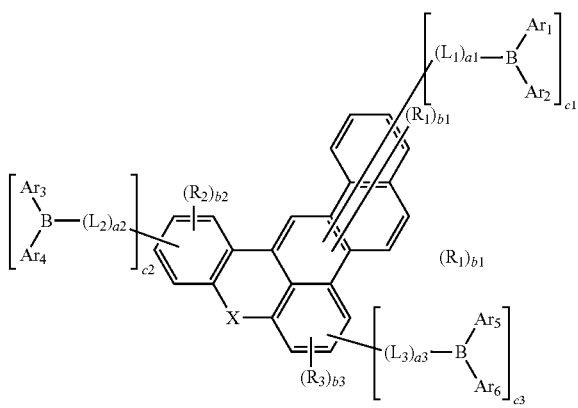

wherein, in Formula 1, X is selected from O, S, and $N(R_{11})$;

when X is O, A is selected from a naphthalene, an anthracene, a phenanthrene, a chrysene, and a pyrene, and ii) when X is S or $N(R_{11})$, A is selected from a benzene, a naphthalene, an anthracene, a phenanthrene, a chrysene, and a pyrene;

in Formulae 1B and 1C,

X is selected from O, S, $N(R_{11})$, $Si(R_{12})(R_{13})$ and $C(R_{15})(R_{16})$;

in Formula 1, 1B, and 1C $L_1$ to $L_3$ are each independently selected from:

a phenylene group, and a phenylene group substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group a1 to a3 are each independently selected from 0 and 1;

$Ar_1$ to $Ar_6$ are each independently selected from a group represented by one of Formulae 6-1 to 6-28:

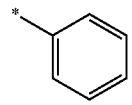

Formula 6-1

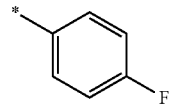

Formula 6-2

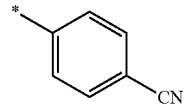

Formula 6-3

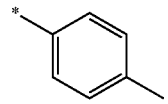

Formula 6-4

-continued
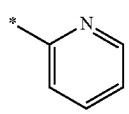
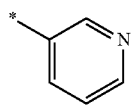
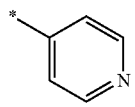
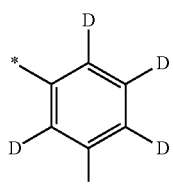
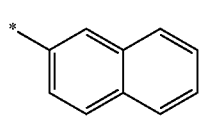
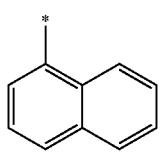
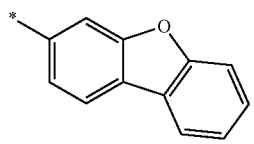
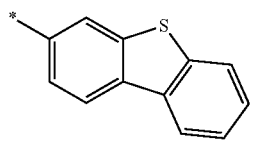
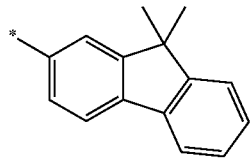
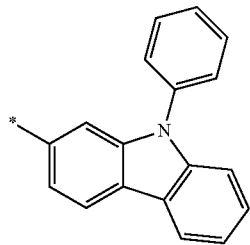
-continued
Formula 6-5
Formula 6-6
Formula 6-7
Formula 6-8
Formula 6-9
Formula 6-10
Formula 6-11
Formula 6-12
Formula 6-13
Formula 6-14
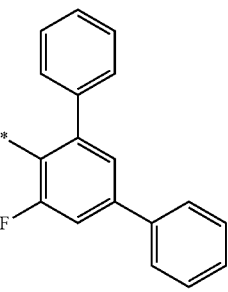
Formula 6-15
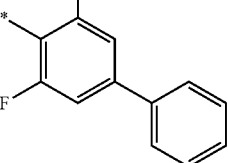
Formula 6-16
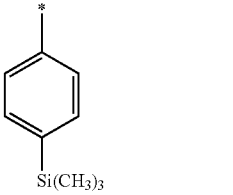
Formula 6-17
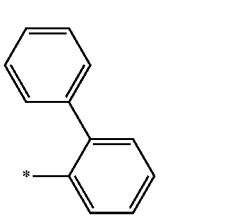
Formula 6-18
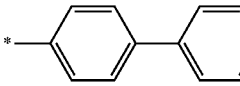
Formula 6-19
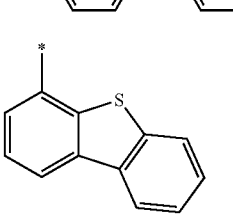
Formula 6-20
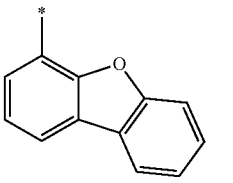
Formula 6-21
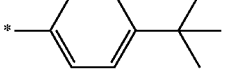
Formula 6-22
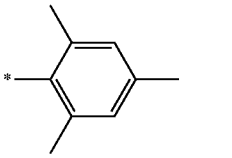
Formula 6-23
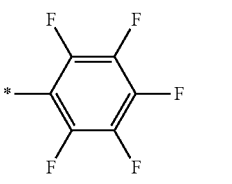

-continued

Formula 6-24

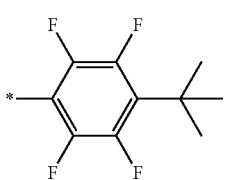

Formula 6-25

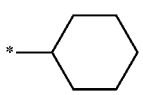

Formula 6-26

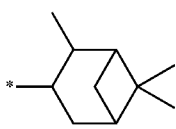

Formula 6-27

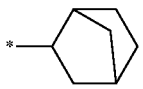

Formula 6-28

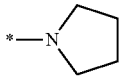

wherein, in Formulae 6-1 to 6-28, * indicates a binding site to an adjacent atom;
c1 to c3 are each independently selected from 0 and 1, provided that a sum of c1, c2, and c3 is 1 or more;
$R_1$ to $R_3$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a methyl group and a phenyl group
b1 to b3 are each independently an integer selected from 0 to 3;
$R_{11}$, $R_{12}$, $R_{13}$, $R_{15}$, and $R_{16}$ are each independently selected from a methyl group and a phenyl group;
and
B is a boron atom.

2. The condensed-cyclic compound as claimed in claim 1, wherein
$L_1$ to $L_3$ are each independently selected from a group represented by one of Formulae 3-1 to 3-3:

Formula 3-1

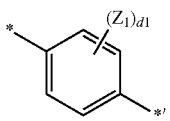

Formula 3-2

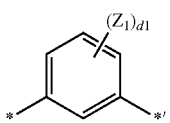

Formula 3-3

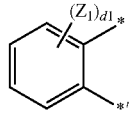

wherein, in Formulae 3-1 to 3-3,
$Z_1$ is selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, and a phenyl group
d1 is an integer selected from 1 to 4;
and
* and *' each indicate a binding site to an adjacent atom.

3. The condensed-cyclic compound as claimed in claim 1, wherein
$L_1$ to $L_3$ are each independently selected from a group represented by one of Formulae 4-1, 4-3, 4-8, 4-10, 4-17, 4-24, 4-26, and 4-28:

Formula 4-1

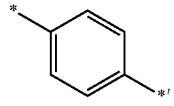

Formula 4-3

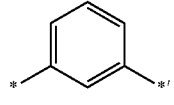

Formula 4-8

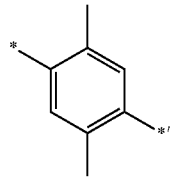

Formula 4-10

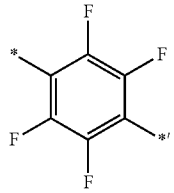

Formula 4-17

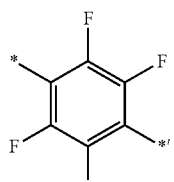

Formula 4-24

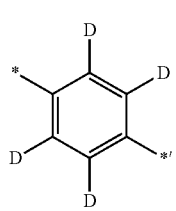

163

-continued

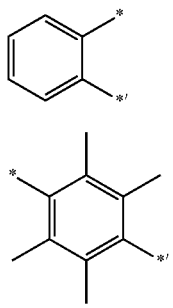

Formula 4-26

Formula 4-28 wherein, in Formulae 4-1, 4-3, 4-8, 4-10, 4-17, 4-24, 4-26, and 4-28, * and *' each indicate a binding site to an adjacent atom.

4. The condensed-cyclic compound as claimed in claim 1, wherein a sum of c1, c2, and c3 is selected from 1 and 2.

5. The condensed-cyclic compound as claimed in claim 1, wherein the condensed-cyclic compound is represented by one of Formulae 1A to 1C:

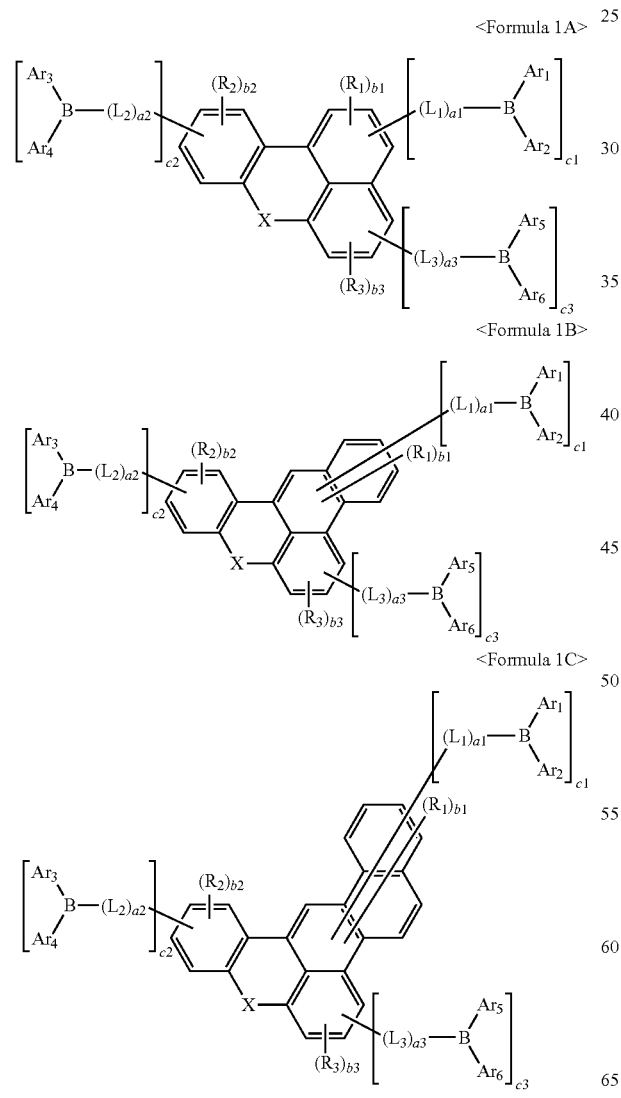

<Formula 1A>

<Formula 1B>

<Formula 1C>

164 wherein, in Formulae 1A, X is selected from S and $N(R_{11})$, in Formulae 1B and 1C, X is selected from O, S, $N(R_{11})$, $Si(R_{12})(R_{13})$, and $C(R_{15})(R_{16})$, and $L_1$ to $L_3$, a1 to a3, $Ar_1$ to $Ar_6$, c1 to c3, $R_1$ to $R_3$, b1 to b3 and $R_{11}$, $R_{12}$, $R_{13}$, $R_{15}$, and $R_{16}$ are the same as defined in claim 1.

6. The condensed-cyclic compound as claimed in claim 1, wherein the condensed-cyclic compound is represented by one of Formulae 1-1 to 1-3 and Formulae 2-1 to 2-3:

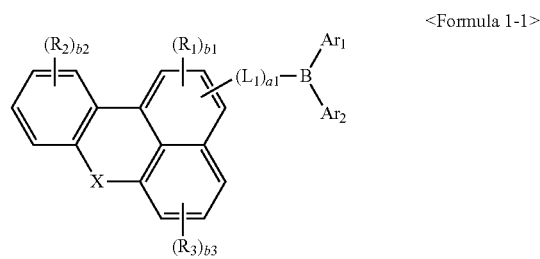

<Formula 1-1>

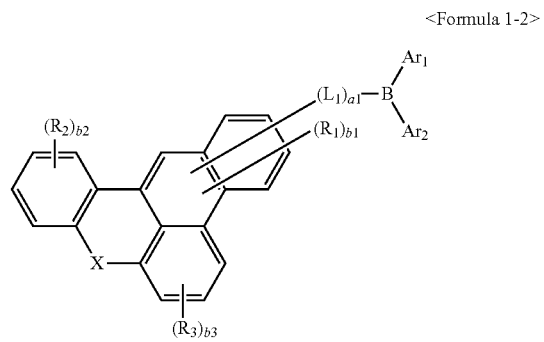

<Formula 1-2>

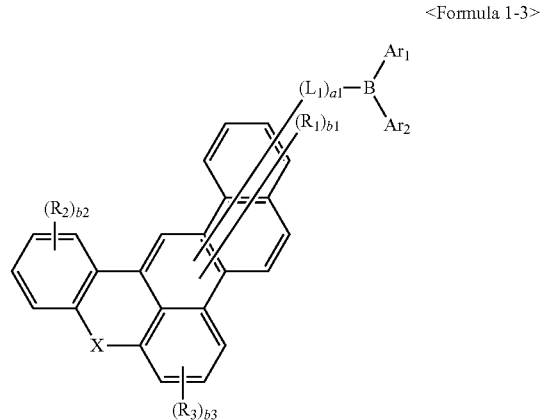

<Formula 1-3>

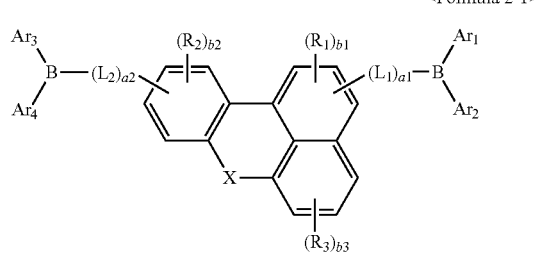

<Formula 2-1>

165
-continued

<Formula 2-2>

[chemical structure with substituents Ar₁, Ar₂, Ar₃, Ar₄, (L₁)ₐ₁, (L₂)ₐ₂, (R₁)b1, (R₂)b2, (R₃)b3, B, X]

<Formula 2-3>

[chemical structure with substituents Ar₁, Ar₂, Ar₃, Ar₄, (L₁)ₐ₁, (L₂)ₐ₂, (R₁)b1, (R₂)b2, (R₃)b3, B, X]

wherein, in Formulae 1-1 and 2-1, X is selected from S and N($R_{11}$), in Formulae 1-2, 1-3, 2-2 and 2-3, X is selected from O, S, N($R_{11}$), Si($R_{12}$)($R_{13}$), and C($R_{15}$)($R_{16}$), and in Formulae 1-1 to 1-3 and Formulae 2-1 to 2-3, $L_1$, $L_2$, a1, a2, $Ar_1$ to $Ar_4$, $R_1$ to $R_3$, b1 to b3, $R_{11}$, $R_{12}$, $R_{13}$, $R_{15}$, and $R_{16}$ are the same as defined in claim 1.

7. The condensed-cyclic compound as claimed in claim 1, wherein the condensed-cyclic compound is represented by one selected from Formulae 1-1(1) to 1-3(1) and Formulae 2-1(1) to 2-3(1):

<Formula 1-1(1)>

[chemical structure]

166
-continued

<Formula 1-2(1)>

[chemical structure]

<Formula 1-3(1)>

[chemical structure]

<Formula 2-1(1)>

[chemical structure]

<Formula 2-2(1)>

[chemical structure]

<Formula 2-3(1)>

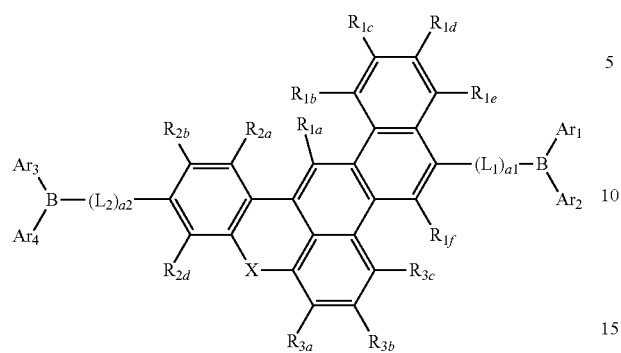

wherein,
in Formulae 1-1(1) and 2-1(1), X is selected from S and N($R_{11}$),
in Formulae 1-2(1), 1-3(1), 2-2(1) and 2-3(1), X is selected from O, S, N($R_{11}$), Si($R_{12}$)($R_{13}$), and C($R_{15}$)($R_{16}$),
in Formulae 1-1(1) to 1-3(1) and Formulae 2-1(1) to 2-3(1), $L_1$, $L_2$, a1, a2, $Ar_1$ to $Ar_4$ and $R_{11}$, $R_{12}$, $R_{13}$, $R_{15}$, and $R_{16}$ are the same as defined in claim 1, and $R_{1a}$ to $R_{1f}$, $R_{2a}$ to $R_{2c}$, and $R_{3a}$ to $R_{3c}$ are the same as defined in connection with $R_1$ as described in claim 1.

8. The condensed-cyclic compound as claimed in claim 7, wherein
$Ar_1$ to $Ar_4$ are each independently selected from Formulae 6-1 to 6-28, and
$R_{1a}$ to $R_{1f}$, $R_{2a}$ to $R_{2c}$, and $R_{3a}$ to $R_{3c}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a methyl group, and a group represented by Formula 6-1:

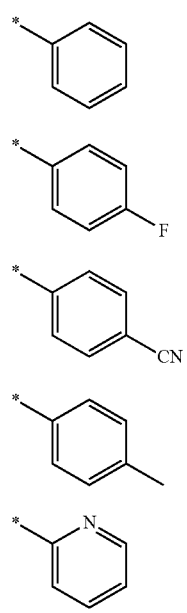

Formula 6-1

Formula 6-2

Formula 6-3

Formula 6-4

Formula 6-5

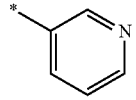

Formula 6-6

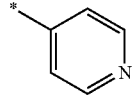

Formula 6-7

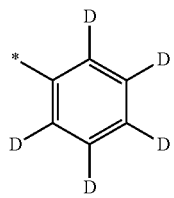

Formula 6-8

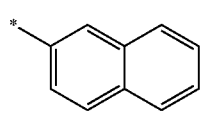

Formula 6-9

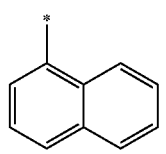

Formula 6-10

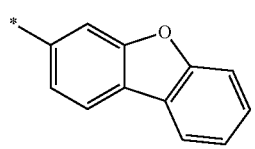

Formula 6-11

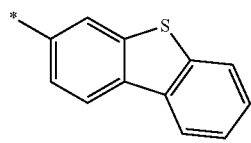

Formula 6-12

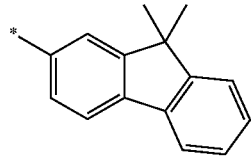

Formula 6-13

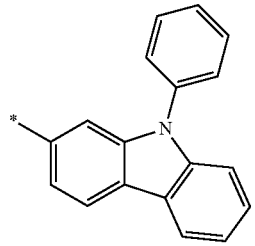

Formula 6-14

Formula 6-15
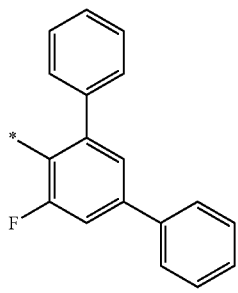
Formula 6-16
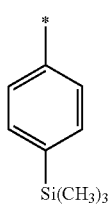
Formula 6-17
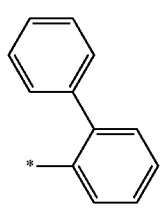
Formula 6-18
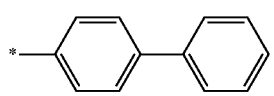
Formula 6-19
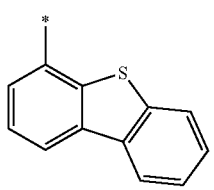
Formula 6-20
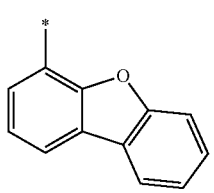
Formula 6-21
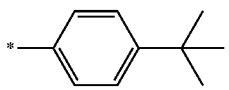
Formula 6-22
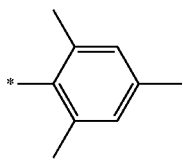
Formula 6-23
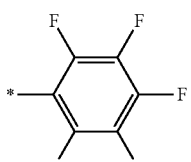
Formula 6-24
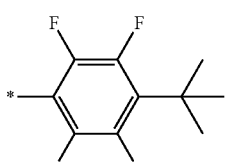
Formula 6-25
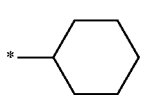
Formula 6-26
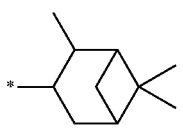
Formula 6-27
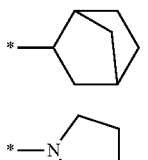
Formula 6-28
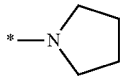
wherein, in Formulae 6-1 to 6-28, * indicates a binding site to an adjacent atom.
9. The condensed-cyclic compound as claimed in claim 1, wherein the condensed-cyclic compound is represented by one of Compounds 14 to 26, 40 to 169 and 182 to 231:
14
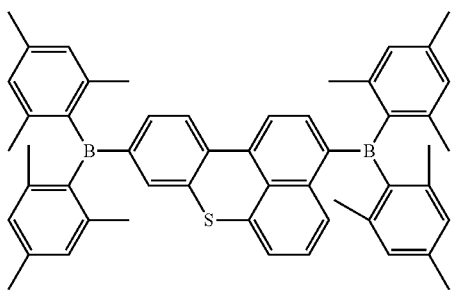
15
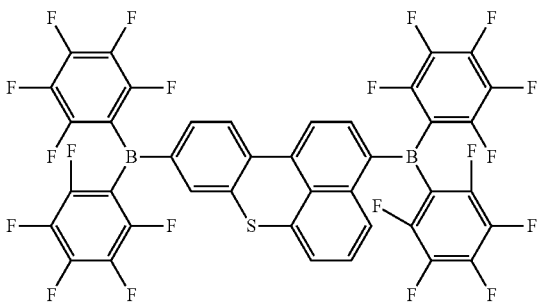

-continued
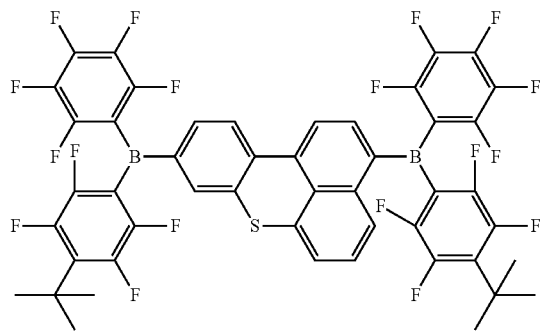
16
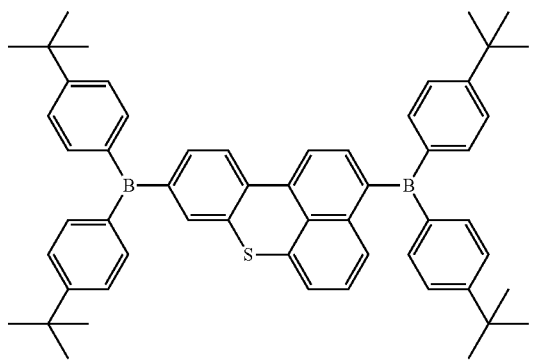
17
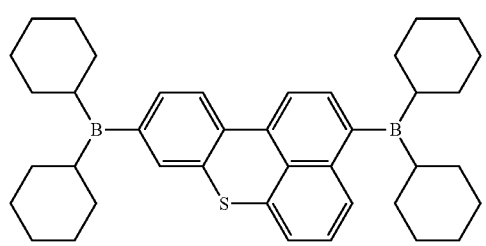
18
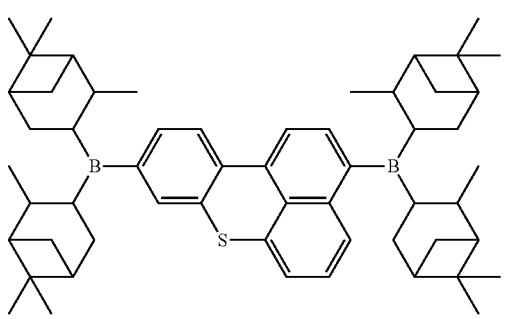
19
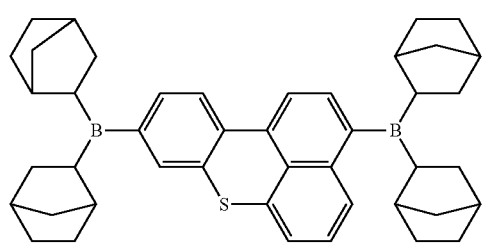
20
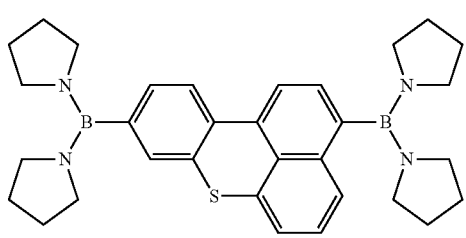
21
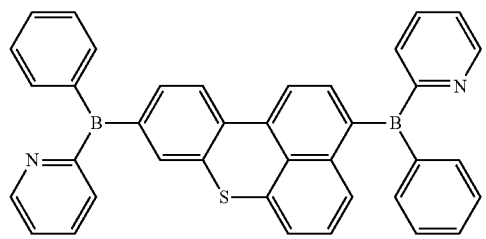
22
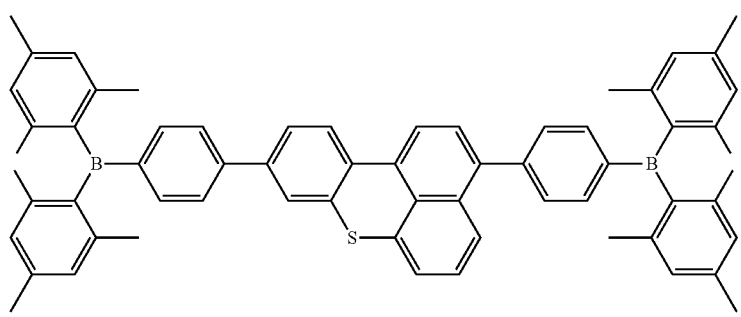
23

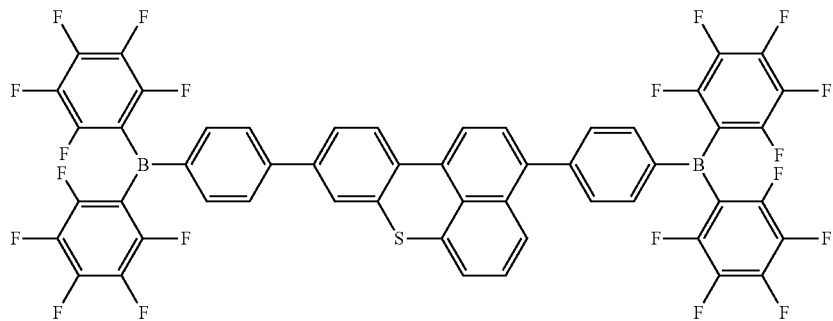
24
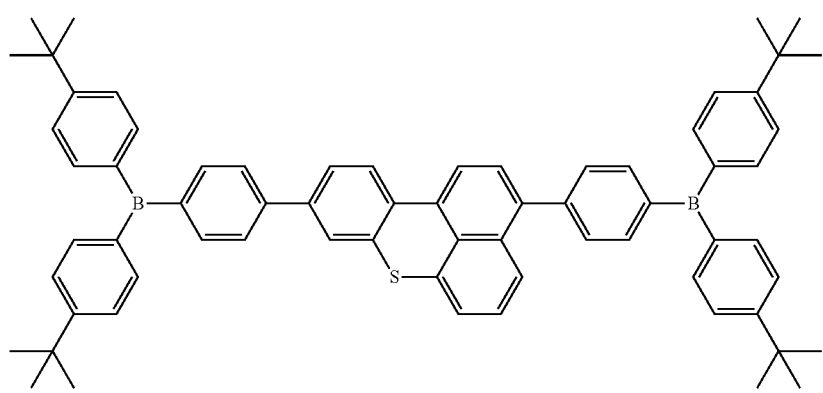
25
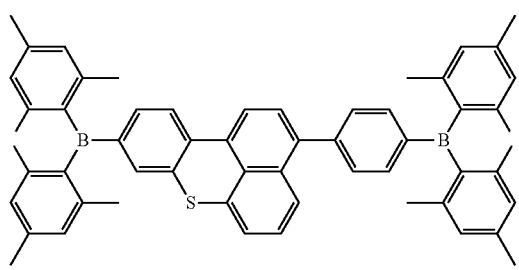
26
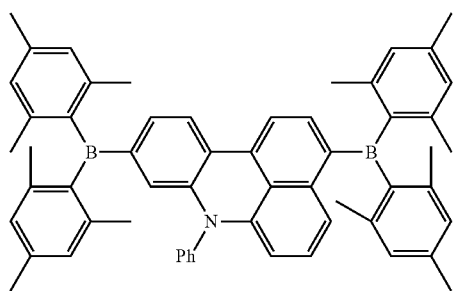
40
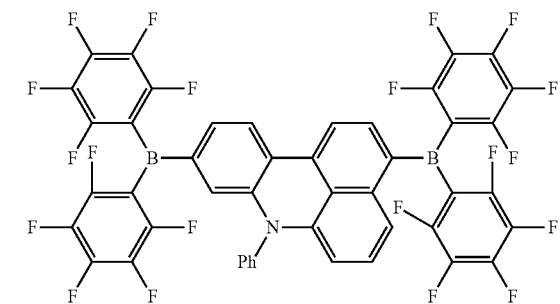
41

-continued
42
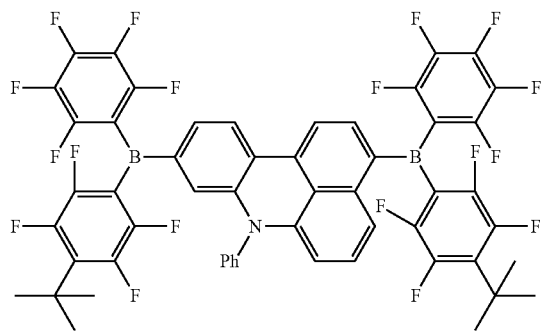
43
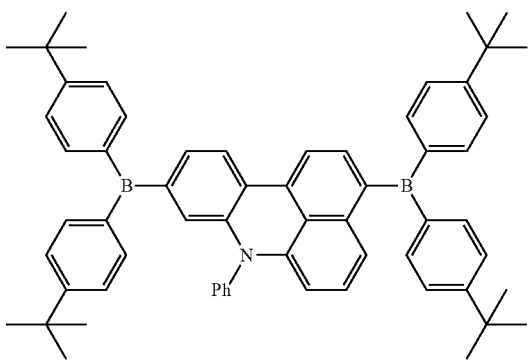
44
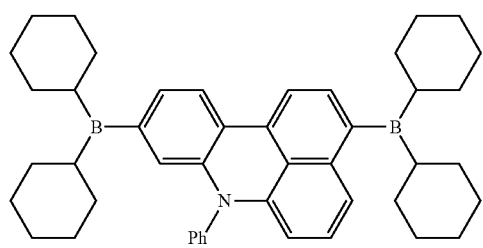
45
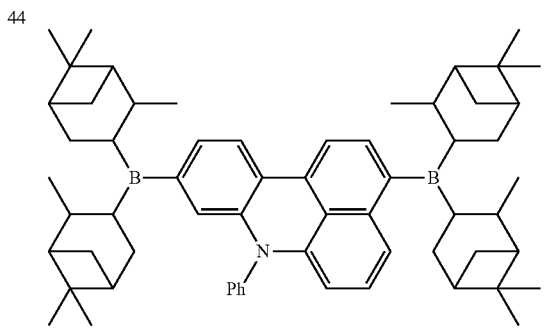
46
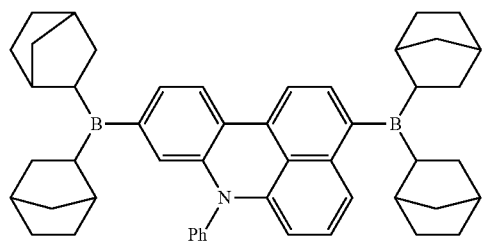
47
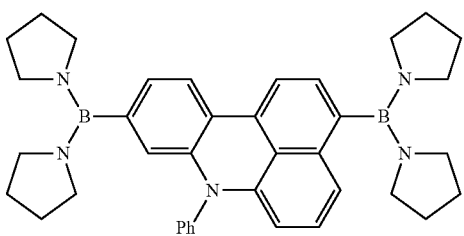
48
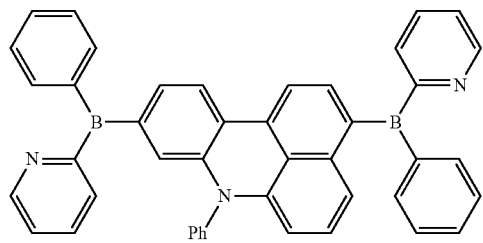
49
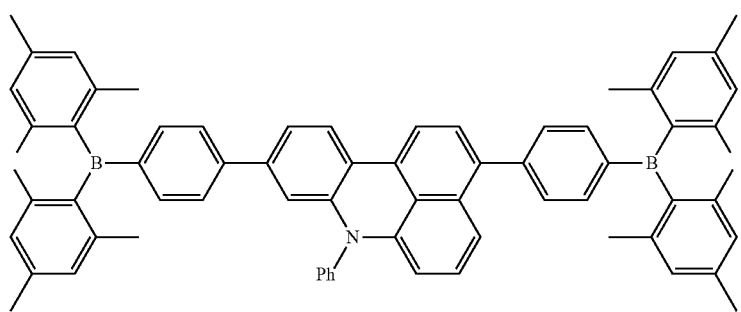

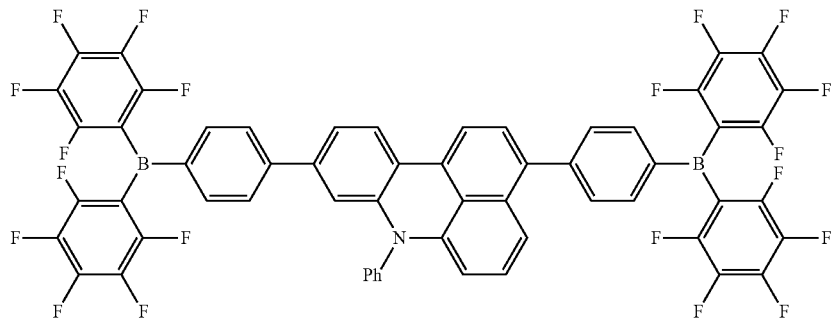
50
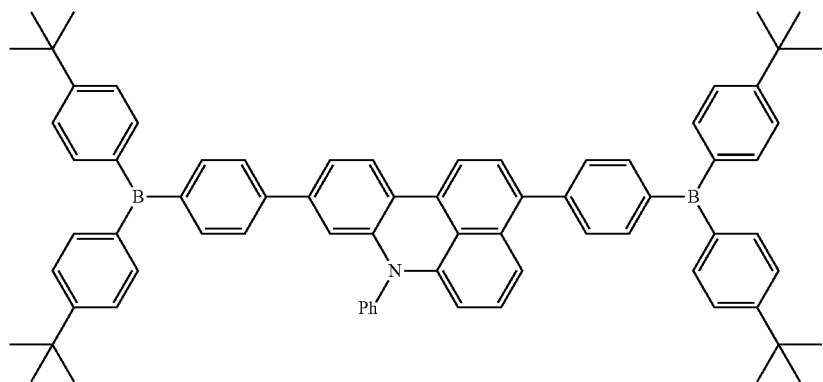
51
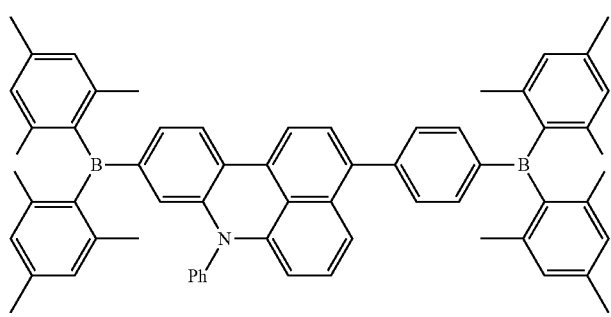
52
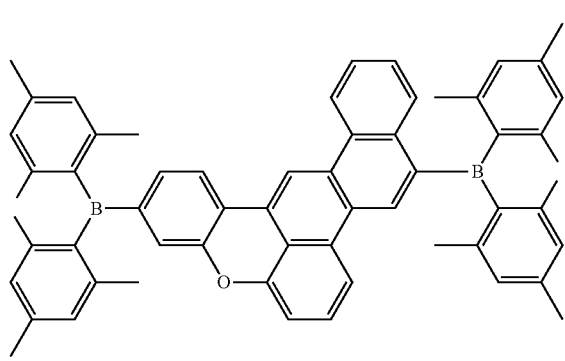
53

-continued
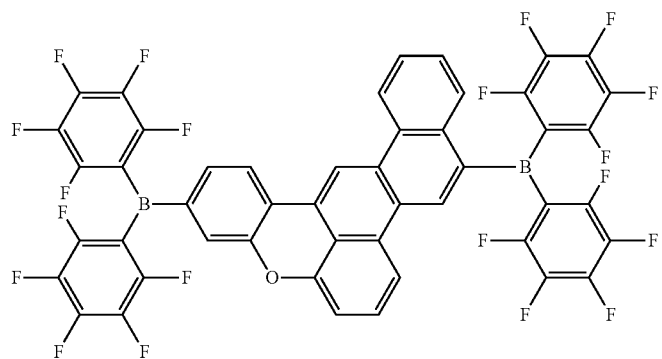
54
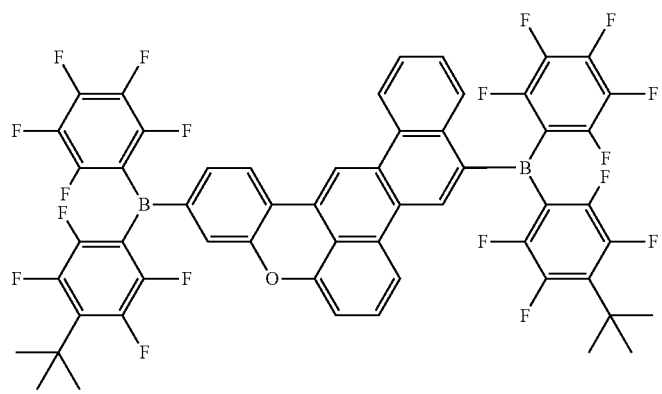
55
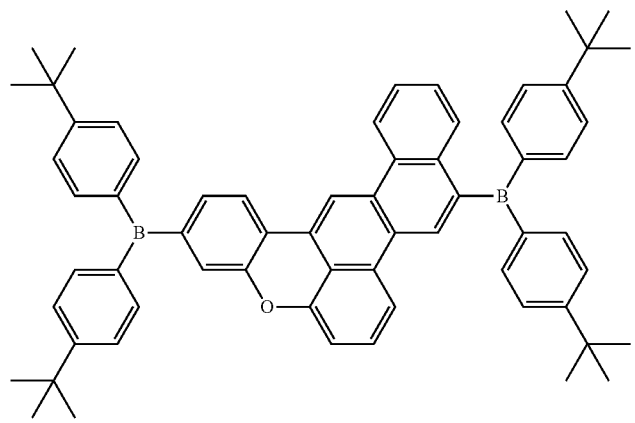
56
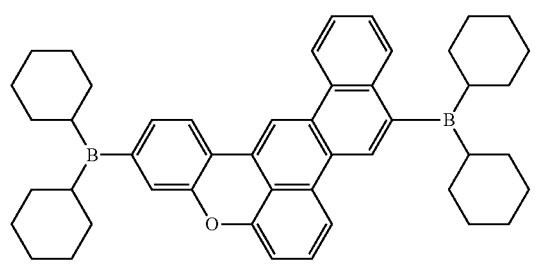
57
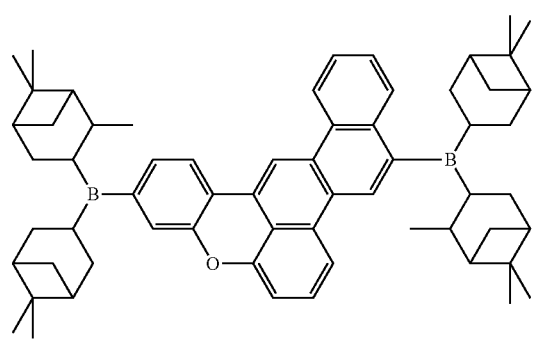
58

59
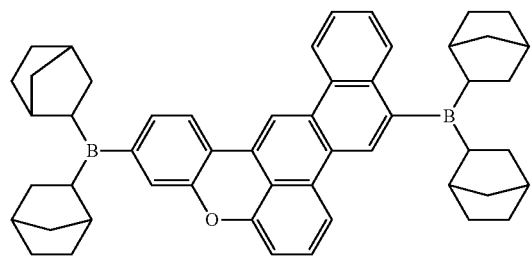
60
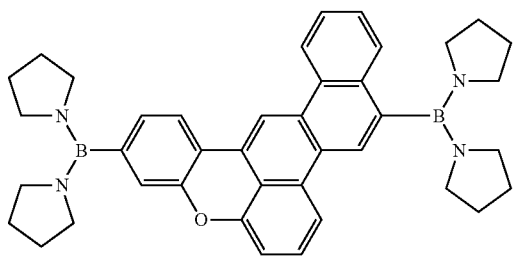
61
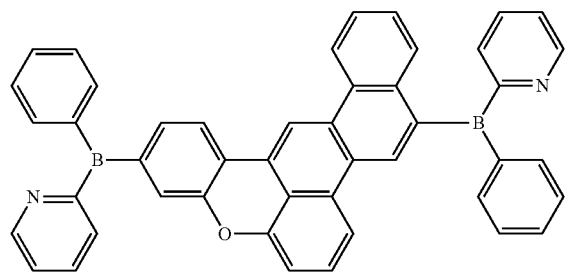
62
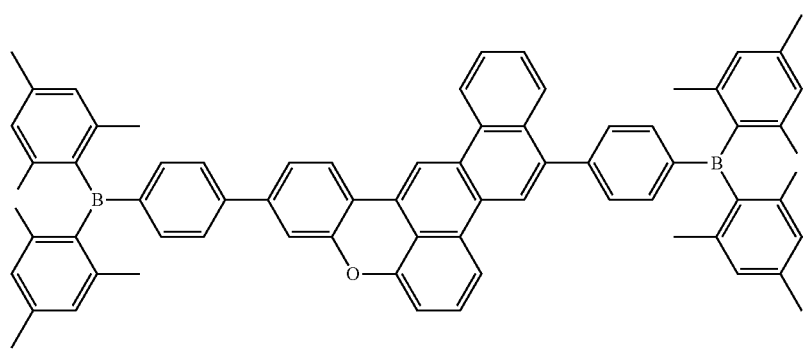
63
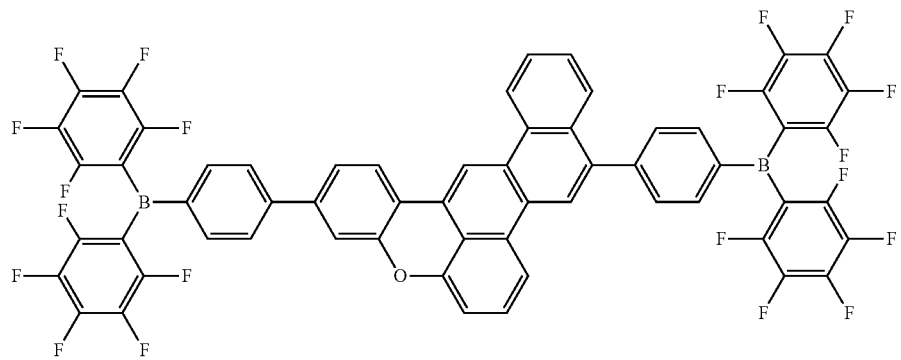

-continued
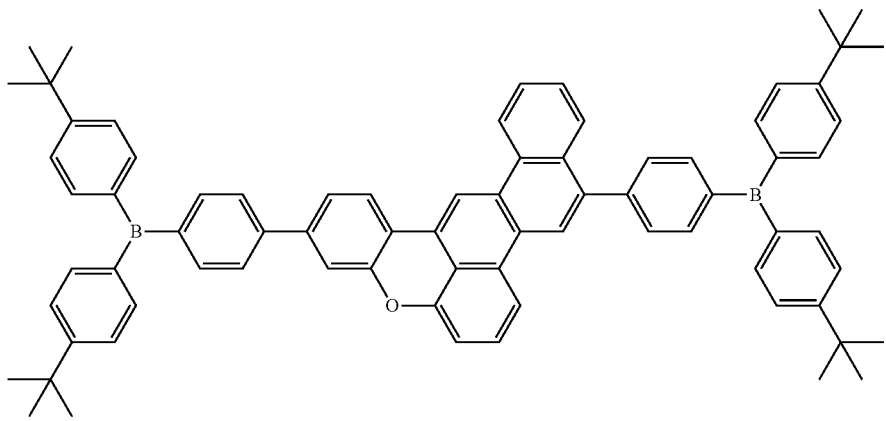
64
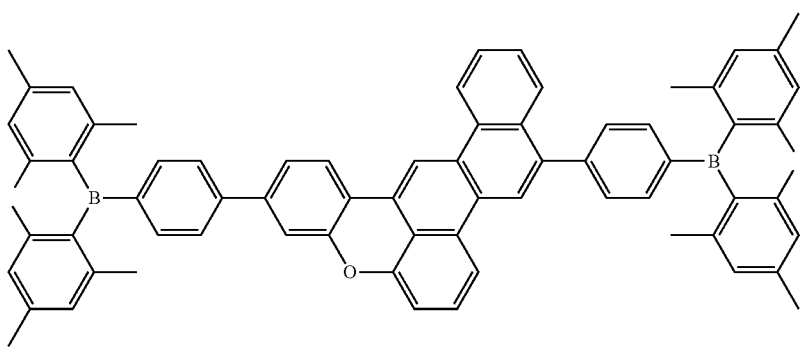
65
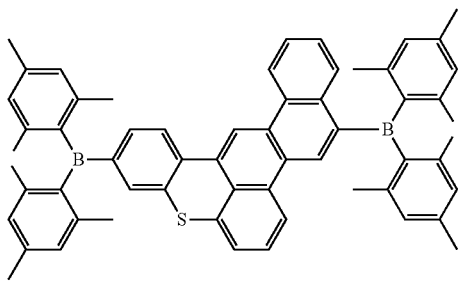
66
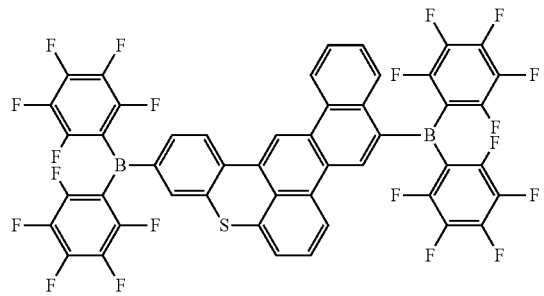
67
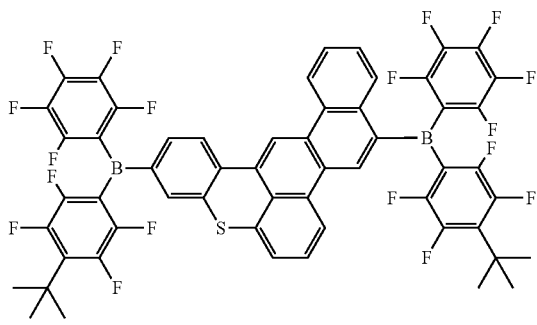
68
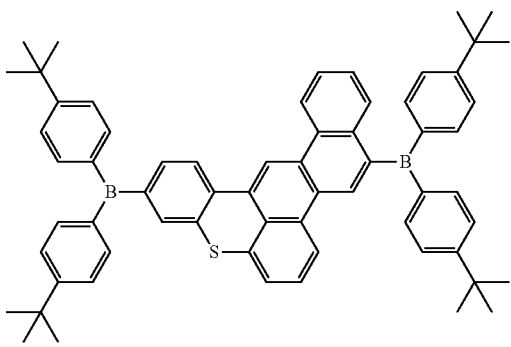
69

-continued
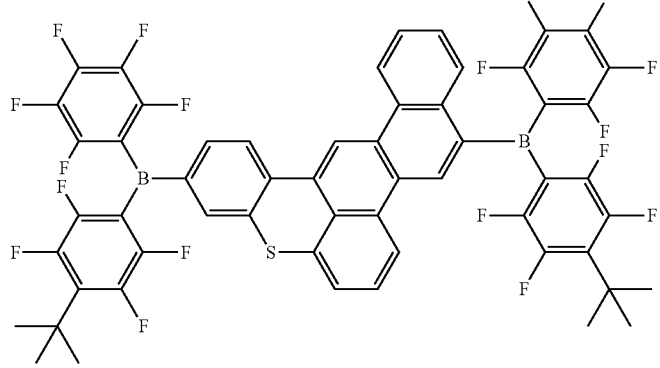
68
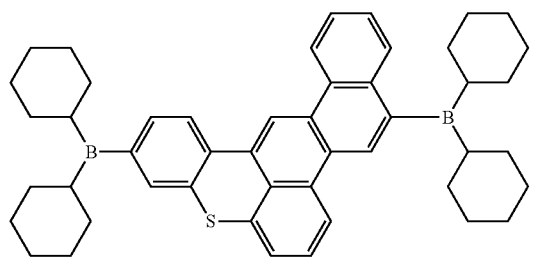
70
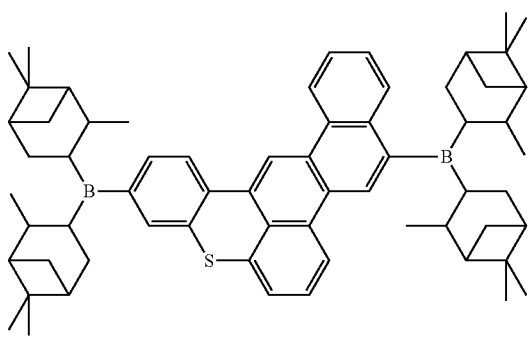
71
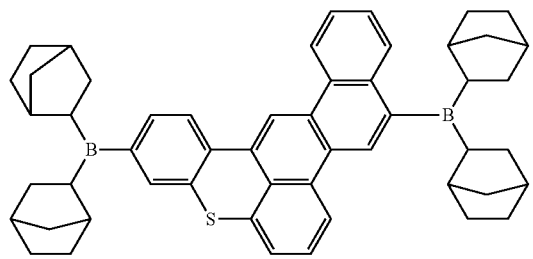
72
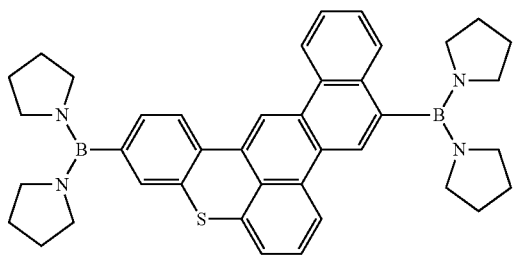
73
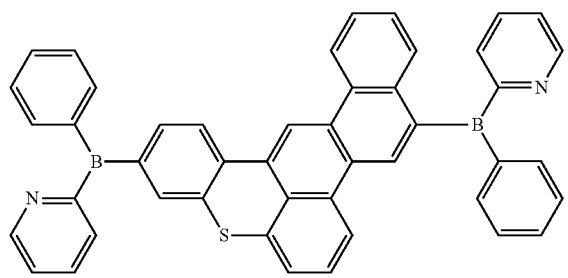
74
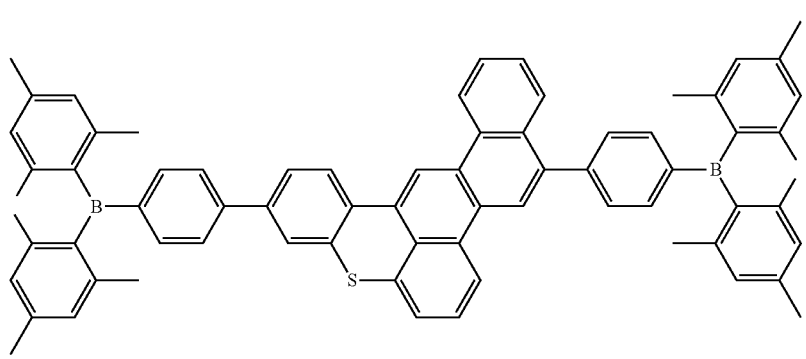
75

76
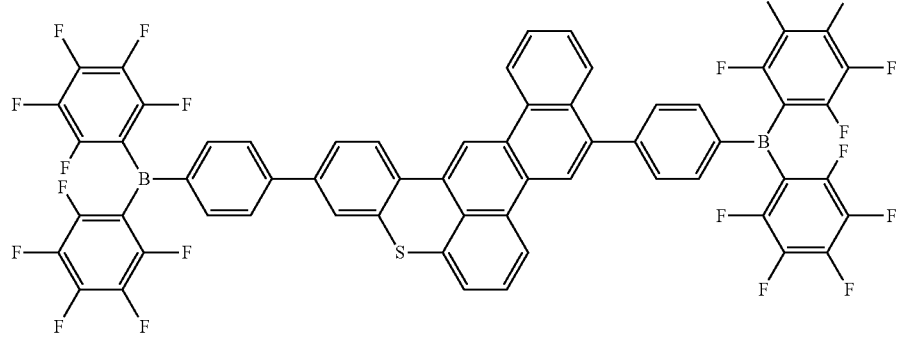
77
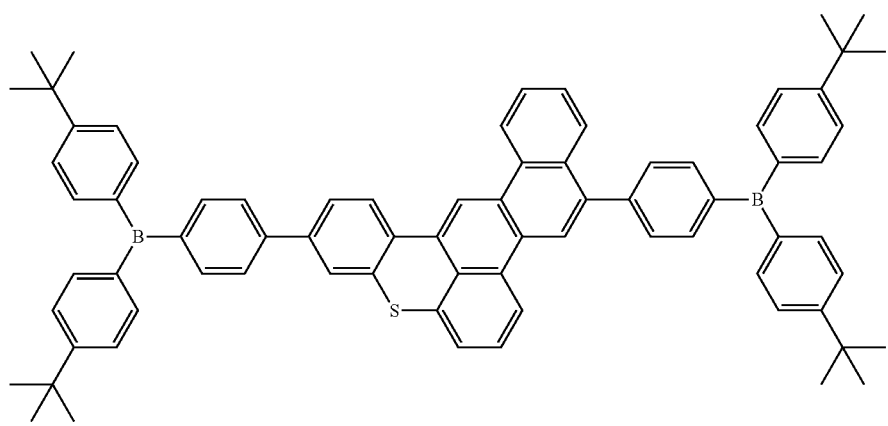
78
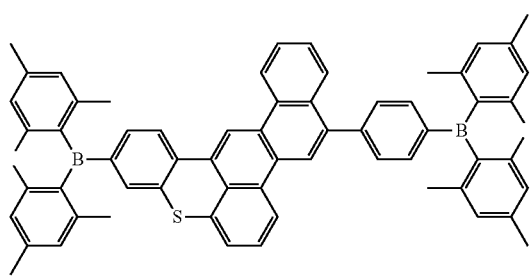
79
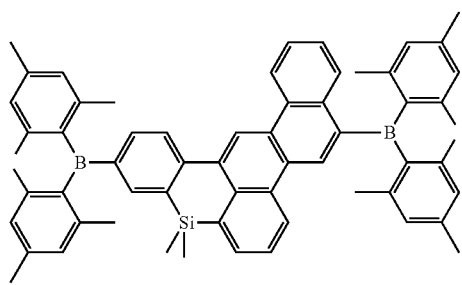
80
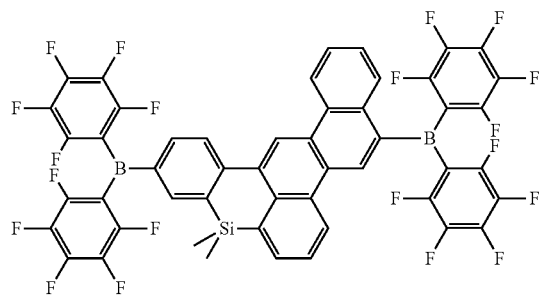

-continued
81
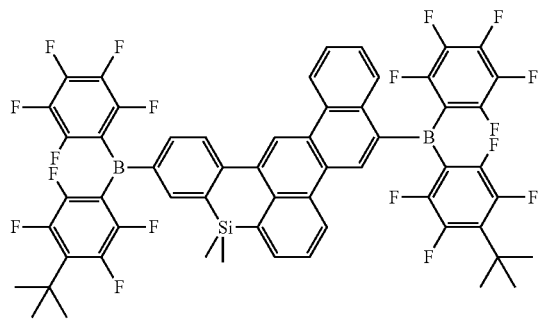
82
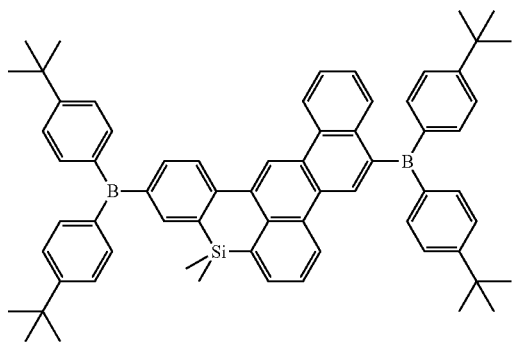
83
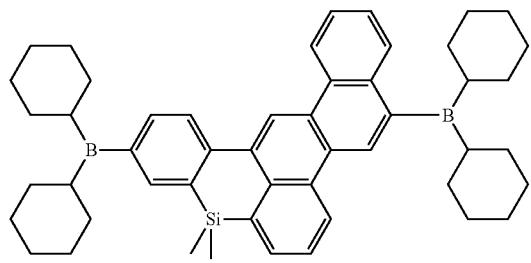
84
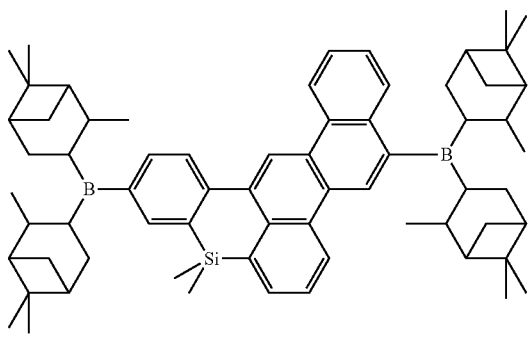
85
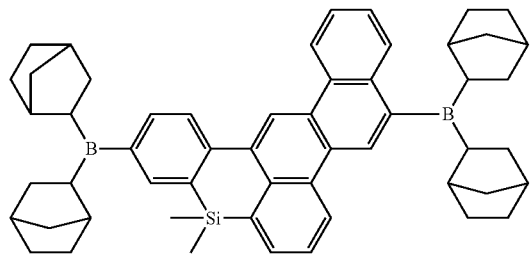
86
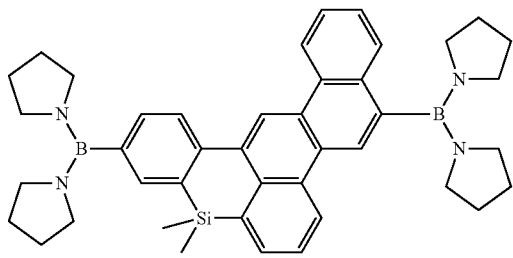
87
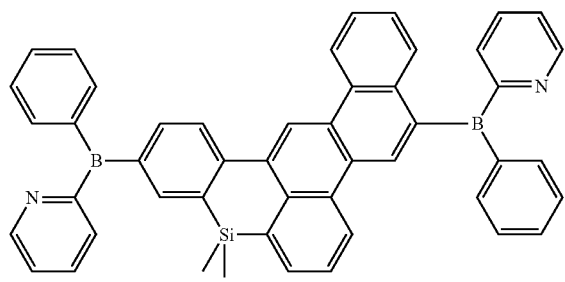
88
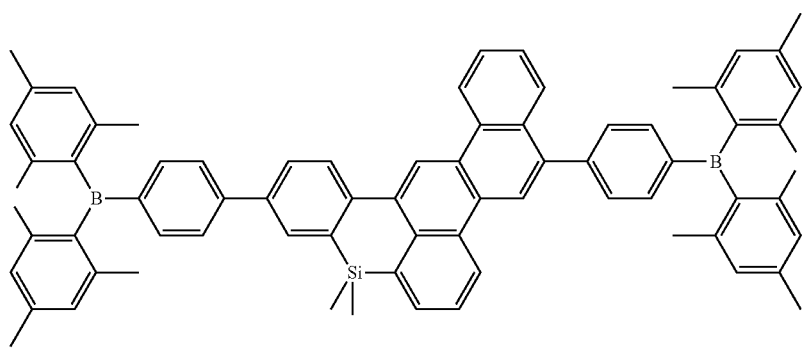

-continued
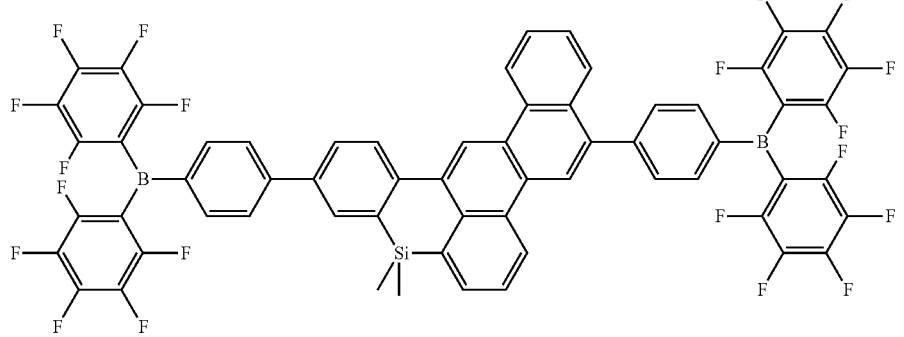
89
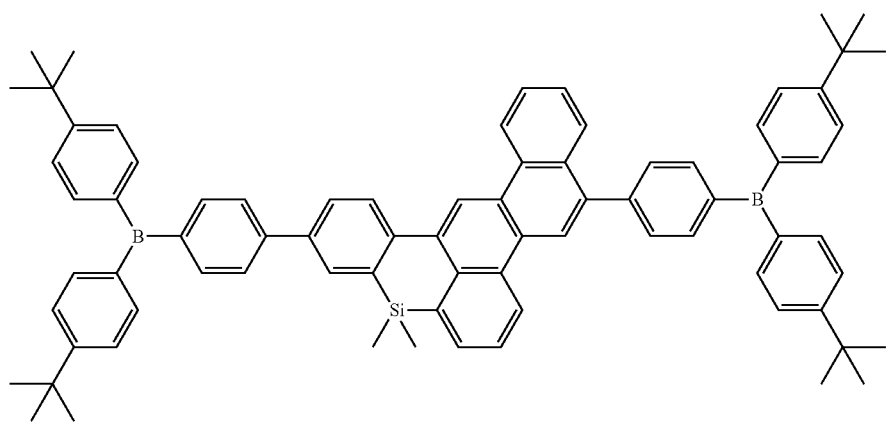
90
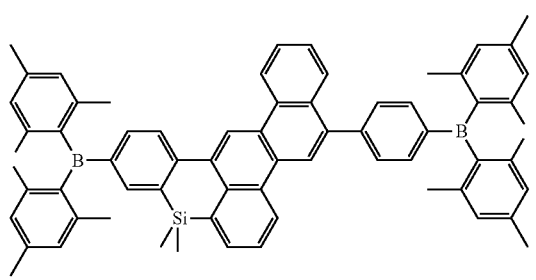
91
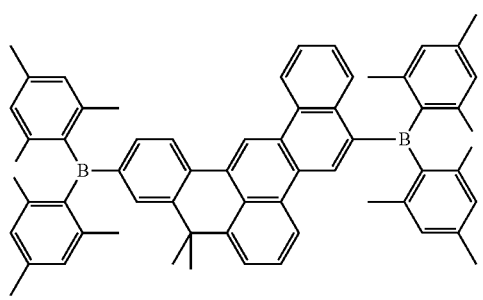
92
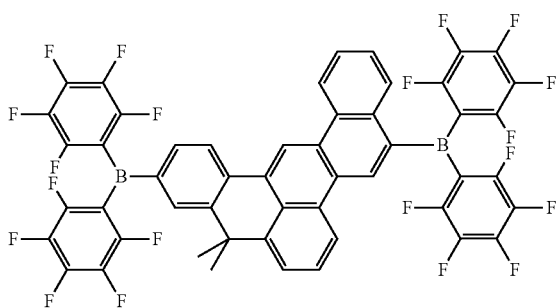
93

-continued
94
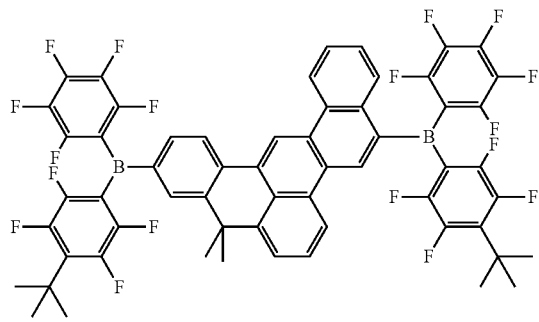
95
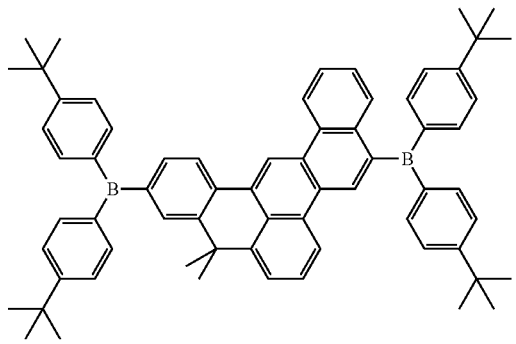
96
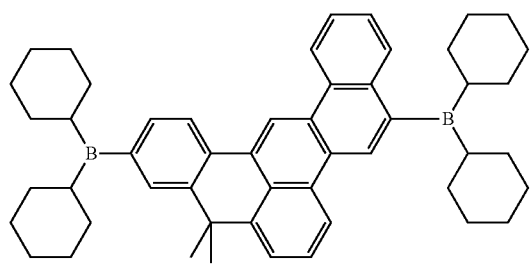
97
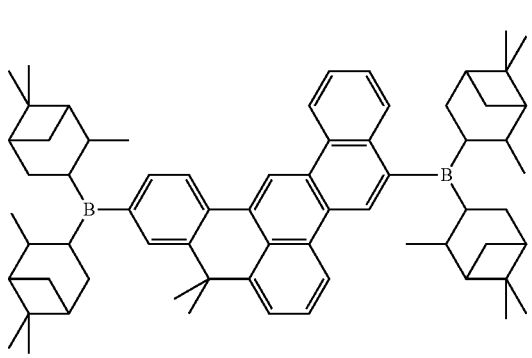
98
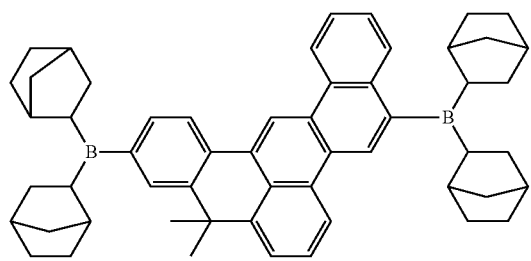
99
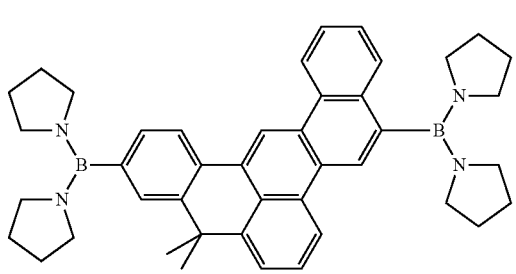
100
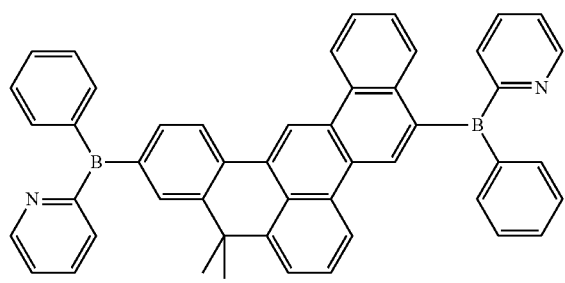
101
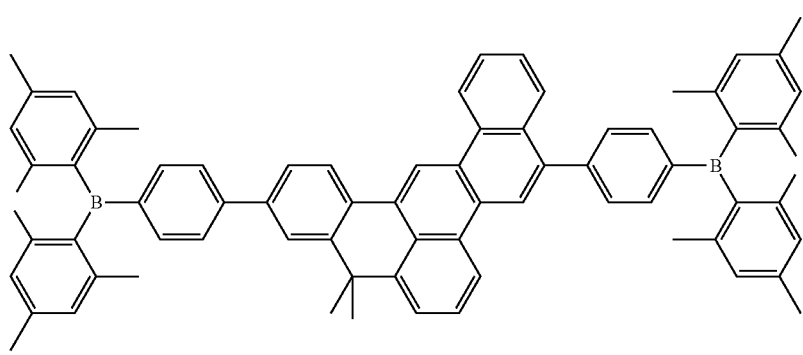

-continued
102
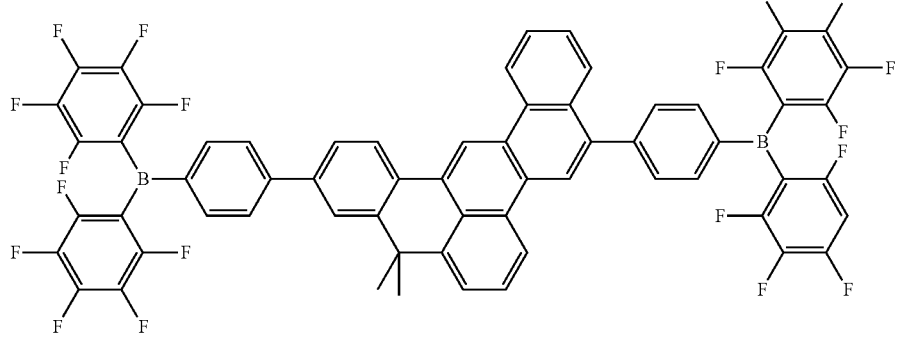
103
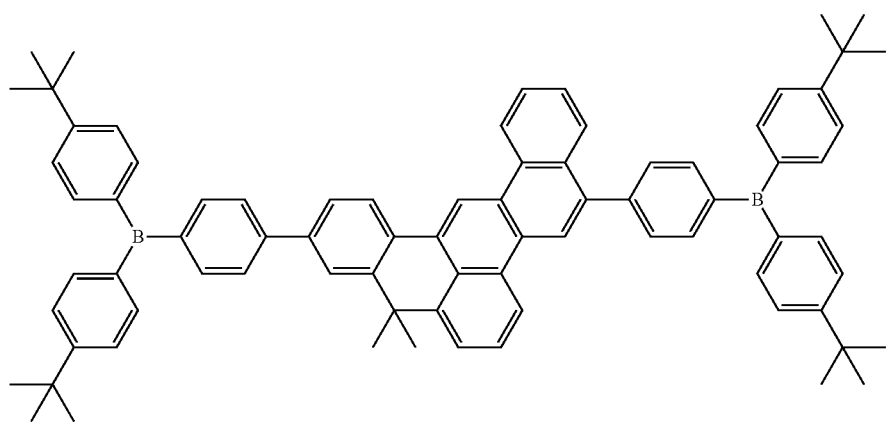
104
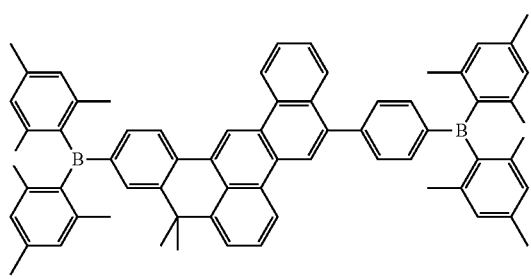
105
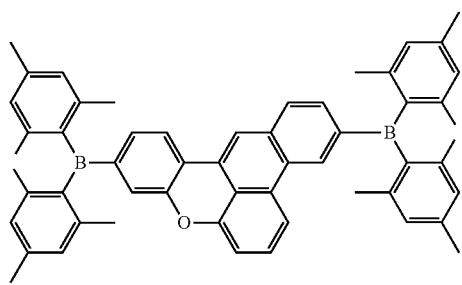
106
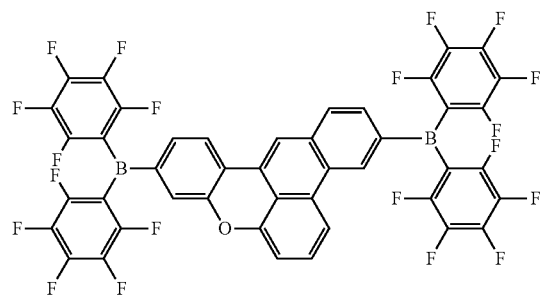

-continued
107
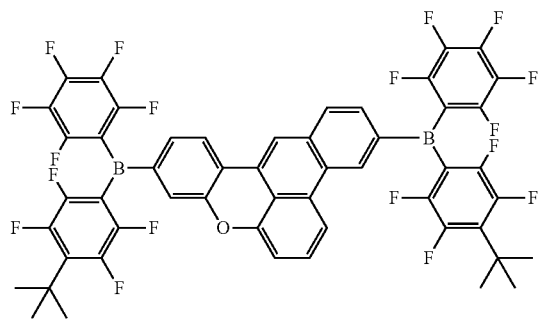
108
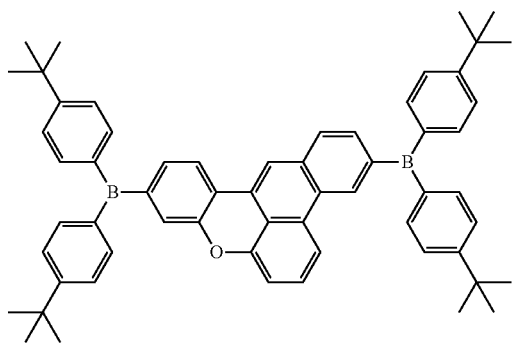
109
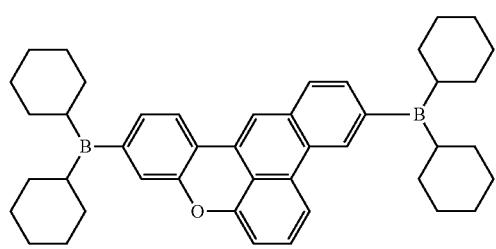
110
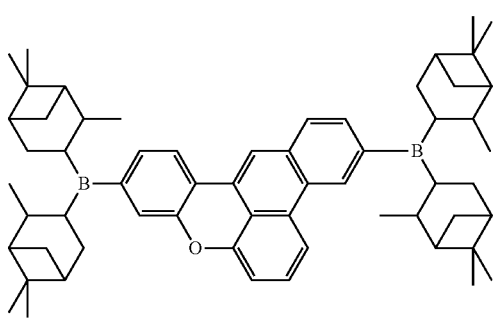
111
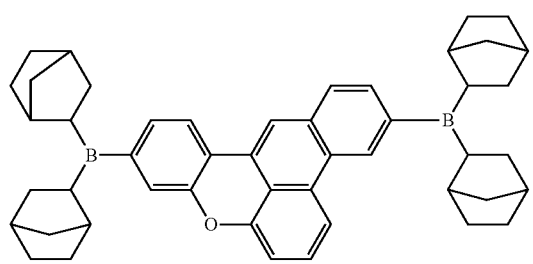
112
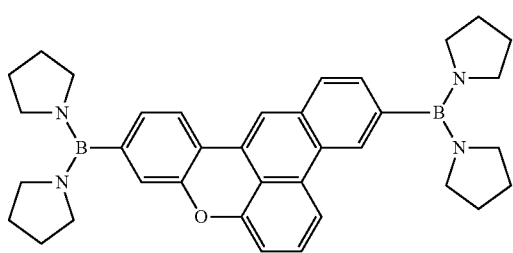
113
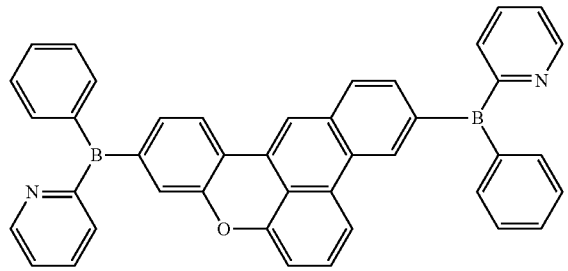
114
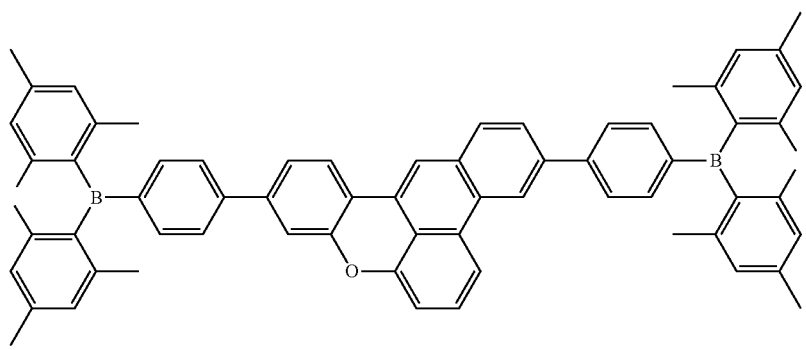

-continued
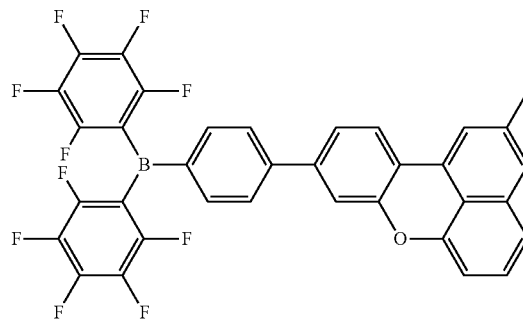 115
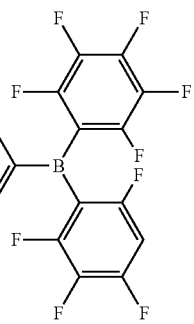
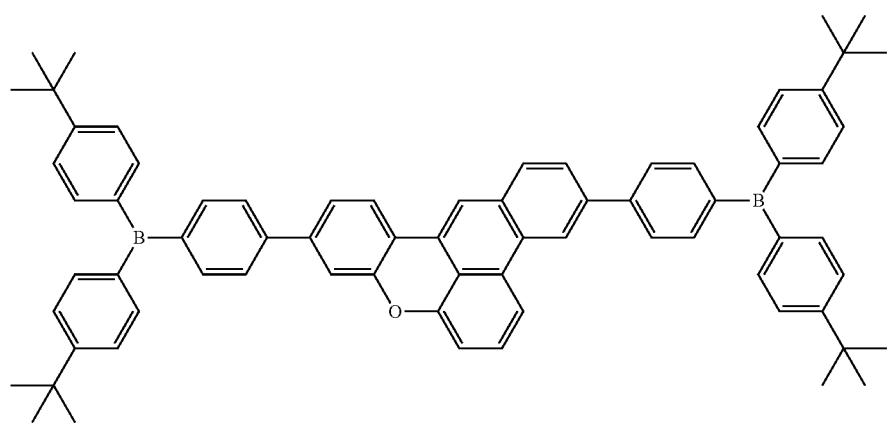 116
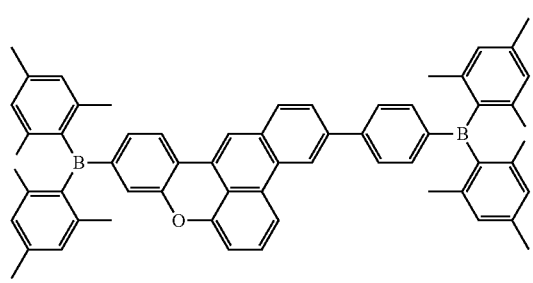 117
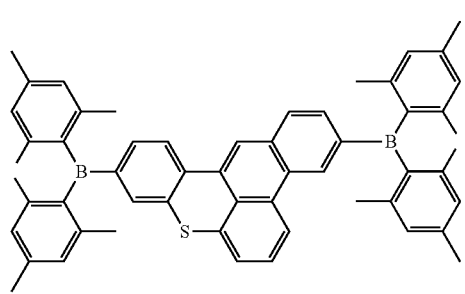 118
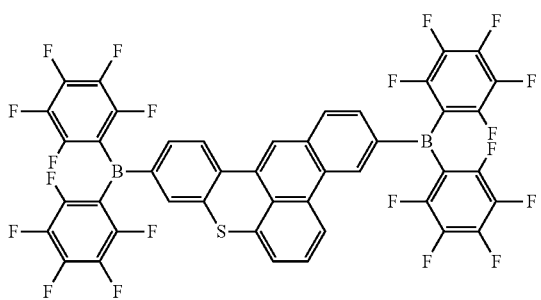 119

-continued
120
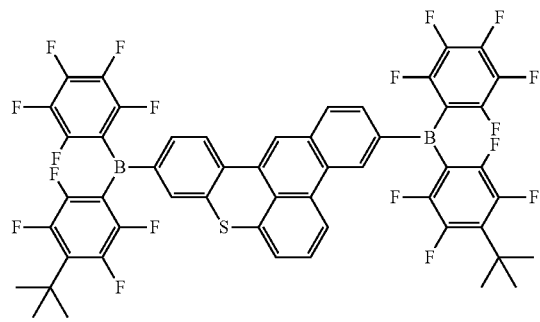
121
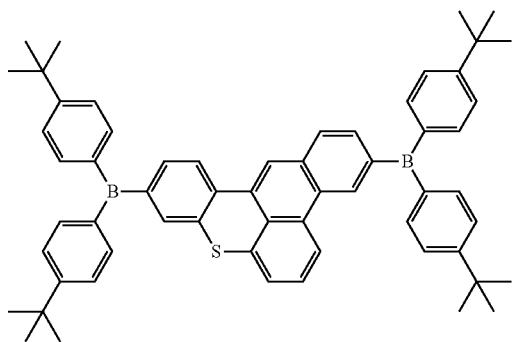
122
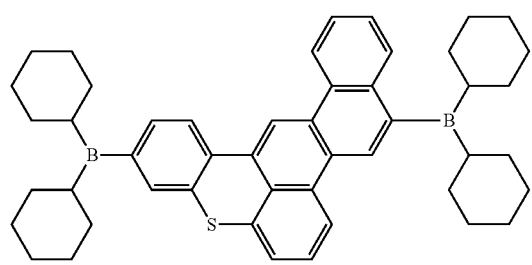
123
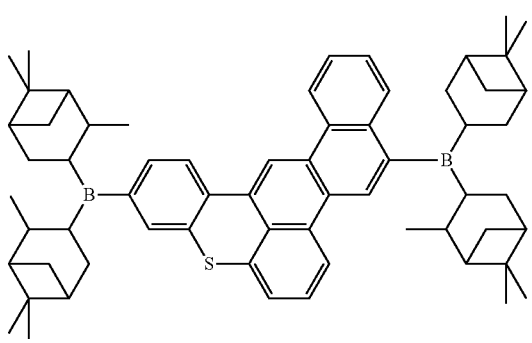
124
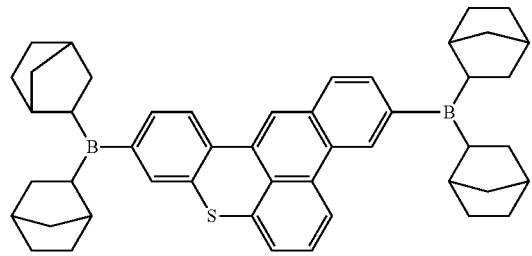
125
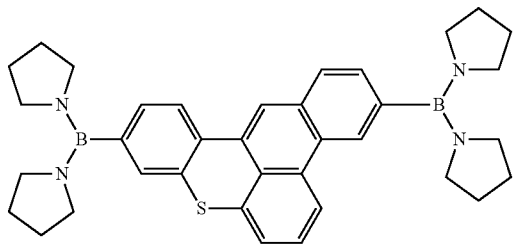
126
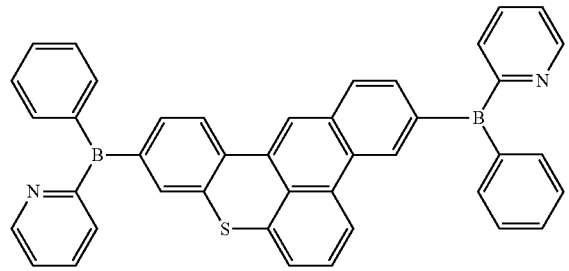
127
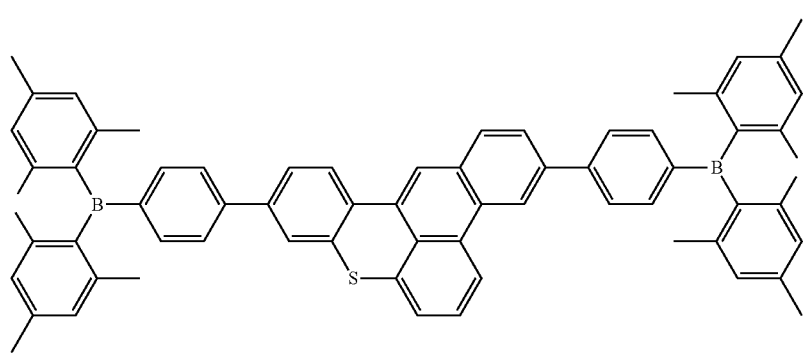

128
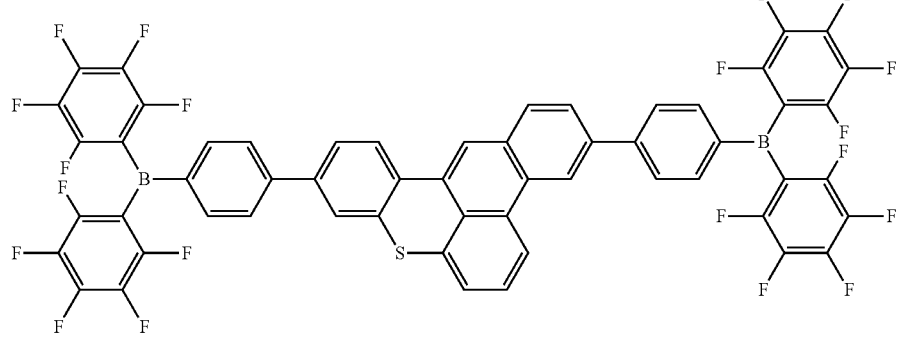
129
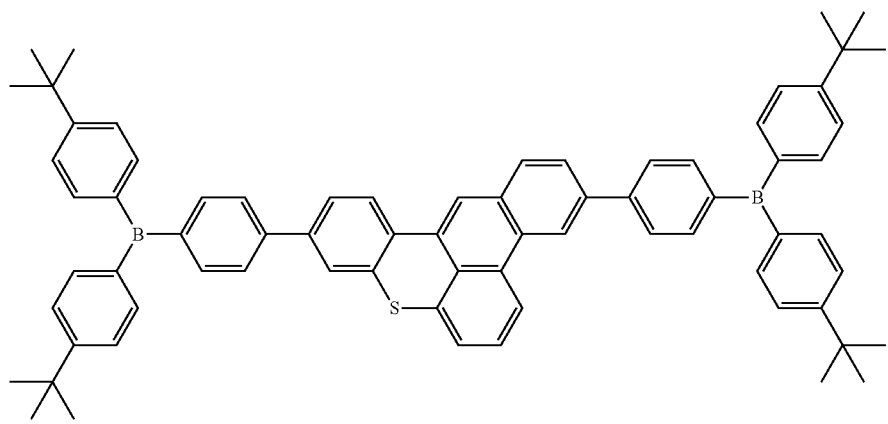
130
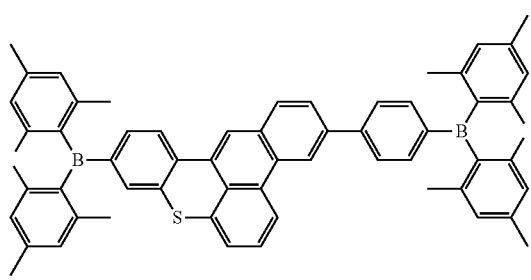
131
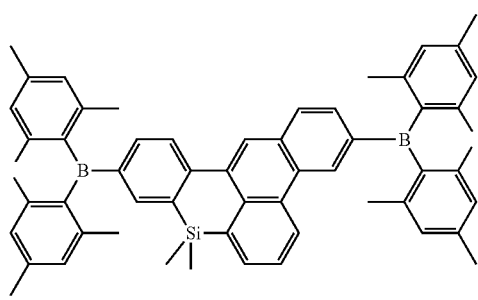
132
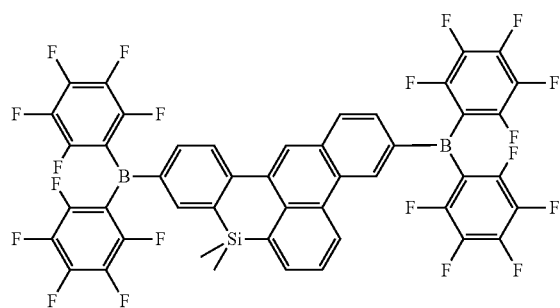

133
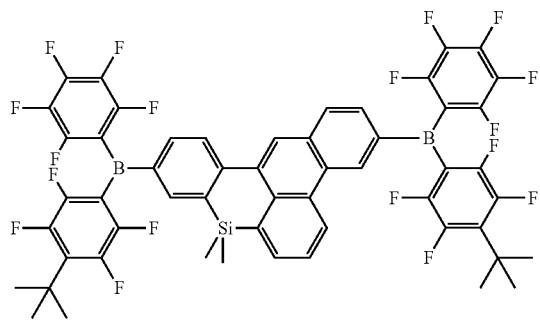
134
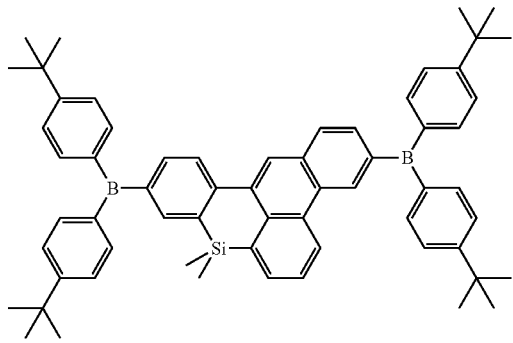
135
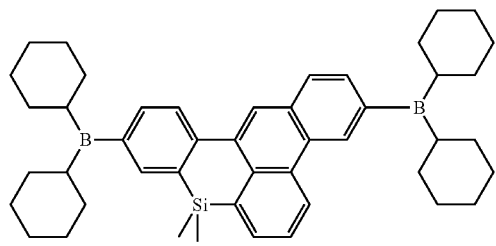
136
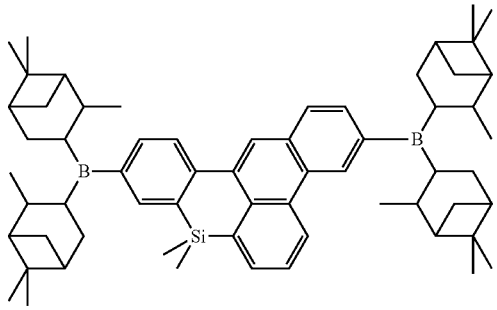
137
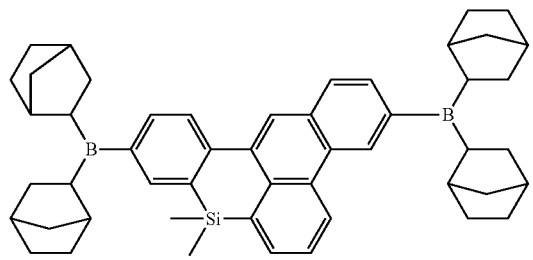
138
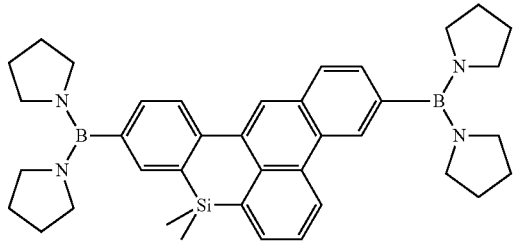
139
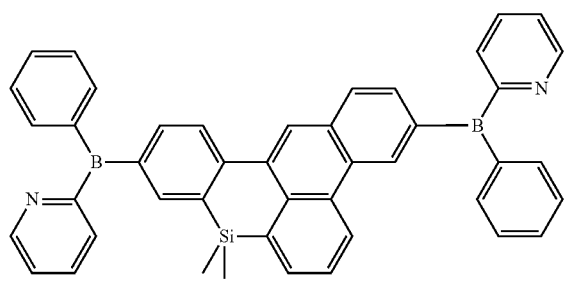
140
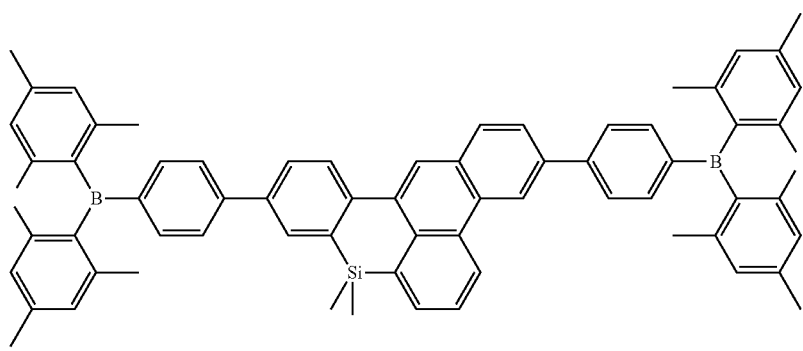

141
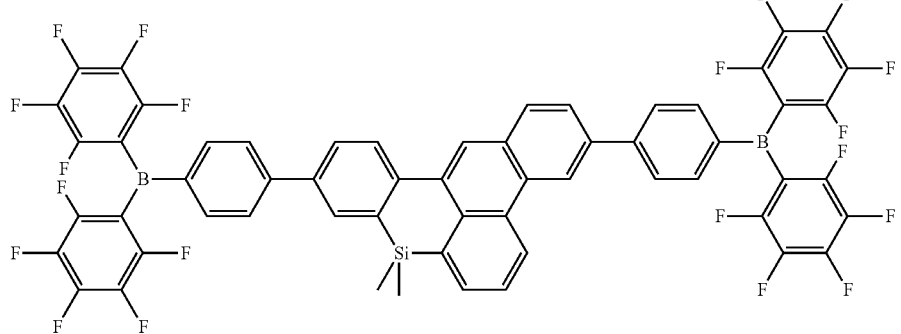
142
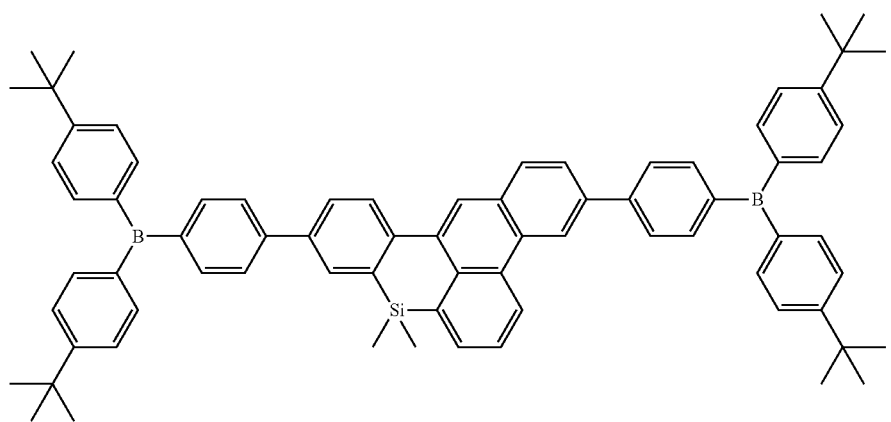
143
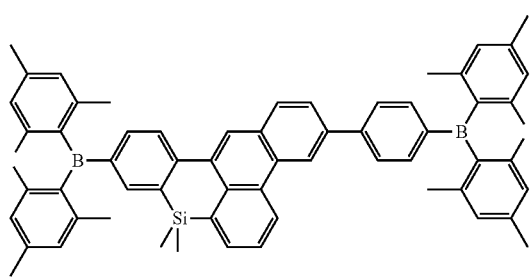
144
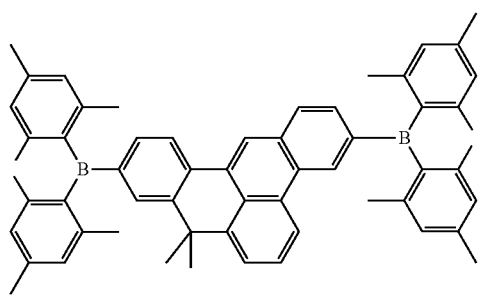
145
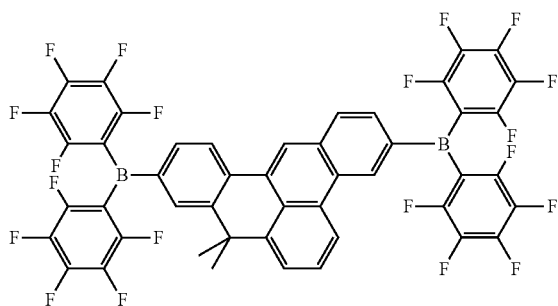

-continued
146
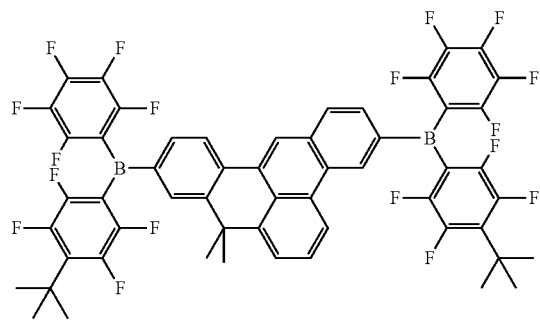
147
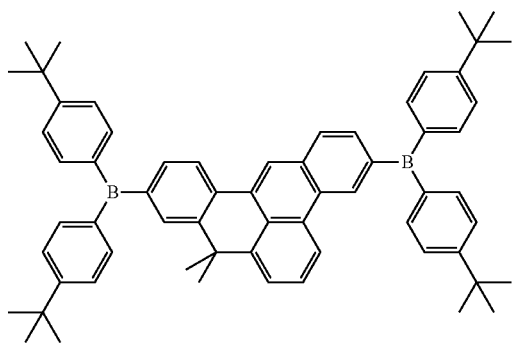
148
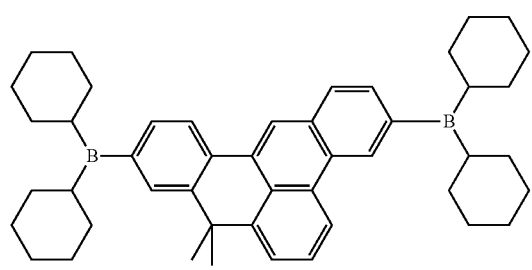
149
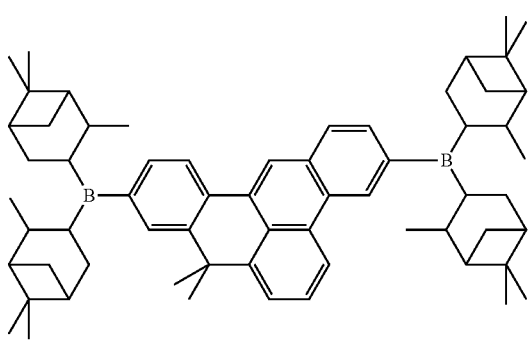
150
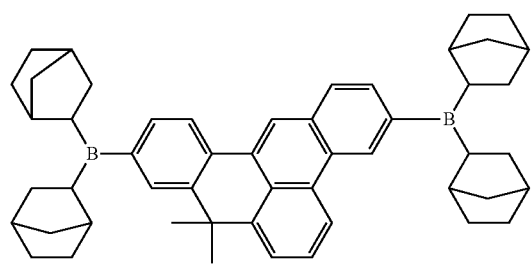
151
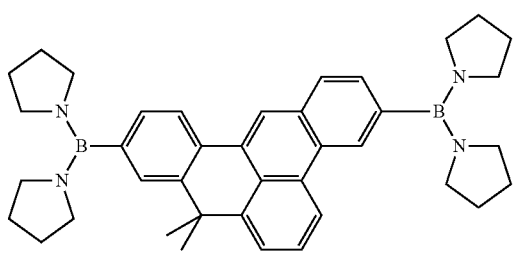
152
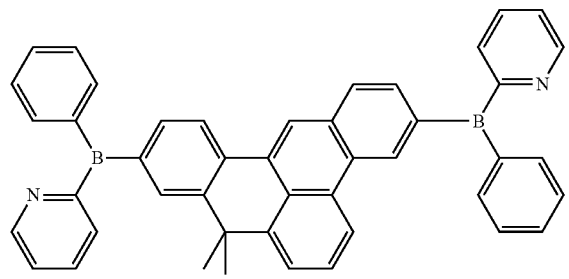
153
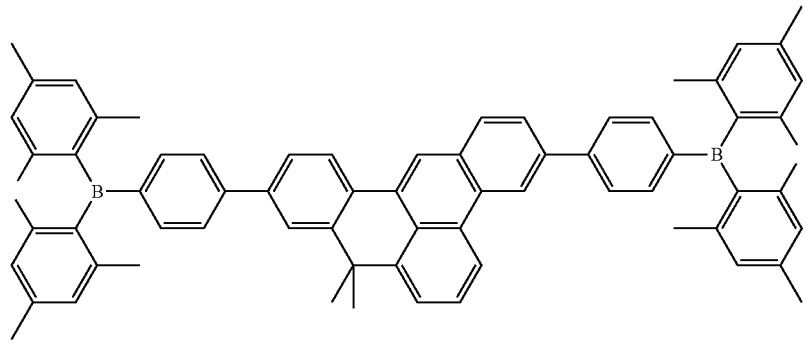

154
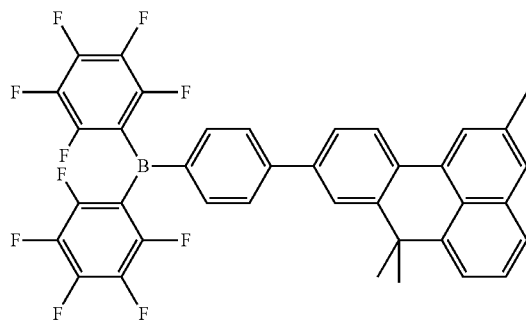
155
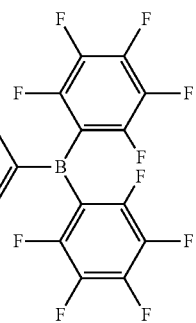
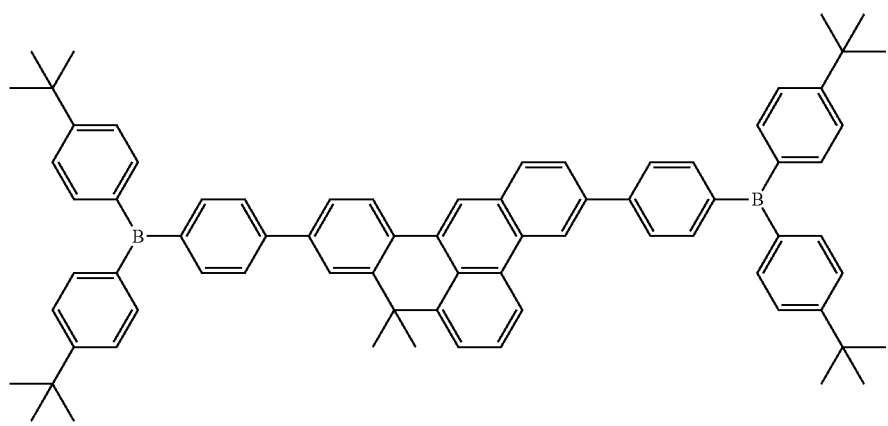
156
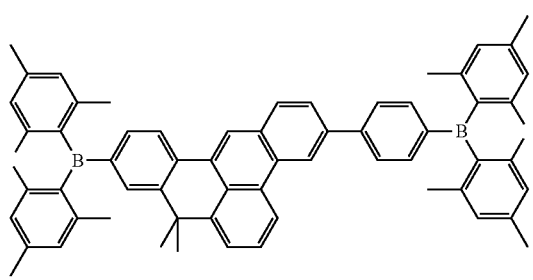
157
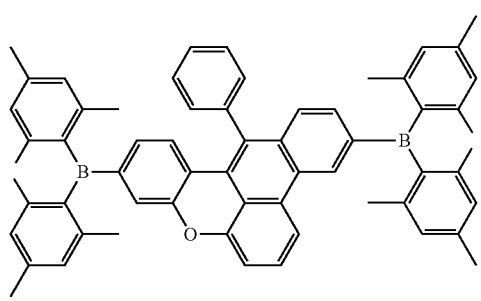
158
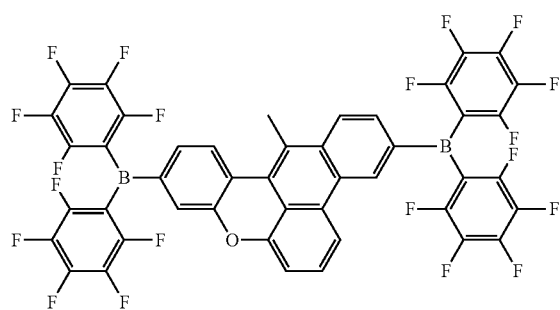

-continued
159
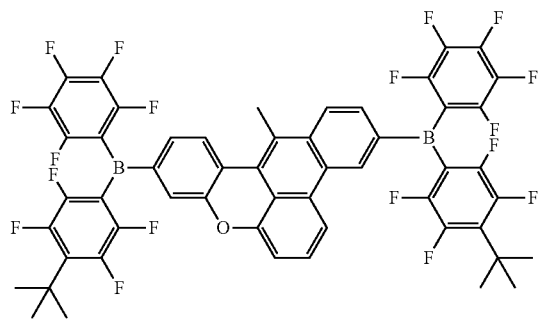
160
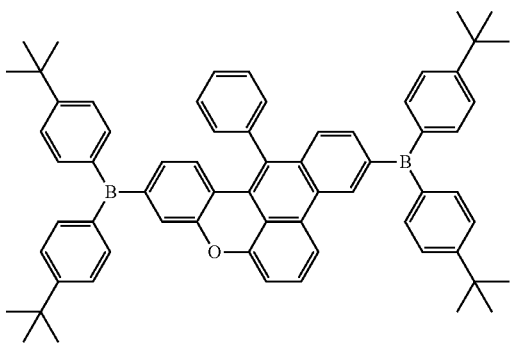
161
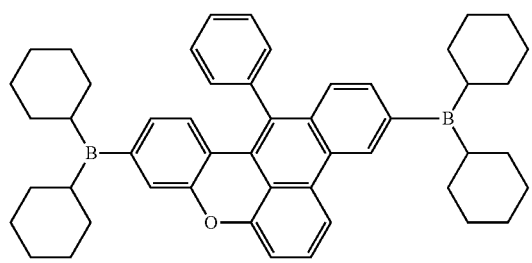
162
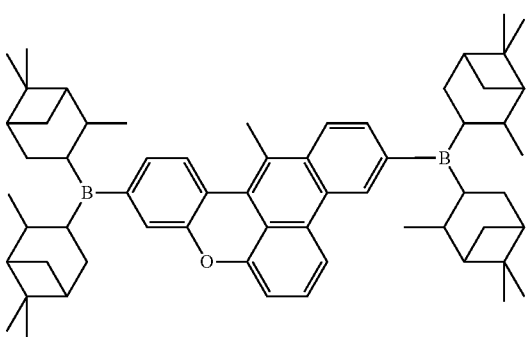
163
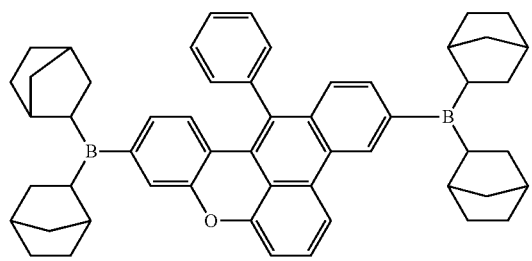
164
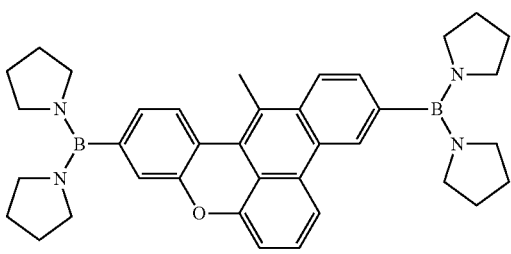
165
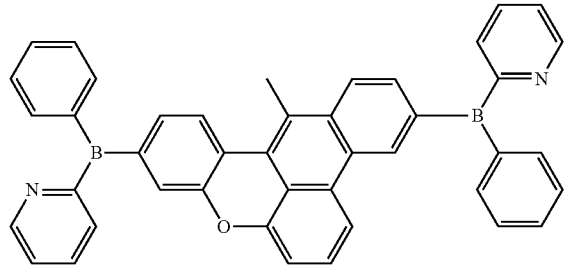
166
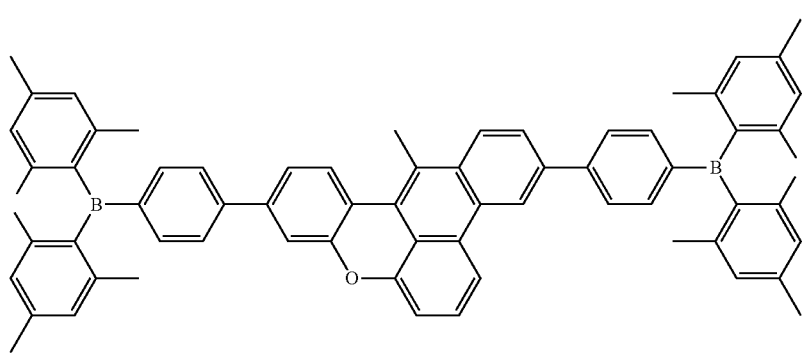

167
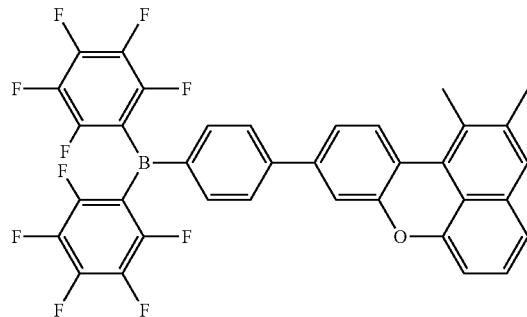
168
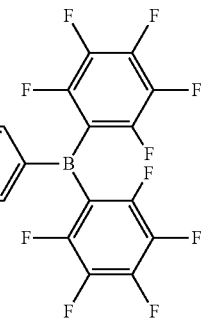
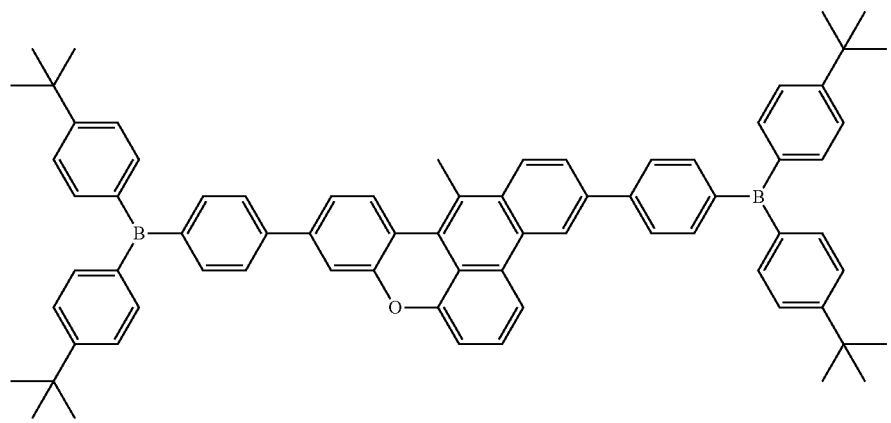
169
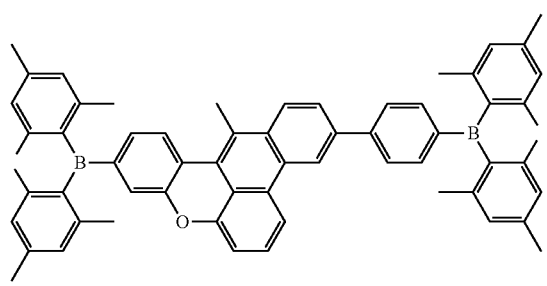
182
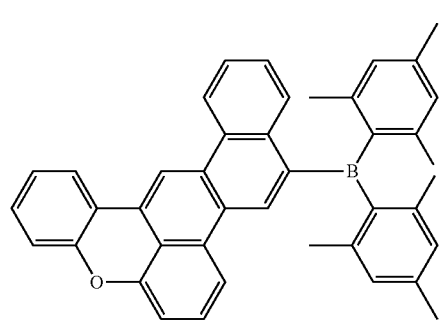
183
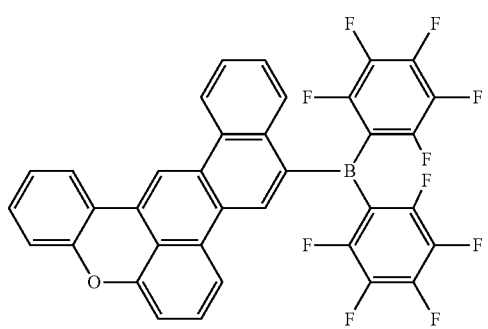

-continued
184
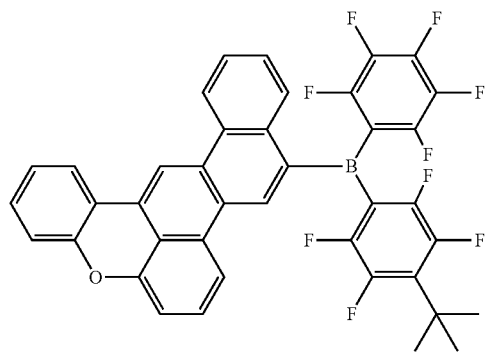
185
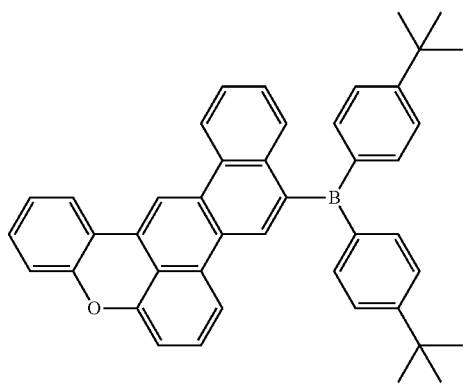
186
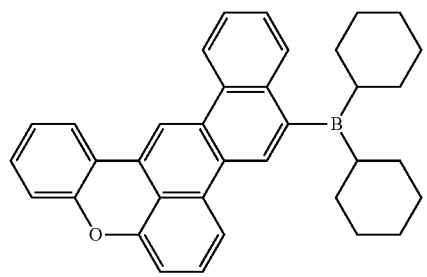
187
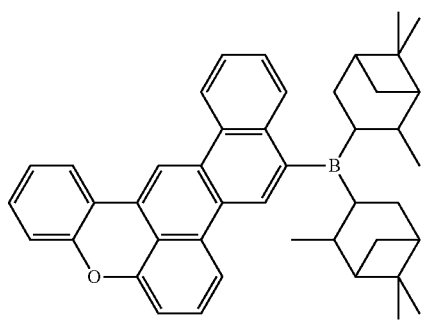
188
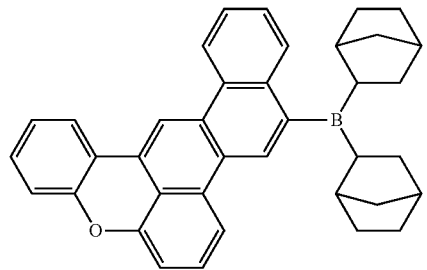
189
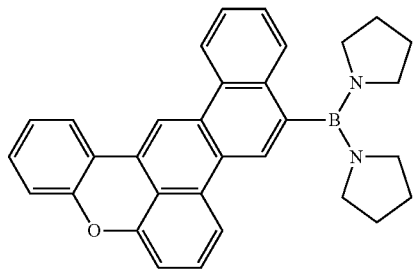
190
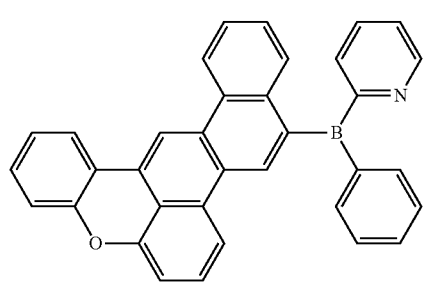
191
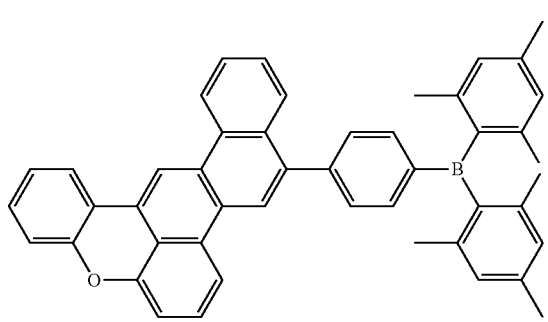
192
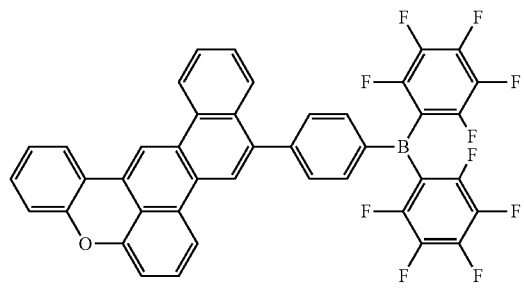
193
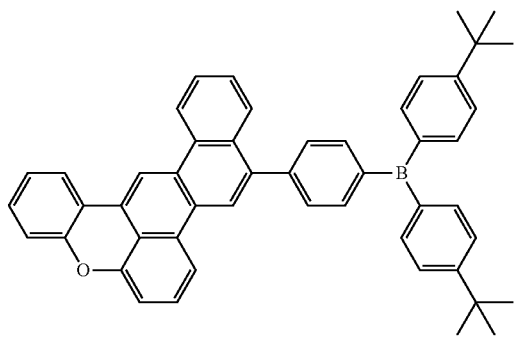

-continued
194
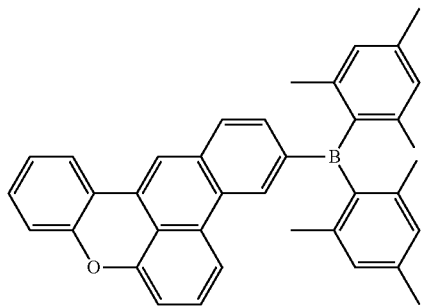
195
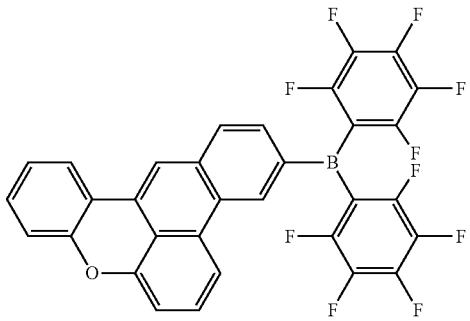
196
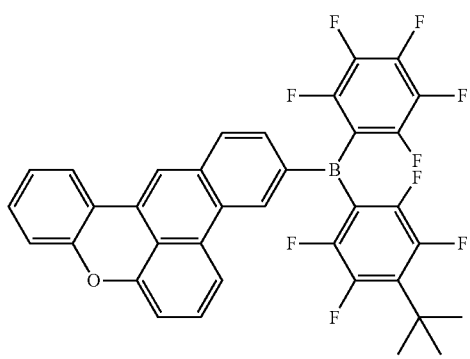
197
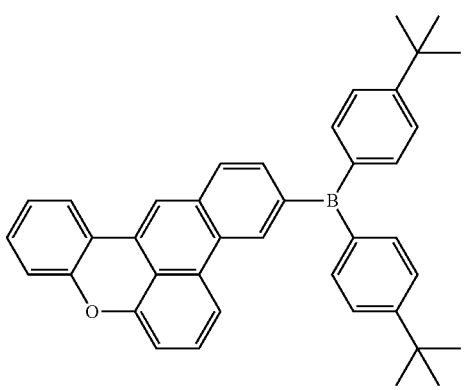
198
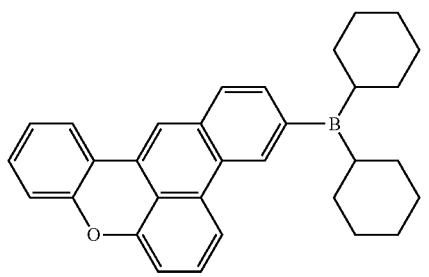
196
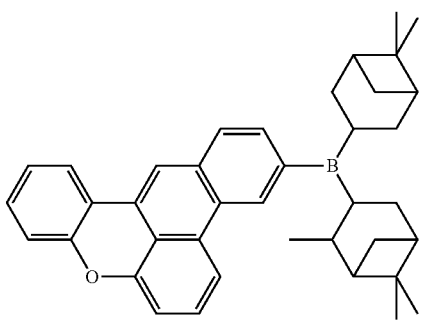
200
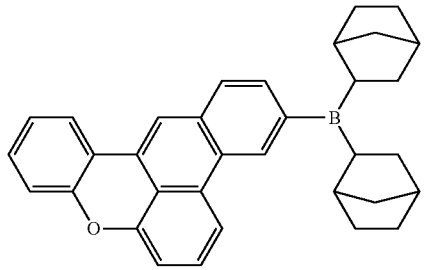
201
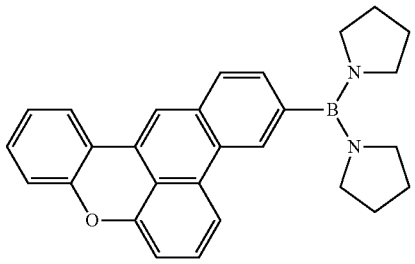
202
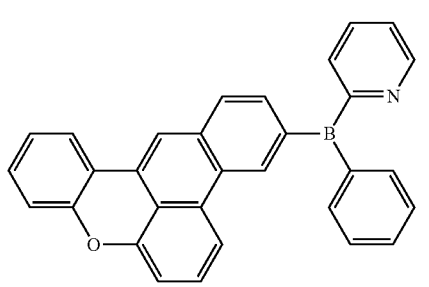
203
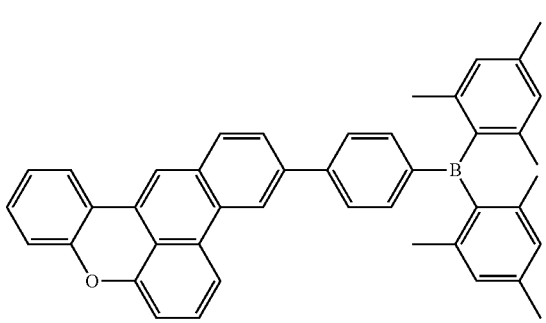

-continued
204
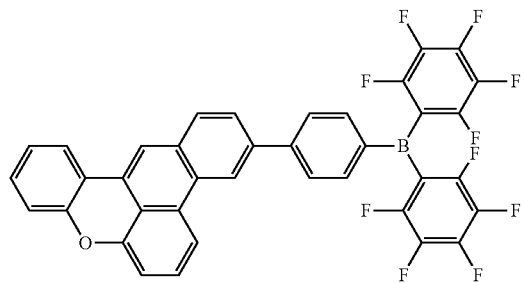
205
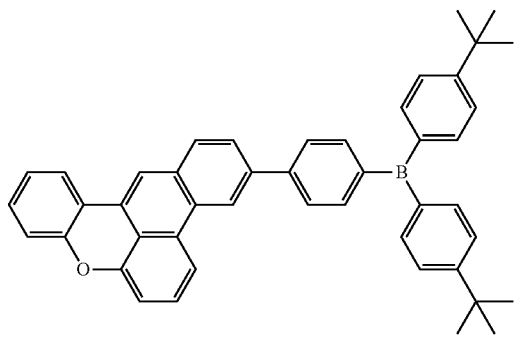
206
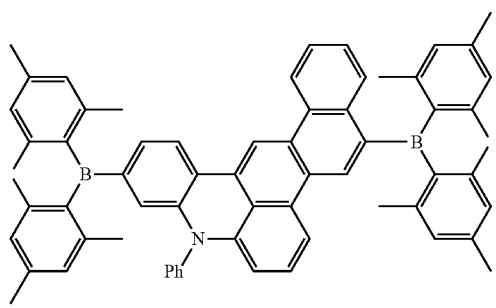
207
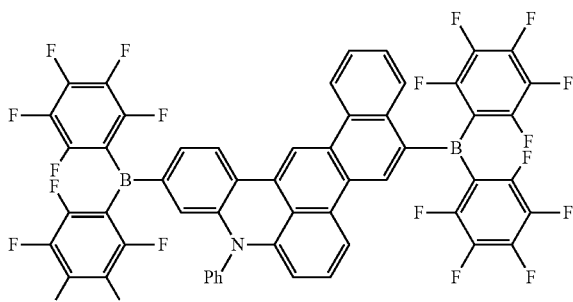
208
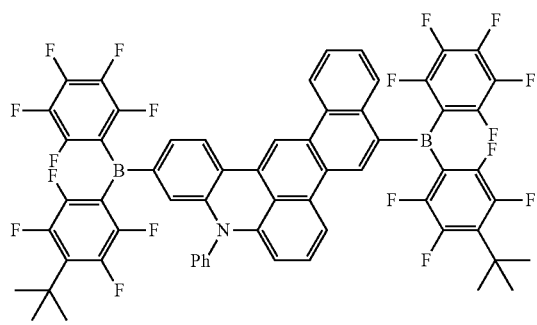
209
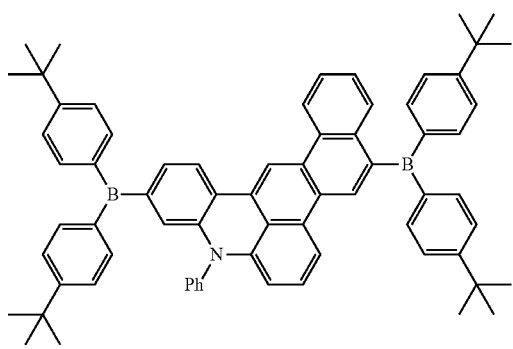
210
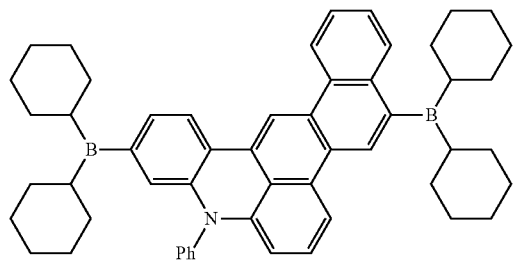
211
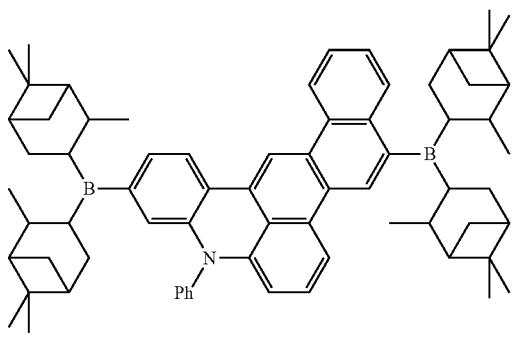
212
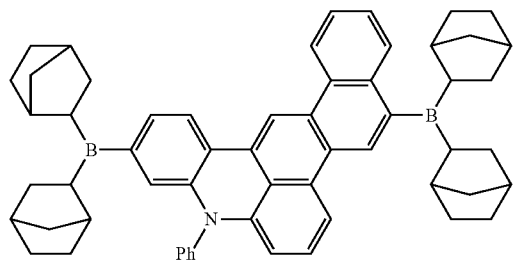
213
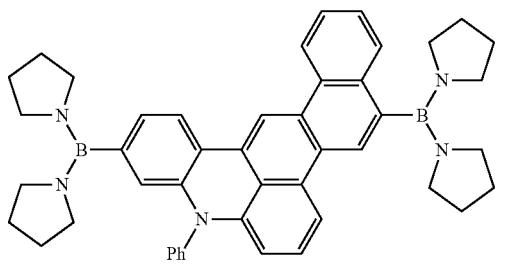

214
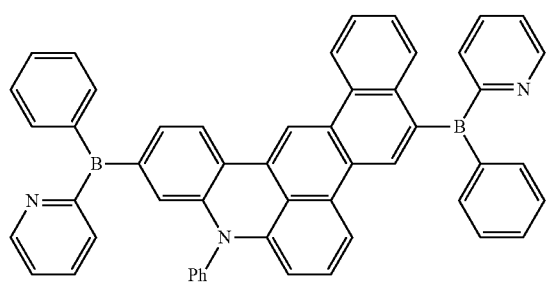
215
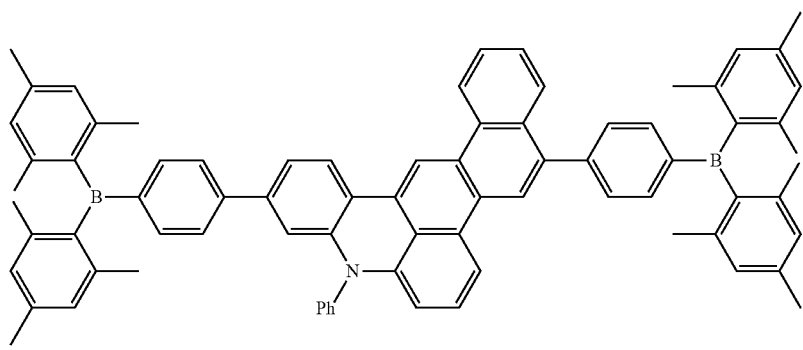
216
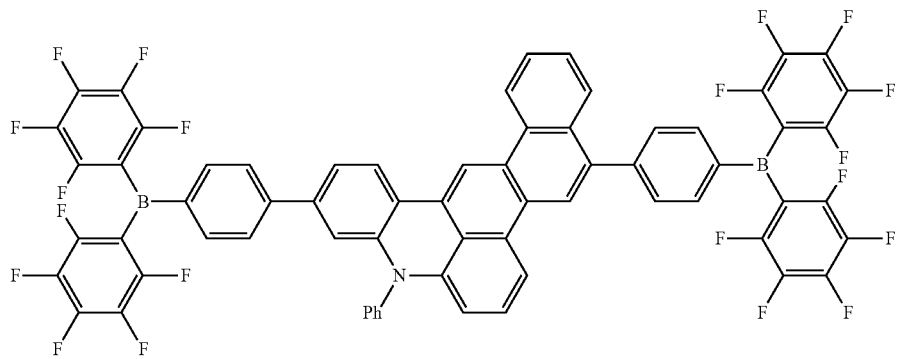
217
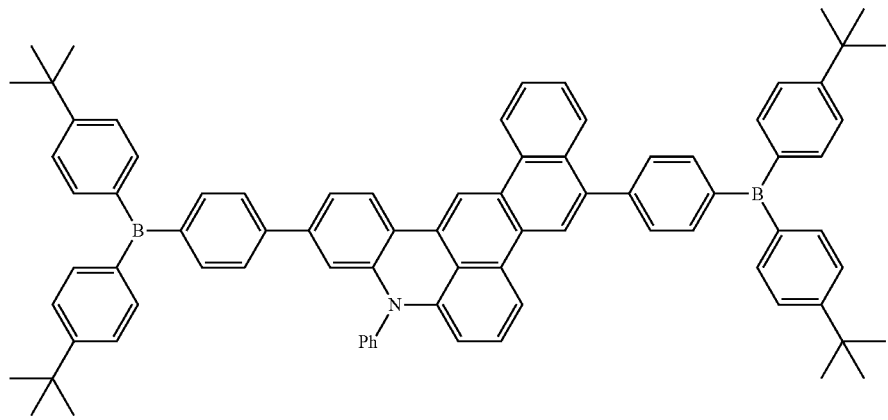

-continued
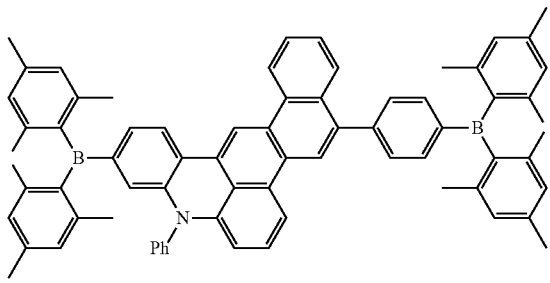
218
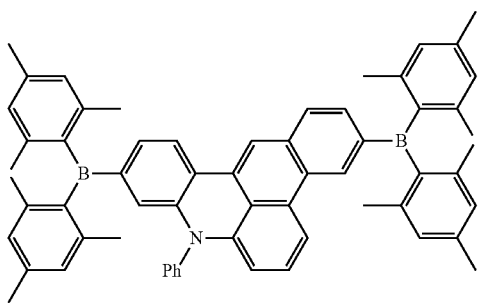
219
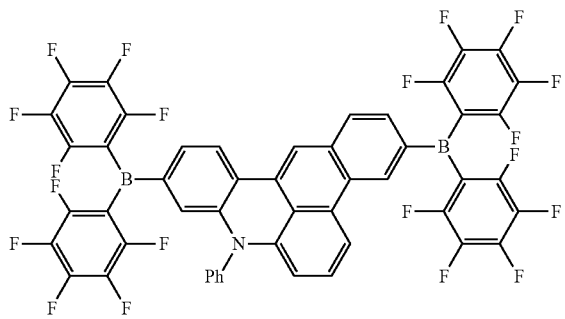
220
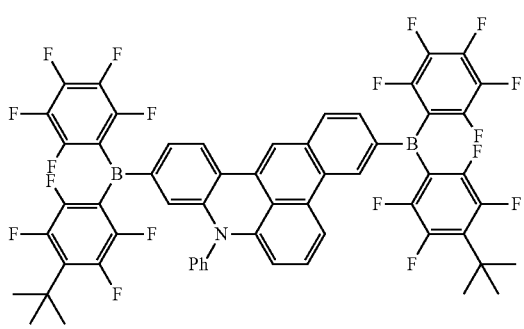
221
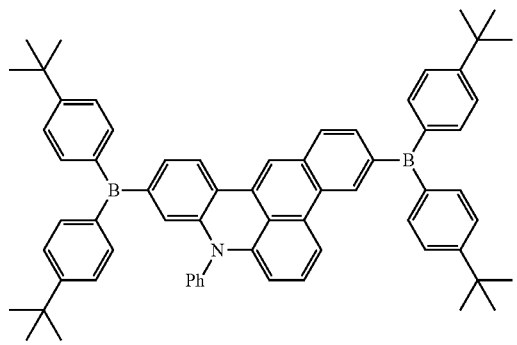
222
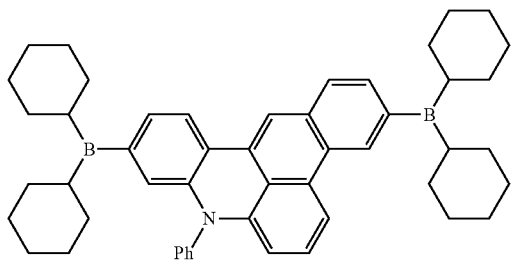
223
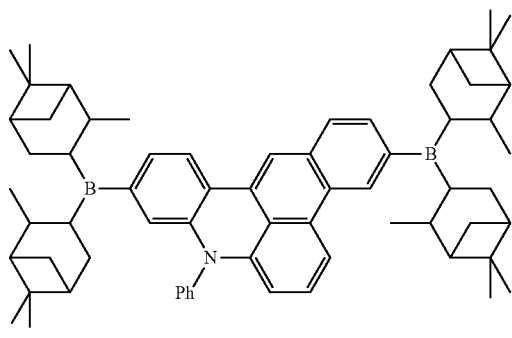
224
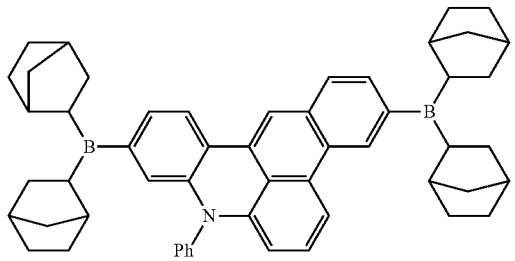
225
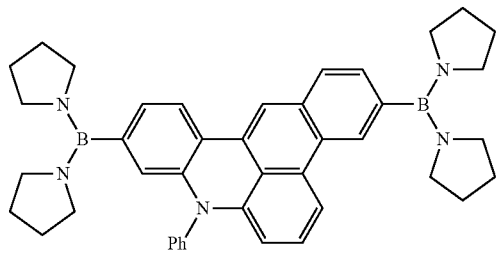
226

227
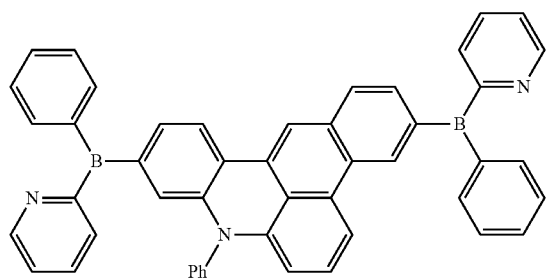
228
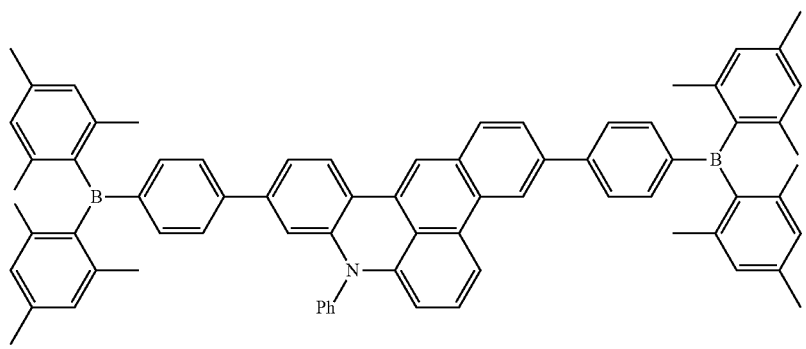
229
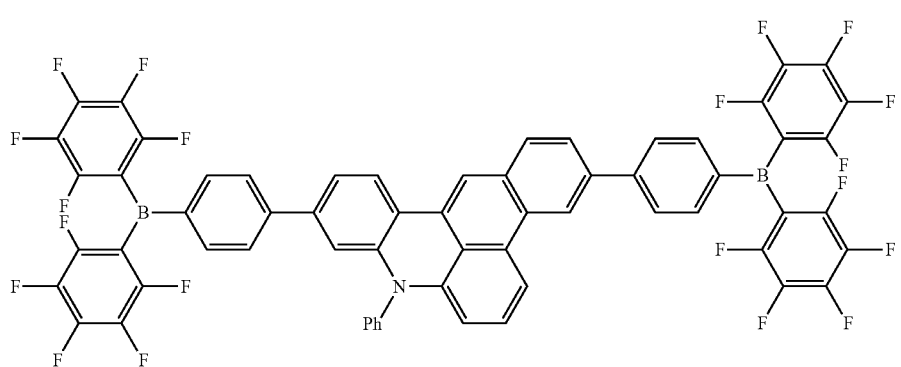
230
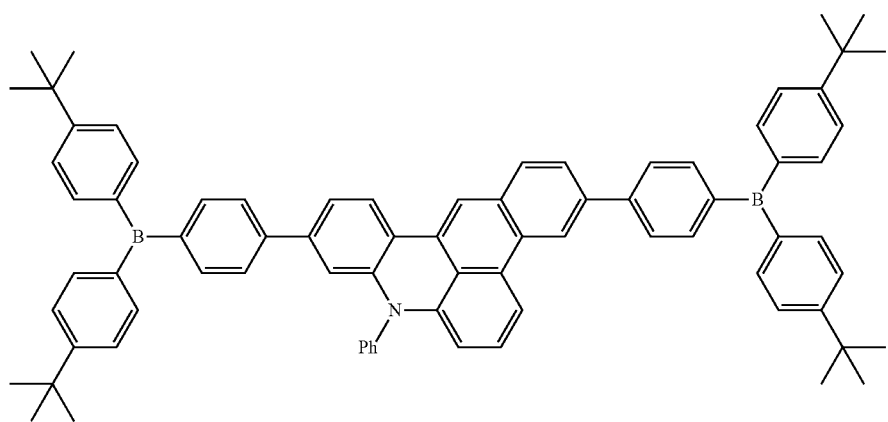

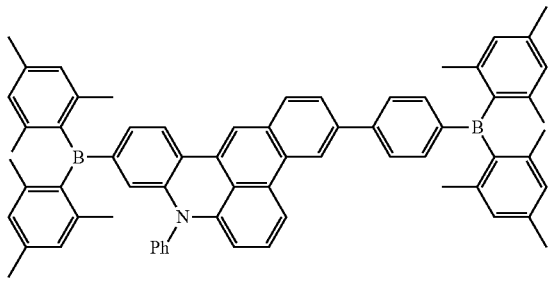

10. An organic light-emitting device comprising a first electrode; a second electrode facing the first electrode; and an organic layer between the first electrode and the second electrode, the organic layer including an emission layer, wherein the organic layer includes the condensed-cyclic compound represented by Formula 1 as claimed in claim 1.

11. The organic light-emitting device as claimed in claim 10, wherein
the first electrode is an anode,
the second electrode is a cathode,
and the organic layer includes i) a hole transport region between the first electrode and the emission layer, the hole transport region including at least one selected from a hole injection layer, a hole transport layer, a buffer layer, and an electron blocking layer and ii) an electron transport region between the emission layer and the second electrode, the electron transport region including at least one selected from a hole blocking layer, an electron transport layer, and an electron injection layer,
wherein at least one selected from the hole transport region and the emission layer includes the condensed-cyclic compound represented by Formula 1.

12. The organic light-emitting device as claimed in claim 10, wherein the emission layer further includes a host.

* * * * *